US007041813B2

(12) United States Patent
Haanes et al.

(10) Patent No.: US 7,041,813 B2
(45) Date of Patent: *May 9, 2006

(54) CANINE HERPES VIRUS ALPHA TRANSINDUCING FACTOR NUCLEIC ACID MOLECULES

(75) Inventors: Elizabeth J. Haanes, Berthoud, CO (US); Rexann S. Frank, Wellington, CO (US)

(73) Assignee: Heska Corporation, Loveland, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/156,275

(22) Filed: May 28, 2002

(65) Prior Publication Data
US 2003/0049844 A1    Mar. 13, 2003

Related U.S. Application Data

(60) Continuation of application No. 09/399,118, filed on Sep. 20, 1999, now abandoned, which is a division of application No. 09/092,409, filed on Jan. 29, 1998, now Pat. No. 6,159,478, which is a division of application No. 08/680,726, filed on Jul. 12, 1996, now Pat. No. 5,804,197, which is a continuation-in-part of application No. 08/602,010, filed on Feb. 15, 1996, now Pat. No. 5,753,235.

(51) Int. Cl.
*C12N 21/02* (2006.01)
*C12N 21/04* (2006.01)
*C12P 15/82* (2006.01)
*C07K 14/00* (2006.01)

(52) U.S. Cl. ............... 536/23.7; 536/23.72; 424/147.1; 424/229.1; 424/186.1; 424/199.1; 435/235.1; 435/69.1; 435/69.3; 435/325; 435/365.1; 530/350

(58) Field of Classification Search ............. 424/229.1, 424/147.1, 186.1, 199.1; 435/235.1, 69.1, 435/69.3, 235, 325, 365.1; 530/388.3, 350; 536/23.7, 23.72
See application file for complete search history.

(56) References Cited

U.S. PATENT DOCUMENTS

| 5,223,424 | A | 6/1993 | Cochran et al. ............ 435/236 |
| 5,266,489 | A | 11/1993 | Rey-Senelonge et al. ..................... 435/320.1 |
| 5,310,668 | A | 5/1994 | Ellis et al. ................ 435/172.3 |
| 5,324,664 | A | 6/1994 | Nunberg et al. ......... 435/320.1 |

FOREIGN PATENT DOCUMENTS

WO    WO 95/26751    10/1995

OTHER PUBLICATIONS

J. Gene. Virol. 1996, vol. 77, pp. 37-48.*
Binn, et al., "Viruses Recovered from Laboratory Dogs with Respiratory Disease," pp. 140-145, P.S.E.B.M., v. 126.
Breeden, et al., "Identification and Transcriptional Mapping of Genes Encoded at the IR/Us Junction of Equine Herpesvirus Type 1," pp. 649-660, *Virology*, 191 (1992).
Carmichael, "*Herpesvirus canls*: Aspects of Pathogenesis and Immune Response," pp. 1714-1721, J.A.V.M.A., vol. 156 (Jun. 15, 1970).
de Wind, et al., "Ribonucleotide reductase-deficient mutants of pseudorabies virus are avirulent for pigs and induce partial protective immunity," pp. 351-359, *Journal of General Virology*, 74 (1993).
Elton, et al., "Sequence analysis of the 4.7-kb *Bam*HI-*Eco*RI fragment of the equine herpesvirus type-1 short unique region," pp. 203-208, Elsevier Science Publishers B.V. 0378-1119/91 (1991).
Graham, et al., "A New Technique for the Assay of Infectivity of Human Adenovirus 5 DNA," pp. 456-467, *Virology*, 52 (1973).
Holliday, et al., "Inhibition of herpes simplex virus types 1 and 2 replication in vitro by mercurithio analogs of deoxyuridine," pp. 197-203, *Antiviral Research*, 16 (1991).
Kit, et al., "Nucleotide Sequence Changes in Thymidine Kinase Gene of Herpes Simplex Virus Type 2 Clones from an isolate of a Patient Treated with Acyclovir," pp. 1483-1490, *Antimicrobial Agents and Chemotherapy*, vol. 31, No. 10 (Oct. 1987).
Kit, et al., "Thymidine Kinase (TK) Induction after Infection of TK-Deficient Rabbit Cell Mutants with Bovine Herpesvirus Type 1 (BHV-1): Isolation of TK⁻ BHV-1 Mutants," pp. 381-389, *Virology*, 130 (1983).

(Continued)

*Primary Examiner*—James Housel
*Assistant Examiner*—Baoqun Li
(74) *Attorney, Agent, or Firm*—Heska Corporation

(57) ABSTRACT

The present invention includes novel recombinant canine herpes virus (CHV) and novel recombinant CHV genomes, and particularly to those CHV and CHV genomes that contain heterologous nucleic acid molecules. The present invention also relates to the use of such genomes and viruses in a variety of applications, including as therapeutic compositions to protect animals from disease. The present invention also relates to novel isolated CHV nucleic acid molecules, to CHV proteins encoded by such nucleic acid molecules, and to antibodies raised against such CHV proteins as well as to the use of such CHV nucleic acid molecules, proteins and antibodies as therapeutic compositions to protect an animal from CHV. The present invention also includes constructs comprising CHV nucleic acid molecules that include heterologous nucleic acid molecules, to recombinant vectors including such constructs, and to the use of such constructs and vectors in the production of recombinant CHV and recombinant CHV genomes.

17 Claims, 5 Drawing Sheets

OTHER PUBLICATIONS

Lees, et al., "The Epstein-Barr Virus Candidate Vaccine Antigen gp340/220 is Highly Conserved between Virus Types A and B," pp. 578-586, *Virology*, 195 (1993).

Liang, et al., "Identification and Deletion Mutagenesis of the Bovine Herpesvirus 1 dUTPase Gene and a Gene Homologous to Herpes Simplex Virus UL49.5," pp. 42-50, *Virology*, 195 (1993).

Limbach, et al., "Nucleotide sequence of the genes encoding the canine herpesvirus gB, gC and gC homologues," pp. 2029-2039, *Journal of General Virology*, 75 (1994).

McGeoch, et al., The Complete DNA Sequence of the Long Unique Region in the Genome of Herpes Simplex Virus Type 1, pp. 1531-1574, *Journal of General Virology*, 69 (1988).

McGeoch, et al., "Sequence Determination and Genetic Content of the Short Unique Region in the Genome of Herpes Simplex Virus Type 1," pp. 1-13, 1985 Academic Press Inc. (London) Ltd.

Meignier, et al., "Virulence of and Establishment of Latency by Genetically Engineered Deletion Mutants of Herpes Simplex Virus 1," pp. 251-254, *Virology*, 162 (1988).

Meinkoth, et al., "Hybridization of Nucleic Acids Immobilized on Solid Supports," pp. 267-284, *Analytical Biochemistry*, 138 (1984).

Nunberg, et al., "Identification of the Thymidine Kinase Gene of Feline Herpesvirus: Use of Degenerate Oligonucleotides in the Polymerase Chain Reaction to Isolate Herpesvirus Gene Homologs," pp. 3240-3249, *Journal of Virology*, vol. 63, No. 8 (Aug. 1989).

Peterson, et al., "Propagation and Quantitation of Animal Herpesviruses in Eight Cell Culture Systems," pp. 93-98, *Comp. Immun. Microbiol. Infect. Dis.*, vol. 11, No. 2 (1988).

Rémond, et al., "Gene organization in the $U_L$ region and inverted repeats of the canine herpesvirus genome," pp. 37-48, *Journal of General Virology*, 77 (1996).

Rémond, et al., "Sequence of the canine herpesvirus thymidine kinase gene: taxon-preferred amino acid residues in the alphaherpesviral thymidine kinases," pp. 341-354, *Virus Research*, 39 (1995).

Riggio, et al., "DNA sequence of a gene cluster in the equine herpesvirus-4 genome which contains a newly identified herpesvirus gene encoding a membrane protein," pp. 171-178, *Archives of Virology*, 133 (1993).

Robertson, et al., Evolution of the herpes thymidine kinase: Identification and comparison of the equine herpesvirus 1 thymidine kinase gene reveals similarity to a cell-encoded thymidylate kinase, pp. 11303-11317, *Nucleic Acids Research*, vol. 16, No. 23 (1988).

Simard, et al., "Sequencing and 5'- and 3'-end Transcript Mapping of the Gene Encoding the Small Subunit of Ribonucleotide Reductase from Bovine Herpesvirus Type-1," pp. 689-701, *Virology*, 190 (1992).

Spatz, et al., "Identification of the feline herpesvirus type 1 (FHV-1) genes encoding glycoproteins G, D, I and E: expression of FHV-1 glycoprotein D in vaccinia and raccoon poxviruses," pp. 1235-1244, *Journal of General Virology*, 75 (1994).

Tack, et al., The Complete DNA Sequence and the Genetic Organization of the Short Unique Region ($U_2$) of the Bovine Herpesvrius Type 1 (ST Strain), pp. 409-421, *Virology*, 199 (1994).

Telford, et al., "The DNA Sequence of Equine Herpesvirus-1," pp. 304, 316, *Virology*, 189 (1992).

van Zijl, et al., "Regeneration of Herpesviruses from Molecularly Cloned Subgenomic Fragments," pp. 2191-2195, *Journal of Virology*, vol. 61, No. 6 (Jun. 1988).

Walboomers, et al., "A New Method for the Isolation of Herpes Simplex Virus Type 2 DNA," pp. 256-258, *Virology*, 74 (1976).

Wolff, et al., "Detect Gene Transfer into Mouse Muscle in Vivo," pp. 1465-1468, *Science*, vol. 247 (Mar. 23, 1990).

Pyles, et al., 1994, *J. Virol.*, vol. 68(7), pp. 4514-4524.

Feng, et al., 1985, *J. Mol. Evol. 21*, pp. 112-125.

Haanes, et al., 1998, *Virus Research*, vol. 53, pp. 151-162.

Johnson, et al., 1993, *J. Mol. Biol. 233*, pp. 716-738.

Schulze, et al., 1998, *Vet Pathol*, vol. 35, pp. 209-217.

Smith, K.C., 1997, *The Veterinary Journal*, vol. 153, pp. 253-268.

Tyack, et al., 1997, *DNA Sequence—The Journal of Sequencing and Mapping*, vol. 7(6), pp. 365-368.

\* cited by examiner

SEQUENCE LISTING (1) GENERAL INFORMATION:

(iii) NUMBER OF SEQUENCES: 92

(2) INFORMATION FOR SEQ ID NO: 1:

(i) SEQUENCE CHARACTERISTICS:
      (A) LENGTH: 5495 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

```
CTGCAGTGTA TTTAAAAAAT AAAATCTATG AATGAAATCT ATGAATGAAA TCTATGAATG     60
AAATCTATGA ATGAAATCTA TGAATGAAAT CTATGAATGA ATCTATGAA TGAAATCTAT    120
GAATGAAATC TATGAATGAA ATCTATGAAT GAAATCTATG AATGAAATCT ATGAATGAAA   180
TCTATGAATG AAATCTATGA ATGAAATCTA TGAATGAAAT CTATGAATGA ATCTATGAA    240
TGAAATCTAT GAATGAAATC TATGAATGAA ATCTATGAAT GAAATCTATG AATGAAATCT   300
ATGAGACAAG TATTTTAAAA ATATTTTAAA TTTATAAGGT TAAGTACAGT AGGCGGTTGG   360
GTAAACATTT TTAGTTTTTC AAGTTTTTAG TTTTTCTGGT ATCCTACCCA ACACAAATGC   420
ATCTTCGGAT ACATTTATTT TAAGAGAGTA ATCACTTTTT AGAATATATC TTATTGGTGG   480
TACATTTATA AATTTTGGAC CATCCCAATA ACACTTCGAT TCCACAAGCG AAGAAGGTAC   540
TTCCATAAGC TGAGAAGCGT TTACTTGATT GTAGGGAGAA CTTGGCGTTT CAAAATCCTT   600
TAGAACGTAT AGTCTGCAAT ACATAGGTTC AATATCATCT TCATACCTCT CATCAGGATA   660
TGAAAATGGA AGTTTCACAA AGGTTCCATC ACGAAGCTTT TTGAAGAATC GTACATCCGT   720
AGGTGGTGTA GGAACAATAG TGAAGGCGTG CGGTTCACCC TGGTTTTTCA CACGTGCAAG   780
CGCTGGTGTG GTTTTAGGGC GAACTGGAAA ATAACCAGGC GGAACTTGTG CGTAGAATCC   840
TTCATTAAGT TCTCCACGAC AGCGTCTGAA GTATGATGGC ATATTAGCTT GATCGGAGTT   900
GTTATCAAAT AGAGCAAATG AAGCACTCAT TTTAAAACTT TTTAGTTAAG CTTTAAAAAC   960
AAGTGAAGAT TTAAAAATGT AGGATAAAAT GCCAGTTTAT ATACAGTAAG AATATGGGAG  1020
TGGTTCACAT AAAAAACCAG AATTTCAGGT TTACATCTAC TGTTTATTCA CAACAAATAT  1080
AAACAAACTT AGTTTCCACA TAAACATGAA CTAAATAGAG ATGAACGTTG AGCGTTGGTA  1140
GGTTGTGTAG AAGACATACC ATCGTTTTCA TTTTTGGTTA TTGTTTTGGC GCGCCTTGAA  1200
AATAATCGTT TAAAAATATT TGGTTTGGAT AGCCTTTTCA TAGGTTTCAC CCCATGCAAG  1260
TCATCCTCTT CTGGTTCAGG AATTTCTTCA TAACCATTAT GGGATATTAT TGCACACATA  1320
AATGATTCGA TTACCGGGGG GGCAGAACGT GTCTCATTTA TATAAAGAGA ATCACATACA  1380
TCGCTTATAG AACATGTAGA ACTGTCAGAA TCCTCTTTAA AACTATTTTT AATTTCACAA  1440
TTAGTTTCTT CTAGTTCATT ATCCACCATC GCATTAGCGT ATTTCCAAAT ATCATTCTCT  1500
GAGGAATAAT GAGATGCAGA GCATGAAGAA GAGGATGAGG AGGAGGAGGA TGAAGATGAG  1560
GATATAGAGG GACATCTTGG AGAGCTTTCA AGTTGAATG GAGTATTAAA TGTTGTACCA  1620
TAAAAAATGT CACTTAACAT AGGGGGTACT TTAAAGGAGG ACAGAAAGGT GTCTAATACA  1680
GGTACCCATA TAAACGAGGG GCAATAAACA CTCCCAGAAT CATCGATATG TTTTACATTA  1740
TTTTTGGAAA TCTCAAGACA CTCAGGTTTC CAGGATGGTT CCGGCCATTC ACATGATACA  1800
TATGCATAAA TTAGTCGCTT TGGTCCTGGG ATATTAGAAA TGACTGGCTC ACATAAATCC  1860
GCTGCACCGA AACCCATAG ATTAAGAGGA TAGTTTCCAA ATATACCAGA GTTTAGATAG  1920
TTATACCCCG AAACAGCCGA TTTCCATTCG ATGCTAGCCC CAGGTTTATC CTCATAAAAT  1980
AAAAAGTCCT CCTCCTCCCC CTCCGTTGGT TTTAAAAATT TACTATTAGA GGTTGATGTT  2040
CTTACTATAG GCCTTGAAAC TCTAGGTAGA TGTTTTATAG AGTCCATAAA ATAACATAAG  2100
TTTGCAGATC GTAATATTAT AGGCATAGCC AATCGTGTGA GAGAAAGGAT ATAGCATTGT  2160
CTAGCCATAA AACACCAAAG ATCAGGATGA ACATCTTGGG AGTTTCCTGG TAACGCCCCA  2220
```

```
TTTTTGTCAA TAAACGTAAC AATATTAACT TCAACCACAC CCATAATTAA ATTTTATGTA    2280

TGAATCCAAT AAAGGTTAAT ACACACCTAA TTTATGTTAT AATTTTAGAA GAAGCTGCAG    2340

TTGATGAGTT GATATTAACA TAACAATTTC ACAATTACCT GATATGGCAA AGTGTACCAC    2400

CGAAAAGTTT TGTTGTATCA GCGTGAATAG AGAATCTTCT GTCGATCCAG AAGACTTCTA    2460

TAAACCGGTT CCTCTAACTT CAGATTTGAT TGAAGAGGAT AACCTACATC AAGACAAAAT    2520

AATGGATGAG GATTTATACT CGGATTTTAG TGATGATGAC TTTATGGATT ATACAAAAAA    2580

TCCAACTGAA AGTGAAAATG AAAGAGAAAG TGACGAAGAA GTTGAAGAAA GTTATGAAAG    2640

TGATGAAGAT AAAAAAAGTT TATCTCCTAC TAAAAGCGAA GGAATTGAAG CGGCTGAAGC    2700

GCTAAAGTTT TCTGTTGTTA AATCGTTAAC GCCTGGGTCA GAAGGAAGAG TTTTTATTGC    2760

TCTTAAAAAA GATAAAGATA CAAGCTATAA GGTAATTTTA AAAATTGGAC AAAGGGGAAA    2820

CACGCTTGTG GAATCGTTAA TTTTGAGAAA TATTAGTCAC CAATCTATAA TTAAACTTCA    2880

AGACACTCTT TTTTATAAAG AGTTAACATG TTTGGTGTTA CCGTATTATA AATATGATCT    2940

ATATAATTTT TTAATGGATC ATGGGAAATC TCTGTCTTTT GAATCTGTAA TTAAAATTGA    3000

AAAACAAATA TTAACTGGAC TTCAATATAT TCATGGAAAA AAAATTATTC ATCGAGATAT    3060

AAAAACTGAA AATATTTTCT TGGATAATGA CTCTAATGTT TGTATAGGTG ATTTTGGGGC    3120

TTCTCAATTT CCTGTTTCCT CACCAGATTA TTTGGGAATT GCGGGACTA TTGAAACTAA    3180

TGCTCCTGAA GTTCTATCAA AGGATGCGTA CAACTGTAAA GCTGATATTT GGAGTGCTGG    3240

TATAATTTTA TTTGAAATGC TTGCATATCC TAATGTTTTG TTTGAGGAGG AAGAAAGAGA    3300

TAGTAGCGAT TTAATAAACA ATTGTAATCT TCATCTTATA AAAATTATAT CAACTCTGAA    3360

GATTAACCCA AATGAATTTC CATCTGATTT GGAATCTAAT CTAGTAAAAC ATTTTATAAA    3420

ATATGCTAAT AATGATAGAC CTCCATTTAC ACGATATAAT CGTCTAAATA ACCTTAAATT    3480

ACATCTCGAT GGTGAATTTT TAATTCATAA AATGCTAACA TTTGATGCAT CTCTACGACC    3540

AAGTGCGGAA GAACTATTAT CCTATCAGAT TTTTAGTAAA CAATAAATTT CATAAAAATG    3600

GGCGTGGAAT TTTTTATTGT TTTATATAAA ACGGGTGTTT GAAAGCTCTT TTTTATTAAT    3660

TTTATTTTA CATCCTAGCT ACAATATTAT AGTTATCATG TTGTATACGC TGTTTTTTGT     3720

TTTTTATTTT AAGGTAGTTT TATCTCGCAT AGCTCCGCTA GAGTTGTGTT ATGCGGATCC    3780

TAAAGAAAAT ACAACTGAAC CTACACAACT TCCTACAGGG GAACAATCTA AGACTCTTAT    3840

TCCCGTGGTA ACAAACGGAT ATGTTGAATA CTCTAAAGGA TGTGAACTAC GATTACTAGA    3900

TACATATGTA AATGTATCTT CACGACCAGA AAAAAAGGTT AATGCTACAA TTGGATGGTC    3960

ATTTGATCTT GGTTGTCAAA TTCCTTTAAT TTATAGAGAA TATTATAATT GTACTGGTAA    4020

TATAATACCA TCACCAGAAA CTTGTGATGG TTATTCTTTA ACTTTGGTAA AATCTGAAAG    4080

TATATCATCT TATGCACTTG TTAATGTTAG TTTGCTTATT CAACCAGGAA TTTTTGATTC    4140

TGGTAGATAT TTATACTCAC TTGTTTTTGG AAACGATAGT TATAACGGAA GAATTGAAGT    4200

TCGAGTGGAT AATGAGACAG ACTATCCATG TTTTATGATG CATGGATTGA CTGTAAAAAA    4260

GGGTGATAAA CTTCATATTC CTTATAAACC ATCCACAAAT CCTAATCATA AACGATATAG    4320

AGGTTGTTTT CCAATATCAA ATACTGAGCT ATGGAATAAT ATTAGTGATG AAAGTGTTGG    4380

TAGATATTCA TATGATGAAG AATATGAAGA ATATGAAGAA GAAACGAAG ATTTTGAAGA     4440

TCTACAATCA AAAGATTGCC GCAAATCCAA TCTTTTTGAT ATGAAGAAGA CTTTTAATTT    4500

GGCTGCAGGT TCTCAAAGTT TATTGATTGC TAGTTTGGGT AAATCAATTT CAGAACAACC    4560

GTGGTCATTT AAAATTAATG AAAGTTATGA ACTTTTTAAT AATTTGTCTA TCACCCTTCA    4620
```

```
ATCGGAAGAA GATTCTAATA TACTGAATCC TGAAATTGTA ACGTTTACCA CACCACCACC      4680

TACTGAAAAT ACACATATGT TTATGTCAAA TAATGAAACT ATGTATGAAG AAGAAAGTGT      4740

TTTAAGCATT ATTCAATTGT TTAACAATGG TTATAATAAT TGTAATACCC ATATAAAGGT      4800

AATTGGATTT GGAACAATTA TCTTTATTAT TTTATTTTTT GTTGCTGTGT TTTTTTGTGG      4860

ATATACTTGT GTATTAAACT CTCGTATTAA AATGATTAAC CATGCTTATA TACAACCCCA      4920

GAAATTAAAT TTTTATGATA TTTAATAAAA CTATTATGAA ACTTCTTATA ACTTATTTGT      4980

TTTTATTAAA TGGGTTGGGT TGGTTTTAAA ATTACATACG TGTATTAAGA ATTAACATCA      5040

TAAAGGACAC ACCCATGAAA AACATTTAAA TTCTATTAAT TTGAACGGAT TAAACATTTT      5100

CTCATTTTAA GAGTTGCTAC GACTTTTGAT AGTAAAATGA TTAAACTTCT ATTTATCTTA      5160

TTTTATTTTA ACCCAATAAC TGGATATAAA TGGGTAGACC CTCCTCGTAG GTATAATTAC      5220

ACCGTTTTAA GAATGATTCC AGATATTCCA AATCCAATGG ATCCTTCTAA AAACGCTGAA      5280

GTTCGGTATG TAACTTCTAC TGACCCATGT GATATGGTTG CTTTGATTTC TAATCCAAAT      5340

ATAGAATCTA CAATTAAAAC GATTCAATTT GTGCAAAAGA AAAAATTTTA CAATGCATCT      5400

CTTAGTTGGT TTAAAGTTGG AGATGATTGT ACATATCCAA TATATTTAAT TCAATATTTT      5460

GATTGTGATC CTCAAAGAGA ATTTGGCATA TGTTT                                5495

(2) INFORMATION FOR SEQ ID NO: 2:

(i) SEQUENCE CHARACTERISTICS:
        (A) LENGTH: 5495 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

AAACATATGC CAAATTCTCT TTGAGGATCA CAATCAAAAT ATTGAATTAA ATATATTGGA        60

TATGTACAAT CATCTCCAAC TTTAAACCAA CTAAGAGATG CATTGTAAAA TTTTTTCTTT       120

TGCACAAATT GAATCGTTTT AATTGTAGAT TCTATATTTG GATTAGAAAT CAAAGCAACC       180

ATATCACATG GGTCAGTAGA AGTTACATAC CGAACTTCAG CGTTTTTAGA AGGATCCATT       240

GGATTTGGAA TATCTGGAAT CATTCTTAAA ACGGTGTAAT TATACCTACG AGGAGGGTCT       300

ACCCATTTAT ATCCAGTTAT TGGGTTAAAA TAAAATAAGA TAAATAGAAG TTTAATCATT       360

TTACTATCAA AAGTCGTAGC AACTCTTAAA ATGAGAAAAT GTTTAATCCG TTCAAATTAA       420

TAGAATTTAA ATGTTTTTCA TGGGTGTGTC CTTTATGATG TTAATTCTTA ATACACGTAT       480

GTAATTTTAA AACCAACCCA ACCCATTTAA TAAAACAAA TAAGTTATAA GAAGTTTCAT        540

AATAGTTTTA TTAAATATCA TAAAAATTTA ATTTCTGGGG TTGTATATAA GCATGGTTAA       600

TCATTTTAAT ACGAGAGTTT AATACACAAG TATATCCACA AAAAAACACA GCAACAAAAA       660

ATAAAATAAT AAAGATAATT GTTCCAAATC CAATTACCTT TATATGGGTA TTACAATTAT       720

TATAACCATT GTTAAACAAT TGAATAATGC TTAAAACACT TCTTCTTCA TACATAGTTT        780

CATTATTTGA CATAAACATA TGTGTATTTT CAGTAGGTGG TGGTGTGGTA AACGTTACAA       840

TTTCAGGATT CAGTATATTA GAATCTTCTT CCGATTGAAG GGTGATAGAC AAATTATTAA       900

AAAGTTCATA ACTTTCATTA ATTTTAAATG ACCACGGTTG TTCTGAAATT GATTTACCCA       960

AACTAGCAAT CAATAAACTT TGAGAACCTG CAGCCAAATT AAAAGTCTTC TTCATATCAA      1020

AAAGATTGGA TTTGCGGCAA TCTTTTGATT GTAGATCTTC AAAATCTTCG TTTTCTTCTT      1080
```

```
CATATTCTTC ATATTCTTCA TCATATGAAT ATCTACCAAC ACTTTCATCA CTAATATTAT      1140

TCCATAGCTC AGTATTTGAT ATTGGAAAAC AACCTCTATA TCGTTTATGA TTAGGATTTG      1200

TGGATGGTTT ATAAGGAATA TGAAGTTTAT CACCCTTTTT TACAGTCAAT CCATGCATCA      1260

TAAAACATGG ATAGTCTGTC TCATTATCCA CTCGAACTTC AATTCTTCCG TTATAACTAT      1320

CGTTTCCAAA AACAAGTGAG TATAAATATC TACCAGAATC AAAAATTCCT GGTTGAATAA      1380

GCAAACTAAC ATTAACAAGT GCATAAGATG ATATACTTTC AGATTTTACC AAAGTTAAAG      1440

AATAACCATC ACAAGTTTCT GGTGATGGTA TTATATTACC AGTACAATTA TAATATTCTC      1500

TATAAATTAA AGGAATTTGA CAACCAAGAT CAAATGACCA TCCAATTGTA GCATTAACCT      1560

TTTTTTCTGG TCGTGAAGAT ACATTTACAT ATGTATCTAG TAATCGTAGT TCACATCCTT      1620

TAGAGTATTC AACATATCCG TTTGTTACCA CGGGAATAAG AGTCTTAGAT TGTTCCCCTG      1680

TAGGAAGTTG TGTAGGTTCA GTTGTATTTT CTTTAGGATC CGCATAACAC AACTCTAGCG      1740

GAGCTATGCG AGATAAAACT ACCTTAAAAT AAAAAACAAA AACAGCGTA TACAACATGA       1800

TAACTATAAT ATTGTAGCTA GGATGTAAAA ATAAAATTAA TAAAAAGAG CTTTCAAACA       1860

CCCGTTTTAT ATAAAACAAT AAAAAATTCC ACGCCCATTT TTATGAAATT TATTGTTTAC      1920

TAAAAATCTG ATAGGATAAT AGTTCTTCCG CACTTGGTCG TAGAGATGCA TCAAATGTTA      1980

GCATTTATG AATTAAAAAT TCACCATCGA GATGTAATTT AAGGTTATTT AGACGATTAT       2040

ATCGTGTAAA TGGAGGTCTA TCATTATTAG CATATTTTAT AAAATGTTTT ACTAGATTAG     2100

ATTCCAAATC AGATGGAAAT TCATTTGGGT TAATCTTCAG AGTTGATATA ATTTTTATAA      2160

GATGAAGATT ACAATTGTTT ATTAAATCGC TACTATCTCT TTCTTCCTCC TCAAACAAAA     2220

CATTAGGATA TGCAAGCATT TCAAATAAAA TTATACCAGC ACTCCAAATA TCAGCTTTAC      2280

AGTTGTACGC ATCCTTTGAT AGAACTTCAG GAGCATTAGT TTCAATAGTC CCGCAATTC       2340

CCAAATAATC TGGTGAGGAA ACAGGAAATT GAGAAGCCCC AAAATCACCT ATACAAACAT      2400

TAGAGTCATT ATCCAAGAAA ATATTTTCAG TTTTTATATC TCGATGAATA ATTTTTTTC       2460

CATGAATATA TTGAAGTCCA GTTAATATTT GTTTTTCAAT TTTAATTACA GATTCAAAAG      2520

ACAGAGATTT CCCATGATCC ATTAAAAAAT TATATAGATC ATATTTATAA TACGGTAACA      2580

CCAAACATGT TAACTCTTTA TAAAAAAGAG TGTCTTGAAG TTTAATTATA GATTGGTGAC      2640

TAATATTTCT CAAAATTAAC GATTCCACAA GCGTGTTTCC CCTTTGTCCA ATTTTTAAAA      2700

TTACCTTATA GCTTGTATCT TTATCTTTTT TAAGAGCAAT AAAAACTCTT CCTTCTGACC      2760

CAGGCGTTAA CGATTTAACA ACAGAAAACT TTAGCGCTTC AGCCGCTTCA ATTCCTTCGC      2820

TTTTAGTAGG AGATAAACTT TTTTTATCTT CATCACTTTC ATAACTTTCT TCAACTTCTT      2880

CGTCACTTTC TCTTTCATTT TCACTTTCAG TTGGATTTTT TGTATAATCC ATAAAGTCAT      2940

CATCACTAAA ATCCGAGTAT AAATCCTCAT CCATTATTTT GTCTTGATGT AGGTTATCCT      3000

CTTCAATCAA ATCTGAAGTT AGAGGAACCG GTTTATAGAA GTCTTCTGGA TCGACAGAAG      3060

ATTCTCTATT CACGCTGATA CAACAAAACT TTTCGGTGGT ACACTTTGCC ATATCAGGTA     3120

ATTGTGAAAT TGTTATGTTA ATATCAACTC ATCAACTGCA GCTTCTTCTA AAATTATAAC      3180

ATAAATTAGG TGTGTATTAA CCTTTATTGG ATTCATACAT AAAATTTAAT TATGGGTGTG      3240

GTTGAAGTTA ATATTGTTAC GTTTATTGAC AAAAATGGGG CGTTACCAGG AAACTCCCAA      3300

GATGTTCATC CTGATCTTTG GTGTTTTATG GCTAGACAAT GCTATATCCT TTCTCTCACA      3360

CGATTGGCTA TGCCTATAAT ATTACGATCT GCAAACTTAT GTTATTTTAT GGACTCTATA      3420
```

-continued

```
AAACATCTAC CTAGAGTTTC AAGGCCTATA GTAAGAACAT CAACCTCTAA TAGTAAATTT    3480

TTAAAACCAA CGGAGGGGGA GGAGGAGGAC TTTTTATTTT ATGAGGATAA ACCTGGGGCT    3540

AGCATCGAAT GGAAATCGGC TGTTTCGGGG TATAACTATC TAAACTCTGG TATATTTGGA    3600

AACTATCCTC TTAATCTATG GGTTTTCGGT GCAGCGGATT TATGTGAGCC AGTCATTTCT    3660

AATATCCCAG GACCAAAGCG ACTAATTTAT GCATATGTAT CATGTGAATG GCCGGAACCA    3720

TCCTGGAAAC CTGAGTGTCT TGAGATTTCC AAAAATAATG TAAAACATAT CGATGATTCT    3780

GGGAGTGTTT ATTGCCCCTC GTTTATATGG GTACCTGTAT TAGACACCTT TCTGTCCTCC    3840

TTTAAAGTAC CCCCTATGTT AAGTGACATT TTTTATGGTA CAACATTTAA TACTCCATTC    3900

AACTTTGAAA GCTCTCCAAG ATGTCCCTCT ATATCCTCAT CTTCATCCTC CTCCTCCTCA    3960

TCCTCTTCTT CATGCTCTGC ATCTCATTAT TCCTCAGAGA ATGATATTTG GAAATACGCT    4020

AATGCGATGG TGGATAATGA ACTAGAAGAA ACTAATTGTG AAATTAAAAA TAGTTTTAAA    4080

GAGGATTCTG ACAGTTCTAC ATGTTCTATA AGCGATGTAT GTGATTCTCT TTATATAAAT    4140

GAGACACGTT CTGCCCCCCC GGTAATCGAA TCATTTATGT GTGCAATAAT ATCCCATAAT    4200

GGTTATGAAG AAATTCCTGA ACCAGAAGAG GATGACTTGC ATGGGGTGAA ACCTATGAAA    4260

AGGCTATCCA AACCAAATAT TTTTAAACGA TTATTTTCAA GGCGCGCCAA AACAATAACC    4320

AAAAATGAAA ACGATGGTAT GTCTTCTACA CAACCTACCA ACGCTCAACG TTCATCTCTA    4380

TTTAGTTCAT GTTTATGTGG AAACTAAGTT TGTTTATATT TGTTGTGAAT AAACAGTAGA    4440

TGTAAACCTG AAATTCTGGT TTTTTATGTG AACCACTCCC ATATTCTTAC TGTATATAAA    4500

CTGGCATTTT ATCCTACATT TTTAAATCTT CACTTGTTTT TAAAGCTTAA CTAAAAAGTT    4560

TTAAAATGAG TGCTTCATTT GCTCTATTTG ATAACAACTC CGATCAAGCT AATATGCCAT    4620

CATACTTCAG ACGCTGTCGT GGAGAACTTA ATGAAGGATT CTACGCACAA GTTCCGCCTG    4680

GTTATTTTCC AGTTCGCCCT AAAACCACAC CAGCGCTTGC ACGTGTGAAA AACCAGGGTG    4740

AACCGCACGC CTTCACTATT GTTCCTACAC CACCTACGGA TGTACGATTC TTCAAAAAGC    4800

TTCGTGATGG AACCTTTGTG AAACTTCCAT TTTCATATCC TGATGAGAGG TATGAAGATG    4860

ATATTGAACC TATGTATTGC AGACTATACG TTCTAAAGGA TTTTGAAACG CCAAGTTCTC    4920

CCTACAATCA AGTAAACGCT TCTCAGCTTA TGGAAGTACC TTCTTCGCTT GTGGAATCGA    4980

AGTGTTATTG GGATGGTCCA AAATTTATAA ATGTACCACC AATAAGATAT ATTCTAAAAA    5040

GTGATTACTC TCTTAAAATA AATGTATCCG AAGATGCATT TGTGTTGGGT AGGATACCAG    5100

AAAAACTAAA AACTTGAAAA ACTAAAAATG TTTACCCAAC CGCCTACTGT ACTTAACCTT    5160

ATAAATTTAA AATATTTTTA AAATACTTGT CTCATAGATT TCATTCATAG ATTTCATTCA    5220

TAGATTTCAT TCATAGATTT CATTCATAGA TTTCATTCAT AGATTTCATT CATAGATTTC    5280

ATTCATAGAT TTCATTCATA GATTTCATTC ATAGATTTCA TTCATAGATT TCATTCATAG    5340

ATTTCATTCA TAGATTTCAT TCATAGATTT CATTCATAGA TTTCATTCAT AGATTTCATT    5400

CATAGATTTC ATTCATAGAT TTCATTCATA GATTTCATTC ATAGATTTCA TTCATAGATT    5460

TCATTCATAG ATTTTATTTT TTAAATACAC TGCAG                               5495
```

(2) INFORMATION FOR SEQ ID NO: 3:

(i) SEQUENCE CHARACTERISTICS:
        (A) LENGTH: 552 base pairs
        (B) TYPE: nucleic acid
        (C) STRANDEDNESS: single
        (D) TOPOLOGY: linear (ii) MOLECULE TYPE: cDNA (ix) FEATURE:
    (A) NAME/KEY: CDS
    (B) LOCATION: 1..552

(xi) SEQUENCE DESCRIPTION: SEQ ID NO: 3:

```
ATG AGT GCT TCA TTT GCT CTA TTT GAT AAC AAC TCC GAT CAA GCT AAT        48
Met Ser Ala Ser Phe Ala Leu Phe Asp Asn Asn Ser Asp Gln Ala Asn
 1               5                  10                  15

ATG CCA TCA TAC TTC AGA CGC TGT CGT GGA GAA CTT AAT GAA GGA TTC        96
Met Pro Ser Tyr Phe Arg Arg Cys Arg Gly Glu Leu Asn Glu Gly Phe
                20                  25                  30

TAC GCA CAA GTT CCG CCT GGT TAT TTT CCA GTT CGC CCT AAA ACC ACA       144
Tyr Ala Gln Val Pro Pro Gly Tyr Phe Pro Val Arg Pro Lys Thr Thr
         35                  40                  45

CCA GCG CTT GCA CGT GTG AAA AAC CAG GGT GAA CCG CAC GCC TTC ACT       192
Pro Ala Leu Ala Arg Val Lys Asn Gln Gly Glu Pro His Ala Phe Thr
     50                  55                  60

ATT GTT CCT ACA CCA CCT ACG GAT GTA CGA TTC TTC AAA AAG CTT CGT       240
Ile Val Pro Thr Pro Pro Thr Asp Val Arg Phe Phe Lys Lys Leu Arg
 65                  70                  75                  80

GAT GGA ACC TTT GTG AAA CTT CCA TTT TCA TAT CCT GAT GAG AGG TAT       288
Asp Gly Thr Phe Val Lys Leu Pro Phe Ser Tyr Pro Asp Glu Arg Tyr
                 85                  90                  95

GAA GAT GAT ATT GAA CCT ATG TAT TGC AGA CTA TAC GTT CTA AAG GAT       336
Glu Asp Asp Ile Glu Pro Met Tyr Cys Arg Leu Tyr Val Leu Lys Asp
            100                 105                 110

TTT GAA ACG CCA AGT TCT CCC TAC AAT CAA GTA AAC GCT TCT CAG CTT       384
Phe Glu Thr Pro Ser Ser Pro Tyr Asn Gln Val Asn Ala Ser Gln Leu
        115                 120                 125

ATG GAA GTA CCT TCT TCG CTT GTG GAA TCG AAG TGT TAT TGG GAT GGT       432
Met Glu Val Pro Ser Ser Leu Val Glu Ser Lys Cys Tyr Trp Asp Gly
    130                 135                 140

CCA AAA TTT ATA AAT GTA CCA CCA ATA AGA TAT ATT CTA AAA AGT GAT       480
Pro Lys Phe Ile Asn Val Pro Pro Ile Arg Tyr Ile Leu Lys Ser Asp
145                 150                 155                 160

TAC TCT CTT AAA ATA AAT GTA TCC GAA GAT GCA TTT GTG TTG GGT AGG       528
Tyr Ser Leu Lys Ile Asn Val Ser Glu Asp Ala Phe Val Leu Gly Arg
                165                 170                 175

ATA CCA GAA AAA CTA AAA ACT TGA                                       552
Ile Pro Glu Lys Leu Lys Thr *
            180
```

(2) INFORMATION FOR SEQ ID NO: 4:

(i) SEQUENCE CHARACTERISTICS:
        (A) LENGTH: 183 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Ser Ala Ser Phe Ala Leu Phe Asp Asn Asn Ser Asp Gln Ala Asn
 1               5                  10                  15

Met Pro Ser Tyr Phe Arg Arg Cys Arg Gly Glu Leu Asn Glu Gly Phe
                20                  25                  30

Tyr Ala Gln Val Pro Pro Gly Tyr Phe Pro Val Arg Pro Lys Thr Thr
         35                  40                  45

Pro Ala Leu Ala Arg Val Lys Asn Gln Gly Glu Pro His Ala Phe Thr
     50                  55                  60
```

```
Ile Val Pro Thr Pro Thr Asp Val Arg Phe Phe Lys Lys Leu Arg
 65                  70                  75                  80

Asp Gly Thr Phe Val Lys Leu Pro Phe Ser Tyr Pro Asp Glu Arg Tyr
                 85                  90                  95

Glu Asp Asp Ile Glu Pro Met Tyr Cys Arg Leu Tyr Val Leu Lys Asp
            100                 105                 110

Phe Glu Thr Pro Ser Ser Pro Tyr Asn Gln Val Asn Ala Ser Gln Leu
            115                 120                 125

Met Glu Val Pro Ser Ser Leu Val Glu Ser Lys Cys Tyr Trp Asp Gly
130                 135                 140

Pro Lys Phe Ile Asn Val Pro Pro Ile Arg Tyr Ile Leu Lys Ser Asp
145                 150                 155                 160

Tyr Ser Leu Lys Ile Asn Val Ser Glu Asp Ala Phe Val Leu Gly Arg
                165                 170                 175

Ile Pro Glu Lys Leu Lys Thr
                180

(2) INFORMATION FOR SEQ ID NO: 5:

(i) SEQUENCE CHARACTERISTICS:
        (A) LENGTH: 1176 base pairs
        (B) TYPE: nucleic acid
        (C) STRANDEDNESS: single
        (D) TOPOLOGY: linear (ii) MOLECULE TYPE: cDNA (ix) FEATURE:
         (A) NAME/KEY: CDS
         (B) LOCATION: 1..1176

(xi) SEQUENCE DESCRIPTION: SEQ ID NO: 5:

ATG GGT GTG GTT GAA GTT AAT ATT GTT ACG TTT ATT GAC AAA AAT GGG      48
Met Gly Val Val Glu Val Asn Ile Val Thr Phe Ile Asp Lys Asn Gly
 1               5                  10                  15

GCG TTA CCA GGA AAC TCC CAA GAT GTT CAT CCT GAT CTT TGG TGT TTT      96
Ala Leu Pro Gly Asn Ser Gln Asp Val His Pro Asp Leu Trp Cys Phe
                20                  25                  30

ATG GCT AGA CAA TGC TAT ATC CTT TCT CTC ACA CGA TTG GCT ATG CCT     144
Met Ala Arg Gln Cys Tyr Ile Leu Ser Leu Thr Arg Leu Ala Met Pro
            35                  40                  45

ATA ATA TTA CGA TCT GCA AAC TTA TGT TAT TTT ATG GAC TCT ATA AAA     192
Ile Ile Leu Arg Ser Ala Asn Leu Cys Tyr Phe Met Asp Ser Ile Lys
50                  55                  60

CAT CTA CCT AGA GTT TCA AGG CCT ATA GTA AGA ACA TCA ACC TCT AAT     240
His Leu Pro Arg Val Ser Arg Pro Ile Val Arg Thr Ser Thr Ser Asn
 65                 70                  75                  80

AGT AAA TTT TTA AAA CCA ACG GAG GGG GAG GAG GAG GAC TTT TTA TTT     288
Ser Lys Phe Leu Lys Pro Thr Glu Gly Glu Glu Glu Asp Phe Leu Phe
                85                  90                  95

TAT GAG GAT AAA CCT GGG GCT AGC ATC GAA TGG AAA TCG GCT GTT TCG     336
Tyr Glu Asp Lys Pro Gly Ala Ser Ile Glu Trp Lys Ser Ala Val Ser
            100                 105                 110

GGG TAT AAC TAT CTA AAC TCT GGT ATA TTT GGA AAC TAT CCT CTT AAT     384
Gly Tyr Asn Tyr Leu Asn Ser Gly Ile Phe Gly Asn Tyr Pro Leu Asn
        115                     120                 125

CTA TGG GTT TTC GGT GCA GCG GAT TTA TGT GAG CCA GTC ATT TCT AAT     432
Leu Trp Val Phe Gly Ala Ala Asp Leu Cys Glu Pro Val Ile Ser Asn
130                 135                 140

ATC CCA GGA CCA AAG CGA CTA ATT TAT GCA TAT GTA TCA TGT GAA TGG     480
```

```
Ile Pro Gly Pro Lys Arg Leu Ile Tyr Ala Tyr Val Ser Cys Glu Trp
145                 150                 155                 160

CCG GAA CCA TCC TGG AAA CCT GAG TGT CTT GAG ATT TCC AAA AAT AAT      528
Pro Glu Pro Ser Trp Lys Pro Glu Cys Leu Glu Ile Ser Lys Asn Asn
                165                 170                 175

GTA AAA CAT ATC GAT GAT TCT GGG AGT GTT TAT TGC CCC TCG TTT ATA      576
Val Lys His Ile Asp Asp Ser Gly Ser Val Tyr Cys Pro Ser Phe Ile
                180                 185                 190

TGG GTA CCT GTA TTA GAC ACC TTT CTG TCC TCC TTT AAA GTA CCC CCT      624
Trp Val Pro Val Leu Asp Thr Phe Leu Ser Ser Phe Lys Val Pro Pro
            195                 200                 205

ATG TTA AGT GAC ATT TTT TAT GGT ACA ACA TTT AAT ACT CCA TTC AAC      672
Met Leu Ser Asp Ile Phe Tyr Gly Thr Thr Phe Asn Thr Pro Phe Asn
    210                 215                 220

TTT GAA AGC TCT CCA AGA TGT CCC TCT ATA TCC TCA TCT TCA TCC TCC      720
Phe Glu Ser Ser Pro Arg Cys Pro Ser Ile Ser Ser Ser Ser Ser Ser
225                 230                 235                 240

TCC TCC TCA TCC TCT TCT TCA TGC TCT GCA TCT CAT TAT TCC TCA GAG      768
Ser Ser Ser Ser Ser Ser Ser Cys Ser Ala Ser His Tyr Ser Ser Glu
                245                 250                 255

AAT GAT ATT TGG AAA TAC GCT AAT GCG ATG GTG GAT AAT GAA CTA GAA      816
Asn Asp Ile Trp Lys Tyr Ala Asn Ala Met Val Asp Asn Glu Leu Glu
                260                 265                 270

GAA ACT AAT TGT GAA ATT AAA AAT AGT TTT AAA GAG GAT TCT GAC AGT      864
Glu Thr Asn Cys Glu Ile Lys Asn Ser Phe Lys Glu Asp Ser Asp Ser
            275                 280                 285

TCT ACA TGT TCT ATA AGC GAT GTA TGT GAT TCT CTT TAT ATA AAT GAG      912
Ser Thr Cys Ser Ile Ser Asp Val Cys Asp Ser Leu Tyr Ile Asn Glu
        290                 295                 300

ACA CGT TCT GCC CCC CCG GTA ATC GAA TCA TTT ATG TGT GCA ATA ATA      960
Thr Arg Ser Ala Pro Pro Val Ile Glu Ser Phe Met Cys Ala Ile Ile
305                 310                 315                 320

TCC CAT AAT GGT TAT GAA GAA ATT CCT GAA CCA GAA GAG GAT GAC TTG     1008
Ser His Asn Gly Tyr Glu Glu Ile Pro Glu Pro Glu Glu Asp Asp Leu
                325                 330                 335

CAT GGG GTG AAA CCT ATG AAA AGG CTA TCC AAA CCA AAT ATT TTT AAA     1056
His Gly Val Lys Pro Met Lys Arg Leu Ser Lys Pro Asn Ile Phe Lys
                340                 345                 350

CGA TTA TTT TCA AGG CGC GCC AAA ACA ATA ACC AAA AAT GAA AAC GAT     1104
Arg Leu Phe Ser Arg Arg Ala Lys Thr Ile Thr Lys Asn Glu Asn Asp
            355                 360                 365

GGT ATG TCT TCT ACA CAA CCT ACC AAC GCT CAA CGT TCA TCT CTA TTT     1152
Gly Met Ser Ser Thr Gln Pro Thr Asn Ala Gln Arg Ser Ser Leu Phe
        370                 375                 380

AGT TCA TGT TTA TGT GGA AAC TAA                                     1176
Ser Ser Cys Leu Cys Gly Asn *
385                 390
```

(2) INFORMATION FOR SEQ ID NO: 6:

(i) SEQUENCE CHARACTERISTICS:
        (A) LENGTH: 391 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Gly Val Val Glu Val Asn Ile Val Thr Phe Ile Asp Lys Asn Gly
1               5                   10                  15

Ala Leu Pro Gly Asn Ser Gln Asp Val His Pro Asp Leu Trp Cys Phe
```

```
                20                  25                  30
Met Ala Arg Gln Cys Tyr Ile Leu Ser Leu Thr Arg Leu Ala Met Pro
                35                  40                  45

Ile Ile Leu Arg Ser Ala Asn Leu Cys Tyr Phe Met Asp Ser Ile Lys
    50                  55                  60

His Leu Pro Arg Val Ser Arg Pro Ile Val Arg Thr Ser Thr Ser Asn
65                  70                  75                  80

Ser Lys Phe Leu Lys Pro Thr Glu Gly Glu Glu Asp Phe Leu Phe
                85                  90                  95

Tyr Glu Asp Lys Pro Gly Ala Ser Ile Glu Trp Lys Ser Ala Val Ser
                100                 105                 110

Gly Tyr Asn Tyr Leu Asn Ser Gly Ile Phe Gly Asn Tyr Pro Leu Asn
                115                 120                 125

Leu Trp Val Phe Gly Ala Ala Asp Leu Cys Glu Pro Val Ile Ser Asn
    130                 135                 140

Ile Pro Gly Pro Lys Arg Leu Ile Tyr Ala Tyr Val Ser Cys Glu Trp
145                 150                 155                 160

Pro Glu Pro Ser Trp Lys Pro Glu Cys Leu Glu Ile Ser Lys Asn Asn
                165                 170                 175

Val Lys His Ile Asp Asp Ser Gly Ser Val Tyr Cys Pro Ser Phe Ile
                180                 185                 190

Trp Val Pro Val Leu Asp Thr Phe Leu Ser Ser Phe Lys Val Pro Pro
    195                 200                 205

Met Leu Ser Asp Ile Phe Tyr Gly Thr Thr Phe Asn Thr Pro Phe Asn
    210                 215                 220

Phe Glu Ser Ser Pro Arg Cys Pro Ser Ile Ser Ser Ser Ser Ser Ser
225                 230                 235                 240

Ser Ser Ser Ser Ser Ser Cys Ser Ala Ser His Tyr Ser Ser Glu
                245                 250                 255

Asn Asp Ile Trp Lys Tyr Ala Asn Ala Met Val Asp Asn Glu Leu Glu
                260                 265                 270

Glu Thr Asn Cys Glu Ile Lys Asn Ser Phe Lys Glu Asp Ser Asp Ser
    275                 280                 285

Ser Thr Cys Ser Ile Ser Asp Val Cys Asp Ser Leu Tyr Ile Asn Glu
    290                 295                 300

Thr Arg Ser Ala Pro Pro Val Ile Glu Ser Phe Met Cys Ala Ile Ile
305                 310                 315                 320

Ser His Asn Gly Tyr Glu Glu Ile Pro Glu Pro Glu Glu Asp Asp Leu
                325                 330                 335

His Gly Val Lys Pro Met Lys Arg Leu Ser Lys Pro Asn Ile Phe Lys
                340                 345                 350

Arg Leu Phe Ser Arg Arg Ala Lys Thr Ile Thr Lys Asn Glu Asn Asp
                355                 360                 365

Gly Met Ser Ser Thr Gln Pro Thr Asn Ala Gln Arg Ser Ser Leu Phe
                370                 375                 380

Ser Ser Cys Leu Cys Gly Asn
385                 390
```

(2) INFORMATION FOR SEQ ID NO: 7:

(i) SEQUENCE CHARACTERISTICS:
        (A) LENGTH: 1203 base pairs
        (B) TYPE: nucleic acid
        (C) STRANDEDNESS: single
        (D) TOPOLOGY: linear -continued (ii) MOLECULE TYPE: cDNA (ix) FEATURE:
    (A) NAME/KEY: CDS
    (B) LOCATION: 1..1203

(xi) SEQUENCE DESCRIPTION: SEQ ID NO: 7:

```
ATG GCA AAG TGT ACC ACC GAA AAG TTT TGT TGT ATC AGC GTG AAT AGA        48
Met Ala Lys Cys Thr Thr Glu Lys Phe Cys Cys Ile Ser Val Asn Arg
 1               5                  10                  15

GAA TCT TCT GTC GAT CCA GAA GAC TTC TAT AAA CCG GTT CCT CTA ACT        96
Glu Ser Ser Val Asp Pro Glu Asp Phe Tyr Lys Pro Val Pro Leu Thr
             20                  25                  30

TCA GAT TTG ATT GAA GAG GAT AAC CTA CAT CAA GAC AAA ATA ATG GAT       144
Ser Asp Leu Ile Glu Glu Asp Asn Leu His Gln Asp Lys Ile Met Asp
         35                  40                  45

GAG GAT TTA TAC TCG GAT TTT AGT GAT GAT GAC TTT ATG GAT TAT ACA       192
Glu Asp Leu Tyr Ser Asp Phe Ser Asp Asp Asp Phe Met Asp Tyr Thr
     50                  55                  60

AAA AAT CCA ACT GAA AGT GAA AAT GAA AGA GAA AGT GAC GAA GAA GTT       240
Lys Asn Pro Thr Glu Ser Glu Asn Glu Arg Glu Ser Asp Glu Glu Val
 65                  70                  75                  80

GAA GAA AGT TAT GAA AGT GAT GAA GAT AAA AAA AGT TTA TCT CCT ACT       288
Glu Glu Ser Tyr Glu Ser Asp Glu Asp Lys Lys Ser Leu Ser Pro Thr
                 85                  90                  95

AAA AGC GAA GGA ATT GAA GCG GCT GAA GCG CTA AAG TTT TCT GTT GTT       336
Lys Ser Glu Gly Ile Glu Ala Ala Glu Ala Leu Lys Phe Ser Val Val
            100                 105                 110

AAA TCG TTA ACG CCT GGG TCA GAA GGA AGA GTT TTT ATT GCT CTT AAA       384
Lys Ser Leu Thr Pro Gly Ser Glu Gly Arg Val Phe Ile Ala Leu Lys
        115                 120                 125

AAA GAT AAA GAT ACA AGC TAT AAG GTA ATT TTA AAA ATT GGA CAA AGG       432
Lys Asp Lys Asp Thr Ser Tyr Lys Val Ile Leu Lys Ile Gly Gln Arg
    130                 135                 140

GGA AAC ACG CTT GTG GAA TCG TTA ATT TTG AGA AAT ATT AGT CAC CAA       480
Gly Asn Thr Leu Val Glu Ser Leu Ile Leu Arg Asn Ile Ser His Gln
145                 150                 155                 160

TCT ATA ATT AAA CTT CAA GAC ACT CTT TTT TAT AAA GAG TTA ACA TGT       528
Ser Ile Ile Lys Leu Gln Asp Thr Leu Phe Tyr Lys Glu Leu Thr Cys
                165                 170                 175

TTG GTG TTA CCG TAT TAT AAA TAT GAT CTA TAT AAT TTT TTA ATG GAT       576
Leu Val Leu Pro Tyr Tyr Lys Tyr Asp Leu Tyr Asn Phe Leu Met Asp
            180                 185                 190

CAT GGG AAA TCT CTG TCT TTT GAA TCT GTA ATT AAA ATT GAA AAA CAA       624
His Gly Lys Ser Leu Ser Phe Glu Ser Val Ile Lys Ile Glu Lys Gln
        195                 200                 205

ATA TTA ACT GGA CTT CAA TAT ATT CAT GGA AAA AAA ATT ATT CAT CGA       672
Ile Leu Thr Gly Leu Gln Tyr Ile His Gly Lys Lys Ile Ile His Arg
    210                 215                 220

GAT ATA AAA ACT GAA AAT ATT TTC TTG GAT AAT GAC TCT AAT GTT TGT       720
Asp Ile Lys Thr Glu Asn Ile Phe Leu Asp Asn Asp Ser Asn Val Cys
225                 230                 235                 240

ATA GGT GAT TTT GGG GCT TCT CAA TTT CCT GTT TCC TCA CCA GAT TAT       768
Ile Gly Asp Phe Gly Ala Ser Gln Phe Pro Val Ser Ser Pro Asp Tyr
                245                 250                 255

TTG GGA ATT GCG GGG ACT ATT GAA ACT AAT GCT CCT GAA GTT CTA TCA       816
Leu Gly Ile Ala Gly Thr Ile Glu Thr Asn Ala Pro Glu Val Leu Ser
            260                 265                 270

AAG GAT GCG TAC AAC TGT AAA GCT GAT ATT TGG AGT GCT GGT ATA ATT       864
Lys Asp Ala Tyr Asn Cys Lys Ala Asp Ile Trp Ser Ala Gly Ile Ile
```

```
                275                 280                 285
TTA TTT GAA ATG CTT GCA TAT CCT AAT GTT TTG TTT GAG GAG GAA GAA      912
Leu Phe Glu Met Leu Ala Tyr Pro Asn Val Leu Phe Glu Glu Glu Glu
    290                 295                 300

AGA GAT AGT AGC GAT TTA ATA AAC AAT TGT AAT CTT CAT CTT ATA AAA      960
Arg Asp Ser Ser Asp Leu Ile Asn Asn Cys Asn Leu His Leu Ile Lys
305                 310                 315                 320

ATT ATA TCA ACT CTG AAG ATT AAC CCA AAT GAA TTT CCA TCT GAT TTG     1008
Ile Ile Ser Thr Leu Lys Ile Asn Pro Asn Glu Phe Pro Ser Asp Leu
                325                 330                 335

GAA TCT AAT CTA GTA AAA CAT TTT ATA AAA TAT GCT AAT AAT GAT AGA     1056
Glu Ser Asn Leu Val Lys His Phe Ile Lys Tyr Ala Asn Asn Asp Arg
            340                 345                 350

CCT CCA TTT ACA CGA TAT AAT CGT CTA AAT AAC CTT AAA TTA CAT CTC     1104
Pro Pro Phe Thr Arg Tyr Asn Arg Leu Asn Asn Leu Lys Leu His Leu
        355                 360                 365

GAT GGT GAA TTT TTA ATT CAT AAA ATG CTA ACA TTT GAT GCA TCT CTA     1152
Asp Gly Glu Phe Leu Ile His Lys Met Leu Thr Phe Asp Ala Ser Leu
370                 375                 380

CGA CCA AGT GCG GAA GAA CTA TTA TCC TAT CAG ATT TTT AGT AAA CAA     1200
Arg Pro Ser Ala Glu Glu Leu Leu Ser Tyr Gln Ile Phe Ser Lys Gln
385                 390                 395                 400

TAA                                                                  1203
*

(2) INFORMATION FOR SEQ ID NO: 8:

(i) SEQUENCE CHARACTERISTICS:
        (A) LENGTH: 400 amino acids
        (B) TYPE: amino acid
        (D) TOPOLOGY: linear (ii) MOLECULE TYPE: protein (xi) SEQUENCE DESCRIPTION: SEQ ID NO: 8:

Met Ala Lys Cys Thr Thr Glu Lys Phe Cys Cys Ile Ser Val Asn Arg
1               5                   10                  15

Glu Ser Ser Val Asp Pro Glu Asp Phe Tyr Lys Pro Val Pro Leu Thr
                20                  25                  30

Ser Asp Leu Ile Glu Glu Asp Asn Leu His Gln Asp Lys Ile Met Asp
            35                  40                  45

Glu Asp Leu Tyr Ser Asp Phe Ser Asp Asp Phe Met Asp Tyr Thr
    50                  55                  60

Lys Asn Pro Thr Glu Ser Glu Asn Glu Arg Glu Ser Asp Glu Glu Val
65                  70                  75                  80

Glu Glu Ser Tyr Glu Ser Asp Glu Asp Lys Lys Ser Leu Ser Pro Thr
                85                  90                  95

Lys Ser Glu Gly Ile Glu Ala Ala Glu Ala Leu Lys Phe Ser Val Val
                100                 105                 110

Lys Ser Leu Thr Pro Gly Ser Glu Gly Arg Val Phe Ile Ala Leu Lys
            115                 120                 125

Lys Asp Lys Asp Thr Ser Tyr Lys Val Ile Leu Lys Ile Gly Gln Arg
130                 135                 140

Gly Asn Thr Leu Val Glu Ser Leu Ile Leu Arg Asn Ile Ser His Gln
145                 150                 155                 160

Ser Ile Ile Lys Leu Gln Asp Thr Leu Phe Tyr Lys Glu Leu Thr Cys
                165                 170                 175

Leu Val Leu Pro Tyr Tyr Lys Tyr Asp Leu Tyr Asn Phe Leu Met Asp
```

-continued

```
            180                 185                 190
His Gly Lys Ser Leu Ser Phe Glu Ser Val Ile Lys Ile Glu Lys Gln
            195                 200                 205
Ile Leu Thr Gly Leu Gln Tyr Ile His Gly Lys Lys Ile Ile His Arg
    210                 215                 220
Asp Ile Lys Thr Glu Asn Ile Phe Leu Asp Asn Asp Ser Asn Val Cys
225                 230                 235                 240
Ile Gly Asp Phe Gly Ala Ser Gln Phe Pro Val Ser Ser Pro Asp Tyr
                245                 250                 255
Leu Gly Ile Ala Gly Thr Ile Glu Thr Asn Ala Pro Glu Val Leu Ser
            260                 265                 270
Lys Asp Ala Tyr Asn Cys Lys Ala Asp Ile Trp Ser Ala Gly Ile Ile
        275                 280                 285
Leu Phe Glu Met Leu Ala Tyr Pro Asn Val Leu Phe Glu Glu Glu Glu
    290                 295                 300
Arg Asp Ser Ser Asp Leu Ile Asn Asn Cys Asn Leu His Leu Ile Lys
305                 310                 315                 320
Ile Ile Ser Thr Leu Lys Ile Asn Pro Asn Glu Phe Pro Ser Asp Leu
                325                 330                 335
Glu Ser Asn Leu Val Lys His Phe Ile Lys Tyr Ala Asn Asn Asp Arg
            340                 345                 350
Pro Pro Phe Thr Arg Tyr Asn Arg Leu Asn Asn Leu Lys Leu His Leu
        355                 360                 365
Asp Gly Glu Phe Leu Ile His Lys Met Leu Thr Phe Asp Ala Ser Leu
    370                 375                 380
Arg Pro Ser Ala Glu Glu Leu Leu Ser Tyr Gln Ile Phe Ser Lys Gln
385                 390                 395                 400
```

(2) INFORMATION FOR SEQ ID NO: 9:

(i) SEQUENCE CHARACTERISTICS:
      (A) LENGTH: 1248 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..1248

(xi) SEQUENCE DESCRIPTION: SEQ ID NO: 9:

```
ATG TTG TAT ACG CTG TTT TTT GTT TTT TAT TTT AAG GTA GTT TTA TCT      48
Met Leu Tyr Thr Leu Phe Phe Val Phe Tyr Phe Lys Val Val Leu Ser
1               5                   10                  15

CGC ATA GCT CCG CTA GAG TTG TGT TAT GCG GAT CCT AAA GAA AAT ACA      96
Arg Ile Ala Pro Leu Glu Leu Cys Tyr Ala Asp Pro Lys Glu Asn Thr
            20                  25                  30

ACT GAA CCT ACA CAA CTT CCT ACA GGG GAA CAA TCT AAG ACT CTT ATT     144
Thr Glu Pro Thr Gln Leu Pro Thr Gly Glu Gln Ser Lys Thr Leu Ile
        35                  40                  45

CCC GTG GTA ACA AAC GGA TAT GTT GAA TAC TCT AAA GGA TGT GAA CTA     192
Pro Val Val Thr Asn Gly Tyr Val Glu Tyr Ser Lys Gly Cys Glu Leu
    50                  55                  60

CGA TTA CTA GAT ACA TAT GTA AAT GTA TCT TCA CGA CCA GAA AAA AAG     240
Arg Leu Leu Asp Thr Tyr Val Asn Val Ser Ser Arg Pro Glu Lys Lys
65                  70                  75                  80

GTT AAT GCT ACA ATT GGA TGG TCA TTT GAT CTT GGT TGT CAA ATT CCT     288
```

```
                Val Asn Ala Thr Ile Gly Trp Ser Phe Asp Leu Gly Cys Gln Ile Pro
                            85                  90                  95

TTA ATT TAT AGA GAA TAT TAT AAT TGT ACT GGT AAT ATA ATA CCA TCA              336
Leu Ile Tyr Arg Glu Tyr Tyr Asn Cys Thr Gly Asn Ile Ile Pro Ser
                100                 105                 110

CCA GAA ACT TGT GAT GGT TAT TCT TTA ACT TTG GTA AAA TCT GAA AGT              384
Pro Glu Thr Cys Asp Gly Tyr Ser Leu Thr Leu Val Lys Ser Glu Ser
            115                 120                 125

ATA TCA TCT TAT GCA CTT GTT AAT GTT AGT TTG CTT ATT CAA CCA GGA              432
Ile Ser Ser Tyr Ala Leu Val Asn Val Ser Leu Leu Ile Gln Pro Gly
        130                 135                 140

ATT TTT GAT TCT GGT AGA TAT TTA TAC TCA CTT GTT TTT GGA AAC GAT              480
Ile Phe Asp Ser Gly Arg Tyr Leu Tyr Ser Leu Val Phe Gly Asn Asp
145                 150                 155                 160

AGT TAT AAC GGA AGA ATT GAA GTT CGA GTG GAT AAT GAG ACA GAC TAT              528
Ser Tyr Asn Gly Arg Ile Glu Val Arg Val Asp Asn Glu Thr Asp Tyr
                165                 170                 175

CCA TGT TTT ATG ATG CAT GGA TTG ACT GTA AAA AAG GGT GAT AAA CTT              576
Pro Cys Phe Met Met His Gly Leu Thr Val Lys Lys Gly Asp Lys Leu
            180                 185                 190

CAT ATT CCT TAT AAA CCA TCC ACA AAT CCT AAT CAT AAA CGA TAT AGA              624
His Ile Pro Tyr Lys Pro Ser Thr Asn Pro Asn His Lys Arg Tyr Arg
        195                 200                 205

GGT TGT TTT CCA ATA TCA AAT ACT GAG CTA TGG AAT AAT ATT AGT GAT              672
Gly Cys Phe Pro Ile Ser Asn Thr Glu Leu Trp Asn Asn Ile Ser Asp
210                 215                 220

GAA AGT GTT GGT AGA TAT TCA TAT GAT GAA GAA TAT GAA GAA TAT GAA              720
Glu Ser Val Gly Arg Tyr Ser Tyr Asp Glu Glu Tyr Glu Glu Tyr Glu
225                 230                 235                 240

GAA GAA AAC GAA GAT TTT GAA GAT CTA CAA TCA AAA GAT TGC CGC AAA              768
Glu Glu Asn Glu Asp Phe Glu Asp Leu Gln Ser Lys Asp Cys Arg Lys
                245                 250                 255

TCC AAT CTT TTT GAT ATG AAG AAG ACT TTT AAT TTG GCT GCA GGT TCT              816
Ser Asn Leu Phe Asp Met Lys Lys Thr Phe Asn Leu Ala Ala Gly Ser
            260                 265                 270

CAA AGT TTA TTG ATT GCT AGT TTG GGT AAA TCA ATT TCA GAA CAA CCG              864
Gln Ser Leu Leu Ile Ala Ser Leu Gly Lys Ser Ile Ser Glu Gln Pro
        275                 280                 285

TGG TCA TTT AAA ATT AAT GAA AGT TAT GAA CTT TTT AAT AAT TTG TCT              912
Trp Ser Phe Lys Ile Asn Glu Ser Tyr Glu Leu Phe Asn Asn Leu Ser
    290                 295                 300

ATC ACC CTT CAA TCG GAA GAA GAT TCT AAT ATA CTG AAT CCT GAA ATT              960
Ile Thr Leu Gln Ser Glu Glu Asp Ser Asn Ile Leu Asn Pro Glu Ile
305                 310                 315                 320

GTA ACG TTT ACC ACA CCA CCA CCT ACT GAA AAT ACA CAT ATG TTT ATG             1008
Val Thr Phe Thr Thr Pro Pro Pro Thr Glu Asn Thr His Met Phe Met
                325                 330                 335

TCA AAT AAT GAA ACT ATG TAT GAA GAA GAA AGT GTT TTA AGC ATT ATT             1056
Ser Asn Asn Glu Thr Met Tyr Glu Glu Glu Ser Val Leu Ser Ile Ile
            340                 345                 350

CAA TTG TTT AAC AAT GGT TAT AAT AAT TGT AAT ACC CAT ATA AAG GTA             1104
Gln Leu Phe Asn Asn Gly Tyr Asn Asn Cys Asn Thr His Ile Lys Val
        355                 360                 365

ATT GGA TTT GGA ACA ATT ATC TTT ATT ATT TTA TTT TTT GTT GCT GTG             1152
Ile Gly Phe Gly Thr Ile Ile Phe Ile Ile Leu Phe Phe Val Ala Val
    370                 375                 380

TTT TTT TGT GGA TAT ACT TGT GTA TTA AAC TCT CGT ATT AAA ATG ATT             1200
Phe Phe Cys Gly Tyr Thr Cys Val Leu Asn Ser Arg Ile Lys Met Ile
385                 390                 395                 400
```

```
AAC CAT GCT TAT ATA CAA CCC CAG AAA TTA AAT TTT TAT GAT ATT TAA      1248
Asn His Ala Tyr Ile Gln Pro Gln Lys Leu Asn Phe Tyr Asp Ile *
            405                 410                 415
```

(2) INFORMATION FOR SEQ ID NO: 10:

(i) SEQUENCE CHARACTERISTICS:
        (A) LENGTH: 415 amino acids
        (B) TYPE: amino acid
        (D) TOPOLOGY: linear (ii) MOLECULE TYPE: protein (xi) SEQUENCE DESCRIPTION: SEQ ID NO: 10:

```
Met Leu Tyr Thr Leu Phe Phe Val Phe Tyr Phe Lys Val Val Leu Ser
 1               5                  10                  15

Arg Ile Ala Pro Leu Glu Leu Cys Tyr Ala Asp Pro Lys Glu Asn Thr
                20                  25                  30

Thr Glu Pro Thr Gln Leu Pro Thr Gly Glu Gln Ser Lys Thr Leu Ile
                35                  40                  45

Pro Val Val Thr Asn Gly Tyr Val Glu Tyr Ser Lys Gly Cys Glu Leu
            50                  55                  60

Arg Leu Leu Asp Thr Tyr Val Asn Val Ser Ser Arg Pro Glu Lys Lys
 65                  70                  75                  80

Val Asn Ala Thr Ile Gly Trp Ser Phe Asp Leu Gly Cys Gln Ile Pro
                85                  90                  95

Leu Ile Tyr Arg Glu Tyr Tyr Asn Cys Thr Gly Asn Ile Ile Pro Ser
                100                 105                 110

Pro Glu Thr Cys Asp Gly Tyr Ser Leu Thr Leu Val Lys Ser Glu Ser
                115                 120                 125

Ile Ser Ser Tyr Ala Leu Val Asn Val Ser Leu Leu Ile Gln Pro Gly
            130                 135                 140

Ile Phe Asp Ser Gly Arg Tyr Leu Tyr Ser Leu Val Phe Gly Asn Asp
145                 150                 155                 160

Ser Tyr Asn Gly Arg Ile Glu Val Arg Val Asp Asn Glu Thr Asp Tyr
                165                 170                 175

Pro Cys Phe Met Met His Gly Leu Thr Val Lys Lys Gly Asp Lys Leu
                180                 185                 190

His Ile Pro Tyr Lys Pro Ser Thr Asn Pro Asn His Lys Arg Tyr Arg
                195                 200                 205

Gly Cys Phe Pro Ile Ser Asn Thr Glu Leu Trp Asn Asn Ile Ser Asp
            210                 215                 220

Glu Ser Val Gly Arg Tyr Ser Tyr Asp Glu Glu Tyr Glu Glu Tyr Glu
225                 230                 235                 240

Glu Glu Asn Glu Asp Phe Glu Asp Leu Gln Ser Lys Asp Cys Arg Lys
                245                 250                 255

Ser Asn Leu Phe Asp Met Lys Lys Thr Phe Asn Leu Ala Ala Gly Ser
                260                 265                 270

Gln Ser Leu Leu Ile Ala Ser Leu Gly Lys Ser Ile Ser Glu Gln Pro
                275                 280                 285

Trp Ser Phe Lys Ile Asn Glu Ser Tyr Glu Leu Phe Asn Asn Leu Ser
                290                 295                 300

Ile Thr Leu Gln Ser Glu Glu Asp Ser Asn Ile Leu Asn Pro Glu Ile
305                 310                 315                 320

Val Thr Phe Thr Thr Pro Pro Thr Glu Asn Thr His Met Phe Met
                325                 330                 335
```

```
Ser Asn Asn Glu Thr Met Tyr Glu Glu Glu Ser Val Leu Ser Ile Ile
            340                 345                 350

Gln Leu Phe Asn Asn Gly Tyr Asn Asn Cys Asn Thr His Ile Lys Val
            355                 360                 365

Ile Gly Phe Gly Thr Ile Phe Ile Ile Leu Phe Phe Val Ala Val
            370                 375             380

Phe Phe Cys Gly Tyr Thr Cys Val Leu Asn Ser Arg Ile Lys Met Ile
385                 390                 395                 400

Asn His Ala Tyr Ile Gln Pro Gln Lys Leu Asn Phe Tyr Asp Ile
            405                 410                 415
```

(2) INFORMATION FOR SEQ ID NO: 11:

(i) SEQUENCE CHARACTERISTICS:
        (A) LENGTH: 357 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..357

(xi) SEQUENCE DESCRIPTION: SEQ ID NO: 11:

```
ATG ATT AAA CTT CTA TTT ATC TTA TTT TAT TTT AAC CCA ATA ACT GGA      48
Met Ile Lys Leu Leu Phe Ile Leu Phe Tyr Phe Asn Pro Ile Thr Gly
  1               5                  10                  15

TAT AAA TGG GTA GAC CCT CCT CGT AGG TAT AAT TAC ACC GTT TTA AGA      96
Tyr Lys Trp Val Asp Pro Pro Arg Arg Tyr Asn Tyr Thr Val Leu Arg
                 20                  25                  30

ATG ATT CCA GAT ATT CCA AAT CCA ATG GAT CCT TCT AAA AAC GCT GAA     144
Met Ile Pro Asp Ile Pro Asn Pro Met Asp Pro Ser Lys Asn Ala Glu
             35                  40                  45

GTT CGG TAT GTA ACT TCT ACT GAC CCA TGT GAT ATG GTT GCT TTG ATT     192
Val Arg Tyr Val Thr Ser Thr Asp Pro Cys Asp Met Val Ala Leu Ile
         50                  55                  60

TCT AAT CCA AAT ATA GAA TCT ACA ATT AAA ACG ATT CAA TTT GTG CAA     240
Ser Asn Pro Asn Ile Glu Ser Thr Ile Lys Thr Ile Gln Phe Val Gln
 65                  70                  75                  80

AAG AAA AAA TTT TAC AAT GCA TCT CTT AGT TGG TTT AAA GTT GGA GAT     288
Lys Lys Lys Phe Tyr Asn Ala Ser Leu Ser Trp Phe Lys Val Gly Asp
                 85                  90                  95

GAT TGT ACA TAT CCA ATA TAT TTA ATT CAA TAT TTT GAT TGT GAT CCT     336
Asp Cys Thr Tyr Pro Ile Tyr Leu Ile Gln Tyr Phe Asp Cys Asp Pro
            100                 105                 110

CAA AGA GAA TTT GGC ATA TGT                                         357
Gln Arg Glu Phe Gly Ile Cys
        115
```

(2) INFORMATION FOR SEQ ID NO: 12:

(i) SEQUENCE CHARACTERISTICS:
        (A) LENGTH: 119 amino acids
        (B) TYPE: amino acid
        (D) TOPOLOGY: linear (ii) MOLECULE TYPE: protein (xi) SEQUENCE DESCRIPTION: SEQ ID NO: 12:

```
Met Ile Lys Leu Leu Phe Ile Leu Phe Tyr Phe Asn Pro Ile Thr Gly
  1               5                  10                  15
```

```
Tyr Lys Trp Val Asp Pro Pro Arg Arg Tyr Asn Tyr Thr Val Leu Arg
             20                  25                  30

Met Ile Pro Asp Ile Pro Asn Pro Met Asp Pro Ser Lys Asn Ala Glu
         35                  40                  45

Val Arg Tyr Val Thr Ser Thr Asp Pro Cys Asp Met Val Ala Leu Ile
 50                  55                  60

Ser Asn Pro Asn Ile Glu Ser Thr Ile Lys Thr Ile Gln Phe Val Gln
 65                  70                  75                  80

Lys Lys Lys Phe Tyr Asn Ala Ser Leu Ser Trp Phe Lys Val Gly Asp
             85                  90                  95

Asp Cys Thr Tyr Pro Ile Tyr Leu Ile Gln Tyr Phe Asp Cys Asp Pro
             100                 105                 110

Gln Arg Glu Phe Gly Ile Cys
             115
```

(2) INFORMATION FOR SEQ ID NO: 13:

(i) SEQUENCE CHARACTERISTICS:
        (A) LENGTH: 743 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

```
CGAAGCGGGA GGAGGATGCT GGTTATGATA TACCATCTCC AAATTTAGTT CAAATAAAAC    60

CGGGATATAG TTACCTTTTT TGTCTTCCTA TTTTTCAATT AGAAATGAAA AACCCACCAA   120

TCGCTTGTAT TTTTGGTAGA TCATCCTTAA ATTCAAGCGG AATAATTGTT CTTCCAACTA   180

TATGGAAACC AAAAACAATT TGTCAATTTT TTATTAAAAA TATATCCTCT AAAACTGTAA   240

CTATAGAAAA AGGTCAGAGA ATAGCTCAGT TAGTTCTTTT AAAAAACAAT CAACCACTAT   300

GGTTACAACC ACAAATTAAT TGTCATTCTT TATTTCCAAA GTCAAACTAT TTAAGCTTAT   360

CAAATCGAGA ATGTGATATG TGGAAGTTTA CAGAAGATCT GAATTTTGAA GCACCGAAAA   420

GTTTACGAGG AATAAATGGA TTTGGATCCA CGGGATTGTA AAATTCGTTA ATAAAGTTAT   480

ATTTAAAGTG CCAAACTTTC ACGTGTCATT TTTTTGGGAC CGTTTCTTTT TTGTTTAGTC   540

GATAAAATAT TTTCAGTTTC CATAGAACTT ATTAGAGGTT CTGTATCTAG TATATCTGTA   600

GAATTATTTT CATCATATTT AACGGTTTGA AGAGATAAGG GTTTTGTTGT ATTAGAATCT   660

ATACCAAGGG TTTTTTCTAA AACCGCTACA TCTGCCATAA CAATATTATT TTCTGAAGTC   720

ATTTTTATGG CTTGGGCACC ACC                                          743
```

(2) INFORMATION FOR SEQ ID NO: 14:

(i) SEQUENCE CHARACTERISTICS:
        (A) LENGTH: 743 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

```
GGTGGTGCCC AAGCCATAAA AATGACTTCA GAAAATAATA TTGTTATGGC AGATGTAGCG    60

GTTTTAGAAA AAACCCTTGG TATAGATTCT AATACAACAA AACCCTTATC TCTTCAAACC   120

GTTAAATATG ATGAAAATAA TTCTACAGAT ATACTAGATA CAGAACCTCT AATAAGTTCT   180
```

```
ATGGAAACTG AAAATATTTT ATCGACTAAA CAAAAAAGAA ACGGTCCCAA AAAAATGACA        240

CGTGAAAGTT TGGCACTTTA AATATAACTT TATTAACGAA TTTTACAATC CCGTGGATCC        300

AAATCCATTT ATTCCTCGTA AACTTTTCGG TGCTTCAAAA TTCAGATCTT CTGTAAACTT        360

CCACATATCA CATTCTCGAT TTGATAAGCT TAAATAGTTT GACTTTGGAA ATAAAGAATG        420

ACAATTAATT TGTGGTTGTA ACCATAGTGG TTGATTGTTT TTTAAAAGAA CTAACTGAGC        480

TATTCTCTGA CCTTTTTCTA TAGTTACAGT TTTAGAGGAT ATATTTTTAA TAAAAAATTG        540

ACAAATTGTT TTTGGTTTCC ATATAGTTGG AAGAACAATT ATTCCGCTTG AATTTAAGGA        600

TGATCTACCA AAAATACAAG CGATTGGTGG GTTTTTCATT TCTAATTGAA AAATAGGAAG        660

ACAAAAAAGG TAACTATATC CCGGTTTTAT TTGAACTAAA TTTGGAGATG GTATATCATA        720

ACCAGCATCC TCCTCCCGCT TCG                                                743
```

(2) INFORMATION FOR SEQ ID NO: 15:

(i) SEQUENCE CHARACTERISTICS:
    (A) LENGTH: 459 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 1..459

(xi) SEQUENCE DESCRIPTION: SEQ ID NO: 15:

```
AAG CGG GAG GAG GAT GCT GGT TAT GAT ATA CCA TCT CCA AAT TTA GTT        48
Lys Arg Glu Glu Asp Ala Gly Tyr Asp Ile Pro Ser Pro Asn Leu Val
 1               5                  10                  15

CAA ATA AAA CCG GGA TAT AGT TAC CTT TTT TGT CTT CCT ATT TTT CAA        96
Gln Ile Lys Pro Gly Tyr Ser Tyr Leu Phe Cys Leu Pro Ile Phe Gln
             20                  25                  30

TTA GAA ATG AAA AAC CCA CCA ATC GCT TGT ATT TTT GGT AGA TCA TCC       144
Leu Glu Met Lys Asn Pro Pro Ile Ala Cys Ile Phe Gly Arg Ser Ser
         35                  40                  45

TTA AAT TCA AGC GGA ATA ATT GTT CTT CCA ACT ATA TGG AAA CCA AAA       192
Leu Asn Ser Ser Gly Ile Ile Val Leu Pro Thr Ile Trp Lys Pro Lys
     50                  55                  60

ACA ATT TGT CAA TTT TTT ATT AAA AAT ATA TCC TCT AAA ACT GTA ACT       240
Thr Ile Cys Gln Phe Phe Ile Lys Asn Ile Ser Ser Lys Thr Val Thr
 65                  70                  75                  80

ATA GAA AAA GGT CAG AGA ATA GCT CAG TTA GTT CTT TTA AAA AAC AAT       288
Ile Glu Lys Gly Gln Arg Ile Ala Gln Leu Val Leu Leu Lys Asn Asn
                 85                  90                  95

CAA CCA CTA TGG TTA CAA CCA CAA ATT AAT TGT CAT TCT TTA TTT CCA       336
Gln Pro Leu Trp Leu Gln Pro Gln Ile Asn Cys His Ser Leu Phe Pro
            100                 105                 110

AAG TCA AAC TAT TTA AGC TTA TCA AAT CGA GAA TGT GAT ATG TGG AAG       384
Lys Ser Asn Tyr Leu Ser Leu Ser Asn Arg Glu Cys Asp Met Trp Lys
        115                 120                 125

TTT ACA GAA GAT CTG AAT TTT GAA GCA CCG AAA AGT TTA CGA GGA ATA       432
Phe Thr Glu Asp Leu Asn Phe Glu Ala Pro Lys Ser Leu Arg Gly Ile
    130                 135                 140

AAT GGA TTT GGA TCC ACG GGA TTG TAA                                   459
Asn Gly Phe Gly Ser Thr Gly Leu  *
145                 150
```

(2) INFORMATION FOR SEQ ID NO: 16:

(i) SEQUENCE CHARACTERISTICS:
    (A) LENGTH: 152 amino acids
    (B) TYPE: amino acid
    (D) TOPOLOGY: linear (ii) MOLECULE TYPE: protein (xi) SEQUENCE DESCRIPTION: SEQ ID NO: 16:

```
Lys Arg Glu Glu Asp Ala Gly Tyr Asp Ile Pro Ser Pro Asn Leu Val
  1               5                  10                  15

Gln Ile Lys Pro Gly Tyr Ser Tyr Leu Phe Cys Leu Pro Ile Phe Gln
             20                  25                  30

Leu Glu Met Lys Asn Pro Pro Ile Ala Cys Ile Phe Gly Arg Ser Ser
         35                  40                  45

Leu Asn Ser Ser Gly Ile Ile Val Leu Pro Thr Ile Trp Lys Pro Lys
 50                  55                  60

Thr Ile Cys Gln Phe Phe Ile Lys Asn Ile Ser Ser Lys Thr Val Thr
 65                  70                  75                  80

Ile Glu Lys Gly Gln Arg Ile Ala Gln Leu Val Leu Leu Lys Asn Asn
                 85                  90                  95

Gln Pro Leu Trp Leu Gln Pro Gln Ile Asn Cys His Ser Leu Phe Pro
            100                 105                 110

Lys Ser Asn Tyr Leu Ser Leu Ser Asn Arg Glu Cys Asp Met Trp Lys
            115                 120                 125

Phe Thr Glu Asp Leu Asn Phe Glu Ala Pro Lys Ser Leu Arg Gly Ile
130                 135                 140

Asn Gly Phe Gly Ser Thr Gly Leu
145                 150
```

(2) INFORMATION FOR SEQ ID NO: 17:

(i) SEQUENCE CHARACTERISTICS:
    (A) LENGTH: 579 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 54..503

(xi) SEQUENCE DESCRIPTION: SEQ ID NO: 17:

```
AATTATTACT CTAAATCTCA CTTCATTATA CTTATATAAT AATATAAAAC CTT ATG        56
                                                          Met
                                                            1

TTT GTC ATT ATT AAC TTA ACA CTA GAT GGT ACT ATA AAG CTA ACT TAC      104
Phe Val Ile Ile Asn Leu Thr Leu Asp Gly Thr Ile Lys Leu Thr Tyr
      5                  10                  15

AAT ATA AAT AGT AAG ATT AGT TTA TAT AAA TTA CAT TTA ATG GCT TTA      152
Asn Ile Asn Ser Lys Ile Ser Leu Tyr Lys Leu His Leu Met Ala Leu
         20                  25                  30

CCA GAT AAC GTT TTT AGT ATT ATT AAT GAA AAT TAT ATC GAT GGA ATT      200
Pro Asp Asn Val Phe Ser Ile Ile Asn Glu Asn Tyr Ile Asp Gly Ile
 35                  40                  45

TTA ACT ATG AAA ATG GGT GAA GAA ATA GAA AGC TCA TCA CCA TTA AAT      248
Leu Thr Met Lys Met Gly Glu Glu Ile Glu Ser Ser Ser Pro Leu Asn
 50                  55                  60                  65

GAA ACA AAT GTT AAT ATA GAT CAA CAT ACA ATA GAT ATT TTT GAT TAC      296
Glu Thr Asn Val Asn Ile Asp Gln His Thr Ile Asp Ile Phe Asp Tyr
```

```
                    70                  75                  80
GAT TCA GAT AAT GGA TGT TAT TAT AGT GAA AGA GAT AAT GAA ACC GCA      344
Asp Ser Asp Asn Gly Cys Tyr Tyr Ser Glu Arg Asp Asn Glu Thr Ala
            85                  90                  95

ACT CTT TTT TTA AAA CGT GTT GGT TAT AGA GAA ACC TCA AAA AAG CGT      392
Thr Leu Phe Leu Lys Arg Val Gly Tyr Arg Glu Thr Ser Lys Lys Arg
        100                 105                 110

AAA CGG ATT TGT GGA TTT ATT GTT TTA GCA ATT TTT ATG GTT ATT ATA      440
Lys Arg Ile Cys Gly Phe Ile Val Leu Ala Ile Phe Met Val Ile Ile
    115                 120                 125

TTA TGT TTT TTA TCA ATA ATT TTG GGA GTT TTT ATA GCG CCT CAT ATT      488
Leu Cys Phe Leu Ser Ile Ile Leu Gly Val Phe Ile Ala Pro His Ile
130                 135                 140                 145

TAT AAA GGC CTA TAG TAAGAACATC AACCTCTAAT AGGTAAATTT TTAAAACCAA      543
Tyr Lys Gly Leu  *
                150

CGGAGGGGGA GGAGGAGGAC TTTTTATTTT ATGAGA                              579

(2) INFORMATION FOR SEQ ID NO: 18:

(i) SEQUENCE CHARACTERISTICS:
        (A) LENGTH: 149 amino acids
        (B) TYPE: amino acid
        (D) TOPOLOGY: linear (ii) MOLECULE TYPE: protein (xi) SEQUENCE DESCRIPTION: SEQ ID NO: 18:

Met Phe Val Ile Ile Asn Leu Thr Leu Asp Gly Thr Ile Lys Leu Thr
 1               5                  10                  15

Tyr Asn Ile Asn Ser Lys Ile Ser Leu Tyr Lys Leu His Leu Met Ala
            20                  25                  30

Leu Pro Asp Asn Val Phe Ser Ile Ile Asn Glu Asn Tyr Ile Asp Gly
        35                  40                  45

Ile Leu Thr Met Lys Met Gly Glu Glu Ile Glu Ser Ser Ser Pro Leu
    50                  55                  60

Asn Glu Thr Asn Val Asn Ile Asp Gln His Thr Ile Asp Ile Phe Asp
65                  70                  75                  80

Tyr Asp Ser Asp Asn Gly Cys Tyr Tyr Ser Glu Arg Asp Asn Glu Thr
            85                  90                  95

Ala Thr Leu Phe Leu Lys Arg Val Gly Tyr Arg Glu Thr Ser Lys Lys
        100                 105                 110

Arg Lys Arg Ile Cys Gly Phe Ile Val Leu Ala Ile Phe Met Val Ile
    115                 120                 125

Ile Leu Cys Phe Leu Ser Ile Ile Leu Gly Val Phe Ile Ala Pro His
    130                 135                 140

Ile Tyr Lys Gly Leu
145

(2) INFORMATION FOR SEQ ID NO: 19:

(i) SEQUENCE CHARACTERISTICS:
        (A) LENGTH: 579 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:
```

```
TCTCATAAAA TAAAAAGTCC TCCTCCTCCC CCTCCGTTGG TTTTAAAAAT TTACCTATTA      60

GAGGTTGATG TTCTTACTAT AGGCCTTTAT AAATATGAGG CGCTATAAAA ACTCCCAAAA     120

TTATTGATAA AAAACATAAT ATAATAACCA TAAAAATTGC TAAAACAATA AATCCACAAA     180

TCCGTTTACG CTTTTTTGAG GTTTCTCTAT AACCAACACG TTTTAAAAAA AGAGTTGCGG     240

TTTCATTATC TCTTTCACTA TAATAACATC CATTATCTGA ATCGTAATCA AAAATATCTA     300

TTGTATGTTG ATCTATATTA ACATTTGTTT CATTTAATGG TGATGAGCTT TCTATTTCTT     360

CACCCATTTT CATAGTTAAA ATTCCATCGA TATAATTTTC ATTAATAATA CTAAAAACGT     420

TATCTGGTAA AGCCATTAAA TGTAATTTAT ATAAACTAAT CTTACTATTT ATATTGTAAG     480

TTAGCTTTAT AGTACCATCT AGTGTTAAGT TAATAATGAC AAACATAAGG TTTTATATTA     540

TTATATAAGT ATAATGAAGT GAGATTTAGA GTAATAATT                            579

(2) INFORMATION FOR SEQ ID NO: 20:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

ATGTTTGTCA TTATTAACTT AACACTAGAT GGTACTATAA AGCTAACTTA CAATATAAAT      60

AGTAAGATTA GTTTATATAA ATTACATTTA ATGGCTTTAC CAGATAACGT TTTTAGTATT     120

ATTAATGAAA ATTATATCGA TGGAATTTTA ACTATGAAAA TGGGTGAAGA AATAGAAAGC     180

TCATCACCAT TAAATGAAAC AAATGTTAAT ATAGATCAAC ATACAATAGA TATTTTTGAT     240

TACGATTCAG ATAATGGATG TTATTATAGT GAAAGAGATA ATGAAACCGC AACTCTTTTT     300

TTAAAACGTG TTGGTTATAG AGAAACCTCA AAAAAGCGTA AACGGATTTG TGGATTTATT     360

GTTTTAGCAA TTTTTATGGT TATTATATTA TGTTTTTTAT CAATAATTTT GGGAGTTTTT     420

ATAGCGCCTC ATATTTATAA AGGCCTATAG                                      450

(2) INFORMATION FOR SEQ ID NO: 21:

(i) SEQUENCE CHARACTERISTICS:
        (A) LENGTH: 294 base pairs
        (B) TYPE: nucleic acid
        (C) STRANDEDNESS: single
        (D) TOPOLOGY: linear (ii) MOLECULE TYPE: cDNA (ix) FEATURE:
         (A) NAME/KEY: CDS
         (B) LOCATION: 3..293

(ix) FEATURE:
         (A) NAME/KEY: R = A or G
         (B) LOCATION: 49

(xi) SEQUENCE DESCRIPTION: SEQ ID NO: 21:

TC CAA AGT GTT TTT GTT TCA TTG TCT TAT TCT TGG AGC CAC CGA CGA         47
   Gln Ser Val Phe Val Ser Leu Ser Tyr Ser Trp Ser His Arg Arg
    1               5                  10                  15

CRG TTT GAG TGT ATA TTT CAT CCA ATT TTA TTT AAT CAT GGT ATT GTG        95
Xaa Phe Glu Cys Ile Phe His Pro Ile Leu Phe Asn His Gly Ile Val
                20                  25                  30

AAT TTG GAA AAT AAC CCT TTG ACA TTT AAG GAA CTA CAA AAA ATA AAT       143
```

```
                Asn Leu Glu Asn Asn Pro Leu Thr Phe Lys Glu Leu Gln Lys Ile Asn
                                 35                  40                  45

TAT AGA CGT CAT ATT CTT GGT TTA CCA TTG ATT AGA GCT GGA TTG GTA                 191
Tyr Arg Arg His Ile Leu Gly Leu Pro Leu Ile Arg Ala Gly Leu Val
         50                  55                  60

GAA GAA GAT AAT CAA CCT TTA ATG ATA CCT CCA GAG TTT TCC AGT AAA                 239
Glu Glu Asp Asn Gln Pro Leu Met Ile Pro Pro Glu Phe Ser Ser Lys
 65                  70                  75

CTA CCT CGA ACA ATA GGA TTT TTA ACT CAA CAA ATT AGA GCC AAA ATG                 287
Leu Pro Arg Thr Ile Gly Phe Leu Thr Gln Gln Ile Arg Ala Lys Met
 80                  85                  90                  95

GAA GCT T                                                                       294
Glu Ala (2) INFORMATION FOR SEQ ID NO: 22:

(i) SEQUENCE CHARACTERISTICS:
          (A) LENGTH: 97 amino acids
          (B) TYPE: amino acid
          (D) TOPOLOGY: linear (ii) MOLECULE TYPE: protein (ix) FEATURE:
          (A) NAME/KEY: Xaa = Arg or Gln
          (B) LOCATION: 16

(xi) SEQUENCE DESCRIPTION: SEQ ID NO: 22:

Gln Ser Val Phe Val Ser Leu Ser Tyr Ser Trp Ser His Arg Arg Xaa
 1               5                  10                  15

Phe Glu Cys Ile Phe His Pro Ile Leu Phe Asn His Gly Ile Val Asn
                 20                  25                  30

Leu Glu Asn Asn Pro Leu Thr Phe Lys Glu Leu Gln Lys Ile Asn Tyr
             35                  40                  45

Arg Arg His Ile Leu Gly Leu Pro Leu Ile Arg Ala Gly Leu Val Glu
         50                  55                  60

Glu Asp Asn Gln Pro Leu Met Ile Pro Pro Glu Phe Ser Ser Lys Leu
 65                  70                  75                  80

Pro Arg Thr Ile Gly Phe Leu Thr Gln Gln Ile Arg Ala Lys Met Glu
                 85                  90                  95

Ala (2) INFORMATION FOR SEQ ID NO: 23:

(i) SEQUENCE CHARACTERISTICS:
          (A) LENGTH: 294 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 23:

AAGCTTCCAT TTTGGCTCTA ATTTGTTGAG TTAAAAATCC TATTGTTCGA GGTAGTTTAC      60

TGGAAAACTC TGGAGGTATC ATTAAAGGTT GATTATCTTC TTCTACCAAT CCAGCTCTAA     120

TCAATGGTAA ACCAAGAATA TGACGTCTAT AATTTATTTT TTGTAGTTCC TTAAATGTCA     180

AAGGGTTATT TTCCAAATTC ACAATACCAT GATTAAATAA AATTGGATGA AATATACACT     240

CAAACYGTCG TCGGTGGCTC CAAGAATAAG ACAATGAAAC AAAAACACTT TGGA           294

(2) INFORMATION FOR SEQ ID NO: 24:
```

(i) SEQUENCE CHARACTERISTICS:
    (A) LENGTH: 291 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 24:

```
CAAAGTGTTT TTGTTTCATT GTCTTATTCT TGGAGCCACC GACGACRGTT TGAGTGTATA    60

TTTCATCCAA TTTTATTTAA TCATGGTATT GTGAATTTGG AAAATAACCC TTTGACATTT   120

AAGGAACTAC AAAAAATAAA TTATAGACGT CATATTCTTG GTTTACCATT GATTAGAGCT   180

GGATTGGTAG AAGAAGATAA TCAACCTTTA ATGATACCTC CAGAGTTTTC CAGTAAACTA   240

CCTCGAACAA TAGGATTTTT AACTCAACAA ATTAGAGCCA AAATGGAAGC T            291
```

(2) INFORMATION FOR SEQ ID NO: 25:

(i) SEQUENCE CHARACTERISTICS:
        (A) LENGTH: 146 base pairs
        (B) TYPE: nucleic acid
        (C) STRANDEDNESS: single
        (D) TOPOLOGY: linear (ii) MOLECULE TYPE: cDNA (ix) FEATURE:
    (A) NAME/KEY: CDS
    (B) LOCATION: 1..146

(xi) SEQUENCE DESCRIPTION: SEQ ID NO: 25:

```
CTA GAA GAT TAT ATA ACA CAT CGA ATT AAT GCC GAT ATT TCA GAG GTT     48
Leu Glu Asp Tyr Ile Thr His Arg Ile Asn Ala Asp Ile Ser Glu Val
 1               5                  10                  15

GGT GTA TTG AGA AAT TAT ATT TCT GCT GAT AGA CAG AGT TTA AAA GTT     96
Gly Val Leu Arg Asn Tyr Ile Ser Ala Asp Arg Gln Ser Leu Lys Val
                20                  25                  30

TCT GAT AGA GAG TTT ATT AAT TAT ATT TAC TTG GCA CAT TTT GAA AGC    146
Ser Asp Arg Glu Phe Ile Asn Tyr Ile Tyr Leu Ala His Phe Glu Ser
            35                  40                  45
```

(2) INFORMATION FOR SEQ ID NO: 26:

(i) SEQUENCE CHARACTERISTICS:
        (A) LENGTH: 48 amino acids
        (B) TYPE: amino acid
        (D) TOPOLOGY: linear (ii) MOLECULE TYPE: protein (xi) SEQUENCE DESCRIPTION: SEQ ID NO: 26:

```
Leu Glu Asp Tyr Ile Thr His Arg Ile Asn Ala Asp Ile Ser Glu Val
 1               5                  10                  15

Gly Val Leu Arg Asn Tyr Ile Ser Ala Asp Arg Gln Ser Leu Lys Val
                20                  25                  30

Ser Asp Arg Glu Phe Ile Asn Tyr Ile Tyr Leu Ala His Phe Glu Ser
            35                  40                  45
```

(2) INFORMATION FOR SEQ ID NO: 27:

(i) SEQUENCE CHARACTERISTICS:
        (A) LENGTH: 146 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 27:

AAGCTTTCAA AATGTGCCAA GTAAATATAA TTAATAAACT CTCTATCAGA AACTTTTAAA      60

CTCTGTCTAT CAGCAGAAAT ATAATTTCTC AATACACCAA CCTCTGAAAT ATCGGCATTA     120

ATTCGATGTG TTATATAATC TTCTAG                                         146

(2) INFORMATION FOR SEQ ID NO: 28:

(i) SEQUENCE CHARACTERISTICS:
           (A) LENGTH: 144 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO: 28:

CTAGAAGATT ATATAACACA TCGAATTAAT GCCGATATTT CAGAGGTTGG TGTATTGAGA      60

AATTATATTT CTGCTGATAG ACAGAGTTTA AAAGTTTCTG ATAGAGAGTT TATTAATTAT     120

ATTTACTTGG CACATTTTGA AAGC                                           144

(2) INFORMATION FOR SEQ ID NO: 29:

(i) SEQUENCE CHARACTERISTICS:
           (A) LENGTH: 161 base pairs
           (B) TYPE: nucleic acid
           (C) STRANDEDNESS: single
           (D) TOPOLOGY: linear (ii) MOLECULE TYPE: DNA (genomic)

(ix) FEATURE:
           (A) NAME/KEY: CDS
           (B) LOCATION: 3..161

(xi) SEQUENCE DESCRIPTION: SEQ ID NO: 29:

TT ATG TCA GTG GAC GTT ATA TTT CTC GAT GAC CAA CAT CTG TCA GTA         47
   Met Ser Val Asp Val Ile Phe Leu Asp Asp Gln His Leu Ser Val
   1               5                   10                  15

AAT AAT TAT AGC GGA ACT ATT GAG TTT ATT CAT TTT AAT AAC TCT TGT        95
Asn Asn Tyr Ser Gly Thr Ile Glu Phe Ile His Phe Asn Asn Ser Cys
                20                  25                  30

TAT ACC GTT TAT CAA ACT ATT GAA TAT TTT TCT TGT CCT CGC ATT TTT       143
Tyr Thr Val Tyr Gln Thr Ile Glu Tyr Phe Ser Cys Pro Arg Ile Phe
            35                  40                  45

AAT AAT GCT TTT AGA TCT                                               161
Asn Asn Ala Phe Arg Ser
        50

(2) INFORMATION FOR SEQ ID NO: 30:

(i) SEQUENCE CHARACTERISTICS:
           (A) LENGTH: 53 amino acids
           (B) TYPE: amino acid
           (D) TOPOLOGY: linear (ii) MOLECULE TYPE: protein (xi) SEQUENCE DESCRIPTION: SEQ ID NO: 30:

Met Ser Val Asp Val Ile Phe Leu Asp Asp Gln His Leu Ser Val Asn
1               5                   10                  15

Asn Tyr Ser Gly Thr Ile Glu Phe Ile His Phe Asn Asn Ser Cys Tyr

```
                20                  25                  30
Thr Val Tyr Gln Thr Ile Glu Tyr Phe Ser Cys Pro Arg Ile Phe Asn
        35                  40                  45

Asn Ala Phe Arg Ser
    50

(2) INFORMATION FOR SEQ ID NO: 31:

(i) SEQUENCE CHARACTERISTICS:
        (A) LENGTH: 161 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 31:

AGATCTAAAA GCATTATTAA AAATGCGAGG ACAAGAAAAA TATTCAATAG TTTGATAAAC      60

GGTATAACAA GAGTTATTAA AATGAATAAA CTCAATAGTT CCGCTATAAT TATTTACTGA     120

CAGATGTTGG TCATCGAGAA ATATAACGTC CACTGACATA A                         161

(2) INFORMATION FOR SEQ ID NO: 32:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 32:

ATGTCAGTGG ACGTTATATT TCTCGATGAC CAACATCTGT CAGTAAATAA TTATAGCGGA      60

ACTATTGAGT TTATTCATTT TAATAACTCT TGTTATACCG TTTATCAAAC TATTGAATAT     120

TTTTCTTGTC CTCGCATTTT TAATAATGCT TTTAGATCT                            159

(2) INFORMATION FOR SEQ ID NO: 33:

(i) SEQUENCE CHARACTERISTICS:
        (A) LENGTH: 261 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..261

(xi) SEQUENCE DESCRIPTION: SEQ ID NO: 33:

GGT GGT GCC CAA GCC ATA AAA ATG ACT TCA GAA AAT AAT ATT GTT ATG        48
Gly Gly Ala Gln Ala Ile Lys Met Thr Ser Glu Asn Asn Ile Val Met
 1               5                  10                  15

GCA GAT GTA GCG GTT TTA GAA AAA ACC CTT GGT ATA GAT TCT AAT ACA        96
Ala Asp Val Ala Val Leu Glu Lys Thr Leu Gly Ile Asp Ser Asn Thr
             20                  25                  30

ACA AAA CCC TTA TCT CTT CAA ACC GTT AAA TAT GAT GAA AAT AAT TCT       144
Thr Lys Pro Leu Ser Leu Gln Thr Val Lys Tyr Asp Glu Asn Asn Ser
         35                  40                  45

ACA GAT ATA CTA GAT ACA GAA CCT CTA ATA AGT TCT ATG GAA ACT GAA       192
Thr Asp Ile Leu Asp Thr Glu Pro Leu Ile Ser Ser Met Glu Thr Glu
     50                  55                  60
```

```
AAT ATT TTA TCG ACT AAA CAA AAA AGA AAC GGT CCC AAA AAA ATG ACA      240
Asn Ile Leu Ser Thr Lys Gln Lys Arg Asn Gly Pro Lys Lys Met Thr
 65              70                  75                  80

CGT GAA AGT TTG GCA CTT TAA                                          261
Arg Glu Ser Leu Ala Leu  *
                 85
```

(2) INFORMATION FOR SEQ ID NO: 34:

(i) SEQUENCE CHARACTERISTICS:
        (A) LENGTH: 86 amino acids
        (B) TYPE: amino acid
        (D) TOPOLOGY: linear (ii) MOLECULE TYPE: protein (xi) SEQUENCE DESCRIPTION: SEQ ID NO: 34:

```
Gly Gly Ala Gln Ala Ile Lys Met Thr Ser Glu Asn Asn Ile Val Met
 1               5                  10                  15

Ala Asp Val Ala Val Leu Glu Lys Thr Leu Gly Ile Asp Ser Asn Thr
                 20                  25                  30

Thr Lys Pro Leu Ser Leu Gln Thr Val Lys Tyr Asp Glu Asn Asn Ser
             35                  40                  45

Thr Asp Ile Leu Asp Thr Glu Pro Leu Ile Ser Ser Met Glu Thr Glu
         50                  55                  60

Asn Ile Leu Ser Thr Lys Gln Lys Arg Asn Gly Pro Lys Lys Met Thr
 65              70                  75                  80

Arg Glu Ser Leu Ala Leu
                 85
```

(2) INFORMATION FOR SEQ ID NO: 35:

(i) SEQUENCE CHARACTERISTICS:
        (A) LENGTH: 280 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..280

(xi) SEQUENCE DESCRIPTION: SEQ ID NO: 35:

```
T GCA TTA AAT TTT ATT AAA TTA GAA AAA AAT AAT CCA GTA TAT TAT        46
  Ala Leu Asn Phe Ile Lys Leu Glu Lys Asn Asn Pro Val Tyr Tyr
   1               5                  10                  15

TTT CCG GAA CCT ATG GCA TTC TGG CGT ATC ATC CTA GAA ACA GAT ATT      94
Phe Pro Glu Pro Met Ala Phe Trp Arg Ile Ile Leu Glu Thr Asp Ile
                 20                  25                  30

GTG CAA GGT ATA TAC TCA GTA CAA GAC CGG AAG CTG CGT GGT GAA TTA     142
Val Gln Gly Ile Tyr Ser Val Gln Asp Arg Lys Leu Arg Gly Glu Leu
             35                  40                  45

AGC CTA AAT GAT GCG TCA TTA ATT ACA GCT CAA CTT CAA ACT AAA TTT     190
Ser Leu Asn Asp Ala Ser Leu Ile Thr Ala Gln Leu Gln Thr Lys Phe
         50                  55                  60

TCT ACG CCA TAT ATT TTA CTT CAT TCC AAT GTA TCC AAA TTT TTT GGA     238
Ser Thr Pro Tyr Ile Leu Leu His Ser Asn Val Ser Lys Phe Phe Gly
 65              70                  75

GAA AAT GTA ACA TTT GGA ATT CCG GAA GTA ATA TTT ATT TTT             280
Glu Asn Val Thr Phe Gly Ile Pro Glu Val Ile Phe Ile Phe
 80                  85                  90
```

(2) INFORMATION FOR SEQ ID NO: 36:

(i) SEQUENCE CHARACTERISTICS:
        (A) LENGTH: 93 amino acids
        (B) TYPE: amino acid
        (D) TOPOLOGY: linear (ii) MOLECULE TYPE: protein (xi) SEQUENCE DESCRIPTION: SEQ ID NO: 36:

```
Ala Leu Asn Phe Ile Lys Leu Glu Lys Asn Asn Pro Val Tyr Tyr Phe
 1               5                  10                  15

Pro Glu Pro Met Ala Phe Trp Arg Ile Ile Leu Glu Thr Asp Ile Val
                20                  25                  30

Gln Gly Ile Tyr Ser Val Gln Asp Arg Lys Leu Arg Gly Glu Leu Ser
            35                  40                  45

Leu Asn Asp Ala Ser Leu Ile Thr Ala Gln Leu Gln Thr Lys Phe Ser
        50                  55                  60

Thr Pro Tyr Ile Leu Leu His Ser Asn Val Ser Lys Phe Phe Gly Glu
65                  70                  75                  80

Asn Val Thr Phe Gly Ile Pro Glu Val Ile Phe Ile Phe
                85                  90
```

(2) INFORMATION FOR SEQ ID NO: 37:

(i) SEQUENCE CHARACTERISTICS:
        (A) LENGTH: 280 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 37:

```
AAAAATAAAT ATTACTTCCG GAATTCCAAA TGTTACATTT TCTCCAAAAA ATTTGGATAC      60
ATTGGAATGA AGTAAAATAT ATGGCGTAGA AAATTTAGTT TGAAGTTGAG CTGTAATTAA     120
TGACGCATCA TTTAGGCTTA ATTCACCACG CAGCTTCCGG TCTTGTACTG AGTATATACC     180
TTGCACAATA TCTGTTTCTA GGATGATACG CCAGAATGCC ATAGGTTCCG GAAAATAATA     240
TACTGGATTA TTTTTTTCTA ATTTAATAAA ATTTAATGCA                           280
```

(2) INFORMATION FOR SEQ ID NO: 38:

(i) SEQUENCE CHARACTERISTICS:
        (A) LENGTH: 279 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 38:

```
GCATTAAATT TTATTAAATT AGAAAAAAAT AATCCAGTAT ATTATTTTCC GGAACCTATG      60
GCATTCTGGC GTATCATCCT AGAAACAGAT ATTGTGCAAG GTATATACTC AGTACAAGAC     120
CGGAAGCTGC GTGGTGAATT AAGCCTAAAT GATGCGTCAT TAATTACAGC TCAACTTCAA     180
ACTAAATTTT CTACGCCATA TATTTTACTT CATTCCAATG TATCCAAATT TTTTGGAGAA     240
AATGTAACAT TTGGAATTCC GGAAGTAATA TTTATTTTT                            279
```

(2) INFORMATION FOR SEQ ID NO: 39:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: misc_feature
    (B) LOCATION: 1..27
    (D) OTHER INFORMATION: /label= primer (ix) FEATURE:
    (A) NAME/KEY: N = Inosine
    (B) LOCATION: 11

(ix) FEATURE:
    (A) NAME/KEY: N = Inosine
    (B) LOCATION: 17

(ix) FEATURE:
    (A) NAME/KEY: N = Inosine
    (B) LOCATION: 20

(xi) SEQUENCE DESCRIPTION: SEQ ID NO: 39:

GGCGAATTCC NAARMGNGAN GARGAYG                     27

(2) INFORMATION FOR SEQ ID NO: 40:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..24
        (D) OTHER INFORMATION: /label= primer (ix) FEATURE:
        (A) NAME/KEY: N = Inosine
        (B) LOCATION: 11

(ix) FEATURE:
        (A) NAME/KEY: N = Inosine
        (B) LOCATION: 16

(ix) FEATURE:
        (A) NAME/KEY: N = Inosine
        (B) LOCATION: 22

(xi) SEQUENCE DESCRIPTION: SEQ ID NO: 40:

CGCGGATCCG NTNSWNCCYA ANCC                        24

(2) INFORMATION FOR SEQ ID NO: 41:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..26
        (D) OTHER INFORMATION: /label= primer (ix) FEATURE:
        (A) NAME/KEY: N = Inosine (B) LOCATION: 18

(ix) FEATURE:
         (A) NAME/KEY: N = Inosine
         (B) LOCATION: 24

(xi) SEQUENCE DESCRIPTION: SEQ ID NO: 41:

GGCGAATTCT AYCAYWSNCA YGTNTA                                              26

(2) INFORMATION FOR SEQ ID NO: 42:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: misc_feature
         (B) LOCATION: 1..30
         (D) OTHER INFORMATION: /label= primer (ix) FEATURE:
         (A) NAME/KEY: N = Inosine
         (B) LOCATION: 16

(ix) FEATURE:
         (A) NAME/KEY: N = Inosine
         (B) LOCATION: 19

(ix) FEATURE:
         (A) NAME/KEY: N = Inosine
         (B) LOCATION: 24

(ix) FEATURE:
         (A) NAME/KEY: N = Inosine
         (B) LOCATION: 25

(ix) FEATURE:
         (A) NAME/KEY: N = Inosine
         (B) LOCATION: 28

(xi) SEQUENCE DESCRIPTION: SEQ ID NO: 42:

CGCGGATCCR TCRTTNSWNG GDANNSWNGT                                          30

(2) INFORMATION FOR SEQ ID NO: 43:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: misc_feature
         (B) LOCATION: 1..20
         (D) OTHER INFORMATION: /label= primer (ix) FEATURE:
         (A) NAME/KEY: N = Inosine
         (B) LOCATION: 12

(ix) FEATURE:
         (A) NAME/KEY: N = Inosine
         (B) LOCATION: 18

(ix) FEATURE:
         (A) NAME/KEY: N = Inosine
         (B) LOCATION: 21

(xi) SEQUENCE DESCRIPTION: SEQ ID NO: 43:

```
GGCGAATTCG GNAARWSNAC NRC                                              23

(2) INFORMATION FOR SEQ ID NO: 44:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..20
        (D) OTHER INFORMATION: /label= primer (ix) FEATURE:
        (A) NAME/KEY: N = Inosine
        (B) LOCATION: 15

(xi) SEQUENCE DESCRIPTION: SEQ ID NO: 44:

GGCGGATCCG GTTGNCKRTC                                                  20

(2) INFORMATION FOR SEQ ID NO: 45:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..30
        (D) OTHER INFORMATION: /label= label (xi) SEQUENCE DESCRIPTION: SEQ ID NO: 45:

CGCGGATCCA AGGTAATAAG TCAAAATGAG                                       30

(2) INFORMATION FOR SEQ ID NO: 46:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..29
        (D) OTHER INFORMATION: /label= primer (xi) SEQUENCE DESCRIPTION: SEQ ID NO: 46:

CGCGGATCCG ACAAAAACAA AAAGTAATG                                        29

(2) INFORMATION FOR SEQ ID NO: 47:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(ix) FEATURE:
```

```
        (A) NAME/KEY: misc_feature
        (B) LOCATION: 1..26
        (D) OTHER INFORMATION: /label= primer (ix) FEATURE:
        (A) NAME/KEY: N = Inosine
        (B) LOCATION: 11

(ix) FEATURE:
        (A) NAME/KEY: N = Inosine
        (B) LOCATION: 20

(xi) SEQUENCE DESCRIPTION: SEQ ID NO: 47:

CCGAATTCYT NATGATHYTN ATHGARGG                                              28

(2) INFORMATION FOR SEQ ID NO: 48:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..29
        (D) OTHER INFORMATION: /label= primer (ix) FEATURE:
        (A) NAME/KEY: N = Inosine
        (B) LOCATION: 21

(xi) SEQUENCE DESCRIPTION: SEQ ID NO: 48:

CCGGATCCYT CRAARAARTT NGTRTGYTT                                             29

(2) INFORMATION FOR SEQ ID NO: 49:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..35
        (D) OTHER INFORMATION: /label= primer (xi) SEQUENCE DESCRIPTION: SEQ ID NO: 49:

TCCCCCGGGG GCGCGCCTTG ACATTGATTA TTGAC                                      35

(2) INFORMATION FOR SEQ ID NO: 50:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..35
        (D) OTHER INFORMATION: /label= primer (xi) SEQUENCE DESCRIPTION: SEQ ID NO: 50:

GCCCTTAAGG GGCGCGCCAA TGCGATGCAA TTTCC                                      35
```

(2) INFORMATION FOR SEQ ID NO: 51:

(i) SEQUENCE CHARACTERISTICS:
        (A) LENGTH: 10592 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 51:

```
CTGCAGTGTA TTTAAAAAAT AAAAATCTAT GAATGAAATC TATGAATGAA ATCTATGAAT     60

GAAATCTATG AATGAAATCT ATGAATGAAA TCTATGAATG AAATCTATGA ATGAAATCTA    120

TGAATGAAAT CTATGAATGA AATCTATGAA TGAAATCTAT GAATGAAATC TATGAATGAA    180

ATCTATGAAT GAAATCTATG AATGAAATCT ATGAATGAAA TCTATGAATG AAATCTATGA    240

ATGAAATCTA TGAATGAAAT CTATGAATGA AATCTATGAA TGAAATCTAT GAGACAAAGT    300

AATTTTTAAA AATATTTTAA ATTTTATTAA GAGTATAGGT TACAAGGTTT AATGCGTTGG    360

GTAAACATTT TAGTTTTCAA GTTTTAGTTT TCTGGTATCT ACCAACACAA ATGCATCTTC    420

GGATACATTA TTTAGAGAGT AATCACTTTT TAGAATATAT CTTATTGGTG GTACATTTAT    480

AAATTTTGGA CCATCCCAAT AACACTTCGA TTCCACAAGC GAAGAAGGTA CTTCCATAAG    540

CTGAGAAGCG TTTACTTGAT TGTAGGGAGA ACTTGGCGTT TCAAAATCCT TTAGAACGTA    600

TAGTCTGCAA TACATAGGTT CAATATCATC TTCATACCTC TCATCAGGAT ATGAAAATGG    660

AAGTTTCACA AAGGTTCCAT CACGAAGCTT TTTGAAGAAT CGTACATCCG TAGGTGGTGT    720

AGGAACAATA GTGAAGGCGT GCGGTTCACC CTGGTTTTTC ACACGTGCAA GCGCTGGTGT    780

GGTTTTAGGG CGAACTGGAA ATAACCAGG CGGAACTTGT GCGTAGAATC CTTCATTAAG     840

TTCTCCACGA CAGCGTCTGA AGTATGATGG CATATTAGCT TGATCGGAGT TGTTATCAAA    900

TAGAGCAAAT GAAGCACTCA TTTTAAAACT TTTTAGTTAA GCTTTAAAAA CAAGTGAAGA    960

TTTAAAAATG TAGGATAAAA TGCCAGTTTA TATACAGTAA GAATATGGGA GTGGTTCACA   1020

TAAAAAACCA GAATTTCAGG TTTACATCTA CTGTTTATTC ACAACAAATA TAAACAAACT   1080

TAGTTTCCAC ATAAACATGA ACTAAATAGA GATGAACGTT GAGCGTTGGT AGGTTGTGTA   1140

GAAGACATAC CATCGTTTTC ATTTTTGGTT ATTGTTTTGG CGCGCCTTGA AAATAATCGT   1200

TTAAAAATAT TTGGTTTGGA TAGCCTTTTC ATAGGTTTCA CCCCATGCAA GTCATCCTCT   1260

TCTGGTTCAG GAATTTCTTC ATAACCATTA TGGGATATTA TTGCACACAT AAATGATTCG   1320

ATTACCGGGG GGGCAGAACG TGTCTCATTT ATATAAAGAG AATCACATAC ATCGCTTATA   1380

GAACATGTAG AACTGTCAGA ATCCTCTTTA AAACTATTTT TAATTTCACA ATTAGTTTCT   1440

TCTAGTTCAT TATCCACCAT CGCATTAGCG TATTTCCAAA TATCATTCTC TGAGGAATAA   1500

TGAGATGCAG AGCATGAAGA AGAGGATGAG GAGGAGGAGG ATGAAGATGA GGATATAGAG   1560

GGACATCTTG GAGAGCTTTC AAAGTTGAAT GGAGTATTAA ATGTTGTACC ATAAAAAATG   1620

TCACTTAACA TAGGGGGTAC TTTAAAGGAG GACAGAAAGG TGTCTAATAC AGGTACCCAT   1680

ATAAACGAGG GGCAATAAAC ACTCCCAGAA TCATCGATAT GTTTTACATT ATTTTTGGAA   1740

ATCTCAAGAC ACTCAGGTTT CCAGGATGGT TCCGGCCATT CACATGATAC ATATGCATAA   1800

ATTAGTCGCT TTGGTCCTGG GATATTAGAA ATGACTGGCT CACATAAATC CGCTGCACCG   1860

AAAACCCATA GATTAAGAGG ATAGTTTCCA AATATACCAG AGTTTAGATA GTTATACCCC   1920

GAAACAGCCG ATTTCCATTC GATGCTAGCC CCAGGTTTAT CCTCATAAAA TAAAAAGTCC   1980
```

```
TCCTCCTCCC CCTCCGTTGG TTTTAAAAAT TTACTATTAG AGGTTGATGT TCTTACTATA    2040

GGCCTTGAAA CTCTAGGTAG ATGTTTTATA GAGTCCATAA AATAACATAA GTTTGCAGAT    2100

CGTAATATTA TAGGCATAGC CAATCGTGTG AGAGAAAGGA TATAGCATTG TCTAGCCATA    2160

AAACACCAAA GATCAGGATG AACATCTTGG GAGTTTCCTG GTAACGCCCC ATTTTTGTCA    2220

ATAAACGTAA CAATATTAAC TTCAACCACA CCCATAATTA AATTTTATGT ATGAATCCAA    2280

TAAAGGTTAA TACACACCTA ATTTATGTTA TAATTTTAGA AGAAGCTGCA GTTGATGAGT    2340

TGATATTAAC ATAACAATTT CACAATTACC TGATATGGCA AAGTGTACCA CCGAAAAGTT    2400

TTGTTGTATC AGCGTGAATA GAGAATCTTC TGTCGATCCA GAAGACTTCT ATAAACCGGT    2460

TCCTCTAACT TCAGATTTGA TTGAAGAGGA TAACCTACAT CAAGACAAAA TAATGGATGA    2520

GGATTTATAC TCGGATTTTA GTGATGATGA CTTTATGGAT TATACAAAAA ATCCAACTGA    2580

AAGTGAAAAT GAAAGAGAAA GTGACGAAGA AGTTGAAGAA AGTTATGAAA GTGATGAAGA    2640

TAAAAAAAGT TTATCTCCTA CTAAAAGCGA AGGAATTGAA GCGGCTGAAG CGCTAAAGTT    2700

TTCTGTTGTT AAATCGTTAA CGCCTGGGTC AGAAGGAAGA GTTTTTATTG CTCTTAAAAA    2760

AGATAAAGAT ACAAGCTATA AGGTAATTTT AAAAATTGGA CAAAGGGGAA ACACGCTTGT    2820

GGAATCGTTA ATTTTGAGAA ATATTAGTCA CCAATCTATA ATTAAACTTC AAGCACTCT    2880

TTTTTATAAA GAGTTAACAT GTTTGGTGTT ACCGTATTAT AAATATGATC TATATAATTT    2940

TTTAATGGAT CATGGGAAAT CTCTGTCTTT TGAATCTGTA ATTAAAATTG AAAAACAAAT    3000

ATTAACTGGA CTTCAATATA TTCATGGAAA AAAAATTATT CATCGAGATA TAAAAACTGA    3060

AAATATTTTC TTGGATAATG ACTCTAATGT TTGTATAGGT GATTTTGGGG CTTCTCAATT    3120

TCCTGTTTCC TCACCAGATT ATTTGGGAAT TGCGGGGACT ATTGAAACTA ATGCTCCTGA    3180

AGTTCTATCA AAGGATGCGT ACAACTGTAA AGCTGATATT TGGAGTGCTG GTATAATTTT    3240

ATTTGAAATG CTTGCATATC CTAATGTTTT GTTTGAGGAG GAAGAAAGAG ATAGTAGCGA    3300

TTTAATAAAC AATTGTAATC TTCATCTTAT AAAAATTATA TCAACTCTGA AGATTAACCC    3360

AAATGAATTT CCATCTGATT TGGAATCTAA TCTAGTAAAA CATTTTATAA AATATGCTAA    3420

TAATGATAGA CCTCCATTTA CACGATATAA TCGTCTAAAT AACCTTAAAT TACATCTCGA    3480

TGGTGAATTT TTAATTCATA AAATGCTAAC ATTTGATGCA TCTCTACGAC CAAGTGCGGA    3540

AGAACTATTA TCCTATCAGA TTTTTAGTAA ACAATAAATT TCATAAAAAT GGGCGTGGAA    3600

TTTTTTATTG TTTTATATAA AACGGGTGTT TGAAAGCTCT TTTTTATTAA TTTTATTTTT    3660

ACATCCTAGC TACAATATTA TAGTTATCAT GTTGTATACG CTGTTTTTTG TTTTTTATTT    3720

TAAGGTAGTT TTATCTCGCA TAGCTCCGCT AGAGTTGTGT TATGCGGATC CTAAAGAAAA    3780

TACAACTGAA CCTACACAAC TTCCTACAGG GGAACAATCT AAGACTCTTA TTCCCGTGGT    3840

AACAAACGGA TATGTTGAAT ACTCTAAAGG ATGTGAACTA CGATTACTAG ATACATATGT    3900

AAATGTATCT TCACGACCAG AAAAAAAGGT TAATGCTACA ATTGGATGGT CATTTGATCT    3960

TGGTTGTCAA ATTCCTTTAA TTTATAGAGA ATATTATAAT TGTACTGGTA ATATAATACC    4020

ATCACCAGAA ACTTGTGATG GTTATTCTTT AACTTTGGTA AAATCTGAAA GTATATCATC    4080

TTATGCACTT GTTAATGTTA GTTTGCTTAT TCAACCAGGA ATTTTTGATT CTGGTAGATA    4140

TTTATACTCA CTTGTTTTTG GAAACGATAG TTATAACGGA AGAATTGAAG TTCGAGTGGA    4200

TAATGAGACA GACTATCCAT GTTTTATGAT GCATGGATTG ACTGTAAAAA AGGGTGATAA    4260

ACTTCATATT CCTTATAAAC CATCCACAAA TCCTAATCAT AAACGATATA GAGGTTGTTT    4320
```

-continued

| | |
|---|---|
| TCCAATATCA AATACTGAGC TATGGAATAA TATTAGTGAT GAAAGTGTTG GTAGATATTC | 4380 |
| ATATGATGAA GAATATGAAG AATATGAAGA AGAAAACGAA GATTTTGAAG ATCTACAATC | 4440 |
| AAAAGATTGC CGCAAATCCA ATCTTTTTGA TATGAAGAAG ACTTTTAATT TGGCTGCAGG | 4500 |
| TTCTCAAAGT TTATTGATTG CTAGTTTGGG TAAATCAATT TCAGAACAAC CGTGGTCATT | 4560 |
| TAAAATTAAT GAAAGTTATG AACTTTTTAA TAATTTGTCT ATCACCCTTC AATCGGAAGA | 4620 |
| AGATTCTAAT ATACTGAATC CTGAAATTGT AACGTTTACC ACACCACCAC CTACTGAAAA | 4680 |
| TACACATATG TTTATGTCAA ATAATGAAAC TATGTATGAA GAAGAAAGTG TTTTAAGCAT | 4740 |
| TATTCAATTG TTTAACAATG GTTATAATAA TTGTAATACC CATATAAAGG TAATTGGATT | 4800 |
| TGGAACAATT ATCTTTATTA TTTTATTTTT TGTTGCTGTG TTTTTTTGTG GATATACTTG | 4860 |
| TGTATTAAAC TCTCGTATTA AAATGATTAA CCATGCTTAT ATACAACCCC AGAAATTAAA | 4920 |
| TTTTTATGAT ATTTAATAAA ACTATTATGA AACTTCTTAT AACTTATTTG TTTTTATTAA | 4980 |
| ATGGGTTGGG TTGGTTTTAA AATTACATAC GTGTATTAAG AATTAACATC ATAAAGGACA | 5040 |
| CACCCATGAA AAACATTTAA ATTCTATTAA TTTGAACGGA TTAAACATTT TCTCATTTTA | 5100 |
| AGAGTTGCTA CGACTTTTGA TAGTAAAATG ATTAAACTTC TATTTATCTT ATTTTATTTT | 5160 |
| AACCCAATAA CTGGATATAA ATGGGTAGAC CCTCCTCGTA GGTATAATTA CACCGTTTTA | 5220 |
| AGAATGATTC CAGATATTCC AAATCCAATG GATCCTTCTA AAAACGCTGA AGTTCGGTAT | 5280 |
| GTAACTTCTA CTGACCCATG TGATATGGTT GCTTTGATTT CTAATCCAAA TATAGAATCT | 5340 |
| ACAATTAAAA CGATTCAATT TGTGCAAAAG AAAAAATTTT ACAATGCATC TCTTAGTTGG | 5400 |
| TTTAAAGTTG GAGATGATTG TACATATCCA ATATATTTAA TTCAATATTT TGATTGTGAT | 5460 |
| CCTCAAAGAG AATTTGGCAT ATGTTTAAAA AGATCTCCAG ATTTTTGGAA ACCATCGTTA | 5520 |
| GTTGGTTACA CATTTTTAAC TGATGATGAA TTGGGATTAG TTTTAGCTGC CCCCGCTCCA | 5580 |
| TTTAATCAAG GTCAATATAG ACGGGTTATT CAAATTGAAA ATGAAGTTTT TTATACTGAT | 5640 |
| TTTATGGTTC AATTACCACG AGAAACTTGT TATTTTCTA AAGAAGATAA ATTTGAACCA | 5700 |
| ACTTTTATGG AATGGTGTAA GGAATCTAGA TCTGTAGGAG CATCAAAAGT TGACGATGAA | 5760 |
| CTTTTTTATC TAAATAGAGC TGGTCCCCAA ACCCTGCTTA ATATTATGT TATTAAAGAT | 5820 |
| TTTTATAGAC TTAACGGTAG AGAACCTCCA ATAAAATTTA AGAAGCTCT TAGATACGAT | 5880 |
| ATACCATATA AAGTGAATGA TAAATTTGAT GATGAATTAC CATCGAGGCC ACATATTAGT | 5940 |
| AATACTATTA ATAAAACTAT TAAAGAAATT GTAAATCTTG AAGATTATTT TAAAAATACA | 6000 |
| AATGTTATAG ATACTACTAC CCCAACACCA ATAAATAATA CCCCAAAAAA TATAACCGTG | 6060 |
| GGAATTGTTA TAATTATATT AATAATACTA TTTATAATTG GATTTTTTGT TTATAAAAGA | 6120 |
| CAAAAAATAT ATAATAATTA TAAAAAATTA ACAACAAATG TTTAGCCTTT ATAAATTAAT | 6180 |
| TTACAGAATA AACAACTGGG CGGTCTTTTG TTTAATAAAA ATTCATGTAC CTACAACTTT | 6240 |
| TATTCACTTG CAAGAGGGTT GAGACCAGAT TACTTATAAC TATGTTTCTA CCTATTTTAT | 6300 |
| TTCTTTTTTT ATATGGTGTA AATGGATTTG TTTACAAAGG TACGTATATA AGTATGTTTT | 6360 |
| TAAATACTAG TTCTGGCTTT TCTATTTTTC CCGATGATAA ATTTATTGTC AGTGGACGTT | 6420 |
| TATTATTTCT CGATGACCAA CATCTGTCAG TAAATAATTA TAGCGGAACT ATTGAGTTTA | 6480 |
| TTCATTTTAA TAACTCTTGT TATACCGTTT ATCAAACTAT TGAATATTTT TCTTGTCCTC | 6540 |
| GCATTTTTAA TAATGCTTTT AGATCTTGTT TAAAAAAGGT ATCAAAACAT CATGAAAGTC | 6600 |
| AACTTCGGAT AAATTCATCT ATAGAAAACG GTGTTTTGTT GGAATTACA AATCCTAAAC | 6660 |
| CAAATGATTC AGGTGTTTAT TTTATACGAG TTCAATTGGA AAATAATAAA ACAGATGTGT | 6720 |

| | |
|---|---|
| TTGGAATACC TGCATTTATT TATTCCTTTA ATATGTCAAA CGAAGTAAAT AAATCAAACT | 6780 |
| TCGATGATGT TACTACATCT TTATATACCT CATCACACCC TTCTTCCCAA ACTATTACAC | 6840 |
| CTATCTATTT AAATGAAAAA CACGAACCGA TATGTCATAC TGTAAAAAAG GATGAAAATG | 6900 |
| TGTATGAACT TTTACTAGGT TTGCATGGAA ATATAACTGA TGATATTTTT CTCGATGAGG | 6960 |
| ATTCTGAATT GCTTAAAAGA GTAAATATAC CTACAACGAC AAATAATTAT ATATTTAAGC | 7020 |
| CTTACCTAGA CCAACGTAAT AGAAAATTTT TAATTATTGT AATTTCGATT TCGATAATTT | 7080 |
| TACTTATTCT TTTGGTATTA ATTGGATCAA TTATTAACAA TATTATTCGT AGACACTTTT | 7140 |
| CTTCTTCTAG GCGTATTTAT CGTCCTAAAG GTAACTCGGA ATCTGAAAAT ATAGAACTGA | 7200 |
| CATGTGGGGA AAACTCAGTA AACAAAAATA ATCCATTACC AAAAAAACCT AACCGCCAAA | 7260 |
| AAAGATCTTC AACTATTCAA AGGGAGACAT CTCTTGAAAC TATTAAGGAA GAAGTATAAT | 7320 |
| TTTAAAAATA TTTACCTACG TAGGTTGATG ACGACTTGTA TGACTAAAAA TTAGAATTTA | 7380 |
| AATGATGAAA ATTTTTTAAA AATAATATAG TATTCCAAAG AGCCTTTTAG GAAAATCATC | 7440 |
| AAGTCTCCAT TTCTCCAATC TTTACGATGT TTCGTTTATT TTTTTTAATC GCGTCTACAT | 7500 |
| TATGTTCGGT AAGATTTGGT TTTTCAACAA TTCGTAATGT TATTGTTTCT GAAAAATCTG | 7560 |
| GATTTGTAAT TGATGGTTAT AGTACTAACC CACCATTTAA TGAGACTAAA AAATTTACTA | 7620 |
| GAGGATGGGT ATTTTTACAA ACCCCCCCTT CTTATTGTAA AGATGGGATA TCAATATCTA | 7680 |
| ATATATGCAT TGAACGTAAT ATTTGTGAAG AAGATATTTT TTTGAATAAA CGATGTACAA | 7740 |
| TTAAAACTAT TAATTATCCC TTAGCTGTAG CAGATTTTGA GATTAGTAAT AATACTATTA | 7800 |
| AAAAAATAAA TGATGTTTAT TTTGTTAATG ATAGTGTTTT TCCAATAATA ACTACAAATA | 7860 |
| AAAGTGGTAT CCATATCACA AATGTGACTA TAAATAATTC TGGAATTTAT ACATTGTATG | 7920 |
| AAAATAATGA TAAGTGGAGT CATCAATCAA AAATCTTGGT AACTATAAAG AAAAAGAAA | 7980 |
| CAGTAATTAC TAAACCTAAA GTATATATAA AAAAACATGG TGGATTTTTT CATGTAAAAA | 8040 |
| ATTATCACTC TCATGTATTT GTACCAAATG ATTCATTTAA AATTGAACTT AATCTTGAAT | 8100 |
| CGGAAATTTA TGATTCTGAA TTTTCAGCAA GTATTGATTG GTATTATATG AAAACTAGCT | 8160 |
| CGGAATGTTC AGTGTTTCAT ATATATGAAA CTTGTATATT TCACCCTCAT GCAAACTCTT | 8220 |
| GTTTGAATCC AATAAACCCA TTGTGTAGTT TTACTTCCCC TTTGAGGGCA ACATCACTAA | 8280 |
| TTAATAGATT TTATTTTAGA TGTAAACCTG AAGGTAAAAA CTGGACAACT GATTGTATAA | 8340 |
| ACACCTTTTC TATTAATGCA GATAAACATA TTAAACAGCA TTCAAATAAT GTAGATTTGA | 8400 |
| TTTTTTTAAA TACTCCAACT AATGCATCTG GTTTGTATGT TTTTATTCTT AAGTATAATG | 8460 |
| GTCATCCAGA GGCTTGGACA TATACTTTGG TTTCAACGGT TAAAAATTTT ATGAATGTAA | 8520 |
| TTAAGGATAT GACACGCCCC CTTTTGTCAA ATAATAAAAT GAAAAAACCT GAGCATTCTA | 8580 |
| CTCAACCACC AACCATAACC AACATAACAC CTGGCTTTAA ATCTAAAAAT TGGGTAGATA | 8640 |
| AATATATAAT TTCAGTAGCG GTGGTTTCTT GTATTACTAT TGTTATATTG ATTGTGGTAA | 8700 |
| TAACCTTTTG TGTTCATCAA TGTATCGGTT TAAATCGTAA ACCATATGAA ATTATAAACC | 8760 |
| CATTTAATAC AGCTTATAAA AGTATACCTA CAAATGAAAA AATATTCTT CATTTTGCTG | 8820 |
| AAGTAACAGA ATCTGATTAT TCCTCCGACG AATCCTTCGA CAGTGACTCA GAAGAGCTAA | 8880 |
| ATCAACGAGG TGAAACAATA CAACAAGGGA AAAAGGAACA ATCTGGATAT ACTATTTGGT | 8940 |
| TTAATGAAGA TTTAGAAGAA TCCGTCTCCA AAAAACTTAA CCAACCAAAC TATTCAAAAA | 9000 |
| TAATTAATAG CTTAAAATCA ATCCAGAATG AATAAATCTA AACTCTCATT TAAAGAAAAA | 9060 |

```
AACGCTATAT ATGAATTTAA AAATATTTTA TCAAACACTT CATTGTCAAC TTTTCCTGTA      9120

TTATCGTTTA ATGAGGAGCC AAAATCCAGA TTTTTTAAAA TGTTTAAAAA TATTTTACTG      9180

GAAAAAATAA AAAAAACTTC AATGGATTAT TTAATTTATT GTACTCTAAA AATCTCACTT      9240

TCATTTATAC TTTATAATAA ATAAAATTAT TAAAAAAACT TTATTGTTTT GTCATTATTA      9300

ACTTTAACAC TAGATGGTAC TATAAAGCTA ACTTACAATA TAAATAGTAA GATTAGTTTA      9360

TATAAATTAC ATTTAATGGC TTTACCAGAT AACGTTTTTA GTATTATTAA TGAAAATTAT      9420

ATCGATGGAA TTTTAACTAT GAAAATGGGT GAAGAAATAG AAAGCTCATC ACCATTAAAT      9480

GAAACAAATG TTAATATAGA TCAACATACA ATAGATATTT TTGATTACGA TTCAGATAAT      9540

GGATGTTATT ATAGTGAAAG AGATAATGAA ACCGCAACTC TTTTTTTAAA ACGTGTTGGT      9600

TATAGAGAAA CCTCAAAAAA GCGTAAACGG ATTTGTGGAT TTATTGTTTT AGCAATTTTT      9660

ATGGTTATTA TATTATGTTT TTTATCAATA ATTTTGGGAG TTTTTATAGC GCCTCATATT      9720

TATAAAGGCC TATAGTAAGA ACATCAACCT CTAATAGTAA ATTTTTAAAA CCAACGGAGG      9780

GGGAGGAGGA GGACTTTTTA TTTTATGAGG ATAAACCTGG GGCTAGCATC GAATGGAAAT      9840

CGGCTGTTTC GGGGTATAAC TATCTAAACT CTGGTATATT TGGAAACTAT CCTCTTAATC      9900

TATGGGTTTT CGGTGCAGCG GATTTATGTG AGCCAGTCAT TTCTAATATC CCAGGACCAA      9960

AGCGACTAAT TTATGCATAT GTATCATGTG AATGGCCGGA ACCATCCTGG AAACCTGAGT      10020

GTCTTGAGAT TTCCAAAAAT AATGTAAAAC ATATCGATGA TTCTGGGAGT GTTTATTGCC      10080

CCTCGTTTAT ATGGGTACCT GTATTAGACA CCTTTCTGTC CTCCTTTAAA GTACCCCCTA      10140

TGTTAAGTGA CATTTTTTAT GGTACAACAT TTAATACTCC ATTCAACTTT GAAAGCTCTC      10200

CAAGATGTCC CTCTATATCC TCATCTTCAT CCTCCTCCTC CTCATCCTCT TCTTCATGCT      10260

CTGCATCTCA TTATTCCTCA GAGAATGATA TTTGGAAATA CGCTAATGCG ATGGTGGATA      10320

ATGAACTAGA AGAAACTAAT TGTGAAATTA AAAATAGTTT TAAAGAGGAT TCTGACAGTT      10380

CTACATGTTC TATAAGCGAT GTATGTGATT CTCTTTATAT AAATGAGACA CGTTCTGCCC      10440

CCCCGGTAAT CGAATCATTT ATGTGTGCAA TAATATCCCA TAATGGTTAT GAAGAAATTC      10500

CTGAACCAGA AGAGGATGAC TTGCATGGGG TGAAACCTAT GAAAAGGCTA TCCAAACCAA      10560

ATATTTTTAA ACGATTATTT TCAAGGCGCG CC                                   10592

(2) INFORMATION FOR SEQ ID NO: 52:

(i) SEQUENCE CHARACTERISTICS:
        (A) LENGTH: 10592 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 52:

GGCGCGCCTT GAAAATAATC GTTTAAAAAT ATTTGGTTTG GATAGCCTTT TCATAGGTTT       60

CACCCCATGC AAGTCATCCT CTTCTGGTTC AGGAATTTCT TCATAACCAT TATGGGATAT      120

TATTGCACAC ATAAATGATT CGATTACCGG GGGGGCAGAA CGTGTCTCAT TTATATAAAG      180

AGAATCACAT ACATCGCTTA TAGAACATGT AGAACTGTCA GAATCCTCTT TAAAACTATT      240

TTTAATTTCA CAATTAGTTT CTTCTAGTTC ATTATCCACC ATCGCATTAG CGTATTTCCA      300

AATATCATTC TCTGAGGAAT AATGAGATGC AGAGCATGAA GAAGAGGATG AGGAGGAGGA      360

GGATGAAGAT GAGGATATAG AGGGACATCT TGGAGAGCTT TCAAAGTTGA ATGGAGTATT      420
```

```
AAATGTTGTA CCATAAAAAA TGTCACTTAA CATAGGGGGT ACTTTAAAGG AGGACAGAAA      480

GGTGTCTAAT ACAGGTACCC ATATAAACGA GGGGCAATAA ACACTCCCAG AATCATCGAT      540

ATGTTTTACA TTATTTTTGG AAATCTCAAG ACACTCAGGT TTCCAGGATG GTTCCGGCCA      600

TTCACATGAT ACATATGCAT AAATTAGTCG CTTTGGTCCT GGGATATTAG AAATGACTGG      660

CTCACATAAA TCCGCTGCAC CGAAAACCCA TAGATTAAGA GGATAGTTTC CAAATATACC      720

AGAGTTTAGA TAGTTATACC CCGAAACAGC CGATTTCCAT TCGATGCTAG CCCCAGGTTT      780

ATCCTCATAA AATAAAAAGT CCTCCTCCTC CCCCTCCGTT GGTTTTAAAA ATTTACTATT      840

AGAGGTTGAT GTTCTTACTA TAGGCCTTTA TAAATATGAG GCGCTATAAA AACTCCCAAA      900

ATTATTGATA AAAACATAA TATAATAACC ATAAAAATTG CTAAAACAAT AAATCCACAA      960

ATCCGTTTAC GCTTTTTTGA GGTTTCTCTA TAACCAACAC GTTTTAAAAA AAGAGTTGCG     1020

GTTTCATTAT CTCTTTCACT ATAATAACAT CCATTATCTG AATCGTAATC AAAAATATCT     1080

ATTGTATGTT GATCTATATT AACATTTGTT TCATTTAATG GTGATGAGCT TTCTATTTCT     1140

TCACCCATTT TCATAGTTAA AATTCCATCG ATATAATTTT CATTAATAAT ACTAAAAACG     1200

TTATCTGGTA AAGCCATTAA ATGTAATTTA TATAAACTAA TCTTACTATT TATATTGTAA     1260

GTTAGCTTTA TAGTACCATC TAGTGTTAAA GTTAATAATG ACAAAACAAT AAAGTTTTTT     1320

TAATAATTTT ATTTATTATA AAGTATAAAT GAAAGTGAGA TTTTTAGAGT ACAATAAATT     1380

AAATAATCCA TTGAAGTTTT TTTTATTTTT TCCAGTAAAA TATTTTTAAA CATTTTAAAA     1440

AATCTGGATT TTGGCTCCTC ATTAAACGAT AATACAGGAA AAGTTGACAA TGAAGTGTTT     1500

GATAAAATAT TTTTAAATTC ATATATAGCG TTTTTTTCTT TAAATGAGAG TTTAGATTTA     1560

TTCATTCTGG ATTGATTTTA AGCTATTAAT TATTTTTGAA TAGTTTGGTT GGTTAAGTTT     1620

TTTGGAGACG GATTCTTCTA AATCTTCATT AAACCAAATA GTATATCCAG ATTGTTCCTT     1680

TTTCCCTTGT TGTATTGTTT CACCTCGTTG ATTTAGCTCT TCTGAGTCAC TGTCGAAGGA     1740

TTCGTCGGAG GAATAATCAG ATTCTGTTAC TTCAGCAAAA TGAAGAATAT TTTTTTCATT     1800

TGTAGGTATA CTTTTATAAG CTGTATTAAA TGGGTTTATA ATTTCATATG GTTTACGATT     1860

TAAACCGATA CATTGATGAA CACAAAAGGT TATTACCACA ATCAATATAA CAATAGTAAT     1920

ACAAGAAACC ACCGCTACTG AAATTATATA TTTATCTACC CAATTTTTAG ATTTAAAGCC     1980

AGGTGTTATG TTGGTTATGG TTGGTGGTTG AGTAGAATGC TCAGGTTTTT TCATTTTATT     2040

ATTTGACAAA AGGGGGCGTG TCATATCCTT AATTACATTC ATAAAATTTT TAACCGTTGA     2100

AACCAAAGTA TATGTCCAAG CCTCTGGATG ACCATTATAC TTAAGAATAA AAACATACAA     2160

ACCAGATGCA TTAGTTGGAG TATTTAAAAA AATCAAATCT ACATTATTTG AATGCTGTTT     2220

AATATGTTTA TCTGCATTAA TAGAAAAGGT GTTTATACAA TCAGTTGTCC AGTTTTTACC     2280

TTCAGGTTTA CATCTAAAAT AAAATCTATT AATTAGTGAT GTTGCCCTCA AGGGGAAGT      2340

AAAACTACAC AATGGGTTTA TTGGATTCAA ACAAGAGTTT GCATGAGGGT GAAATATACA     2400

AGTTTCATAT ATATGAAACA CTGAACATTC CGAGCTAGTT TTCATATAAT ACCAATCAAT     2460

ACTTGCTGAA AATTCAGAAT CATAAATTTC CGATTCAAGA TTAAGTTCAA TTTTAAATGA     2520

ATCATTTGGT ACAAATACAT GAGAGTGATA ATTTTTTACA TGAAAAAATC CACCATGTTT     2580

TTTTATATAT ACTTTAGGTT TAGTAATTAC TGTTTCTTTT TTCTTTATAG TTACCAAGAT     2640

TTTTGATTGA TGACTCCACT TATCATTATT TTCATACAAT GTATAAATTC CAGAATTATT     2700

TATAGTCACA TTTGTGATAT GGATACCACT TTTATTTGTA GTTATTATTG GAAAACACT      2760

ATCATTAACA AAATAAACAT CATTTATTTT TTAATAGTA TTATTACTAA TCTCAAAATC      2820
```

```
TGCTACAGCT AAGGGATAAT TAATAGTTTT AATTGTACAT CGTTTATTCA AAAAAATATC    2880

TTCTTCACAA ATATTACGTT CAATGCATAT ATTAGATATT GATATCCCAT CTTTACAATA    2940

AGAAGGGGGG GTTTGTAAAA ATACCCATCC TCTAGTAAAT TTTTTAGTCT CATTAAATGG    3000

TGGGTTAGTA CTATAACCAT CAATTACAAA TCCAGATTTT TCAGAAACAA TAACATTACG    3060

AATTGTTGAA AAACCAAATC TTACCGAACA TAATGTAGAC GCGATTAAAA AAAATAAACG    3120

AAACATCGTA AAGATTGGAG AAATGGAGAC TTGATGATTT TCCTAAAAGG CTCTTTGGAA    3180

TACTATATTA TTTTTAAAAA ATTTTCATCA TTTAAATTCT AATTTTTAGT CATACAAGTC    3240

GTCATCAACC TACGTAGGTA AATATTTTTA AAATTATACT TCTTCCTTAA TAGTTTCAAG    3300

AGATGTCTCC CTTTGAATAG TTGAAGATCT TTTTTGGCGG TTAGGTTTTT TTGGTAATGG    3360

ATTATTTTTG TTTACTGAGT TTTCCCCACA TGTCAGTTCT ATATTTTCAG ATTCCGAGTT    3420

ACCTTTAGGA CGATAAATAC GCCTAGAAGA AGAAAAGTGT CTACGAATAA TATTGTTAAT    3480

AATTGATCCA ATTAATACCA AAAGAATAAG TAAAATTATC GAAATCGAAA TTACAATAAT    3540

TAAAAATTTT CTATTACGTT GGTCTAGGTA AGGCTTAAAT ATATAATTAT TTGTCGTTGT    3600

AGGTATATTT ACTCTTTTAA GCAATTCAGA ATCCTCATCG AGAAAAATAT CATCAGTTAT    3660

ATTTCCATGC AAACCTAGTA AAAGTTCATA CACATTTTCA TCCTTTTTTA CAGTATGACA    3720

TATCGGTTCG TGTTTTTCAT TTAAATAGAT AGGTGTAATA GTTGGGAAG AAGGGTGTGA     3780

TGAGGTATAT AAAGATGTAG TAACATCATC GAAGTTTGAT TTATTTACTT CGTTGACAT    3840

ATTAAAGGAA TAAATAAATG CAGGTATTCC AAACACATCT GTTTTATTAT TTTCCAATTG    3900

AACTCGTATA AAATAAACAC CTGAATCATT TGGTTTAGGA TTTGTAATTT CCAACAAAAC    3960

ACCGTTTTCT ATAGATGAAT TTATCCGAAG TTGACTTTCA TGATGTTTTG ATACCTTTTT    4020

TAAACAAGAT CTAAAAGCAT TATTAAAAAT GCGAGGACAA GAAAAATATT CAATAGTTTG    4080

ATAAACGGTA TAACAAGAGT TATTAAAATG AATAAACTCA ATAGTTCCGC TATAATTATT    4140

TACTGACAGA TGTTGGTCAT CGAGAAATAA TAAACGTCCA CTGACAATAA ATTTATCATC    4200

GGGAAAAATA GAAAAGCCAG AACTAGTATT TAAAAACATA CTTATATACG TACCTTTGTA    4260

AACAAATCCA TTTACACCAT ATAAAAAAAG AAATAAAATA GGTAGAAACA TAGTTATAAG    4320

TAATCTGGTC TCAACCCTCT TGCAAGTGAA TAAAAGTTGT AGGTACATGA ATTTTTATTA    4380

AACAAAAGAC CGCCCAGTTG TTTATTCTGT AAATTAATTT ATAAAGGCTA AACATTTGTT    4440

GTTAATTTTT TATAATTATT ATATATTTTT TGTCTTTTAT AAACAAAAAA TCCAATTATA    4500

AATAGTATTA TTAATATAAT TATAACAATT CCCACGGTTA TATTTTTTGG GGTATTATTT    4560

ATTGGTGTTG GGGTAGTAGT ATCTATAACA TTTGTATTTT TAAATAATC TTCAAGATTT     4620

ACAATTTCTT TAATAGTTTT ATTAATAGTA TTACTAATAT GTGGCCTCGA TGGTAATTCA    4680

TCATCAAATT TATCATTCAC TTTATATGGT ATATCGTATC TAAGAGCTTC TTTAAATTTT    4740

ATTGGAGGTT CTCTACCGTT AAGTCTATAA AAATCTTTAA TAACATAATA TTTAAGCAGG    4800

GTTTGGGGAC CAGCTCTATT TAGATAAAAA AGTTCATCGT CAACTTTTGA TGCTCCTACA    4860

GATCTAGATT CCTTACACCA TTCCATAAAA GTTGGTTCAA ATTTATCTTC TTTAGAAAAA    4920

TAACAAGTTT CTCGTGGTAA TTGAACCATA AAATCAGTAT AAAAAACTTC ATTTTCAATT    4980

TGAATAACCC GTCTATATTG ACCTTGATTA AATGGAGCGG GGGCAGCTAA AACTAATCCC    5040

AATTCATCAT CAGTTAAAAA TGTGTAACCA ACTAACGATG GTTTCCAAAA ATCTGGAGAT    5100

CTTTTTAAAC ATATGCCAAA TTCTCTTTGA GGATCACAAT CAAAATATTG AATTAAATAT    5160
```

```
ATTGGATATG TACAATCATC TCCAACTTTA AACCAACTAA GAGATGCATT GTAAAATTTT    5220

TTCTTTTGCA CAAATTGAAT CGTTTTAATT GTAGATTCTA TATTTGGATT AGAAATCAAA    5280

GCAACCATAT CACATGGGTC AGTAGAAGTT ACATACCGAA CTTCAGCGTT TTTAGAAGGA    5340

TCCATTGGAT TTGGAATATC TGGAATCATT CTTAAAACGG TGTAATTATA CCTACGAGGA    5400

GGGTCTACCC ATTTATATCC AGTTATTGGG TTAAAATAAA ATAAGATAAA TAGAAGTTTA    5460

ATCATTTTAC TATCAAAAGT CGTAGCAACT CTTAAAATGA GAAAATGTTT AATCCGTTCA    5520

AATTAATAGA ATTTAAATGT TTTTCATGGG TGTGTCCTTT ATGATGTTAA TTCTTAATAC    5580

ACGTATGTAA TTTTAAAACC AACCCAACCC ATTTAATAAA AACAAATAAG TTATAAGAAG    5640

TTTCATAATA GTTTTATTAA ATATCATAAA AATTTAATTT CTGGGGTTGT ATATAAGCAT    5700

GGTTAATCAT TTTAATACGA GAGTTTAATA CACAAGTATA TCCACAAAAA AACACAGCAA    5760

CAAAAAATAA AATAATAAAG ATAATTGTTC CAAATCCAAT TACCTTTATA TGGGTATTAC    5820

AATTATTATA ACCATTGTTA AACAATTGAA TAATGCTTAA AACACTTTCT TCTTCATACA    5880

TAGTTTCATT ATTTGACATA AACATATGTG TATTTTCAGT AGGTGGTGGT GTGGTAAACG    5940

TTACAATTTC AGGATTCAGT ATATTAGAAT CTTCTTCCGA TTGAAGGGTG ATAGACAAAT    6000

TATTAAAAAG TTCATAACTT TCATTAATTT TAAATGACCA CGGTTGTTCT GAAATTGATT    6060

TACCCAAACT AGCAATCAAT AAACTTTGAG AACCTGCAGC CAAATTAAAA GTCTTCTTCA    6120

TATCAAAAAG ATTGGATTTG CGGCAATCTT TTGATTGTAG ATCTTCAAAA TCTTCGTTTT    6180

CTTCTTCATA TTCTTCATAT TCTTCATCAT ATGAATATCT ACCAACACTT TCATCACTAA    6240

TATTATTCCA TAGCTCAGTA TTTGATATTG GAAAACAACC TCTATATCGT TTATGATTAG    6300

GATTTGTGGA TGGTTTATAA GGAATATGAA GTTTATCACC CTTTTTTACA GTCAATCCAT    6360

GCATCATAAA ACATGGATAG TCTGTCTCAT TATCCACTCG AACTTCAATT CTTCCGTTAT    6420

AACTATCGTT TCCAAAAACA AGTGAGTATA AATATCTACC AGAATCAAAA ATTCCTGGTT    6480

GAATAAGCAA ACTAACATTA ACAAGTGCAT AAGATGATAT ACTTTCAGAT TTTACCAAAG    6540

TTAAAGAATA ACCATCACAA GTTTCTGGTG ATGGTATTAT ATTACCAGTA CAATTATAAT    6600

ATTCTCTATA AATTAAAGGA ATTTGACAAC CAAGATCAAA TGACCATCCA ATTGTAGCAT    6660

TAACCTTTTT TTCTGGTCGT GAAGATACAT TTACATATGT ATCTAGTAAT CGTAGTTCAC    6720

ATCCTTTAGA GTATTCAACA TATCCGTTTG TTACCACGGG AATAAGAGTC TTAGATTGTT    6780

CCCCTGTAGG AAGTTGTGTA GGTTCAGTTG TATTTTCTTT AGGATCCGCA TAACACAACT    6840

CTAGCGGAGC TATGCGAGAT AAAACTACCT TAAAATAAAA AACAAAAAAC AGCGTATACA    6900

ACATGATAAC TATAATATTG TAGCTAGGAT GTAAAAATAA AATTAATAAA AAAGAGCTTT    6960

CAAACACCCG TTTTATATAA AACAATAAAA AATTCCACGC CCATTTTTAT GAAATTTATT    7020

GTTTACTAAA AATCTGATAG GATAATAGTT CTTCCGCACT TGGTCGTAGA GATGCATCAA    7080

ATGTTAGCAT TTTATGAATT AAAAATTCAC CATCGAGATG TAATTTAAGG TTATTTAGAC    7140

GATTATATCG TGTAAATGGA GGTCTATCAT TATTAGCATA TTTTATAAAA TGTTTTACTA    7200

GATTAGATTC CAAATCAGAT GGAAATTCAT TTGGGTTAAT CTTCAGAGTT GATATAATTT    7260

TTATAAGATG AAGATTACAA TTGTTTATTA AATCGCTACT ATCTCTTTCT TCCTCCTCAA    7320

ACAAAACATT AGGATATGCA AGCATTTCAA ATAAAATTAT ACCAGCACTC CAAATATCAG    7380

CTTTACAGTT GTACGCATCC TTTGATAGAA CTTCAGGAGC ATTAGTTTCA ATAGTCCCCG    7440

CAATTCCCAA ATAATCTGGT GAGGAAACAG GAAATTGAGA AGCCCAAAAA TCACCTATAC    7500

AAACATTAGA GTCATTATCC AAGAAAATAT TTTCAGTTTT TATATCTCGA TGAATAATTT    7560
```

-continued

```
TTTTTCCATG AATATATTGA AGTCCAGTTA ATATTTGTTT TTCAATTTTA ATTACAGATT    7620

CAAAAGACAG AGATTTCCCA TGATCCATTA AAAAATTATA TAGATCATAT TTATAATACG    7680

GTAACACCAA ACATGTTAAC TCTTTATAAA AAAGAGTGTC TTGAAGTTTA ATTATAGATT    7740

GGTGACTAAT ATTTCTCAAA ATTAACGATT CCACAAGCGT GTTTCCCCTT TGTCCAATTT    7800

TTAAAATTAC CTTATAGCTT GTATCTTTAT CTTTTTTAAG AGCAATAAAA ACTCTTCCTT    7860

CTGACCCAGG CGTTAACGAT TTAACAACAG AAAACTTTAG CGCTTCAGCC GCTTCAATTC    7920

CTTCGCTTTT AGTAGGAGAT AAACTTTTTT TATCTTCATC ACTTTCATAA CTTTCTTCAA    7980

CTTCTTCGTC ACTTTCTCTT TCATTTTCAC TTTCAGTTGG ATTTTTTGTA TAATCCATAA    8040

AGTCATCATC ACTAAAATCC GAGTATAAAT CCTCATCCAT TATTTTGTCT TGATGTAGGT    8100

TATCCTCTTC AATCAAATCT GAAGTTAGAG GAACCGGTTT ATAGAAGTCT TCTGGATCGA    8160

CAGAAGATTC TCTATTCACG CTGATACAAC AAAACTTTTC GGTGGTACAC TTTGCCATAT    8220

CAGGTAATTG TGAAATTGTT ATGTTAATAT CAACTCATCA ACTGCAGCTT CTTCTAAAAT    8280

TATAACATAA ATTAGGTGTG TATTAACCTT TATTGGATTC ATACATAAAA TTTAATTATG    8340

GGTGTGGTTG AAGTTAATAT TGTTACGTTT ATTGACAAAA ATGGGGCGTT ACCAGGAAAC    8400

TCCCAAGATG TTCATCCTGA TCTTTGGTGT TTTATGGCTA GACAATGCTA TATCCTTTCT    8460

CTCACACGAT TGGCTATGCC TATAATATTA CGATCTGCAA ACTTATGTTA TTTTATGGAC    8520

TCTATAAAAC ATCTACCTAG AGTTTCAAGG CCTATAGTAA GAACATCAAC CTCTAATAGT    8580

AAATTTTTAA AACCAACGGA GGGGGAGGAG GAGGACTTTT TATTTTATGA GGATAAACCT    8640

GGGGCTAGCA TCGAATGGAA ATCGGCTGTT TCGGGGTATA ACTATCTAAA CTCTGGTATA    8700

TTTGGAAACT ATCCTCTTAA TCTATGGGTT TTCGGTGCAG CGGATTTATG TGAGCCAGTC    8760

ATTTCTAATA TCCCAGGACC AAAGCGACTA ATTTATGCAT ATGTATCATG TGAATGGCCG    8820

GAACCATCCT GGAAACCTGA GTGTCTTGAG ATTTCCAAAA ATAATGTAAA ACATATCGAT    8880

GATTCTGGGA GTGTTTATTG CCCCTCGTTT ATATGGGTAC CTGTATTAGA CACCTTTCTG    8940

TCCTCCTTTA AGTACCCCCC TATGTTAAGT GACATTTTTT ATGGTACAAC ATTTAATACT    9000

CCATTCAACT TTGAAAGCTC TCCAAGATGT CCCTCTATAT CCTCATCTTC ATCCTCCTCC    9060

TCCTCATCCT CTTCTTCATG CTCTGCATCT CATTATTCCT CAGAGAATGA TATTTGGAAA    9120

TACGCTAATG CGATGGTGGA TAATGAACTA GAAGAAACTA ATTGTGAAAT TAAAAATAGT    9180

TTTAAAGAGG ATTCTGACAG TTCTACATGT TCTATAAGCG ATGTATGTGA TTCTCTTTAT    9240

ATAAATGAGA CACGTTCTGC CCCCCCGGTA ATCGAATCAT TTATGTGTGC AATAATATCC    9300

CATAATGGTT ATGAAGAAAT TCCTGAACCA GAAGAGGATG ACTTGCATGG GGTGAAACCT    9360

ATGAAAGGC TATCCAAACC AAATATTTTT AAACGATTAT TTTCAAGGCG CGCCAAAACA    9420

ATAACCAAAA ATGAAAACGA TGGTATGTCT TCTACACAAC CTACCAACGC TCAACGTTCA    9480

TCTCTATTTA GTTCATGTTT ATGTGGAAAC TAAGTTTGTT TATATTTGTT GTGAATAAAC    9540

AGTAGATGTA AACCTGAAAT TCTGGTTTTT TATGTGAACC ACTCCCATAT TCTTACTGTA    9600

TATAAACTGG CATTTTATCC TACATTTTTA AATCTTCACT TGTTTTTAAA GCTTAACTAA    9660

AAAGTTTTAA AATGAGTGCT TCATTTGCTC TATTTGATAA CAACTCCGAT CAAGCTAATA    9720

TGCCATCATA CTTCAGACGC TGTCGTGGAG AACTTAATGA AGGATTCTAC GCACAAGTTC    9780

CGCCTGGTTA TTTTCCAGTT CGCCCTAAAA CCACACCAGC GCTTGCACGT GTGAAAAACC    9840

AGGGTGAACC GCACGCCTTC ACTATTGTTC CTACACCACC TACGGATGTA CGATTCTTCA    9900
```

-continued

```
AAAAGCTTCG TGATGGAACC TTTGTGAAAC TTCCATTTTC ATATCCTGAT GAGAGGTATG        9960

AAGATGATAT TGAACCTATG TATTGCAGAC TATACGTTCT AAAGGATTTT GAAACGCCAA       10020

GTTCTCCCTA CAATCAAGTA AACGCTTCTC AGCTTATGGA AGTACCTTCT TCGCTTGTGG       10080

AATCGAAGTG TTATTGGGAT GGTCCAAAAT TTATAAATGT ACCACCAATA AGATATATTC       10140

TAAAAAGTGA TTACTCTCTA AATAATGTAT CCGAAGATGC ATTTGTGTTG GTAGATACCA       10200

GAAAACTAAA ACTTGAAAAC TAAAATGTTT ACCCAACGCA TTAAACCTTG TAACCTATAC       10260

TCTTAATAAA ATTTAAAATA TTTTTAAAAA TTACTTTGTC TCATAGATTT CATTCATAGA       10320

TTTCATTCAT AGATTTCATT CATAGATTTC ATTCATAGAT TTCATTCATA GATTTCATTC       10380

ATAGATTTCA TTCATAGATT TCATTCATAG ATTTCATTCA TAGATTTCAT TCATAGATTT       10440

CATTCATAGA TTTCATTCAT AGATTTCATT CATAGATTTC ATTCATAGAT TTCATTCATA       10500

GATTTCATTC ATAGATTTCA TTCATAGATT TCATTCATAG ATTTCATTCA TAGATTTCAT       10560

TCATAGATTT TTATTTTTTA AATACACTGC AG                                    10592
```

(2) INFORMATION FOR SEQ ID NO: 53:

(i) SEQUENCE CHARACTERISTICS:
        (A) LENGTH: 1038 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1035

(xi) SEQUENCE DESCRIPTION: SEQ ID NO: 53:

```
ATG ATT AAA CTT CTA TTT ATC TTA TTT TAT TTT AAC CCA ATA ACT GGA         48
Met Ile Lys Leu Leu Phe Ile Leu Phe Tyr Phe Asn Pro Ile Thr Gly
 1               5                  10                  15

TAT AAA TGG GTA GAC CCT CCT CGT AGG TAT AAT TAC ACC GTT TTA AGA         96
Tyr Lys Trp Val Asp Pro Pro Arg Arg Tyr Asn Tyr Thr Val Leu Arg
             20                  25                  30

ATG ATT CCA GAT ATT CCA AAT CCA ATG GAT CCT TCT AAA AAC GCT GAA        144
Met Ile Pro Asp Ile Pro Asn Pro Met Asp Pro Ser Lys Asn Ala Glu
         35                  40                  45

GTT CGG TAT GTA ACT TCT ACT GAC CCA TGT GAT ATG GTT GCT TTG ATT        192
Val Arg Tyr Val Thr Ser Thr Asp Pro Cys Asp Met Val Ala Leu Ile
 50                  55                  60

TCT AAT CCA AAT ATA GAA TCT ACA ATT AAA ACG ATT CAA TTT GTG CAA        240
Ser Asn Pro Asn Ile Glu Ser Thr Ile Lys Thr Ile Gln Phe Val Gln
 65                  70                  75                  80

AAG AAA AAA TTT TAC AAT GCA TCT CTT AGT TGG TTT AAA GTT GGA GAT        288
Lys Lys Lys Phe Tyr Asn Ala Ser Leu Ser Trp Phe Lys Val Gly Asp
                 85                  90                  95

GAT TGT ACA TAT CCA ATA TAT TTA ATT CAA TAT TTT GAT TGT GAT CCT        336
Asp Cys Thr Tyr Pro Ile Tyr Leu Ile Gln Tyr Phe Asp Cys Asp Pro
            100                 105                 110

CAA AGA GAA TTT GGC ATA TGT TTA AAA AGA TCT CCA GAT TTT TGG AAA        384
Gln Arg Glu Phe Gly Ile Cys Leu Lys Arg Ser Pro Asp Phe Trp Lys
        115                 120                 125

CCA TCG TTA GTT GGT TAC ACA TTT TTA ACT GAT GAT GAA TTG GGA TTA        432
Pro Ser Leu Val Gly Tyr Thr Phe Leu Thr Asp Asp Glu Leu Gly Leu
    130                 135                 140

GTT TTA GCT GCC CCC GCT CCA TTT AAT CAA GGT CAA TAT AGA CGG GTT        480
Val Leu Ala Ala Pro Ala Pro Phe Asn Gln Gly Gln Tyr Arg Arg Val
```

```
                145               150               155               160
ATT CAA ATT GAA AAT GAA GTT TTT TAT ACT GAT TTT ATG GTT CAA TTA              528
Ile Gln Ile Glu Asn Glu Val Phe Tyr Thr Asp Phe Met Val Gln Leu
                    165               170               175

CCA CGA GAA ACT TGT TAT TTT TCT AAA GAA GAT AAA TTT GAA CCA ACT              576
Pro Arg Glu Thr Cys Tyr Phe Ser Lys Glu Asp Lys Phe Glu Pro Thr
                180               185               190

TTT ATG GAA TGG TGT AAG GAA TCT AGA TCT GTA GGA GCA TCA AAA GTT              624
Phe Met Glu Trp Cys Lys Glu Ser Arg Ser Val Gly Ala Ser Lys Val
            195               200               205

GAC GAT GAA CTT TTT TAT CTA AAT AGA GCT GGT CCC CAA ACC CTG CTT              672
Asp Asp Glu Leu Phe Tyr Leu Asn Arg Ala Gly Pro Gln Thr Leu Leu
        210               215               220

AAA TAT TAT GTT ATT AAA GAT TTT TAT AGA CTT AAC GGT AGA GAA CCT              720
Lys Tyr Tyr Val Ile Lys Asp Phe Tyr Arg Leu Asn Gly Arg Glu Pro
225               230               235               240

CCA ATA AAA TTT AAA GAA GCT CTT AGA TAC GAT ATA CCA TAT AAA GTG              768
Pro Ile Lys Phe Lys Glu Ala Leu Arg Tyr Asp Ile Pro Tyr Lys Val
                245               250               255

AAT GAT AAA TTT GAT GAT GAA TTA CCA TCG AGG CCA CAT ATT AGT AAT              816
Asn Asp Lys Phe Asp Asp Glu Leu Pro Ser Arg Pro His Ile Ser Asn
                    260               265               270

ACT ATT AAT AAA ACT ATT AAA GAA ATT GTA AAT CTT GAA GAT TAT TTT              864
Thr Ile Asn Lys Thr Ile Lys Glu Ile Val Asn Leu Glu Asp Tyr Phe
                275               280               285

AAA AAT ACA AAT GTT ATA GAT ACT ACT ACC CCA ACA CCA ATA AAT AAT              912
Lys Asn Thr Asn Val Ile Asp Thr Thr Thr Pro Thr Pro Ile Asn Asn
        290               295               300

ACC CCA AAA AAT ATA ACC GTG GGA ATT GTT ATA ATT ATA TTA ATA ATA              960
Thr Pro Lys Asn Ile Thr Val Gly Ile Val Ile Ile Leu Ile Ile
305               310               315               320

CTA TTT ATA ATT GGA TTT TTT GTT TAT AAA AGA CAA AAA ATA TAT AAT             1008
Leu Phe Ile Ile Gly Phe Phe Val Tyr Lys Arg Gln Lys Ile Tyr Asn
                325               330               335

AAT TAT AAA AAA TTA ACA ACA AAT GTT TAG                                     1038
Asn Tyr Lys Lys Leu Thr Thr Asn Val
                340               345

(2) INFORMATION FOR SEQ ID NO: 54:

(i) SEQUENCE CHARACTERISTICS:
        (A) LENGTH: 345 amino acids
        (B) TYPE: amino acid
        (D) TOPOLOGY: linear (ii) MOLECULE TYPE: protein (xi) SEQUENCE DESCRIPTION: SEQ ID NO: 54:

Met Ile Lys Leu Leu Phe Ile Leu Phe Tyr Phe Asn Pro Ile Thr Gly
  1               5                  10                  15

Tyr Lys Trp Val Asp Pro Pro Arg Arg Tyr Asn Tyr Thr Val Leu Arg
                 20                  25                  30

Met Ile Pro Asp Ile Pro Asn Pro Met Asp Pro Ser Lys Asn Ala Glu
             35                  40                  45

Val Arg Tyr Val Thr Ser Thr Asp Pro Cys Asp Met Val Ala Leu Ile
         50                  55                  60

Ser Asn Pro Asn Ile Glu Ser Thr Ile Lys Thr Ile Gln Phe Val Gln
 65                  70                  75                  80

Lys Lys Lys Phe Tyr Asn Ala Ser Leu Ser Trp Phe Lys Val Gly Asp
                 85                  90                  95
```

```
Asp Cys Thr Tyr Pro Ile Tyr Leu Ile Gln Tyr Phe Asp Cys Asp Pro
             100                 105                 110

Gln Arg Glu Phe Gly Ile Cys Leu Lys Arg Ser Pro Asp Phe Trp Lys
         115                 120                 125

Pro Ser Leu Val Gly Tyr Thr Phe Leu Thr Asp Asp Glu Leu Gly Leu
     130                 135                 140

Val Leu Ala Ala Pro Ala Pro Phe Asn Gln Gly Gln Tyr Arg Arg Val
145                 150                 155                 160

Ile Gln Ile Glu Asn Glu Val Phe Tyr Thr Asp Phe Met Val Gln Leu
                 165                 170                 175

Pro Arg Glu Thr Cys Tyr Phe Ser Lys Glu Asp Lys Phe Glu Pro Thr
             180                 185                 190

Phe Met Glu Trp Cys Lys Glu Ser Arg Ser Val Gly Ala Ser Lys Val
         195                 200                 205

Asp Asp Glu Leu Phe Tyr Leu Asn Arg Ala Gly Pro Gln Thr Leu Leu
     210                 215                 220

Lys Tyr Tyr Val Ile Lys Asp Phe Tyr Arg Leu Asn Gly Arg Glu Pro
225                 230                 235                 240

Pro Ile Lys Phe Lys Glu Ala Leu Arg Tyr Asp Ile Pro Tyr Lys Val
                 245                 250                 255

Asn Asp Lys Phe Asp Asp Glu Leu Pro Ser Arg Pro His Ile Ser Asn
             260                 265                 270

Thr Ile Asn Lys Thr Ile Lys Glu Ile Val Asn Leu Glu Asp Tyr Phe
         275                 280                 285

Lys Asn Thr Asn Val Ile Asp Thr Thr Thr Pro Thr Pro Ile Asn Asn
     290                 295                 300

Thr Pro Lys Asn Ile Thr Val Gly Ile Val Ile Ile Leu Ile Ile
305                 310                 315                 320

Leu Phe Ile Ile Gly Phe Phe Val Tyr Lys Arg Gln Lys Ile Tyr Asn
                 325                 330                 335

Asn Tyr Lys Lys Leu Thr Thr Asn Val
             340                 345

(2) INFORMATION FOR SEQ ID NO: 55:

(i) SEQUENCE CHARACTERISTICS:
        (A) LENGTH: 1095 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1092

(xi) SEQUENCE DESCRIPTION: SEQ ID NO: 55:

ATG TAC CTA CAA CTT TTA TTC ACT TGC AAG AGG GTT GAG ACC AGA TTA      48
Met Tyr Leu Gln Leu Leu Phe Thr Cys Lys Arg Val Glu Thr Arg Leu
 1               5                  10                  15

CTT ATA ACT ATG TTT CTA CCT ATT TTA TTT CTT TTT TTA TAT GGT GTA      96
Leu Ile Thr Met Phe Leu Pro Ile Leu Phe Leu Phe Leu Tyr Gly Val
             20                  25                  30

AAT GGA TTT GTT TAC AAA GGT ACG TAT ATA AGT ATG TTT TTA AAT ACT     144
Asn Gly Phe Val Tyr Lys Gly Thr Tyr Ile Ser Met Phe Leu Asn Thr
         35                  40                  45

AGT TCT GGC TTT TCT ATT TTT CCC GAT GAT AAA TTT ATT GTC AGT GGA     192
```

```
Ser Ser Gly Phe Ser Ile Phe Pro Asp Asp Lys Phe Ile Val Ser Gly
     50                  55                  60

CGT TTA TTA TTT CTC GAT GAC CAA CAT CTG TCA GTA AAT AAT TAT AGC       240
Arg Leu Leu Phe Leu Asp Asp Gln His Leu Ser Val Asn Asn Tyr Ser
 65                  70                  75                  80

GGA ACT ATT GAG TTT ATT CAT TTT AAT AAC TCT TGT TAT ACC GTT TAT       288
Gly Thr Ile Glu Phe Ile His Phe Asn Asn Ser Cys Tyr Thr Val Tyr
                     85                  90                  95

CAA ACT ATT GAA TAT TTT TCT TGT CCT CGC ATT TTT AAT AAT GCT TTT       336
Gln Thr Ile Glu Tyr Phe Ser Cys Pro Arg Ile Phe Asn Asn Ala Phe
                 100                 105                 110

AGA TCT TGT TTA AAA AAG GTA TCA AAA CAT CAT GAA AGT CAA CTT CGG       384
Arg Ser Cys Leu Lys Lys Val Ser Lys His His Glu Ser Gln Leu Arg
             115                 120                 125

ATA AAT TCA TCT ATA GAA AAC GGT GTT TTG TTG GAA ATT ACA AAT CCT       432
Ile Asn Ser Ser Ile Glu Asn Gly Val Leu Leu Glu Ile Thr Asn Pro
         130                 135                 140

AAA CCA AAT GAT TCA GGT GTT TAT TTT ATA CGA GTT CAA TTG GAA AAT       480
Lys Pro Asn Asp Ser Gly Val Tyr Phe Ile Arg Val Gln Leu Glu Asn
145                 150                 155                 160

AAT AAA ACA GAT GTG TTT GGA ATA CCT GCA TTT ATT TAT TCC TTT AAT       528
Asn Lys Thr Asp Val Phe Gly Ile Pro Ala Phe Ile Tyr Ser Phe Asn
                 165                 170                 175

ATG TCA AAC GAA GTA AAT AAA TCA AAC TTC GAT GAT GTT ACT ACA TCT       576
Met Ser Asn Glu Val Asn Lys Ser Asn Phe Asp Asp Val Thr Thr Ser
             180                 185                 190

TTA TAT ACC TCA TCA CAC CCT TCT TCC CAA ACT ATT ACA CCT ATC TAT       624
Leu Tyr Thr Ser Ser His Pro Ser Ser Gln Thr Ile Thr Pro Ile Tyr
         195                 200                 205

TTA AAT GAA AAA CAC GAA CCG ATA TGT CAT ACT GTA AAA AAG GAT GAA       672
Leu Asn Glu Lys His Glu Pro Ile Cys His Thr Val Lys Lys Asp Glu
210                 215                 220

AAT GTG TAT GAA CTT TTA CTA GGT TTG CAT GGA AAT ATA ACT GAT GAT       720
Asn Val Tyr Glu Leu Leu Leu Gly Leu His Gly Asn Ile Thr Asp Asp
225                 230                 235                 240

ATT TTT CTC GAT GAG GAT TCT GAA TTG CTT AAA AGA GTA AAT ATA CCT       768
Ile Phe Leu Asp Glu Asp Ser Glu Leu Leu Lys Arg Val Asn Ile Pro
                 245                 250                 255

ACA ACG ACA AAT AAT TAT ATA TTT AAG CCT TAC CTA GAC CAA CGT AAT       816
Thr Thr Thr Asn Asn Tyr Ile Phe Lys Pro Tyr Leu Asp Gln Arg Asn
             260                 265                 270

AGA AAA TTT TTA ATT ATT GTA ATT TCG ATT TCG ATA ATT TTA CTT ATT       864
Arg Lys Phe Leu Ile Ile Val Ile Ser Ile Ser Ile Ile Leu Leu Ile
         275                 280                 285

CTT TTG GTA TTA ATT GGA TCA ATT ATT AAC AAT ATT ATT CGT AGA CAC       912
Leu Leu Val Leu Ile Gly Ser Ile Ile Asn Asn Ile Ile Arg Arg His
     290                 295                 300

TTT TCT TCT TCT AGG CGT ATT TAT CGT CCT AAA GGT AAC TCG GAA TCT       960
Phe Ser Ser Ser Arg Arg Ile Tyr Arg Pro Lys Gly Asn Ser Glu Ser
305                 310                 315                 320

GAA AAT ATA GAA CTG ACA TGT GGG GAA AAC TCA GTA AAC AAA AAT AAT      1008
Glu Asn Ile Glu Leu Thr Cys Gly Glu Asn Ser Val Asn Lys Asn Asn
                 325                 330                 335

CCA TTA CCA AAA AAA CCT AAC CGC CAA AAA AGA TCT TCA ACT ATT CAA      1056
Pro Leu Pro Lys Lys Pro Asn Arg Gln Lys Arg Ser Ser Thr Ile Gln
             340                 345                 350

AGG GAG ACA TCT CTT GAA ACT ATT AAG GAA GAA GTA TAA                  1095
Arg Glu Thr Ser Leu Glu Thr Ile Lys Glu Glu Val
         355                 360
```

(2) INFORMATION FOR SEQ ID NO: 56:

(i) SEQUENCE CHARACTERISTICS:
      (A) LENGTH: 364 amino acids
      (B) TYPE: amino acid
      (D) TOPOLOGY: linear (ii) MOLECULE TYPE: protein (xi) SEQUENCE DESCRIPTION: SEQ ID NO: 56:

```
Met Tyr Leu Gln Leu Leu Phe Thr Cys Lys Arg Val Glu Thr Arg Leu
 1               5                  10                  15

Leu Ile Thr Met Phe Leu Pro Ile Leu Phe Leu Phe Leu Tyr Gly Val
                20                  25                  30

Asn Gly Phe Val Tyr Lys Gly Thr Tyr Ile Ser Met Phe Leu Asn Thr
             35                  40                  45

Ser Ser Gly Phe Ser Ile Phe Pro Asp Asp Lys Phe Ile Val Ser Gly
         50                  55                  60

Arg Leu Leu Phe Leu Asp Asp Gln His Leu Ser Val Asn Asn Tyr Ser
 65                  70                  75                  80

Gly Thr Ile Glu Phe Ile His Phe Asn Asn Ser Cys Tyr Thr Val Tyr
                 85                  90                  95

Gln Thr Ile Glu Tyr Phe Ser Cys Pro Arg Ile Phe Asn Asn Ala Phe
                100                 105                 110

Arg Ser Cys Leu Lys Lys Val Ser Lys His His Glu Ser Gln Leu Arg
            115                 120                 125

Ile Asn Ser Ser Ile Glu Asn Gly Val Leu Leu Glu Ile Thr Asn Pro
130                 135                 140

Lys Pro Asn Asp Ser Gly Val Tyr Phe Ile Arg Val Gln Leu Glu Asn
145                 150                 155                 160

Asn Lys Thr Asp Val Phe Gly Ile Pro Ala Phe Ile Tyr Ser Phe Asn
                165                 170                 175

Met Ser Asn Glu Val Asn Lys Ser Asn Phe Asp Asp Val Thr Thr Ser
                180                 185                 190

Leu Tyr Thr Ser Ser His Pro Ser Ser Gln Thr Ile Thr Pro Ile Tyr
        195                 200                 205

Leu Asn Glu Lys His Glu Pro Ile Cys His Thr Val Lys Lys Asp Glu
210                 215                 220

Asn Val Tyr Glu Leu Leu Gly Leu His Gly Asn Ile Thr Asp Asp
225                 230                 235                 240

Ile Phe Leu Asp Glu Asp Ser Glu Leu Leu Lys Arg Val Asn Ile Pro
                245                 250                 255

Thr Thr Thr Asn Asn Tyr Ile Phe Lys Pro Tyr Leu Asp Gln Arg Asn
                260                 265                 270

Arg Lys Phe Leu Ile Ile Val Ile Ser Ile Ser Ile Leu Leu Ile
            275                 280                 285

Leu Leu Val Leu Ile Gly Ser Ile Ile Asn Asn Ile Ile Arg Arg His
        290                 295                 300

Phe Ser Ser Ser Arg Arg Ile Tyr Arg Pro Lys Gly Asn Ser Glu Ser
305                 310                 315                 320

Glu Asn Ile Glu Leu Thr Cys Gly Glu Asn Ser Val Asn Lys Asn Asn
                325                 330                 335

Pro Leu Pro Lys Lys Pro Asn Arg Gln Lys Arg Ser Ser Thr Ile Gln
                340                 345                 350

Arg Glu Thr Ser Leu Glu Thr Ile Lys Glu Glu Val
```

(2) INFORMATION FOR SEQ ID NO: 57:

(i) SEQUENCE CHARACTERISTICS:
       (A) LENGTH: 1569 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 1..1566

(xi) SEQUENCE DESCRIPTION: SEQ ID NO: 57:

```
ATG TTT CGT TTA TTT TTT TTA ATC GCG TCT ACA TTA TGT TCG GTA AGA      48
Met Phe Arg Leu Phe Phe Leu Ile Ala Ser Thr Leu Cys Ser Val Arg
 1               5                  10                  15

TTT GGT TTT TCA ACA ATT CGT AAT GTT ATT GTT TCT GAA AAA TCT GGA      96
Phe Gly Phe Ser Thr Ile Arg Asn Val Ile Val Ser Glu Lys Ser Gly
             20                  25                  30

TTT GTA ATT GAT GGT TAT AGT ACT AAC CCA CCA TTT AAT GAG ACT AAA     144
Phe Val Ile Asp Gly Tyr Ser Thr Asn Pro Pro Phe Asn Glu Thr Lys
         35                  40                  45

AAA TTT ACT AGA GGA TGG GTA TTT TTA CAA ACC CCC CCT TCT TAT TGT     192
Lys Phe Thr Arg Gly Trp Val Phe Leu Gln Thr Pro Pro Ser Tyr Cys
 50                  55                  60

AAA GAT GGG ATA TCA ATA TCT AAT ATA TGC ATT GAA CGT AAT ATT TGT     240
Lys Asp Gly Ile Ser Ile Ser Asn Ile Cys Ile Glu Arg Asn Ile Cys
 65                  70                  75                  80

GAA GAA GAT ATT TTT TTG AAT AAA CGA TGT ACA ATT AAA ACT ATT AAT     288
Glu Glu Asp Ile Phe Leu Asn Lys Arg Cys Thr Ile Lys Thr Ile Asn
                 85                  90                  95

TAT CCC TTA GCT GTA GCA GAT TTT GAG ATT AGT AAT AAT ACT ATT AAA     336
Tyr Pro Leu Ala Val Ala Asp Phe Glu Ile Ser Asn Asn Thr Ile Lys
            100                 105                 110

AAA ATA AAT GAT GTT TAT TTT GTT AAT GAT AGT GTT TTT CCA ATA ATA     384
Lys Ile Asn Asp Val Tyr Phe Val Asn Asp Ser Val Phe Pro Ile Ile
        115                 120                 125

ACT ACA AAT AAA AGT GGT ATC CAT ATC ACA AAT GTG ACT ATA AAT AAT     432
Thr Thr Asn Lys Ser Gly Ile His Ile Thr Asn Val Thr Ile Asn Asn
    130                 135                 140

TCT GGA ATT TAT ACA TTG TAT GAA AAT AAT GAT AAG TGG AGT CAT CAA     480
Ser Gly Ile Tyr Thr Leu Tyr Glu Asn Asn Asp Lys Trp Ser His Gln
145                 150                 155                 160

TCA AAA ATC TTG GTA ACT ATA AAG AAA AAA GAA ACA GTA ATT ACT AAA     528
Ser Lys Ile Leu Val Thr Ile Lys Lys Lys Glu Thr Val Ile Thr Lys
                165                 170                 175

CCT AAA GTA TAT ATA AAA AAA CAT GGT GGA TTT TTT CAT GTA AAA AAT     576
Pro Lys Val Tyr Ile Lys Lys His Gly Gly Phe Phe His Val Lys Asn
            180                 185                 190

TAT CAC TCT CAT GTA TTT GTA CCA AAT GAT TCA TTT AAA ATT GAA CTT     624
Tyr His Ser His Val Phe Val Pro Asn Asp Ser Phe Lys Ile Glu Leu
        195                 200                 205

AAT CTT GAA TCG GAA ATT TAT GAT TCT GAA TTT TCA GCA AGT ATT GAT     672
Asn Leu Glu Ser Glu Ile Tyr Asp Ser Glu Phe Ser Ala Ser Ile Asp
    210                 215                 220

TGG TAT TAT ATG AAA ACT AGC TCG GAA TGT TCA GTG TTT CAT ATA TAT     720
Trp Tyr Tyr Met Lys Thr Ser Ser Glu Cys Ser Val Phe His Ile Tyr
225                 230                 235                 240
```

```
GAA ACT TGT ATA TTT CAC CCT CAT GCA AAC TCT TGT TTG AAT CCA ATA         768
Glu Thr Cys Ile Phe His Pro His Ala Asn Ser Cys Leu Asn Pro Ile
            245                 250                 255

AAC CCA TTG TGT AGT TTT ACT TCC CCT TTG AGG GCA ACA TCA CTA ATT         816
Asn Pro Leu Cys Ser Phe Thr Ser Pro Leu Arg Ala Thr Ser Leu Ile
        260                 265                 270

AAT AGA TTT TAT TTT AGA TGT AAA CCT GAA GGT AAA AAC TGG ACA ACT         864
Asn Arg Phe Tyr Phe Arg Cys Lys Pro Glu Gly Lys Asn Trp Thr Thr
    275                 280                 285

GAT TGT ATA AAC ACC TTT TCT ATT AAT GCA GAT AAA CAT ATT AAA CAG         912
Asp Cys Ile Asn Thr Phe Ser Ile Asn Ala Asp Lys His Ile Lys Gln
290                 295                 300

CAT TCA AAT AAT GTA GAT TTG ATT TTT TTA AAT ACT CCA ACT AAT GCA         960
His Ser Asn Asn Val Asp Leu Ile Phe Leu Asn Thr Pro Thr Asn Ala
305                 310                 315                 320

TCT GGT TTG TAT GTT TTT ATT CTT AAG TAT AAT GGT CAT CCA GAG GCT        1008
Ser Gly Leu Tyr Val Phe Ile Leu Lys Tyr Asn Gly His Pro Glu Ala
            325                 330                 335

TGG ACA TAT ACT TTG GTT TCA ACG GTT AAA AAT TTT ATG AAT GTA ATT        1056
Trp Thr Tyr Thr Leu Val Ser Thr Val Lys Asn Phe Met Asn Val Ile
        340                 345                 350

AAG GAT ATG ACA CGC CCC CTT TTG TCA AAT AAT AAA ATG AAA AAA CCT        1104
Lys Asp Met Thr Arg Pro Leu Leu Ser Asn Asn Lys Met Lys Lys Pro
    355                 360                 365

GAG CAT TCT ACT CAA CCA CCA ACC ATA ACC AAC ATA ACA CCT GGC TTT        1152
Glu His Ser Thr Gln Pro Pro Thr Ile Thr Asn Ile Thr Pro Gly Phe
370                 375                 380

AAA TCT AAA AAT TGG GTA GAT AAA TAT ATA ATT TCA GTA GCG GTG GTT        1200
Lys Ser Lys Asn Trp Val Asp Lys Tyr Ile Ile Ser Val Ala Val Val
385                 390                 395                 400

TCT TGT ATT ACT ATT GTT ATA TTG ATT GTG GTA ATA ACC TTT TGT GTT        1248
Ser Cys Ile Thr Ile Val Ile Leu Ile Val Val Ile Thr Phe Cys Val
            405                 410                 415

CAT CAA TGT ATC GGT TTA AAT CGT AAA CCA TAT GAA ATT ATA AAC CCA        1296
His Gln Cys Ile Gly Leu Asn Arg Lys Pro Tyr Glu Ile Ile Asn Pro
        420                 425                 430

TTT AAT ACA GCT TAT AAA AGT ATA CCT ACA AAT GAA AAA AAT ATT CTT        1344
Phe Asn Thr Ala Tyr Lys Ser Ile Pro Thr Asn Glu Lys Asn Ile Leu
    435                 440                 445

CAT TTT GCT GAA GTA ACA GAA TCT GAT TAT TCC TCC GAC GAA TCC TTC        1392
His Phe Ala Glu Val Thr Glu Ser Asp Tyr Ser Ser Asp Glu Ser Phe
450                 455                 460

GAC AGT GAC TCA GAA GAG CTA AAT CAA CGA GGT GAA ACA ATA CAA CAA        1440
Asp Ser Asp Ser Glu Glu Leu Asn Gln Arg Gly Glu Thr Ile Gln Gln
465                 470                 475                 480

GGG AAA AAG GAA CAA TCT GGA TAT ACT ATT TGG TTT AAT GAA GAT TTA        1488
Gly Lys Lys Glu Gln Ser Gly Tyr Thr Ile Trp Phe Asn Glu Asp Leu
            485                 490                 495

GAA GAA TCC GTC TCC AAA AAA CTT AAC CAA CCA AAC TAT TCA AAA ATA        1536
Glu Glu Ser Val Ser Lys Lys Leu Asn Gln Pro Asn Tyr Ser Lys Ile
        500                 505                 510

ATT AAT AGC TTA AAA TCA ATC CAG AAT GAA TAA                            1569
Ile Asn Ser Leu Lys Ser Ile Gln Asn Glu
    515                 520
```

(2) INFORMATION FOR SEQ ID NO: 58:

(i) SEQUENCE CHARACTERISTICS:
        (A) LENGTH: 522 amino acids
        (B) TYPE: amino acid
        (D) TOPOLOGY: linear -continued (ii) MOLECULE TYPE: protein (xi) SEQUENCE DESCRIPTION: SEQ ID NO: 58:

```
Met Phe Arg Leu Phe Phe Leu Ile Ala Ser Thr Leu Cys Ser Val Arg
  1               5                  10                  15

Phe Gly Phe Ser Thr Ile Arg Asn Val Ile Val Ser Glu Lys Ser Gly
             20                  25                  30

Phe Val Ile Asp Gly Tyr Ser Thr Asn Pro Pro Phe Asn Glu Thr Lys
         35                  40                  45

Lys Phe Thr Arg Gly Trp Val Phe Leu Gln Thr Pro Pro Ser Tyr Cys
 50                  55                  60

Lys Asp Gly Ile Ser Ile Ser Asn Ile Cys Ile Glu Arg Asn Ile Cys
 65                  70                  75                  80

Glu Glu Asp Ile Phe Leu Asn Lys Arg Cys Thr Ile Lys Thr Ile Asn
                 85                  90                  95

Tyr Pro Leu Ala Val Ala Asp Phe Glu Ile Ser Asn Asn Thr Ile Lys
            100                 105                 110

Lys Ile Asn Asp Val Tyr Phe Val Asn Asp Ser Val Phe Pro Ile Ile
        115                 120                 125

Thr Thr Asn Lys Ser Gly Ile His Ile Thr Asn Val Thr Ile Asn Asn
130                 135                 140

Ser Gly Ile Tyr Thr Leu Tyr Glu Asn Asn Asp Lys Trp Ser His Gln
145                 150                 155                 160

Ser Lys Ile Leu Val Thr Ile Lys Lys Glu Thr Val Ile Thr Lys
                165                 170                 175

Pro Lys Val Tyr Ile Lys Lys His Gly Gly Phe Phe His Val Lys Asn
            180                 185                 190

Tyr His Ser His Val Phe Val Pro Asn Asp Ser Phe Lys Ile Glu Leu
        195                 200                 205

Asn Leu Glu Ser Glu Ile Tyr Asp Ser Glu Phe Ser Ala Ser Ile Asp
    210                 215                 220

Trp Tyr Tyr Met Lys Thr Ser Ser Glu Cys Ser Val Phe His Ile Tyr
225                 230                 235                 240

Glu Thr Cys Ile Phe His Pro His Ala Asn Ser Cys Leu Asn Pro Ile
                245                 250                 255

Asn Pro Leu Cys Ser Phe Thr Ser Pro Leu Arg Ala Thr Ser Leu Ile
            260                 265                 270

Asn Arg Phe Tyr Phe Arg Cys Lys Pro Glu Gly Lys Asn Trp Thr Thr
        275                 280                 285

Asp Cys Ile Asn Thr Phe Ser Ile Asn Ala Asp Lys His Ile Lys Gln
290                 295                 300

His Ser Asn Asn Val Asp Leu Ile Phe Leu Asn Thr Pro Thr Asn Ala
305                 310                 315                 320

Ser Gly Leu Tyr Val Phe Ile Leu Lys Tyr Asn Gly His Pro Glu Ala
                325                 330                 335

Trp Thr Tyr Thr Leu Val Ser Thr Val Lys Asn Phe Met Asn Val Ile
            340                 345                 350

Lys Asp Met Thr Arg Pro Leu Leu Ser Asn Asn Lys Met Lys Lys Pro
        355                 360                 365

Glu His Ser Thr Gln Pro Pro Thr Ile Thr Asn Ile Thr Pro Gly Phe
370                 375                 380

Lys Ser Lys Asn Trp Val Asp Lys Tyr Ile Ile Ser Val Ala Val Val
385                 390                 395                 400
```

```
Ser Cys Ile Thr Ile Val Ile Leu Ile Val Val Ile Thr Phe Cys Val
            405                 410                 415

His Gln Cys Ile Gly Leu Asn Arg Lys Pro Tyr Glu Ile Ile Asn Pro
            420                 425                 430

Phe Asn Thr Ala Tyr Lys Ser Ile Pro Thr Asn Glu Lys Asn Ile Leu
            435                 440                 445

His Phe Ala Glu Val Thr Glu Ser Asp Tyr Ser Ser Asp Glu Ser Phe
            450                 455                 460

Asp Ser Asp Ser Glu Glu Leu Asn Gln Arg Gly Glu Thr Ile Gln Gln
465                 470                 475                 480

Gly Lys Lys Glu Gln Ser Gly Tyr Thr Ile Trp Phe Asn Glu Asp Leu
            485                 490                 495

Glu Glu Ser Val Ser Lys Lys Leu Asn Gln Pro Asn Tyr Ser Lys Ile
            500                 505                 510

Ile Asn Ser Leu Lys Ser Ile Gln Asn Glu
            515                 520
```

(2) INFORMATION FOR SEQ ID NO: 59:

(i) SEQUENCE CHARACTERISTICS:
        (A) LENGTH: 237 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..234

(xi) SEQUENCE DESCRIPTION: SEQ ID NO: 59:

```
ATG AAT AAA TCT AAA CTC TCA TTT AAA GAA AAA AAC GCT ATA TAT GAA      48
Met Asn Lys Ser Lys Leu Ser Phe Lys Glu Lys Asn Ala Ile Tyr Glu
 1               5                  10                  15

TTT AAA AAT ATT TTA TCA AAC ACT TCA TTG TCA ACT TTT CCT GTA TTA      96
Phe Lys Asn Ile Leu Ser Asn Thr Ser Leu Ser Thr Phe Pro Val Leu
            20                  25                  30

TCG TTT AAT GAG GAG CCA AAA TCC AGA TTT TTT AAA ATG TTT AAA AAT     144
Ser Phe Asn Glu Glu Pro Lys Ser Arg Phe Phe Lys Met Phe Lys Asn
        35                  40                  45

ATT TTA CTG GAA AAA ATA AAA AAA ACT TCA ATG GAT TAT TTA ATT TAT     192
Ile Leu Leu Glu Lys Ile Lys Lys Thr Ser Met Asp Tyr Leu Ile Tyr
 50                  55                  60

TGT ACT CTA AAA ATC TCA CTT TCA TTT ATA CTT TAT AAT AAA             234
Cys Thr Leu Lys Ile Ser Leu Ser Phe Ile Leu Tyr Asn Lys
65                  70                  75

TAA                                                                  237
```

(2) INFORMATION FOR SEQ ID NO: 60:

(i) SEQUENCE CHARACTERISTICS:
        (A) LENGTH: 78 amino acids
        (B) TYPE: amino acid
        (D) TOPOLOGY: linear (ii) MOLECULE TYPE: protein (xi) SEQUENCE DESCRIPTION: SEQ ID NO: 60:

```
Met Asn Lys Ser Lys Leu Ser Phe Lys Glu Lys Asn Ala Ile Tyr Glu
 1               5                  10                  15
```

```
Phe Lys Asn Ile Leu Ser Asn Thr Ser Leu Ser Thr Phe Pro Val Leu
            20                  25                  30

Ser Phe Asn Glu Glu Pro Lys Ser Arg Phe Phe Lys Met Phe Lys Asn
        35                  40                  45

Ile Leu Leu Glu Lys Ile Lys Lys Thr Ser Met Asp Tyr Leu Ile Tyr
    50                  55                  60

Cys Thr Leu Lys Ile Ser Leu Ser Phe Ile Leu Tyr Asn Lys
65                  70                  75
```

(2) INFORMATION FOR SEQ ID NO: 61:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..357

(xi) SEQUENCE DESCRIPTION: SEQ ID NO: 61:

```
ATG GCT TTA CCA GAT AAC GTT TTT AGT ATT ATT AAT GAA AAT TAT ATC    48
Met Ala Leu Pro Asp Asn Val Phe Ser Ile Ile Asn Glu Asn Tyr Ile
1               5                   10                  15

GAT GGA ATT TTA ACT ATG AAA ATG GGT GAA GAA ATA GAA AGC TCA TCA    96
Asp Gly Ile Leu Thr Met Lys Met Gly Glu Glu Ile Glu Ser Ser Ser
                20                  25                  30

CCA TTA AAT GAA ACA AAT GTT AAT ATA GAT CAA CAT ACA ATA GAT ATT   144
Pro Leu Asn Glu Thr Asn Val Asn Ile Asp Gln His Thr Ile Asp Ile
            35                  40                  45

TTT GAT TAC GAT TCA GAT AAT GGA TGT TAT TAT AGT GAA AGA GAT AAT   192
Phe Asp Tyr Asp Ser Asp Asn Gly Cys Tyr Tyr Ser Glu Arg Asp Asn
        50                  55                  60

GAA ACC GCA ACT CTT TTT TTA AAA CGT GTT GGT TAT AGA GAA ACC TCA   240
Glu Thr Ala Thr Leu Phe Leu Lys Arg Val Gly Tyr Arg Glu Thr Ser
65                  70                  75                  80

AAA AAG CGT AAA CGG ATT TGT GGA TTT ATT GTT TTA GCA ATT TTT ATG   288
Lys Lys Arg Lys Arg Ile Cys Gly Phe Ile Val Leu Ala Ile Phe Met
                85                  90                  95

GTT ATT ATA TTA TGT TTT TTA TCA ATA ATT TTG GGA GTT TTT ATA GCG   336
Val Ile Ile Leu Cys Phe Leu Ser Ile Ile Leu Gly Val Phe Ile Ala
            100                 105                 110

CCT CAT ATT TAT AAA GGC CTA TAG                                   360
Pro His Ile Tyr Lys Gly Leu
        115
```

(2) INFORMATION FOR SEQ ID NO: 62:

(i) SEQUENCE CHARACTERISTICS:
        (A) LENGTH: 119 amino acids
        (B) TYPE: amino acid
        (D) TOPOLOGY: linear (ii) MOLECULE TYPE: protein (xi) SEQUENCE DESCRIPTION: SEQ ID NO: 62:

```
Met Ala Leu Pro Asp Asn Val Phe Ser Ile Ile Asn Glu Asn Tyr Ile
1               5                   10                  15

Asp Gly Ile Leu Thr Met Lys Met Gly Glu Glu Ile Glu Ser Ser Ser
                20                  25                  30
```

-continued

```
Pro Leu Asn Glu Thr Asn Val Asn Ile Asp Gln His Thr Ile Asp Ile
         35                  40                  45

Phe Asp Tyr Asp Ser Asp Asn Gly Cys Tyr Tyr Ser Glu Arg Asp Asn
 50                  55                  60

Glu Thr Ala Thr Leu Phe Leu Lys Arg Val Gly Tyr Arg Glu Thr Ser
 65                  70                  75                  80

Lys Lys Arg Lys Arg Ile Cys Gly Phe Ile Val Leu Ala Ile Phe Met
                 85                  90                  95

Val Ile Ile Leu Cys Phe Leu Ser Ile Ile Leu Gly Val Phe Ile Ala
                100                 105                 110

Pro His Ile Tyr Lys Gly Leu
        115
```

(2) INFORMATION FOR SEQ ID NO: 63:

(i) SEQUENCE CHARACTERISTICS:
        (A) LENGTH: 2044 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 63:

```
AAATTTACTA GAACAGAACC TGGATCTGGT GTTATTTTTT CCAGTAAGCC TATATCCCTT      60

CAGTAATACC CCAAAAACAC CAAAATTTCC ATGGTATGGA GCCACTCATT TGTATAACAA     120

AAATGTTTTT TGTGAAGCTG TACGTCGATG TGCTTCTAAA CATGCTATAG AAGCCGCATC     180

ATCTATTTGG GATTTAAATC CACCACAGTC AAATGAAGAA TTGGAAAAGT TTCTAACTAA     240

AGCGGTTATT CGCATAACCA TATCTGAGGG ACTAGGTATT TTAAAAACTG CAAATACCCC     300

ATTTAGCTGT GGTCAAAAAA CTGCTGATGA TGTTAAATTT AAGTCTCACT CCTCACGTAG     360

GAGTAAGAGT CAGTCAAGAA GTAGACACAG TCGGGGTGAT TTCGACGACA GTAGTGATTA     420

AAGTTTGTTA CACCCACTAA TTTAAATAAA TAAAAAATTT ATATTTAAAG CTATTTGTCT     480

GTCTTTTTTT GTTATATATA TTCTTGCTTA GTGAGAGTAT AAACTATTTT GTTTTTAAAA     540

ATGGAATTTA ACATAGAAGA CTTTGATGAA TCGTTGCTAG GGGCTGTTGG ATACTCTAAT     600

AATTTTAAAG GTAAGCAAAG CCTTCCGATT AAGGCTTCTA GTCCATCATC GTTAATTAAA     660

AATCTTTTAG ATGAATTAAA TTTTCCGGAA GGTCCTAGTT TATTATCTTC TATGGAAAAA     720

TGGAATGAGG ATTTATTTTC CTGCATCCCA AGATTTTTGG AAATCTACAT TGAAAATTCT     780

ATTTTATCAA CATCTGTCGA TGAGGTTATT AAAAATTTGG ATAATTCTTT AAATTATGAT     840

GATGTAATCG ATTTTCAGGT CCATGGACCT GAAACATTTC CAAAAACCCC ATTATTGGAA     900

GAGGAATTGG AAAATTATGT AACATCTGTT CAAAAGTATT TTTTATCTGA ACTTAAAGCT     960

AGAGAAGTTA CATATTCATT TCTACTCACT AAATATTGTA AAGCGCTTTT GTTATATCTT    1020

CGCTATAATA CAAAATCATC GATTAAGGGT AATAAGGACA TAAATGCATT TCACCAAAAA    1080

TTTAAACAAA ATGTGCGGGA ACGTTATTAT AGAGAGGTTG CAAATATAGC ACGATTGTTA    1140

TATTTACATC TGTATTTATC AGTAACTAGG GAAGTGTCTT GGAAACTACA TGCCGATCAA    1200

GTATTACTCC AAAGTGTTTT TGTTTCATTG TCTTATTCTT GGAGCCACCG ACGACAGTTT    1260

GAGTGTATAT TTCATCCAAT TTTATTTAAT CATGGTATTG TGAATTTGGA AAATAACCCT    1320

TTGACATTTA AGGAACTACA AAAAATAAAT TATAGACGTC ATATTCTTGG TTTACCATTG    1380

ATTAGAGCTG GATTGGTAGA AGAAGATAAT CAACCTTTAA TGATACCTCC AGAGTTTTCC    1440
```

-continued

| | |
|---|---|
| AGTAAACTAC CTCGAACAAT AGGATTTTTA ACTCAACAAA TTAGAGCCAA AATGGAAGCT | 1500 |
| TATTCAGACA ACCATCCTGT AACACCAAAA TTTCCTCGTA TTGAACATTC ATATGCTAAA | 1560 |
| CCTATAGATC CTATTAACTA TGGAACTACA ATAGAAGCTA TGATGGACCC ACCATCACCA | 1620 |
| AGCGCTATTT TACCAGGAGA TCCAAATCCT GAAATTAATG TTAAGGTTAA AAGCACTGTT | 1680 |
| TCATCCTTTC AAATTCCACC TAATATTACC TTGGAAGAAC TGGAGTCAGG TGAATATAAT | 1740 |
| TTATTTACAG ATGGTGTTAC CTACAATGAT ATACCTGAAA ATGAGTTAAA TAAAATGTTT | 1800 |
| CAATTATAAT TTTTTTTTAA TTTTTTCCAT TTAAAACGTT AGTATATAAT ATGAGGTTAT | 1860 |
| ATTAATCAAT AACACCAATA TATTGGGGAA TTGCCACTAA GATACACGTG AGTGGTACTT | 1920 |
| TTGTAGTTAG TGGGTATAAA TAAGGTGGGG TAAGGTGGGG TTCAAATCAT TTTTTATTAC | 1980 |
| TCAGTGTTTG CTTAAGAAAT TATATATTTA ATATATTTAC TATGGAAAGA GACCATGGTT | 2040 |
| TTGC | 2044 |

(2) INFORMATION FOR SEQ ID NO: 64:

(i) SEQUENCE CHARACTERISTICS:
        (A) LENGTH: 2044 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 64:

| | |
|---|---|
| GCAAAACCAT GGTCTCTTTC CATAGTAAAT ATATTAAATA TATAATTTCT TAAGCAAACA | 60 |
| CTGAGTAATA AAAAATGATT TGAACCCCAC CTTACCCCAC CTTATTTATA CCCACTAACT | 120 |
| ACAAAAGTAC CACTCACGTG TATCTTAGTG GCAATTCCCC AATATATTGG TGTTATTGAT | 180 |
| TAATATAACC TCATATTATA TACTAACGTT TTAAATGGAA AAAATTAAAA AAAAATTATA | 240 |
| ATTGAAACAT TTTATTTAAC TCATTTTCAG GTATATCATT GTAGGTAACA CCATCTGTAA | 300 |
| ATAAATTATA TTCACCTGAC TCCAGTTCTT CCAAGGTAAT ATTAGGTGGA ATTTGAAAGG | 360 |
| ATGAAACAGT GCTTTTAACC TTAACATTAA TTTCAGGATT TGGATCTCCT GGTAAAATAG | 420 |
| CGCTTGGTGA TGGTGGGTCC ATCATAGCTT CTATTGTAGT TCCATAGTTA ATAGGATCTA | 480 |
| TAGGTTTAGC ATATGAATGT TCAATACGAG GAAATTTTGG TGTTACAGGA TGGTTGTCTG | 540 |
| AATAAGCTTC CATTTTGGCT CTAATTTGTT GAGTTAAAAA TCCTATTGTT CGAGGTAGTT | 600 |
| TACTGGAAAA CTCTGGAGGT ATCATTAAAG GTTGATTATC TTCTTCTACC AATCCAGCTC | 660 |
| TAATCAATGG TAAACCAAGA ATATGACGTC TATAATTTAT TTTTTGTAGT TCCTTAAATG | 720 |
| TCAAAGGGTT ATTTTCCAAA TTCACAATAC CATGATTAAA TAAAATTGGA TGAAATATAC | 780 |
| ACTCAAACTG TCGTCGGTGG CTCCAAGAAT AAGACAATGA AACAAAAACA CTTTGGAGTA | 840 |
| ATACTTGATC GGCATGTAGT TTCCAAGACA CTTCCCTAGT TACTGATAAA TACAGATGTA | 900 |
| AATATAACAA TCGTGCTATA TTTGCAACCT CTCTATAATA ACGTTCCCGC ACATTTTGTT | 960 |
| TAAATTTTTG GTGAAATGCA TTTATGTCCT TATTACCCTT AATCGATGAT TTTGTATTAT | 1020 |
| AGCGAAGATA TAACAAAAGC GCTTTACAAT ATTTAGTGAG TAGAAATGAA TATGTAACTT | 1080 |
| CTCTAGCTTT AAGTTCAGAT AAAAAATACT TTTGAACAGA TGTTACATAA TTTTCCAATT | 1140 |
| CCTCTTCCAA TAATGGGGTT TTTGGAAATG TTTCAGGTCC ATGGACCTGA AAATCGATTA | 1200 |
| CATCATCATA ATTTAAAGAA TTATCCAAAT TTTTAATAAC CTCATCGACA GATGTTGATA | 1260 |
| AAATAGAATT TTCAATGTAG ATTTCCAAAA ATCTTGGGAT GCAGGAAAAT AAATCCTCAT | 1320 |

-continued

```
TCCATTTTTC CATAGAAGAT AATAAACTAG GACCTTCCGG AAAATTTAAT TCATCTAAAA      1380

GATTTTTAAT TAACGATGAT GGACTAGAAG CCTTAATCGG AAGGCTTTGC TTACCTTTAA      1440

AATTATTAGA GTATCCAACA GCCCCTAGCA ACGATTCATC AAAGTCTTCT ATGTTAAATT      1500

CCATTTTTAA AAACAAAATA GTTTATACTC TCACTAAGCA AGAATATATA TAACAAAAAA      1560

AGACAGACAA ATAGCTTTAA ATATAAATTT TTTATTTATT TAAATTAGTG GGTGTAACAA      1620

ACTTTAATCA CTACTGTCGT CGAAATCACC CCGACTGTGT CTACTTCTTG ACTGACTCTT      1680

ACTCCTACGT GAGGAGTGAG ACTTAAATTT AACATCATCA GCAGTTTTTT GACCACAGCT      1740

AAATGGGGTA TTTGCAGTTT TTAAAATACC TAGTCCCTCA GATATGGTTA TGCGAATAAC      1800

CGCTTTAGTT AGAAACTTTT CCAATTCTTC ATTTGACTGT GGTGGATTTA AATCCCAAAT      1860

AGATGATGCG GCTTCTATAG CATGTTTAGA AGCACATCGA CGTACAGCTT CACAAAAAAC      1920

ATTTTTGTTA TACAAATGAG TGGCTCCATA CCATGGAAAT TTTGGTGTTT TTGGGGTATT      1980

ACTGAAGGGA TATAGGCTTA CTGGAAAAAA TAACACCAGA TCCAGGTTCT GTTCTAGTAA      2040

ATTT                                                                  2044
```

(2) INFORMATION FOR SEQ ID NO: 65:

(i) SEQUENCE CHARACTERISTICS:
        (A) LENGTH: 420 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..417

(xi) SEQUENCE DESCRIPTION: SEQ ID NO: 65:

```
AAT TTA CTA GAA CAG AAC CTG GAT CTG GTG TTA TTT TTT CCA GTA AGC        48
Asn Leu Leu Glu Gln Asn Leu Asp Leu Val Leu Phe Phe Pro Val Ser
 1               5                  10                  15

CTA TAT CCC TTC AGT AAT ACC CCA AAA ACA CCA AAA TTT CCA TGG TAT        96
Leu Tyr Pro Phe Ser Asn Thr Pro Lys Thr Pro Lys Phe Pro Trp Tyr
                20                  25                  30

GGA GCC ACT CAT TTG TAT AAC AAA AAT GTT TTT TGT GAA GCT GTA CGT       144
Gly Ala Thr His Leu Tyr Asn Lys Asn Val Phe Cys Glu Ala Val Arg
            35                  40                  45

CGA TGT GCT TCT AAA CAT GCT ATA GAA GCC GCA TCA TCT ATT TGG GAT       192
Arg Cys Ala Ser Lys His Ala Ile Glu Ala Ala Ser Ser Ile Trp Asp
        50                  55                  60

TTA AAT CCA CCA CAG TCA AAT GAA GAA TTG GAA AAG TTT CTA ACT AAA       240
Leu Asn Pro Pro Gln Ser Asn Glu Glu Leu Glu Lys Phe Leu Thr Lys
 65                  70                  75                  80

GCG GTT ATT CGC ATA ACC ATA TCT GAG GGA CTA GGT ATT TTA AAA ACT       288
Ala Val Ile Arg Ile Thr Ile Ser Glu Gly Leu Gly Ile Leu Lys Thr
                85                  90                  95

GCA AAT ACC CCA TTT AGC TGT GGT CAA AAA ACT GCT GAT GAT GTT AAA       336
Ala Asn Thr Pro Phe Ser Cys Gly Gln Lys Thr Ala Asp Asp Val Lys
            100                 105                 110

TTT AAG TCT CAC TCC TCA CGT AGG AGT AAG AGT CAG TCA AGA AGT AGA       384
Phe Lys Ser His Ser Ser Arg Arg Ser Lys Ser Gln Ser Arg Ser Arg
        115                 120                 125

CAC AGT CGG GGT GAT TTC GAC GAC AGT AGT GAT TAA                       420
His Ser Arg Gly Asp Phe Asp Asp Ser Ser Asp
        130                 135
```

(2) INFORMATION FOR SEQ ID NO: 66:

(i) SEQUENCE CHARACTERISTICS:
        (A) LENGTH: 139 amino acids
        (B) TYPE: amino acid
        (D) TOPOLOGY: linear (ii) MOLECULE TYPE: protein (xi) SEQUENCE DESCRIPTION: SEQ ID NO: 66:

```
Asn Leu Leu Glu Gln Asn Leu Asp Leu Val Leu Phe Phe Pro Val Ser
 1               5                  10                  15

Leu Tyr Pro Phe Ser Asn Thr Pro Lys Thr Pro Lys Phe Pro Trp Tyr
             20                  25                  30

Gly Ala Thr His Leu Tyr Asn Lys Asn Val Phe Cys Glu Ala Val Arg
         35                  40                  45

Arg Cys Ala Ser Lys His Ala Ile Glu Ala Ala Ser Ser Ile Trp Asp
     50                  55                  60

Leu Asn Pro Pro Gln Ser Asn Glu Glu Leu Glu Lys Phe Leu Thr Lys
 65                  70                  75                  80

Ala Val Ile Arg Ile Thr Ile Ser Glu Gly Leu Gly Ile Leu Lys Thr
                 85                  90                  95

Ala Asn Thr Pro Phe Ser Cys Gly Gln Lys Thr Ala Asp Asp Val Lys
             100                 105                 110

Phe Lys Ser His Ser Ser Arg Arg Ser Lys Ser Gln Ser Arg Ser Arg
         115                 120                 125

His Ser Arg Gly Asp Phe Asp Asp Ser Ser Asp
     130                 135
```

(2) INFORMATION FOR SEQ ID NO: 67:

(i) SEQUENCE CHARACTERISTICS:
        (A) LENGTH: 1269 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1266

(xi) SEQUENCE DESCRIPTION: SEQ ID NO: 67:

```
ATG GAA TTT AAC ATA GAA GAC TTT GAT GAA TCG TTG CTA GGG GCT GTT      48
Met Glu Phe Asn Ile Glu Asp Phe Asp Glu Ser Leu Leu Gly Ala Val
 1               5                  10                  15

GGA TAC TCT AAT AAT TTT AAA GGT AAG CAA AGC CTT CCG ATT AAG GCT      96
Gly Tyr Ser Asn Asn Phe Lys Gly Lys Gln Ser Leu Pro Ile Lys Ala
             20                  25                  30

TCT AGT CCA TCA TCG TTA ATT AAA AAT CTT TTA GAT GAA TTA AAT TTT     144
Ser Ser Pro Ser Ser Leu Ile Lys Asn Leu Leu Asp Glu Leu Asn Phe
         35                  40                  45

CCG GAA GGT CCT AGT TTA TTA TCT TCT ATG GAA AAA TGG AAT GAG GAT     192
Pro Glu Gly Pro Ser Leu Leu Ser Ser Met Glu Lys Trp Asn Glu Asp
     50                  55                  60

TTA TTT TCC TGC ATC CCA AGA TTT TTG GAA ATC TAC ATT GAA AAT TCT     240
Leu Phe Ser Cys Ile Pro Arg Phe Leu Glu Ile Tyr Ile Glu Asn Ser
 65                  70                  75                  80

ATT TTA TCA ACA TCT GTC GAT GAG GTT ATT AAA AAT TTG GAT AAT TCT     288
Ile Leu Ser Thr Ser Val Asp Glu Val Ile Lys Asn Leu Asp Asn Ser
                 85                  90                  95
```

```
TTA AAT TAT GAT GAT GTA ATC GAT TTT CAG GTC CAT GGA CCT GAA ACA        336
Leu Asn Tyr Asp Asp Val Ile Asp Phe Gln Val His Gly Pro Glu Thr
        100                 105                 110

TTT CCA AAA ACC CCA TTA TTG GAA GAG GAA TTG GAA AAT TAT GTA ACA        384
Phe Pro Lys Thr Pro Leu Leu Glu Glu Glu Leu Glu Asn Tyr Val Thr
        115                 120                 125

TCT GTT CAA AAG TAT TTT TTA TCT GAA CTT AAA GCT AGA GAA GTT ACA        432
Ser Val Gln Lys Tyr Phe Leu Ser Glu Leu Lys Ala Arg Glu Val Thr
        130                 135                 140

TAT TCA TTT CTA CTC ACT AAA TAT TGT AAA GCG CTT TTG TTA TAT CTT        480
Tyr Ser Phe Leu Leu Thr Lys Tyr Cys Lys Ala Leu Leu Leu Tyr Leu
145                 150                 155                 160

CGC TAT AAT ACA AAA TCA TCG ATT AAG GGT AAT AAG GAC ATA AAT GCA        528
Arg Tyr Asn Thr Lys Ser Ser Ile Lys Gly Asn Lys Asp Ile Asn Ala
            165                 170                 175

TTT CAC CAA AAA TTT AAA CAA AAT GTG CGG GAA CGT TAT TAT AGA GAG        576
Phe His Gln Lys Phe Lys Gln Asn Val Arg Glu Arg Tyr Tyr Arg Glu
        180                 185                 190

GTT GCA AAT ATA GCA CGA TTG TTA TAT TTA CAT CTG TAT TTA TCA GTA        624
Val Ala Asn Ile Ala Arg Leu Leu Tyr Leu His Leu Tyr Leu Ser Val
        195                 200                 205

ACT AGG GAA GTG TCT TGG AAA CTA CAT GCC GAT CAA GTA TTA CTC CAA        672
Thr Arg Glu Val Ser Trp Lys Leu His Ala Asp Gln Val Leu Leu Gln
210                 215                 220

AGT GTT TTT GTT TCA TTG TCT TAT TCT TGG AGC CAC CGA CGA CAG TTT        720
Ser Val Phe Val Ser Leu Ser Tyr Ser Trp Ser His Arg Arg Gln Phe
225                 230                 235                 240

GAG TGT ATA TTT CAT CCA ATT TTA TTT AAT CAT GGT ATT GTG AAT TTG        768
Glu Cys Ile Phe His Pro Ile Leu Phe Asn His Gly Ile Val Asn Leu
            245                 250                 255

GAA AAT AAC CCT TTG ACA TTT AAG GAA CTA CAA AAA ATA AAT TAT AGA        816
Glu Asn Asn Pro Leu Thr Phe Lys Glu Leu Gln Lys Ile Asn Tyr Arg
        260                 265                 270

CGT CAT ATT CTT GGT TTA CCA TTG ATT AGA GCT GGA TTG GTA GAA GAA        864
Arg His Ile Leu Gly Leu Pro Leu Ile Arg Ala Gly Leu Val Glu Glu
        275                 280                 285

GAT AAT CAA CCT TTA ATG ATA CCT CCA GAG TTT TCC AGT AAA CTA CCT        912
Asp Asn Gln Pro Leu Met Ile Pro Pro Glu Phe Ser Ser Lys Leu Pro
        290                 295                 300

CGA ACA ATA GGA TTT TTA ACT CAA CAA ATT AGA GCC AAA ATG GAA GCT        960
Arg Thr Ile Gly Phe Leu Thr Gln Gln Ile Arg Ala Lys Met Glu Ala
305                 310                 315                 320

TAT TCA GAC AAC CAT CCT GTA ACA CCA AAA TTT CCT CGT ATT GAA CAT       1008
Tyr Ser Asp Asn His Pro Val Thr Pro Lys Phe Pro Arg Ile Glu His
            325                 330                 335

TCA TAT GCT AAA CCT ATA GAT CCT ATT AAC TAT GGA ACT ACA ATA GAA       1056
Ser Tyr Ala Lys Pro Ile Asp Pro Ile Asn Tyr Gly Thr Thr Ile Glu
        340                 345                 350

GCT ATG ATG GAC CCA CCA TCA CCA AGC GCT ATT TTA CCA GGA GAT CCA       1104
Ala Met Met Asp Pro Pro Ser Pro Ser Ala Ile Leu Pro Gly Asp Pro
        355                 360                 365

AAT CCT GAA ATT AAT GTT AAG GTT AAA AGC ACT GTT TCA TCC TTT CAA       1152
Asn Pro Glu Ile Asn Val Lys Val Lys Ser Thr Val Ser Ser Phe Gln
        370                 375                 380

ATT CCA CCT AAT ATT ACC TTG GAA GAA CTG GAG TCA GGT GAA TAT AAT       1200
Ile Pro Pro Asn Ile Thr Leu Glu Glu Leu Glu Ser Gly Glu Tyr Asn
385                 390                 395                 400

TTA TTT ACA GAT GGT GTT ACC TAC AAT GAT ATA CCT GAA AAT GAG TTA       1248
Leu Phe Thr Asp Gly Val Thr Tyr Asn Asp Ile Pro Glu Asn Glu Leu
```

```
                   405                 410                 415
AAT AAA ATG TTT CAA TTA TAA                                                    1269
Asn Lys Met Phe Gln Leu
            420
```

(2) INFORMATION FOR SEQ ID NO: 68:

(i) SEQUENCE CHARACTERISTICS:
        (A) LENGTH: 422 amino acids
        (B) TYPE: amino acid
        (D) TOPOLOGY: linear (ii) MOLECULE TYPE: protein (xi) SEQUENCE DESCRIPTION: SEQ ID NO: 68:

```
Met Glu Phe Asn Ile Glu Asp Phe Asp Glu Ser Leu Leu Gly Ala Val
 1               5                  10                  15

Gly Tyr Ser Asn Asn Phe Lys Gly Lys Gln Ser Leu Pro Ile Lys Ala
            20                  25                  30

Ser Ser Pro Ser Ser Leu Ile Lys Asn Leu Leu Asp Glu Leu Asn Phe
        35                  40                  45

Pro Glu Gly Pro Ser Leu Ser Ser Met Glu Lys Trp Asn Glu Asp
 50                  55                  60

Leu Phe Ser Cys Ile Pro Arg Phe Leu Glu Ile Tyr Ile Glu Asn Ser
 65                  70                  75                  80

Ile Leu Ser Thr Ser Val Asp Glu Val Ile Lys Asn Leu Asp Asn Ser
                85                  90                  95

Leu Asn Tyr Asp Asp Val Ile Asp Phe Gln Val His Gly Pro Glu Thr
            100                 105                 110

Phe Pro Lys Thr Pro Leu Leu Glu Glu Glu Leu Glu Asn Tyr Val Thr
        115                 120                 125

Ser Val Gln Lys Tyr Phe Leu Ser Glu Leu Lys Ala Arg Glu Val Thr
    130                 135                 140

Tyr Ser Phe Leu Leu Thr Lys Tyr Cys Lys Ala Leu Leu Leu Tyr Leu
145                 150                 155                 160

Arg Tyr Asn Thr Lys Ser Ser Ile Lys Gly Asn Lys Asp Ile Asn Ala
                165                 170                 175

Phe His Gln Lys Phe Lys Gln Asn Val Arg Glu Arg Tyr Tyr Arg Glu
            180                 185                 190

Val Ala Asn Ile Ala Arg Leu Leu Tyr Leu His Leu Tyr Leu Ser Val
        195                 200                 205

Thr Arg Glu Val Ser Trp Lys Leu His Ala Asp Gln Val Leu Leu Gln
    210                 215                 220

Ser Val Phe Val Ser Leu Ser Tyr Ser Trp Ser His Arg Arg Gln Phe
225                 230                 235                 240

Glu Cys Ile Phe His Pro Ile Leu Phe Asn His Gly Ile Val Asn Leu
                245                 250                 255

Glu Asn Asn Pro Leu Thr Phe Lys Glu Leu Gln Lys Ile Asn Tyr Arg
            260                 265                 270

Arg His Ile Leu Gly Leu Pro Leu Ile Arg Ala Gly Leu Val Glu Glu
        275                 280                 285

Asp Asn Gln Pro Leu Met Ile Pro Pro Glu Phe Ser Ser Lys Leu Pro
    290                 295                 300

Arg Thr Ile Gly Phe Leu Thr Gln Gln Ile Arg Ala Lys Met Glu Ala
305                 310                 315                 320

Tyr Ser Asp Asn His Pro Val Thr Pro Lys Phe Pro Arg Ile Glu His
```

```
                  325                 330                 335
Ser Tyr Ala Lys Pro Ile Asp Pro Ile Asn Tyr Gly Thr Thr Ile Glu
            340                 345                 350

Ala Met Met Asp Pro Pro Ser Pro Ser Ala Ile Leu Pro Gly Asp Pro
            355                 360                 365

Asn Pro Glu Ile Asn Val Lys Val Lys Ser Thr Val Ser Ser Phe Gln
            370                 375                 380

Ile Pro Pro Asn Ile Thr Leu Glu Glu Leu Glu Ser Gly Glu Tyr Asn
385                 390                 395                 400

Leu Phe Thr Asp Gly Val Thr Tyr Asn Asp Ile Pro Glu Asn Glu Leu
                405                 410                 415

Asn Lys Met Phe Gln Leu
            420

(2) INFORMATION FOR SEQ ID NO: 69:

(i) SEQUENCE CHARACTERISTICS:
        (A) LENGTH: 626 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 69:

AAGCTTATTG TCCGTGCTTT GCTGATGGTT TCTGGAACTG TCTCCCCTAT TTTAAGATAC        60

AATATAGAAG GAGTAAAATG TAAACTAAGT TCATGGAACC TTACAACCGC TGCCTTTTCT       120

ACCCCATCTA CTGTTAATGA AAAAATTAAT GATGTGGTTG AAACAACTTC AAACCCTTTG       180

AGTAAACTAA AAAAGAATTG TAATAGAGAA AAGGAACTTT CAAAATCAAA AAGTATAGTT       240

TCAGGAGGTG TTAGTGTTCA TGGATTAGAA CAAAGCTGTA GCTCTCATAC CTCCAATTTT       300

CAGAAATGCC CAGATAAAAC CAAGTCATCA AATAAAAATG ATGCAAACAA ACGTGAGTCA       360

AGGGGAAAAA GAAAGTCTGA ACCAATAGTA AATAGTTTTG GAGTCGCAAA AGTTTCATCC       420

AACCCACCGC CATCAAAAAA GAGAGCATCA TCACAATCTA CCGGACCACT TGGACCAATG       480

CCAGAAGAAG GACCGACCCC CAAGGGTGGT TTTAGAAGAA TACCTTCTGG GGATTGTCAT       540

ACCCCAGTTC CAAGGGACAT TGTAAAATCT ATCTACTGTT CACCAGAGAC TGTGAAAGAA       600

TTAACAGATC ATCCATTGTT TCCTGA                                             626

(2) INFORMATION FOR SEQ ID NO: 70:

(i) SEQUENCE CHARACTERISTICS:
        (A) LENGTH: 626 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 70:

TCAGGAAACA ATGGATGATC TGTTAATTCT TTCACAGTCT CTGGTGAACA GTAGATAGAT        60

TTTACAATGT CCCTTGGAAC TGGGGTATGA CAATCCCCAG AAGGTATTCT TCTAAAACCA       120

CCCTTGGGGG TCGGTCCTTC TTCTGGCATT GGTCCAAGTG GTCCGGTAGA TTGTGATGAT       180

GCTCTCTTTT TTGATGGCGG TGGGTTGGAT GAAACTTTTG CGACTCCAAA ACTATTTACT       240

ATTGGTTCAG ACTTTCTTTT TCCCCTTGAC TCACGTTTGT TTGCATCATT TTTATTTGAT       300

GACTTGGTTT TATCTGGGCA TTTCTGAAAA TTGGAGGTAT GAGAGCTACA GCTTTGTTCT       360
```

```
AATCCATGAA CACTAACACC TCCTGAAACT ATACTTTTTG ATTTTGAAAG TTCCTTTTCT      420

CTATTACAAT TCTTTTTTAG TTTACTCAAA GGGTTTGAAG TTGTTTCAAC CACATCATTA      480

ATTTTTTCAT TAACAGTAGA TGGGGTAGAA AAGGCAGCGG TTGTAAGGTT CCATGAACTT      540

AGTTTACATT TTACTCCTTC TATATTGTAT CTTAAAATAG GGGAGACAGT TCCAGAAACC      600

ATCAGCAAAG CACGGACAAT AAGCTT                                          626

(2) INFORMATION FOR SEQ ID NO: 71:

(i) SEQUENCE CHARACTERISTICS:
        (A) LENGTH: 624 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..624

(xi) SEQUENCE DESCRIPTION: SEQ ID NO: 71:

AAG CTT ATT GTC CGT GCT TTG CTG ATG GTT TCT GGA ACT GTC TCC CCT        48
Lys Leu Ile Val Arg Ala Leu Leu Met Val Ser Gly Thr Val Ser Pro
  1               5                  10                  15

ATT TTA AGA TAC AAT ATA GAA GGA GTA AAA TGT AAA CTA AGT TCA TGG        96
Ile Leu Arg Tyr Asn Ile Glu Gly Val Lys Cys Lys Leu Ser Ser Trp
             20                  25                  30

AAC CTT ACA ACC GCT GCC TTT TCT ACC CCA TCT ACT GTT AAT GAA AAA       144
Asn Leu Thr Thr Ala Ala Phe Ser Thr Pro Ser Thr Val Asn Glu Lys
         35                  40                  45

ATT AAT GAT GTG GTT GAA ACA ACT TCA AAC CCT TTG AGT AAA CTA AAA       192
Ile Asn Asp Val Val Glu Thr Thr Ser Asn Pro Leu Ser Lys Leu Lys
     50                  55                  60

AAG AAT TGT AAT AGA GAA AAG GAA CTT TCA AAA TCA AAA AGT ATA GTT       240
Lys Asn Cys Asn Arg Glu Lys Glu Leu Ser Lys Ser Lys Ser Ile Val
 65                  70                  75                  80

TCA GGA GGT GTT AGT GTT CAT GGA TTA GAA CAA AGC TGT AGC TCT CAT       288
Ser Gly Gly Val Ser Val His Gly Leu Glu Gln Ser Cys Ser Ser His
                 85                  90                  95

ACC TCC AAT TTT CAG AAA TGC CCA GAT AAA ACC AAG TCA TCA AAT AAA       336
Thr Ser Asn Phe Gln Lys Cys Pro Asp Lys Thr Lys Ser Ser Asn Lys
            100                 105                 110

AAT GAT GCA AAC AAA CGT GAG TCA AGG GGA AAA AGA AAG TCT GAA CCA       384
Asn Asp Ala Asn Lys Arg Glu Ser Arg Gly Lys Arg Lys Ser Glu Pro
        115                 120                 125

ATA GTA AAT AGT TTT GGA GTC GCA AAA GTT TCA TCC AAC CCA CCG CCA       432
Ile Val Asn Ser Phe Gly Val Ala Lys Val Ser Ser Asn Pro Pro Pro
    130                 135                 140

TCA AAA AAG AGA GCA TCA TCA CAA TCT ACC GGA CCA CTT GGA CCA ATG       480
Ser Lys Lys Arg Ala Ser Ser Gln Ser Thr Gly Pro Leu Gly Pro Met
145                 150                 155                 160

CCA GAA GAA GGA CCG ACC CCC AAG GGT GGT TTT AGA AGA ATA CCT TCT       528
Pro Glu Glu Gly Pro Thr Pro Lys Gly Gly Phe Arg Arg Ile Pro Ser
                165                 170                 175

GGG GAT TGT CAT ACC CCA GTT CCA AGG GAC ATT GTA AAA TCT ATC TAC       576
Gly Asp Cys His Thr Pro Val Pro Arg Asp Ile Val Lys Ser Ile Tyr
            180                 185                 190

TGT TCA CCA GAG ACT GTG AAA GAA TTA ACA GAT CAT CCA TTG TTT CCT       624
Cys Ser Pro Glu Thr Val Lys Glu Leu Thr Asp His Pro Leu Phe Pro
        195                 200                 205
```

(2) INFORMATION FOR SEQ ID NO: 72:

(i) SEQUENCE CHARACTERISTICS:
        (A) LENGTH: 208 amino acids
        (B) TYPE: amino acid
        (D) TOPOLOGY: linear (ii) MOLECULE TYPE: protein (xi) SEQUENCE DESCRIPTION: SEQ ID NO: 72:

```
Lys Leu Ile Val Arg Ala Leu Leu Met Val Ser Gly Thr Val Ser Pro
 1               5                  10                  15

Ile Leu Arg Tyr Asn Ile Glu Gly Val Lys Cys Lys Leu Ser Ser Trp
            20                  25                  30

Asn Leu Thr Thr Ala Ala Phe Ser Thr Pro Ser Thr Val Asn Glu Lys
        35                  40                  45

Ile Asn Asp Val Val Glu Thr Thr Ser Asn Pro Leu Ser Lys Leu Lys
    50                  55                  60

Lys Asn Cys Asn Arg Glu Lys Glu Leu Ser Lys Ser Lys Ser Ile Val
65                  70                  75                  80

Ser Gly Gly Val Ser Val His Gly Leu Glu Gln Ser Cys Ser Ser His
                85                  90                  95

Thr Ser Asn Phe Gln Lys Cys Pro Asp Lys Thr Lys Ser Ser Asn Lys
            100                 105                 110

Asn Asp Ala Asn Lys Arg Glu Ser Arg Gly Lys Arg Lys Ser Glu Pro
        115                 120                 125

Ile Val Asn Ser Phe Gly Val Ala Lys Val Ser Ser Asn Pro Pro Pro
    130                 135                 140

Ser Lys Lys Arg Ala Ser Ser Gln Ser Thr Gly Pro Leu Gly Pro Met
145                 150                 155                 160

Pro Glu Glu Gly Pro Thr Pro Lys Gly Gly Phe Arg Arg Ile Pro Ser
                165                 170                 175

Gly Asp Cys His Thr Pro Val Pro Arg Asp Ile Val Lys Ser Ile Tyr
            180                 185                 190

Cys Ser Pro Glu Thr Val Lys Glu Leu Thr Asp His Pro Leu Phe Pro
        195                 200                 205
```

(2) INFORMATION FOR SEQ ID NO: 73:

(i) SEQUENCE CHARACTERISTICS:
        (A) LENGTH: 655 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 73:

```
AAGCTTGACT TGTTGATTAA AGTTAAAGAA TTGTTTAACA AATTAACATT CTTAGGTCTT      60

CCTCTAGGTC GTTTAATAAC AGGCTCATTT TTGTTGTCTG TAGAGTCATA CCTGTTTTCG     120

AGTTTGTGTT TAGAAGTCAT CATAAACAAG AAGTAGTTTC AGTCAAACCG GTTTTTTGAG     180

ATATACAACC AAGTGGTGGT GGAGGTAATA TAGGAGCTTC TGGTGAAAGC TGTGATGGAT     240

AAAATAATCT GTCTATTATA TCAAAAAATT TGGTTTTTAA ACCTTTGGGT GTATTTATTT     300

TCATAATATC ATCAGCCAAT CCCCGGAGAG CTATAAATGG ATTAACCCAA AATACATCAT     360

TCGTTGATTT GAACCATAAA ATGATTTCTA TTGGGTTACA ATCCGTTCTT ATTATAATTC     420
```

```
CAGAAAGGTT TTTTATATCT TTATTTATTT TTTTATATAT ATTTTTTTCT ATTTGATGAT      480

TACGGCATGG TCCTTGAAGT AGTATATTAA TGTTGTTATA TTGATTTTTA CTCGACGGAA      540

GCATGGTTAA AATATCTTTT ATATACGAAG AAACAATTAG AATTATTAAT GAATTTATTA      600

AACCCCATCT TCTAAAATTG TGGAGAATAT GAAAAATATT CCGTTTTATA TACAA          655

(2) INFORMATION FOR SEQ ID NO: 74:

(i) SEQUENCE CHARACTERISTICS:
        (A) LENGTH: 655 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 74:

TTGTATATAA AACGGAATAT TTTTCATATT CTCCACAATT TTAGAAGATG GGGTTTAATA       60

AATTCATTAA TAATTCTAAT TGTTTCTTCG TATATAAAAG ATATTTTAAC CATGCTTCCG      120

TCGAGTAAAA ATCAATATAA CAACATTAAT ATACTACTTC AAGGACCATG CCGTAATCAT      180

CAAATAGAAA AAAATATATA TAAAAAAATA AATAAGATA TAAAAAACCCT TTCTGGAATT      240

ATAATAAGAA CGGATTGTAA CCCAATAGAA ATCATTTTAT GGTTCAAATC AACGAATGAT      300

GTATTTTGGG TTAATCCATT TATAGCTCTC CGGGGATTGG CTGATGATAT TATGAAAATA      360

AATACACCCA AAGGTTTAAA AACCAAATTT TTTGATATAA TAGACAGATT ATTTTATCCA      420

TCACAGCTTT CACCAGAAGC TCCTATATTA CCTCCACCAC CACTTGGTTG TATATCTCAA      480

AAAACCGGTT TGACTGAAAC TACTTCTTGT TTATGATGAC TTCTAAACAC AAACTCGAAA      540

ACAGGTATGA CTCTACAGAC AACAAAAATG AGCCTGTTAT TAAACGACCT AGAGGAAGAC      600

CTAAGAATGT TAATTTGTTA ACAATTCTT TAACTTTAAT CAACAAGTCA AGCTT          655

(2) INFORMATION FOR SEQ ID NO: 75:

(i) SEQUENCE CHARACTERISTICS:
        (A) LENGTH: 516 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..513

(xi) SEQUENCE DESCRIPTION: SEQ ID NO: 75:

TTG TAT ATA AAA CGG AAT ATT TTT CAT ATT CTC CAC AAT TTT AGA AGA         48
Leu Tyr Ile Lys Arg Asn Ile Phe His Ile Leu His Asn Phe Arg Arg
 1               5                   10                  15

TGG GGT TTA ATA AAT TCA TTA ATA ATT CTA ATT GTT TCT TCG TAT ATA         96
Trp Gly Leu Ile Asn Ser Leu Ile Ile Leu Ile Val Ser Ser Tyr Ile
            20                  25                  30

AAA GAT ATT TTA ACC ATG CTT CCG TCG AGT AAA AAT CAA TAT AAC AAC        144
Lys Asp Ile Leu Thr Met Leu Pro Ser Ser Lys Asn Gln Tyr Asn Asn
        35                  40                  45

ATT AAT ATA CTA CTT CAA GGA CCA TGC CGT AAT CAT CAA ATA GAA AAA        192
Ile Asn Ile Leu Leu Gln Gly Pro Cys Arg Asn His Gln Ile Glu Lys
    50                  55                  60

AAT ATA TAT AAA AAA ATA AAT AAA GAT ATA AAA AAC CTT TCT GGA ATT        240
Asn Ile Tyr Lys Lys Ile Asn Lys Asp Ile Lys Asn Leu Ser Gly Ile
65                  70                  75                  80
```

-continued

```
ATA ATA AGA ACG GAT TGT AAC CCA ATA GAA ATC ATT TTA TGG TTC AAA     288
Ile Ile Arg Thr Asp Cys Asn Pro Ile Glu Ile Ile Leu Trp Phe Lys
             85                  90                  95

TCA ACG AAT GAT GTA TTT TGG GTT AAT CCA TTT ATA GCT CTC CGG GGA     336
Ser Thr Asn Asp Val Phe Trp Val Asn Pro Phe Ile Ala Leu Arg Gly
        100                 105                 110

TTG GCT GAT GAT ATT ATG AAA ATA AAT ACA CCC AAA GGT TTA AAA ACC     384
Leu Ala Asp Asp Ile Met Lys Ile Asn Thr Pro Lys Gly Leu Lys Thr
            115                 120                 125

AAA TTT TTT GAT ATA ATA GAC AGA TTA TTT TAT CCA TCA CAG CTT TCA     432
Lys Phe Phe Asp Ile Ile Asp Arg Leu Phe Tyr Pro Ser Gln Leu Ser
    130                 135                 140

CCA GAA GCT CCT ATA TTA CCT CCA CCA CCA CTT GGT TGT ATA TCT CAA     480
Pro Glu Ala Pro Ile Leu Pro Pro Pro Pro Leu Gly Cys Ile Ser Gln
145                 150                 155                 160

AAA ACC GGT TTG ACT GAA ACT ACT TCT TGT TTA TGA                     516
Lys Thr Gly Leu Thr Glu Thr Thr Ser Cys Leu
                165                 170
```

(2) INFORMATION FOR SEQ ID NO: 76:

(i) SEQUENCE CHARACTERISTICS:
        (A) LENGTH: 171 amino acids
        (B) TYPE: amino acid
        (D) TOPOLOGY: linear (ii) MOLECULE TYPE: protein (xi) SEQUENCE DESCRIPTION: SEQ ID NO: 76:

```
Leu Tyr Ile Lys Arg Asn Ile Phe His Ile Leu His Asn Phe Arg Arg
  1               5                  10                  15

Trp Gly Leu Ile Asn Ser Leu Ile Ile Leu Ile Val Ser Ser Tyr Ile
             20                  25                  30

Lys Asp Ile Leu Thr Met Leu Pro Ser Ser Lys Asn Gln Tyr Asn Asn
         35                  40                  45

Ile Asn Ile Leu Leu Gln Gly Pro Cys Arg Asn His Gln Ile Glu Lys
     50                  55                  60

Asn Ile Tyr Lys Lys Ile Asn Lys Asp Ile Lys Asn Leu Ser Gly Ile
 65                  70                  75                  80

Ile Ile Arg Thr Asp Cys Asn Pro Ile Glu Ile Ile Leu Trp Phe Lys
             85                  90                  95

Ser Thr Asn Asp Val Phe Trp Val Asn Pro Phe Ile Ala Leu Arg Gly
        100                 105                 110

Leu Ala Asp Asp Ile Met Lys Ile Asn Thr Pro Lys Gly Leu Lys Thr
            115                 120                 125

Lys Phe Phe Asp Ile Ile Asp Arg Leu Phe Tyr Pro Ser Gln Leu Ser
    130                 135                 140

Pro Glu Ala Pro Ile Leu Pro Pro Pro Pro Leu Gly Cys Ile Ser Gln
145                 150                 155                 160

Lys Thr Gly Leu Thr Glu Thr Thr Ser Cys Leu
                165                 170
```

(2) INFORMATION FOR SEQ ID NO: 77:

(i) SEQUENCE CHARACTERISTICS:
        (A) LENGTH: 1823 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 77:

```
GCTTTGGACG AGATTTAGGC TGGGAAATTG TTAGTTGAGC ATATTGATTT TCGCATAGTT        60
CATAAATATG GTCTTCGTCA TCATCATCAC AAACTTGATC ATACACATTT TTATACTCAA       120
AAGTTGGAAT AGTTCGTTCG TAAATAGGAT TTTCCCTTTC AATTCGTTGA GATGACTTTC       180
TTCTTACACC GTTTTGTCTC TTAATAGTAG CATATATCGG TTCATCTTCA TATGATGAAA       240
TACGACGGCT GGCCATAATT CTATAAATAA GAGAAGGTTA AAAATAAGTT GCTTAACTGG       300
TTTAGGCAAC TAATAAAATA TCTCTAAAAC ATACCCCCTT TTATATAAAT CTGTGGATTA       360
GTTTCGGATT TCGAAACCCA CCTTCTTATT AGTGTTGCAT CTGACGAAGT TCCCGACTAA       420
CCATTCTCAA ACAGGTTCTA TAAGAATAAC AAAATATCGC AACCCCTACT GTTACCAGGG       480
ATATATAAAA CAAATAGCG GAAGTTGAAG GCGTATTAAT ATTGATACCC CTAGCTGAAC       540
AACTAGAGCT CCAAAACTGT CTCCTAGCTT CAGCTCTAGA ATAATCTAAA CGATCATCGT       600
CGAAGGCATA AACTGAAAAA ATAATGGATA GTAAAAATAC TATCTCCATT GCTTTGATTG       660
AAAAACAAAA ACCTTTTAAT TGGACTATCA ACAAAATAAA TGAAAGCCTT CTGATGACCA       720
ACAACGAAGA AATAAACTTG ACTGAAAATT TTAAAAATAC GGGCACCTTT TATAGCAAGA       780
TAATTGACCT TGAAATCCGA ACTGCTACAT CTAGTCAATA TGCAGTCTTT GTTACACAAA       840
TGTGTTCTGA TGACGAAAAT ATGAATAATA CAAATATTTT TGTTATTAAT GGTGTTATTG       900
ATTCTGGATA TAGAGGAATA GTTAAAGCGT TAGTTTATTA CCATCCAACT GTAGAAAAAT       960
TAAATCCATA CGATCTTAAA ATTAAACTTC CACTAATAGA ACTTAGTAAA GATTTAATAC      1020
CACTATCACC TAGTTTACAT AGTTATAGTG AATTATATAA TTTTTTTAAT GTCTTTAATA      1080
AAAAACGTGA TGAAGATGCT GGTTATGATA TACCATCTCC AAATTTAGTT CAAATAAAAC      1140
CGGGATATAG TTACCTTTTT TGTCTTCCTA TTTTTCAATT AGAAATGAAA AACCCACCAA      1200
TCGCTTGTAT TTTTGGTAGA TCATCCTTAA ATTCAAGCGG AATAATTGTT CTTCCAACTA      1260
TATGGAAACC AAAAACAATT TGTCAATTTT TTATTAAAAA TATATCCTCT AAAACTGTAA      1320
CTATAGAAAA AGGTCAGAGA ATAGCTCAGT TAGTTCTTTT AAAAAACAAT CAACCACTAT      1380
GGTTACAACC ACAAATTAAT TGTCATTCTT TATTTCCAAA GTCAAACTAT TTAAGCTTAT      1440
CAAATCGAGA ATGTGATATG TGGAAGTTTA CAGAAGATCT GAATTTTGAA GCACCGAAAA      1500
GTTTACGAGG AATAAATGGA TTTGGATCCA CGGGATTGTA AAATTCGTTA ATAAAGTTAT      1560
ATTTAAAGTG CCAAACTTTC ACGTGTCATT TTTTTGGGAC CGTTTCTTTT TTGTTTAGTC      1620
GATAAAATAT TTTCAGTTTC CATAGAACTT ATTAGAGGTT CTGTATCTAG TATATCTGTA      1680
GAATTATTTT CATCATATTT AACGGTTTGA AGAGATAAGG GTTTTGTTGT ATTAGAATCT      1740
ATACCAAGGG TTTTTTCTAA AACCGCTACA TCTGCCATAA CAATATTATT TTCTGAAGTC      1800
ATTTTTATGG CTTGGGCACC ACC                                             1823
```

(2) INFORMATION FOR SEQ ID NO: 78:

(i) SEQUENCE CHARACTERISTICS:
        (A) LENGTH: 1823 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 78:

```
GGTGGTGCCC AAGCCATAAA AATGACTTCA GAAAATAATA TTGTTATGGC AGATGTAGCG    60

GTTTTAGAAA AAACCCTTGG TATAGATTCT AATACAACAA AACCCTTATC TCTTCAAACC   120

GTTAAATATG ATGAAAATAA TTCTACAGAT ATACTAGATA CAGAACCTCT AATAAGTTCT   180

ATGGAAACTG AAAATATTTT ATCGACTAAA CAAAAAAGAA ACGGTCCCAA AAAAATGACA   240

CGTGAAAGTT TGGCACTTTA AATATAACTT TATTAACGAA TTTTACAATC CCGTGGATCC   300

AAATCCATTT ATTCCTCGTA AACTTTTCGG TGCTTCAAAA TTCAGATCTT CTGTAAACTT   360

CCACATATCA CATTCTCGAT TTGATAAGCT TAAATAGTTT GACTTTGGAA ATAAAGAATG   420

ACAATTAATT TGTGGTTGTA ACCATAGTGG TTGATTGTTT TTTAAAAGAA CTAACTGAGC   480

TATTCTCTGA CCTTTTTCTA TAGTTACAGT TTTAGAGGAT ATATTTTTAA TAAAAAATTG   540

ACAAATTGTT TTTGGTTTCC ATATAGTTGG AAGAACAATT ATTCCGCTTG AATTTAAGGA   600

TGATCTACCA AAAATACAAG CGATTGGTGG GTTTTTCATT TCTAATTGAA AAATAGGAAG   660

ACAAAAAAGG TAACTATATC CCGGTTTTAT TTGAACTAAA TTTGGAGATG GTATATCATA   720

ACCAGCATCT TCATCACGTT TTTTATTAAA GACATTAAAA AAATTATATA ATTCACTATA   780

ACTATGTAAA CTAGGTGATA GTGGTATTAA ATCTTTACTA AGTTCTATTA GTGGAAGTTT   840

AATTTTAAGA TCGTATGGAT TTAATTTTTC TACAGTTGGA TGGTAATAAA CTAACGCTTT   900

AACTATTCCT CTATATCCAG AATCAATAAC ACCATTAATA ACAAAAATAT TTGTATTATT   960

CATATTTTCG TCATCAGAAC ACATTTGTGT AACAAAGACT GCATATTGAC TAGATGTAGC  1020

AGTTCGGATT TCAAGGTCAA TTATCTTGCT ATAAAAGGTG CCCGTATTTT TAAAATTTTC  1080

AGTCAAGTTT ATTTCTTCGT TGTTGGTCAT CAGAAGGCTT TCATTTATTT TGTTGATAGT  1140

CCAATTAAAA GGTTTTTGTT TTTCAATCAA AGCAATGGAG ATAGTATTTT TACTATCCAT  1200

TATTTTTTCA GTTTATGCCT TCGACGATGA TCGTTTAGAT TATTCTAGAG CTGAAGCTAG  1260

GAGACAGTTT TGGAGCTCTA GTTGTTCAGC TAGGGGTATC AATATTAATA CGCCTTCAAC  1320

TTCCGCTATT TTGTTTTATA TATCCCTGGT AACAGTAGGG GTTGCGATAT TTTGTTATTC  1380

TTATAGAACC TGTTTGAGAA TGGTTAGTCG GGAACTTCGT CAGATGCAAC ACTAATAAGA  1440

AGGTGGGTTT CGAAATCCGA AACTAATCCA CAGATTTATA TAAAAGGGGG TATGTTTTAG  1500

AGATATTTTA TTAGTTGCCT AAACCAGTTA AGCAACTTAT TTTTAACCTT CTCTTATTTA  1560

TAGAATTATG GCCAGCCGTC GTATTTCATC ATATGAAGAT GAACCGATAT ATGCTACTAT  1620

TAAGAGACAA AACGGTGTAA GAAGAAAGTC ATCTCAACGA ATTGAAAGGG AAAATCCTAT  1680

TTACGAACGA ACTATTCCAA CTTTTGAGTA TAAAAATGTG TATGATCAAG TTTGTGATGA  1740

TGATGACGAA GACCATATTT ATGAACTATG CGAAAATCAA TATGCTCAAC TAACAATTTC  1800

CCAGCCTAAA TCTCGTCCAA AGC                                         1823
```

(2) INFORMATION FOR SEQ ID NO: 79:

(i) SEQUENCE CHARACTERISTICS:
        (A) LENGTH: 918 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..915

(xi) SEQUENCE DESCRIPTION: SEQ ID NO: 79:

```
ATG GAT AGT AAA AAT ACT ATC TCC ATT GCT TTG ATT GAA AAA CAA AAA         48
Met Asp Ser Lys Asn Thr Ile Ser Ile Ala Leu Ile Glu Lys Gln Lys
 1               5                  10                  15

CCT TTT AAT TGG ACT ATC AAC AAA ATA AAT GAA AGC CTT CTG ATG ACC         96
Pro Phe Asn Trp Thr Ile Asn Lys Ile Asn Glu Ser Leu Leu Met Thr
                20                  25                  30

AAC AAC GAA GAA ATA AAC TTG ACT GAA AAT TTT AAA AAT ACG GGC ACC        144
Asn Asn Glu Glu Ile Asn Leu Thr Glu Asn Phe Lys Asn Thr Gly Thr
            35                  40                  45

TTT TAT AGC AAG ATA ATT GAC CTT GAA ATC CGA ACT GCT ACA TCT AGT        192
Phe Tyr Ser Lys Ile Ile Asp Leu Glu Ile Arg Thr Ala Thr Ser Ser
        50                  55                  60

CAA TAT GCA GTC TTT GTT ACA CAA ATG TGT TCT GAT GAC GAA AAT ATG        240
Gln Tyr Ala Val Phe Val Thr Gln Met Cys Ser Asp Asp Glu Asn Met
 65              70                  75                  80

AAT AAT ACA AAT ATT TTT GTT ATT AAT GGT GTT ATT GAT TCT GGA TAT        288
Asn Asn Thr Asn Ile Phe Val Ile Asn Gly Val Ile Asp Ser Gly Tyr
                85                  90                  95

AGA GGA ATA GTT AAA GCG TTA GTT TAT TAC CAT CCA ACT GTA GAA AAA        336
Arg Gly Ile Val Lys Ala Leu Val Tyr Tyr His Pro Thr Val Glu Lys
            100                 105                 110

TTA AAT CCA TAC GAT CTT AAA ATT AAA CTT CCA CTA ATA GAA CTT AGT        384
Leu Asn Pro Tyr Asp Leu Lys Ile Lys Leu Pro Leu Ile Glu Leu Ser
        115                 120                 125

AAA GAT TTA ATA CCA CTA TCA CCT AGT TTA CAT AGT TAT AGT GAA TTA        432
Lys Asp Leu Ile Pro Leu Ser Pro Ser Leu His Ser Tyr Ser Glu Leu
130                 135                 140

TAT AAT TTT TTT AAT GTC TTT AAT AAA AAA CGT GAT GAA GAT GCT GGT        480
Tyr Asn Phe Phe Asn Val Phe Asn Lys Lys Arg Asp Glu Asp Ala Gly
145                 150                 155                 160

TAT GAT ATA CCA TCT CCA AAT TTA GTT CAA ATA AAA CCG GGA TAT AGT        528
Tyr Asp Ile Pro Ser Pro Asn Leu Val Gln Ile Lys Pro Gly Tyr Ser
                165                 170                 175

TAC CTT TTT TGT CTT CCT ATT TTT CAA TTA GAA ATG AAA AAC CCA CCA        576
Tyr Leu Phe Cys Leu Pro Ile Phe Gln Leu Glu Met Lys Asn Pro Pro
            180                 185                 190

ATC GCT TGT ATT TTT GGT AGA TCA TCC TTA AAT TCA AGC GGA ATA ATT        624
Ile Ala Cys Ile Phe Gly Arg Ser Ser Leu Asn Ser Ser Gly Ile Ile
        195                 200                 205

GTT CTT CCA ACT ATA TGG AAA CCA AAA ACA ATT TGT CAA TTT TTT ATT        672
Val Leu Pro Thr Ile Trp Lys Pro Lys Thr Ile Cys Gln Phe Phe Ile
    210                 215                 220

AAA AAT ATA TCC TCT AAA ACT GTA ACT ATA GAA AAA GGT CAG AGA ATA        720
Lys Asn Ile Ser Ser Lys Thr Val Thr Ile Glu Lys Gly Gln Arg Ile
225                 230                 235                 240

GCT CAG TTA GTT CTT TTA AAA AAC AAT CAA CCA CTA TGG TTA CAA CCA        768
Ala Gln Leu Val Leu Leu Lys Asn Asn Gln Pro Leu Trp Leu Gln Pro
                245                 250                 255

CAA ATT AAT TGT CAT TCT TTA TTT CCA AAG TCA AAC TAT TTA AGC TTA        816
Gln Ile Asn Cys His Ser Leu Phe Pro Lys Ser Asn Tyr Leu Ser Leu
            260                 265                 270

TCA AAT CGA GAA TGT GAT ATG TGG AAG TTT ACA GAA GAT CTG AAT TTT        864
Ser Asn Arg Glu Cys Asp Met Trp Lys Phe Thr Glu Asp Leu Asn Phe
        275                 280                 285

GAA GCA CCG AAA AGT TTA CGA GGA ATA AAT GGA TTT GGA TCC ACG GGA        912
Glu Ala Pro Lys Ser Leu Arg Gly Ile Asn Gly Phe Gly Ser Thr Gly
    290                 295                 300

TTG TAA                                                                918
Leu
305
```

(2) INFORMATION FOR SEQ ID NO: 80:

(i) SEQUENCE CHARACTERISTICS:
        (A) LENGTH: 305 amino acids
        (B) TYPE: amino acid
        (D) TOPOLOGY: linear (ii) MOLECULE TYPE: protein (xi) SEQUENCE DESCRIPTION: SEQ ID NO: 80:

```
Met Asp Ser Lys Asn Thr Ile Ser Ile Ala Leu Ile Glu Lys Gln Lys
 1               5                  10                  15

Pro Phe Asn Trp Thr Ile Asn Lys Ile Asn Glu Ser Leu Leu Met Thr
            20                  25                  30

Asn Asn Glu Glu Ile Asn Leu Thr Glu Asn Phe Lys Asn Thr Gly Thr
        35                  40                  45

Phe Tyr Ser Lys Ile Ile Asp Leu Glu Ile Arg Thr Ala Thr Ser Ser
    50                  55                  60

Gln Tyr Ala Val Phe Val Thr Gln Met Cys Ser Asp Glu Asn Met
65                  70                  75                  80

Asn Asn Thr Asn Ile Phe Val Ile Asn Gly Val Ile Asp Ser Gly Tyr
                85                  90                  95

Arg Gly Ile Val Lys Ala Leu Val Tyr Tyr His Pro Thr Val Glu Lys
            100                 105                 110

Leu Asn Pro Tyr Asp Leu Lys Ile Lys Leu Pro Leu Ile Glu Leu Ser
        115                 120                 125

Lys Asp Leu Ile Pro Leu Ser Pro Ser Leu His Ser Tyr Ser Glu Leu
130                 135                 140

Tyr Asn Phe Phe Asn Val Phe Asn Lys Lys Arg Asp Glu Asp Ala Gly
145                 150                 155                 160

Tyr Asp Ile Pro Ser Pro Asn Leu Val Gln Ile Lys Pro Gly Tyr Ser
                165                 170                 175

Tyr Leu Phe Cys Leu Pro Ile Phe Gln Leu Glu Met Lys Asn Pro Pro
            180                 185                 190

Ile Ala Cys Ile Phe Gly Arg Ser Ser Leu Asn Ser Ser Gly Ile Ile
        195                 200                 205

Val Leu Pro Thr Ile Trp Lys Pro Lys Thr Ile Cys Gln Phe Phe Ile
210                 215                 220

Lys Asn Ile Ser Ser Lys Thr Val Thr Ile Glu Lys Gly Gln Arg Ile
225                 230                 235                 240

Ala Gln Leu Val Leu Leu Lys Asn Asn Gln Pro Leu Trp Leu Gln Pro
                245                 250                 255

Gln Ile Asn Cys His Ser Leu Phe Pro Lys Ser Asn Tyr Leu Ser Leu
            260                 265                 270

Ser Asn Arg Glu Cys Asp Met Trp Lys Phe Thr Glu Asp Leu Asn Phe
        275                 280                 285

Glu Ala Pro Lys Ser Leu Arg Gly Ile Asn Gly Phe Gly Ser Thr Gly
    290                 295                 300

Leu
305
```

(2) INFORMATION FOR SEQ ID NO: 81:

(i) SEQUENCE CHARACTERISTICS:
        (A) LENGTH: 261 base pairs
        (B) TYPE: nucleic acid (C) STRANDEDNESS: single
        (D) TOPOLOGY: linear (ii) MOLECULE TYPE: cDNA (ix) FEATURE:
        (A) NAME/KEY: CDS
        (B) LOCATION: 1..258

(xi) SEQUENCE DESCRIPTION: SEQ ID NO: 81:

```
ATG GAG ATA GTA TTT TTA CTA TCC ATT ATT TTT TCA GTT TAT GCC TTC      48
Met Glu Ile Val Phe Leu Leu Ser Ile Ile Phe Ser Val Tyr Ala Phe
  1               5                  10                  15

GAC GAT GAT CGT TTA GAT TAT TCT AGA GCT GAA GCT AGG AGA CAG TTT      96
Asp Asp Asp Arg Leu Asp Tyr Ser Arg Ala Glu Ala Arg Arg Gln Phe
             20                  25                  30

TGG AGC TCT AGT TGT TCA GCT AGG GGT ATC AAT ATT AAT ACG CCT TCA     144
Trp Ser Ser Ser Cys Ser Ala Arg Gly Ile Asn Ile Asn Thr Pro Ser
         35                  40                  45

ACT TCC GCT ATT TTG TTT TAT ATA TCC CTG GTA ACA GTA GGG GTT GCG     192
Thr Ser Ala Ile Leu Phe Tyr Ile Ser Leu Val Thr Val Gly Val Ala
     50                  55                  60

ATA TTT TGT TAT TCT TAT AGA ACC TGT TTG AGA ATG GTT AGT CGG GAA     240
Ile Phe Cys Tyr Ser Tyr Arg Thr Cys Leu Arg Met Val Ser Arg Glu
 65                  70                  75                  80

CTT CGT CAG ATG CAA CAC TAA                                         261
Leu Arg Gln Met Gln His
                 85
```

(2) INFORMATION FOR SEQ ID NO: 82:

(i) SEQUENCE CHARACTERISTICS:
        (A) LENGTH: 86 amino acids
        (B) TYPE: amino acid
        (D) TOPOLOGY: linear (ii) MOLECULE TYPE: protein (xi) SEQUENCE DESCRIPTION: SEQ ID NO: 82:

```
Met Glu Ile Val Phe Leu Leu Ser Ile Ile Phe Ser Val Tyr Ala Phe
  1               5                  10                  15

Asp Asp Asp Arg Leu Asp Tyr Ser Arg Ala Glu Ala Arg Arg Gln Phe
             20                  25                  30

Trp Ser Ser Ser Cys Ser Ala Arg Gly Ile Asn Ile Asn Thr Pro Ser
         35                  40                  45

Thr Ser Ala Ile Leu Phe Tyr Ile Ser Leu Val Thr Val Gly Val Ala
     50                  55                  60

Ile Phe Cys Tyr Ser Tyr Arg Thr Cys Leu Arg Met Val Ser Arg Glu
 65                  70                  75                  80

Leu Arg Gln Met Gln His
                 85
```

(2) INFORMATION FOR SEQ ID NO: 83:

(i) SEQUENCE CHARACTERISTICS:
        (A) LENGTH: 255 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..255

(xi) SEQUENCE DESCRIPTION: SEQ ID NO: 83:

```
ATG GCC AGC CGT CGT ATT TCA TCA TAT GAA GAT GAA CCG ATA TAT GCT        48
Met Ala Ser Arg Arg Ile Ser Ser Tyr Glu Asp Glu Pro Ile Tyr Ala
 1               5                  10                  15

ACT ATT AAG AGA CAA AAC GGT GTA AGA AGA AAG TCA TCT CAA CGA ATT        96
Thr Ile Lys Arg Gln Asn Gly Val Arg Arg Lys Ser Ser Gln Arg Ile
            20                  25                  30

GAA AGG GAA AAT CCT ATT TAC GAA CGA ACT ATT CCA ACT TTT GAG TAT       144
Glu Arg Glu Asn Pro Ile Tyr Glu Arg Thr Ile Pro Thr Phe Glu Tyr
        35                  40                  45

AAA AAT GTG TAT GAT CAA GTT TGT GAT GAT GAT GAC GAA GAC CAT ATT       192
Lys Asn Val Tyr Asp Gln Val Cys Asp Asp Asp Asp Glu Asp His Ile
    50                  55                  60

TAT GAA CTA TGC GAA AAT CAA TAT GCT CAA CTA ACA ATT TCC CAG CCT       240
Tyr Glu Leu Cys Glu Asn Gln Tyr Ala Gln Leu Thr Ile Ser Gln Pro
 65                 70                  75                  80

AAA TCT CGT CCA AAG                                                   255
Lys Ser Arg Pro Lys
                85
```

(2) INFORMATION FOR SEQ ID NO: 84:

(i) SEQUENCE CHARACTERISTICS:
        (A) LENGTH: 85 amino acids
        (B) TYPE: amino acid
        (D) TOPOLOGY: linear (ii) MOLECULE TYPE: protein (xi) SEQUENCE DESCRIPTION: SEQ ID NO: 84:

```
Met Ala Ser Arg Arg Ile Ser Ser Tyr Glu Asp Glu Pro Ile Tyr Ala
 1               5                  10                  15

Thr Ile Lys Arg Gln Asn Gly Val Arg Arg Lys Ser Ser Gln Arg Ile
            20                  25                  30

Glu Arg Glu Asn Pro Ile Tyr Glu Arg Thr Ile Pro Thr Phe Glu Tyr
        35                  40                  45

Lys Asn Val Tyr Asp Gln Val Cys Asp Asp Asp Glu Asp His Ile
    50                  55                  60

Tyr Glu Leu Cys Glu Asn Gln Tyr Ala Gln Leu Thr Ile Ser Gln Pro
 65                 70                  75                  80

Lys Ser Arg Pro Lys
                85
```

(2) INFORMATION FOR SEQ ID NO: 85:

(i) SEQUENCE CHARACTERISTICS:
        (A) LENGTH: 749 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 85:

```
AAGCTTTCAA AATGTGCCAA GTAAATATAA TTAATAAACT CTCTATCAGA AACTTTTAAA     60

CTCTGTCTAT CAGCAGAAAT ATAATTTCTC AATACACCAA CCTCTGAAAT ATCGGCATTA    120

ATTCGATGTG TTATATAATC TTCTAGTTTA ACAGCAATCT TTCCTGTAGC ATACCCACTT    180

TGACAACAAA ATTTTGATAA CAAAGAAAAT GATATTAAAT CTATACATTT AAGATTAGTT    240

TTGTTTTGTT GTACAGGTAT TTTATATGTT TCGATAAAAT CTTTTATAGC TTGTAGGTCA    300
```

```
TAGGTATGAA AAGGCTTTAA ACTGTTTGTA GCTTGAAATA GATAAAATCT TGTTGCTAAA      360

ACTAAAGTTT TTTCTTCAGG ACCAAATTTT GAAGTAAACC AAAACGGTGT AGGATTTGTT      420

CCATATATTC GTCTAAAGGC TGCAAGTATT TGTTGTTCGT GATGAATATA TAATAATGTT      480

AACCCATGGC GTCCTTTATT ACATTTCGAT AAGCATGTTT TTATAGATAA TGTAGGGTCA      540

TATTTAGCAG ATTCTAAAGT TCTTCCAGAT TTAGGAGTTA GACGCTCTGT CGTTATAGAT      600

AATATAGTTA TTAAATCATC ATGAATATTA AACGTATGCT GATCATCAAT ACAAGAAAGT      660

ATTAATTTTG TAGAGATTGG GTTTCCATAT AATAAAGATT TAGCTATAAC AGACGCTTCA      720

TAATTATTTT TAATTGAACA TATAAACAT                                        749

(2) INFORMATION FOR SEQ ID NO: 86:

(i) SEQUENCE CHARACTERISTICS:
        (A) LENGTH: 749 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 86:

ATGTTTATAT GTTCAATTAA AAATAATTAT GAAGCGTCTG TTATAGCTAA ATCTTTATTA       60

TATGGAAACC CAATCTCTAC AAAATTAATA CTTTCTTGTA TTGATGATCA GCATACGTTT      120

AATATTCATG ATGATTTAAT AACTATATTA TCTATAACGA CAGAGCGTCT AACTCCTAAA      180

TCTGGAAGAA CTTTAGAATC TGCTAAATAT GACCCTACAT TATCTATAAA AACATGCTTA      240

TCGAAATGTA ATAAAGGACG CCATGGGTTA ACATTATTAT ATATTCATCA CGAACAACAA      300

ATACTTGCAG CCTTTAGACG AATATATGGA ACAAATCCTA CACCGTTTTG GTTTACTTCA      360

AAATTTGGTC CTGAAGAAAA AACTTTAGTT TTAGCAACAA GATTTTATCT ATTTCAAGCT      420

ACAAACAGTT TAAAGCCTTT TCATACCTAT GACCTACAAG CTATAAAAGA TTTTATCGAA      480

ACATATAAAA TACCTGTACA ACAAAACAAA ACTAATCTTA AATGTATAGA TTTAATATCA      540

TTTTCTTTGT TATCAAAATT TTGTTGTCAA AGTGGGTATG CTACAGGAAA GATTGCTGTT      600

AAACTAGAAG ATTATATAAC ACATCGAATT AATGCCGATA TTTCAGAGGT TGGTGTATTG      660

AGAAATTATA TTTCTGCTGA TAGACAGAGT TTAAAAGTTT CTGATAGAGA GTTTATTAAT      720

TATATTTACT TGGCACATTT TGAAAGCTT                                        749

(2) INFORMATION FOR SEQ ID NO: 87:

(i) SEQUENCE CHARACTERISTICS:
        (A) LENGTH: 747 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..747

(xi) SEQUENCE DESCRIPTION: SEQ ID NO: 87:

ATG TTT ATA TGT TCA ATT AAA AAT AAT TAT GAA GCG TCT GTT ATA GCT        48
Met Phe Ile Cys Ser Ile Lys Asn Asn Tyr Glu Ala Ser Val Ile Ala
 1               5                  10                  15

AAA TCT TTA TTA TAT GGA AAC CCA ATC TCT ACA AAA TTA ATA CTT TCT        96
Lys Ser Leu Leu Tyr Gly Asn Pro Ile Ser Thr Lys Leu Ile Leu Ser
```

```
            20                  25                  30
TGT ATT GAT GAT CAG CAT ACG TTT AAT ATT CAT GAT GAT TTA ATA ACT      144
Cys Ile Asp Asp Gln His Thr Phe Asn Ile His Asp Asp Leu Ile Thr
            35                  40                  45

ATA TTA TCT ATA ACG ACA GAG CGT CTA ACT CCT AAA TCT GGA AGA ACT      192
Ile Leu Ser Ile Thr Thr Glu Arg Leu Thr Pro Lys Ser Gly Arg Thr
 50                  55                  60

TTA GAA TCT GCT AAA TAT GAC CCT ACA TTA TCT ATA AAA ACA TGC TTA      240
Leu Glu Ser Ala Lys Tyr Asp Pro Thr Leu Ser Ile Lys Thr Cys Leu
 65                  70                  75                  80

TCG AAA TGT AAT AAA GGA CGC CAT GGG TTA ACA TTA TTA TAT ATT CAT      288
Ser Lys Cys Asn Lys Gly Arg His Gly Leu Thr Leu Leu Tyr Ile His
                85                  90                  95

CAC GAA CAA CAA ATA CTT GCA GCC TTT AGA CGA ATA TAT GGA ACA AAT      336
His Glu Gln Gln Ile Leu Ala Ala Phe Arg Arg Ile Tyr Gly Thr Asn
                100                 105                 110

CCT ACA CCG TTT TGG TTT ACT TCA AAA TTT GGT CCT GAA GAA AAA ACT      384
Pro Thr Pro Phe Trp Phe Thr Ser Lys Phe Gly Pro Glu Glu Lys Thr
                115                 120                 125

TTA GTT TTA GCA ACA AGA TTT TAT CTA TTT CAA GCT ACA AAC AGT TTA      432
Leu Val Leu Ala Thr Arg Phe Tyr Leu Phe Gln Ala Thr Asn Ser Leu
130                 135                 140

AAG CCT TTT CAT ACC TAT GAC CTA CAA GCT ATA AAA GAT TTT ATC GAA      480
Lys Pro Phe His Thr Tyr Asp Leu Gln Ala Ile Lys Asp Phe Ile Glu
145                 150                 155                 160

ACA TAT AAA ATA CCT GTA CAA CAA AAC AAA ACT AAT CTT AAA TGT ATA      528
Thr Tyr Lys Ile Pro Val Gln Gln Asn Lys Thr Asn Leu Lys Cys Ile
                165                 170                 175

GAT TTA ATA TCA TTT TCT TTG TTA TCA AAA TTT TGT TGT CAA AGT GGG      576
Asp Leu Ile Ser Phe Ser Leu Leu Ser Lys Phe Cys Cys Gln Ser Gly
                180                 185                 190

TAT GCT ACA GGA AAG ATT GCT GTT AAA CTA GAA GAT TAT ATA ACA CAT      624
Tyr Ala Thr Gly Lys Ile Ala Val Lys Leu Glu Asp Tyr Ile Thr His
                195                 200                 205

CGA ATT AAT GCC GAT ATT TCA GAG GTT GGT GTA TTG AGA AAT TAT ATT      672
Arg Ile Asn Ala Asp Ile Ser Glu Val Gly Val Leu Arg Asn Tyr Ile
210                 215                 220

TCT GCT GAT AGA CAG AGT TTA AAA GTT TCT GAT AGA GAG TTT ATT AAT      720
Ser Ala Asp Arg Gln Ser Leu Lys Val Ser Asp Arg Glu Phe Ile Asn
225                 230                 235                 240

TAT ATT TAC TTG GCA CAT TTT GAA AGC                                  747
Tyr Ile Tyr Leu Ala His Phe Glu Ser
                245
```

(2) INFORMATION FOR SEQ ID NO: 88:

(i) SEQUENCE CHARACTERISTICS:
        (A) LENGTH: 249 amino acids
        (B) TYPE: amino acid
        (D) TOPOLOGY: linear (ii) MOLECULE TYPE: protein (xi) SEQUENCE DESCRIPTION: SEQ ID NO: 88:

```
Met Phe Ile Cys Ser Ile Lys Asn Asn Tyr Glu Ala Ser Val Ile Ala
 1               5                  10                  15

Lys Ser Leu Leu Tyr Gly Asn Pro Ile Ser Thr Lys Leu Ile Leu Ser
                20                  25                  30

Cys Ile Asp Asp Gln His Thr Phe Asn Ile His Asp Asp Leu Ile Thr
                35                  40                  45
```

```
Ile Leu Ser Ile Thr Thr Glu Arg Leu Thr Pro Lys Ser Gly Arg Thr
     50                  55                  60

Leu Glu Ser Ala Lys Tyr Asp Pro Thr Leu Ser Ile Lys Thr Cys Leu
 65                  70                  75                  80

Ser Lys Cys Asn Lys Gly Arg His Gly Leu Thr Leu Leu Tyr Ile His
                 85                  90                  95

His Glu Gln Gln Ile Leu Ala Ala Phe Arg Arg Ile Tyr Gly Thr Asn
                100                 105                 110

Pro Thr Pro Phe Trp Phe Thr Ser Lys Phe Gly Pro Glu Glu Lys Thr
                115                 120                 125

Leu Val Leu Ala Thr Arg Phe Tyr Leu Phe Gln Ala Thr Asn Ser Leu
130                 135                 140

Lys Pro Phe His Thr Tyr Asp Leu Gln Ala Ile Lys Asp Phe Ile Glu
145                 150                 155                 160

Thr Tyr Lys Ile Pro Val Gln Gln Asn Lys Thr Asn Leu Lys Cys Ile
                165                 170                 175

Asp Leu Ile Ser Phe Ser Leu Leu Ser Lys Phe Cys Cys Gln Ser Gly
                180                 185                 190

Tyr Ala Thr Gly Lys Ile Ala Val Lys Leu Glu Asp Tyr Ile Thr His
                195                 200                 205

Arg Ile Asn Ala Asp Ile Ser Glu Val Gly Val Leu Arg Asn Tyr Ile
210                 215                 220

Ser Ala Asp Arg Gln Ser Leu Lys Val Ser Asp Arg Glu Phe Ile Asn
225                 230                 235                 240

Tyr Ile Tyr Leu Ala His Phe Glu Ser
                245

(2) INFORMATION FOR SEQ ID NO: 89:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..30
        (D) OTHER INFORMATION: /label= primer (xi) SEQUENCE DESCRIPTION: SEQ ID NO: 89:

GCCGGTACCA GGCTTTGGAC GAGATTTAGG                                    30

(2) INFORMATION FOR SEQ ID NO: 90:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..29
        (D) OTHER INFORMATION: /label= primer (xi) SEQUENCE DESCRIPTION: SEQ ID NO: 90:

GCCGAATTCA ATATAATTAA TAAACTCTC                                     29
```

(2) INFORMATION FOR SEQ ID NO: 91:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..28
        (D) OTHER INFORMATION: /label= primer (xi) SEQUENCE DESCRIPTION: SEQ ID NO: 91:

CCGGAATTCG CTTAGTGAGA GTATAAAC                28

(2) INFORMATION FOR SEQ ID NO: 92:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..28
        (D) OTHER INFORMATION: /label= primer (xi) SEQUENCE DESCRIPTION: SEQ ID NO: 92:

CCGGAATTCC CTCATATTAT ATACTAAC                28

CANINE HERPES VIRUS ALPHA TRANSINDUCING FACTOR NUCLEIC ACID MOLECULES

CROSS-REFERENCE TO RELATED APPLICATIONS

The present application is a continuation of U.S. patent application Ser. No. 09/399,118, file date Sep. 20, 1999 now abandoned which is a divisional of U.S. patent application Ser. No. 09/092,409, filed Jan. 29, 1998, now U.S. Pat. No. 6,159,478; which is a divisional of U.S. patent application Ser. No. 08/680,726, filed Jul. 12, 1996, now U.S. Pat. No. 5,804,197; which is a continuation-in-part of U.S. patent application Ser. No. 08/602,010, filed Feb. 15, 1996, now U.S. Pat. No. 5,753,235; all of which are entitled "RECOMBINANT CANINE HERPESVIRUSES." Each of the above-identified patent applications is incorporated herein by reference in its entirety.

FIELD OF THE INVENTION

The present invention relates to canine herpesvirus (CHV), and particularly to novel recombinant CHV and recombinant CHV genomes, including those that contain heterologous nucleic acid molecules. The present invention also relates to the use of such genomes and viruses in a variety of applications, including as therapeutic compositions to protect animals from disease. The present invention also relates to novel isolated CHV nucleic acid molecules, to proteins encoded by such nucleic acid molecules, and to use of such CHV nucleic acid molecules to insert heterologous nucleic acid molecules into CHV genomes.

BACKGROUND OF THE INVENTION

Dogs and other canids are affected by a number of diseases against which it would be desirable to develop protective vaccines. Live vaccines, and particularly live viral vector vaccines, are attractive vaccine vector candidates as they appear to be associated with longer-lasting immunity than inactivated virus vaccines or subunit vaccines. One disadvantage of live vaccines, however, has been that attenuated virus strains often revert to virulence. Another disadvantage has been the host range of a number of viral vaccines. In an attempt to deliver genes to an animal, several viral and bacterial systems, such as poxviruses, adenoviruses, Salmonella, and BCG (*Bacillus Calmette-Guerin*), have been genetically manipulated to generate vectors containing heterologous antigen genes in order to immunize a host with a vaccine in which the antigens are presented in a "live" configuration. See, for example, the following two review articles: Esposito et al., pp. 195–247, 1989, *Advances in Veterinary Science and Comparative Medicine*, Vol. 33; Dougan et al., pp. 271–300, 1989, *Advances in Veterinary Science and Comparative Medicine*, Vol. 33.

Several herpes virus vaccines, such as those based on bovine herpes virus (BHV), cytomegalovirus (CMV), Epstein Barr virus (EBV), equine herpes virus (EHV), feline herpes virus (FHV), herpes simplex virus (HSV), Marek's disease virus (MDV), pseudorabies virus (PRV), turkey herpes virus (HVT), and varicella zoster virus (VZV) have been developed and several have shown at least some efficacy as vaccines against the virus per se or as vectors carrying other genes in certain indications. The listed herpes viruses, however, also have the drawback that even if attenuated, they are subject to reversion.

Canine herpes virus (CHV) infection is a relatively benign infection except in newborn puppies. A few vaccines to protect against CHV infection have been reported including a small-plaque variant CHV vaccine disclosed in U.S. Pat. No. 4,213,965, by Carmichael, issued Jul. 22, 1980. The nucleotide sequences of CHV genes encoding gB, gC, gD and UL45 homologs have been reported by Limbach et al., 1994, *J. Gen. Virol.* 75, 2029–2039, but these proteins, while proposed as vaccine candidates against CHV, were not tested as such by Limbach et al., ibid.

The inventors are not aware of any reports which describe the use of CHV as a vaccine vector, either with respect to inactivating genes in the CHV genome using recombinant DNA techniques, and/or to delivering protective compounds to a canid, in spite of the need to develop safe and efficacious delivery systems to protect canids, and especially dogs, from disease. Two U.S. patents (i.e., U.S. Pat. No. 5,266,489, by Rey-Senelonge et al., issued Nov. 30, 1993; and U.S. Pat. No. 5,223,424, by Cochran et al., issued Jun. 29, 1993) at best speculate on the insertion of genes into certain CHV loci, but neither claims CHV vectors or vaccines, nor provides data supporting such speculations. U.S. Pat. No. 5,266,489, ibid., claimed HVT having a foreign gene inserted into the ribonucleotide reductase (RR) small subunit gene of the HVT genome, but also disclosed without support the insertion of foreign genes into the RR small subunit genes of BHV, CHV, CMV, duck herpes virus, EBV, EHV, FHV, HSV, PRV and VZV. The inventors, however, have demonstrated the inaccuracy of this disclosure in that the inventors have found, and disclosed in the present application, that the CHV genome lacks the RR small subunit gene. That is, the CHV RR small subunit gene does not exist to provide a target for the insertion of foreign genes.

U.S. Pat. No. 5,223,424, ibid., claimed specific hybrid PRV constructs having deletions in the TK, repeat, or and/or gX regions and heterologous sequences inserted into the repeat and/or gX regions, but also proposed without data the ability to insert foreign genes into the repeat region of the CHV genome, even though that genome had not yet been mapped. Also disclosed were certain BHV and HVT constructs and proposals, without data, to delete and insert genes in other herpesviruses, such as EHV and FHV, HSV and MDV. It is also of note that a patent application (now U.S. Pat. No. 5,273,876, by Hock et al, issued Dec. 28, 1993) that was filed significantly later than U.S. Pat. No. 5,223,424, ibid., and shares two co-inventors with U.S. Pat. No. 5,223,424, ibid., states in column 2, lines 57–61, "Among the herpesviruses, only four herpesviruses (herpes simplex of humans, herpes saimiri of monkeys, pseudorabies virus and varicella-zoster virus) have been engineered to contain foreign DNA sequences previous to this disclosure," thereby indicating the lack of CHV, or a number of other, herpes virus vectors.

Thus, there remains a need for new and improved methods to vaccinate canids to protect them from diseases, such as those caused by genetic or metabolic disorders as well as those caused by infectious agents such as protozoan parasites, helminth parasites, ectoparasites, fungi, bacteria, and viruses.

SUMMARY OF THE INVENTION

The present invention relates to a new method to protect animals from disease using a recombinant virus or virus genome. When a recombinant CHV of the present invention is administered to an animal, the virus is able to infect cells within the animal. Infected cells are able to express nucleic acid sequences present on the recombinant CHV genome to produce protective compounds, such as proteins and RNAs, capable of protecting the animal from a variety of diseases. Using methods taught in the present invention, vaccines can be generated that are capable of protecting an animal from any disease for which a protective compound can be produced. As such, the present invention is of extremely broad scope and includes a wide variety of vaccines that have a variety of applications.

The present invention includes a recombinant CHV that comprises a recombinant CHV genome. The invention also includes recombinant CHV genomes. In one embodiment, a recombinant CHV has an inactive gene within its genome, with a preferred recombinant CHV in this embodiment being a CdUTPase negative CHV, a CgC negative CHV, a CgE negative CHV, a CgG negative CHV, a CgI negative CHV, a CPK negative CHV, a CTK negative CHV, a CIR6 negative CHV, a CUS2 negative CHV, a CUS9 negative CHV, a CUL49 negative CHV, a CUL51 negative CHV, a CUL45 negative CHV, a CgD negative CHV, a CgB negative CHV, a CUL48 negative CHV, a CUL52 negative CHV, a CgL negative CHV, a CUL49.5 negative CHV, a CICP0 negative CHV, a CICP4 negative CHV, and/or a CUS8.5 negative CHV. In the case of the CUS8.5 negative CHV, a CUS8.5 negative CHV refers to a CHV in which the CUS8.5 open reading frame is disrupted.

The present invention also includes a recombinant CHV genome that comprises a heterologous nucleic acid molecule, which preferably encodes a protective compound that protects a canid from disease. Such a heterologous nucleic acid molecule can be located in an essential gene, a nonessential gene, and/or in an intergenic region. Insertion of a heterologous nucleic acid into a CHV genome can, but need not, inactivate a gene within that genome. Also included in the present invention are methods to produce a recombinant CHV and a recombinant CHV genome, as well as a canine cell line that complements a defect in a gene essential to CHV reproduction in vitro.

One embodiment of the present invention is a method to increase recombinant CHV plaque forming efficiency. Such a method can include the steps of introducing a recombinant CHV genome into a canine cell expressing CHV alpha transinducing factor and culturing the cell to produce recombinant CHV. In another embodiment, the method includes the steps of co-introducing a recombinant CHV genome and a CHV alpha transinducing factor gene into a canine cell and culturing the cell to produce recombinant CHV. The present invention also includes a canine cell line comprising a CHV alpha transinducing factor gene.

One embodiment of the present invention is a therapeutic composition that includes a recombinant CHV, a recombinant CHV genome, or a mixture thereof. The present invention also includes a method to protect an animal from disease by administering such a therapeutic composition to the animal.

The present invention also includes an isolated CHV nucleic acid molecule that hybridizes under stringent hybridization conditions with at least one of the following nucleic acid regions: a CdUTPase gene, a CgE gene, a CgG gene, a CgI gene, a CPK gene, a CTK gene, a CIR6 gene, a CUS2 gene, a CUS9 gene, a CUL49 gene, a CUL51 gene, a CUL48 gene, a CUL52 gene, a CgL gene, a CUL49.5 gene, a CICP4 gene, a CUS8.5 open reading frame, and/or a region of the CHV genome spanning from about the 3' end of the coding region of the CUL41 gene through about the 3' end of the coding region of the CUL38 gene. Also included are recombinant molecules, recombinant viruses, recombinant vectors, and recombinant cells that include such CHV nucleic acid molecules. The present invention also includes CHV proteins encoded by such CHV nucleic acid molecules and antibodies that selectively bind to such CHV proteins, as well as methods to produce such CHV nucleic acid molecules, recombinant molecules, recombinant viruses, recombinant vectors, recombinant cells, CHV proteins and antibodies. Also included in the present invention are therapeutic compositions including such CHV nucleic acid molecules, CHV proteins and antibodies, as well as methods to use such compositions to protect an animal from disease.

DETAILED DESCRIPTION OF THE INVENTION

Figure 1:
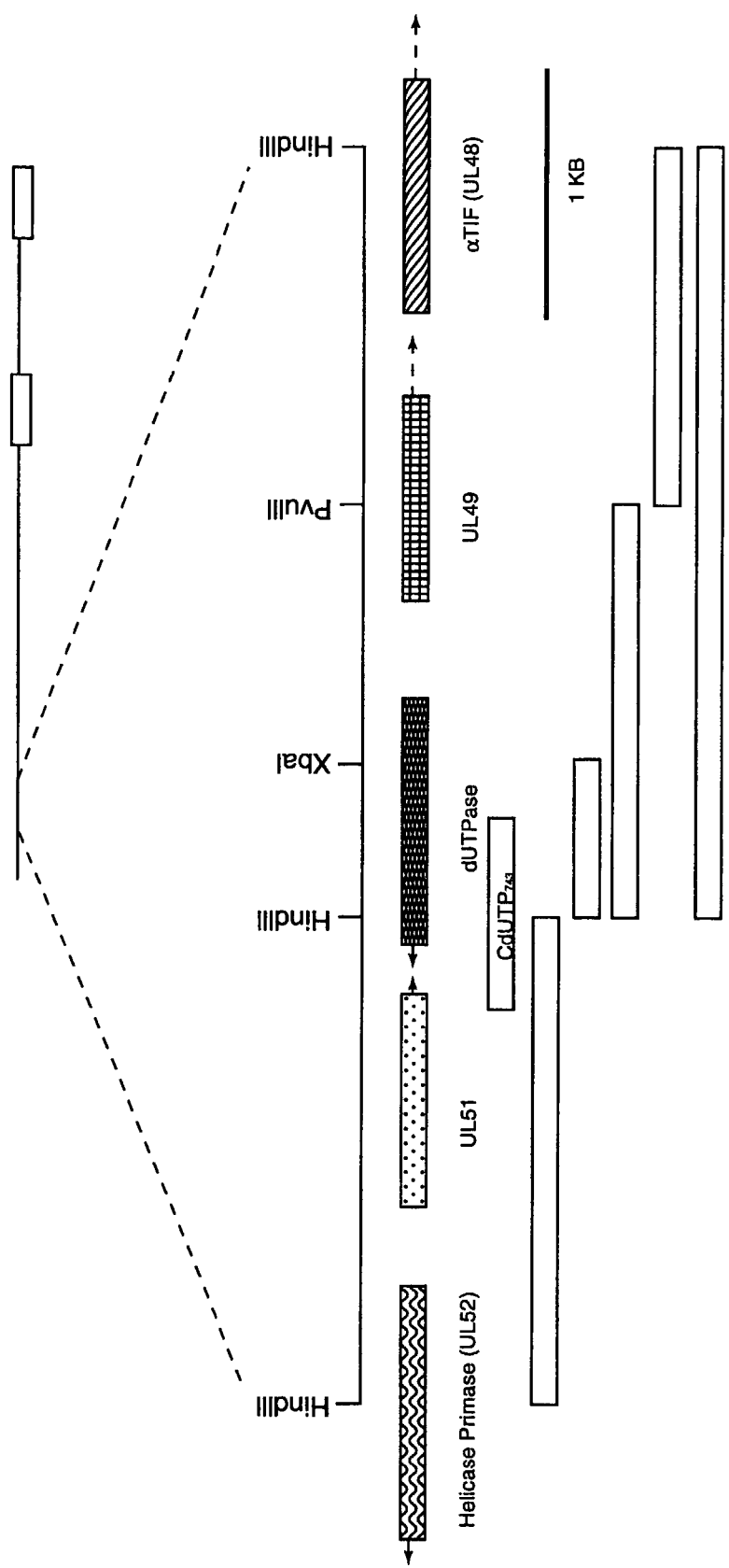
FIG. 1 depicts a schematic map of two contiguous HindIII fragments that include at least portions of CHV UL48 UL49, dUTPase, UL51 and UL52 genes.
Figure 2:
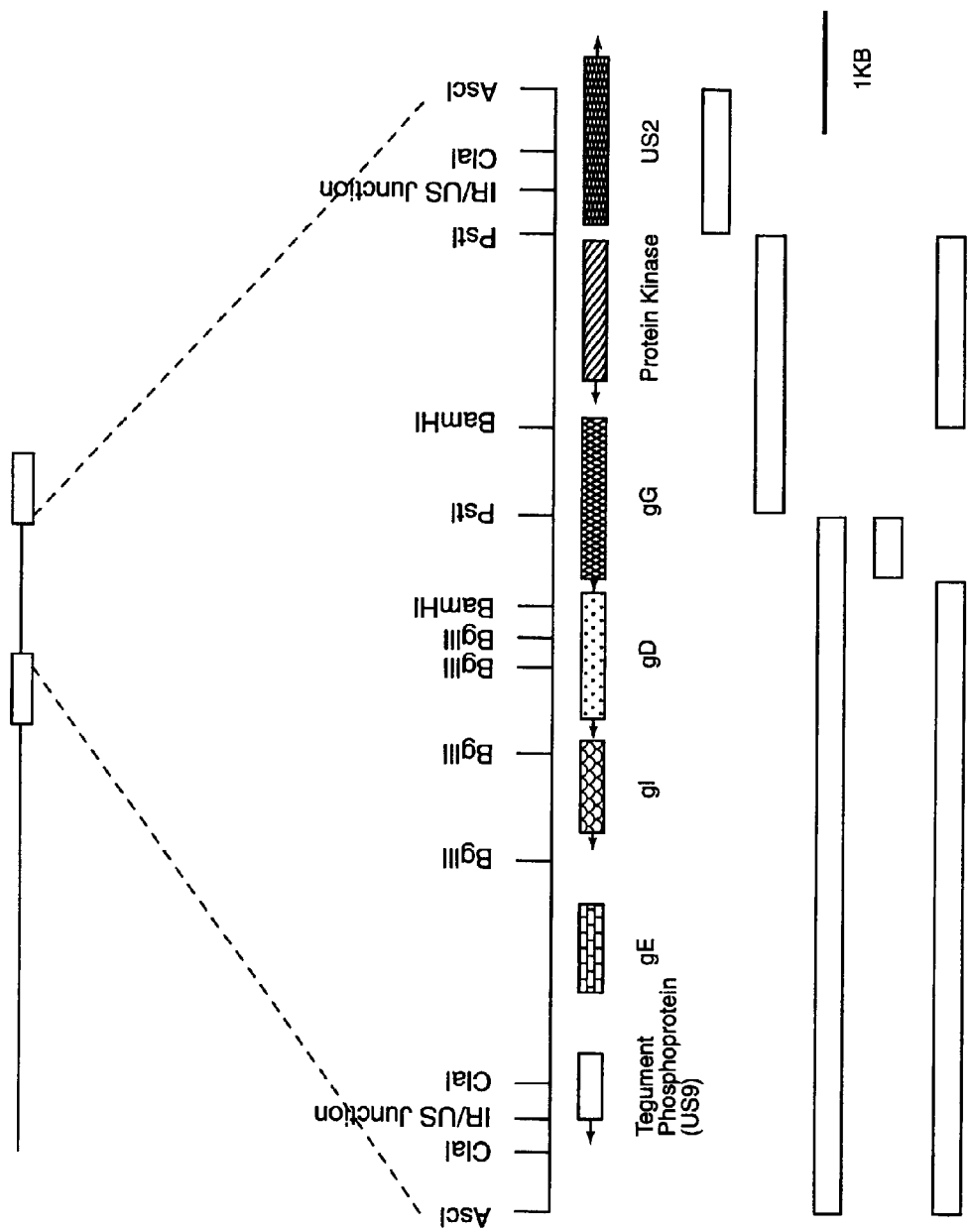
FIG. 2 depicts a schematic map of the AscI fragment that includes the unique short region of CHV.
Figure 3:
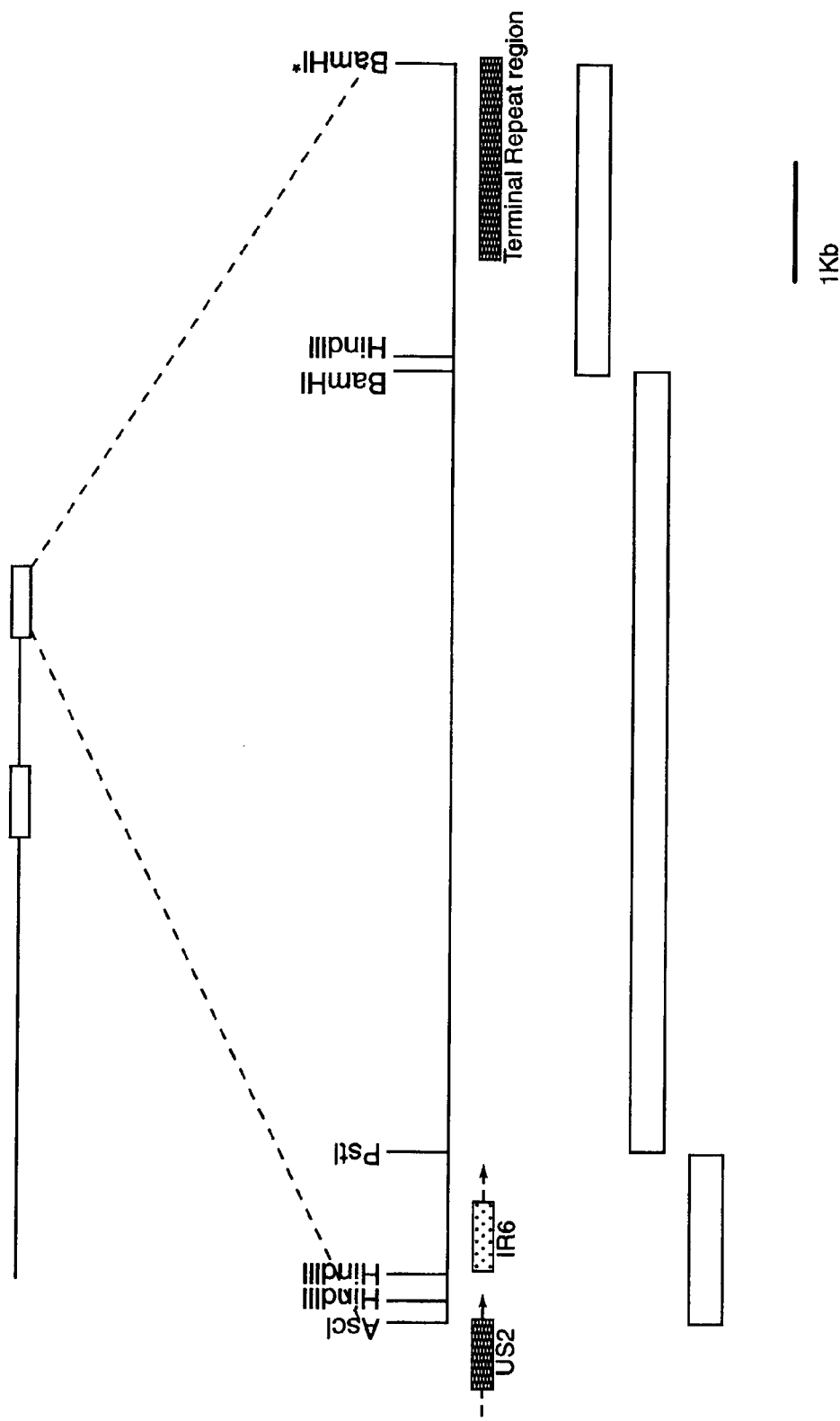
FIG. 3 depicts a schematic map of the AscI/blunt fragment that includes the terminal inverted repeat region of CHV.

The present invention relates to canine herpesviruses (CHV), and particularly to recombinant CHV and recombinant CHV genomes as well as to methods to produce and use such viruses and genomes. The present invention also includes identification of regions of the CHV genome that are preferred targets for deletion and/or for insertion of heterologous nucleic acid molecules. As used herein, the term "canine" refers to "of the family Canidae" and, as such, includes reference to dogs (including wild and domesticated dogs), foxes, wolves, jackals, coyotes, and other members of the family Canidae. Similarly, a "canid" is any member of the family Canidae. As used herein, the term CHV refers to any herpesvirus endogenous to the family Canidae. A particularly preferred CHV of the present invention is a recombinant CHV that infects dogs.

One embodiment of the present invention is the use of a recombinant CHV, and particularly of a CHV having a recombinant CHV genome that includes a (i.e., one or more than one) heterologous nucleic acid molecule, as a live CHV-based therapeutic composition, or vaccine, to protect an animal from a disease against which the heterologous nucleic acid molecule is targeted. Live vaccines are advantageous because they are believed to confer more vigorous and longer-lasting immunity than subunit or killed vaccines. While not being bound by theory, it is believed that such advantages are due to the ability of the genetic information carried by the virus to enter cells of the treated animal, replicate itself, and direct the expression of a protective compound, such as a protective protein or a protective RNA, for extended periods of time. Thus, the therapeutic composition need not be administered frequently and, at least in some embodiments, the virus vaccine can function as a self-booster.

CHV is particularly useful as a delivery vehicle for a heterologous nucleic acid molecule to protect canids from a disease for a variety of reasons, including, but not limited to, CHV's limited host range and pathogenicity. CHV, to the inventors' knowledge, has the most limited host range of any herpesvirus, including FHV, in that CHV's host range appears to be substantially limited to canine cells. As far as the inventors are aware, the only report of CHV infection of a cell type other than canine cells is limited infection of mink lung cells; see, for example, Peterson et al, 1988, *Comp. Immunol. Microbiol. Infect. Diseases* 11, 93–98. This limited host range illustrates the safety of CHV in that the virus apparently cannot be transmitted to a variety of species unrelated to canids.

Furthermore, CHV exhibits only limited pathogenicity. Although the virus has been shown to cause a fatal hemorrhagic disease in hypothermic neonatal pups (i.e., essentially all pups experimentally infected with CHV and maintained at room temperature (i.e., from about 25° C. to 27° C.) within a week of birth die from the infection), CHV causes insignificant respiratory infection in adult dogs; see, for example, Carmichael, 1970, *J. Am. Vet. Med. Assn.* 156, 1714–1721. Moreover, prolonged survival or recovery of experimentally infected neonatal pups maintained at 38.4° C. to 39.5° C. was observed. Adult dogs exposed to CHV do, however, become infected since virus shedding has been shown to occur for at least two weeks post-inoculation; and latency is postulated to occur, since CHV has been isolated from primary cultured cells of normal healthy dogs; see, for example, Carmichael, ibid. Furthermore, maternal antibody, or passive transfer of antibody from seropositive dogs has been shown to protect puppies from an otherwise fatal CHV challenge; see, for example, Carmichael, ibid. Due to its limited pathogenicity, CHV apparently need not be attenuated to the extent required for other viruses used as live vaccine vectors. In addition, vaccination of a dam with CHV can lead to passive protection in her pups.

Another advantage of CHV is its limited temperature range. CHV grows well at temperatures ranging from about 34° C. to about 36° C., with optimal growth occurring at about 35° C. CHV, however, does not grow well at temperatures less than or equal to about 33° C. or at temperatures greater than or equal to about 37° C. As such CHV is significantly more temperature sensitive than any other known wild type herpesvirus, including FHV.

Yet another advantage of CHV is its potential for use as a single, multivalent therapeutic composition against a variety of canine pathogens. That is, the CHV genome can be manipulated to incorporate multiple heterologous nucleic acid molecules without disrupting the ability of the genome to be packaged (i.e., assembled) into a live virus. Examples of multivalent therapeutic compositions are described below.

As far as the inventors are aware, this application is the first report of the genetic engineering of a CHV genome, particularly for the development of efficacious canid vaccines, in spite of a long felt need for efficacious vaccines against canine pathogens. The inventors have developed methods to identify CHV genes and intergenic regions, particularly those having utility as targets for the insertion of heterologous nucleic acid molecules, despite the difficulty of using known herpesvirus sequences to identify such regions due to the AT-rich nature of the CHV genome. The CHV genome contains about 70% adenosine and thymidine residues, compared to other known herpesvirus genomes which, on the average, contain from about 30% to about 58% adenosine and thymidine residues (e.g., HSV, BHV, and PRV contain about 30%, EHV about 54%, and FHV about 58%, adenosine and thymidine residues). As such, it is very difficult to design primers or probes using known herpesvirus sequences to identify CHV analogs.

One embodiment of the present invention is a recombinant CHV. As used herein, a recombinant CHV is a CHV that comprises (i.e., has or includes) a genome that has been genetically engineered (i.e., subjected to recombinant nucleic acid (i.e., DNA or RNA) techniques, such as those disclosed in Sambrook et al., 1989, *Molecular Cloning: A Laboratory Manual*, Cold Spring Harbor Labs Press; Sambrook et al., ibid., is incorporated by reference herein in its entirety) to differ from the genome of a natural CHV isolate (i.e., a herpesvirus endogenous to the family Canidae). Such a genetically engineered genome is referred to herein as a recombinant CHV genome and is described in more detail below.

A recombinant CHV of the present invention includes not only a recombinant CHV genome but also an envelope and capsid in which the genome is packaged. The viral envelope and capsid are preferably a CHV envelope and a CHV capsid, encoded at least in part by CHV genes, thereby imparting to the recombinant CHV the host range of a natural CHV isolate. It is to be noted, however, that the present invention also includes recombinant CHV having envelopes and/or capsids that have been modified to, for example, alter (e.g., broaden, narrow, or completely change) the host range of the recombinant CHV genome. Such modifications can be accomplished by one skilled in the art by, for example, modifying CHV envelope and/or capsid genes and/or replacing such genes with those of another virus. Altered genes can be located on the CHV genome itself and/or in the genome of the cell in which the recombinant virus is produced.

A recombinant CHV genome of the present invention is a CHV genome in which nucleotides have been deleted, inserted, substituted or inverted using recombinant techniques known to those skilled in the art such that the recombinant CHV genome is no longer the same as a natural CHV genome. A recombinant CHV genome of the present invention is capable of effecting expression (e.g., transcription, translation) of coding regions that are operatively linked to regulatory sequences within the genome. As used herein, a coding region is a stretch of nucleotides that encodes an RNA molecule and/or a protein. Coding regions can be endogenous to CHV or can be heterologous nucleic acid molecules of the present invention, which are described in more detail below. The phrase operatively linked refers to the positioning of a coding region in the CHV genome such that the coding region is able to be expressed when the genome is inside a cell. Regulatory sequences include transcription control sequences, translation control sequences, and other regulatory sequences that control the expression of coding regions. Transcription control sequences are sequences which control the initiation, elongation, and termination of transcription. Particularly important transcription control sequences are those which control transcription initiation, such as promoter, enhancer, operator and repressor sequences. Suitable regulatory sequences include any regulatory sequence that can function in the present invention. Preferred regulatory sequences are disclosed herein.

A recombinant CHV genome of the present invention can include a gene that has been inactivated. As used herein, a gene includes a coding region as well as the regulatory sequences involved in expression of that coding region. An inactive gene refers to a gene that no longer exhibits the function of its natural counterpart. Methods to inactivate a gene include, but are not limited to, deletion of one or more nucleotides within the gene, insertion of one or more nucleotides into the gene, replacement of one or more nucleotides within the gene by other nucleotides (i.e., nucleotide substitution), and/or inversion of nucleotides within the gene such that the resulting gene no longer has the function of the corresponding natural gene. Such alterations can be effected anywhere within the gene, such as within the coding region, within the regulatory sequences and/or in regions surrounding the coding region or regulatory sequences such that the alteration(s) cause gene inactivation. In one embodiment, an entire gene or the coding region and/or regulatory sequences thereof can be deleted or replaced.

One embodiment of the present invention is an attenuated recombinant CHV. As used herein, an attenuated CHV is a CHV that does not cause 100% mortality if used to infect canid neonates less than 1 week old that are maintained in room temperature. A preferred attenuated CHV of the present invention causes less than about 90% and preferably less than about 70% mortality when used to infect canid neonates less than 1 week of age maintained at room temperature.

An attenuated recombinant CHV can be produced by inactivating a CHV gene that, due to that gene's inactivation, results in an attenuated virus. Methods to inactivate a gene are disclosed above. An attenuated CHV can be identified by exposing pups less than 1 week old to the recombinant virus to be tested and determining the percentage of exposed pups that die; such an exposure method is disclosed, for example, in Carmichael, ibid. If less than 100% percent of the pups die, the virus being tested is attenuated in accordance with the present invention. Suitable CHV genes to inactivate in order to produce an attenuated CHV include any gene that when inactivated leads to an attenuated virus, as determined using an assay as disclosed above. A preferred attenuated recombinant CHV of the present invention is a CHV having a recombinant genome in which a heterologous nucleic acid molecule is inserted into a gene, the insertion resulting in an attenuated virus.

An attenuated recombinant CHV has utility, for example, as a therapeutic composition to protect an animal from CHV infection and/or as a live CHV-based vaccine carrying a heterologous nucleic acid molecule. It is to be noted, however, that, as disclosed above, it is believed that CHV need not be attenuated for use as a live vaccine vector due to the low pathogenicity of natural CHV, particularly as compared to that of other herpesviruses.

One embodiment of the present invention is a recombinant CHV that can reproduce (i.e., grow) in tissue culture; that is, the virus is a reproduction competent CHV. A reproduction competent CHV is a CHV that upon in vitro infection of an appropriate host cell is able to use host cell machinery, as well as its own regulatory control regions and/or encoded enzymes, to effect self-reproduction, i.e., to form infectious virus.

Reproduction competent recombinant CHV genomes can have gene alterations in one or more genes non-essential for growth in vitro. Suitable gene targets (i.e., genes to alter) include any non-essential CHV gene. A non-essential CHV gene can be identified by altering a CHV gene within a CHV genome (e.g., by genetic engineering or classical mutagenesis) and demonstrating that the altered genome is capable of effecting self-reproduction in tissue culture. Preferred non-essential CHV genes to target include, but are not limited to, a CHV deoxyuridine triphosphate pyrophosphatase (CdUTPase) gene, a CHV glycoprotein C (CgC) gene, a CHV glycoprotein E (CgE) gene, a CHV glycoprotein G (CgG) gene, a CHV glycoprotein I (CgI) gene, a CHV serine-threonine protein kinase US3 (CPK) gene, a CHV thymidine kinase (CTK) gene, a CHV IR6 (CIR6) gene, a CHV US2 (CUS2) gene, a CHV tegument phosphoprotein US9 (CUS9) gene, a CHV membrane protein UL49 (CUL49) gene, a CHV membrane protein CHV UL49.5 (CUL49.5) gene, a CHV regulatory protein ICP0 (cICP0) gene, a CHV membrane protein UL51 (CUL51) gene, and a CHV membrane protein UL45 (CUL45) gene. Particularly preferred non-essential genes to target include a CdUTPase gene, a CgC gene, a CgE gene, a CgG gene, a CgI gene, a CUS2 gene and a CUS9 gene. It is to be noted that CHV regions and genes disclosed herein are named in accordance with herpesvirus nomenclature in that the names include "C" for canine and the rest of the name indicating the corresponding herpes simplex virus (HSV) homolog (e.g., "dUTPase"). For example, the CHV unique short region (CUS) is the shorter region of the CHV genome that has unique sequences, analogous to the US region of HSV; the CHV unique long region (CUL) is the longer region of CHV that has unique sequences, analogous to the UL region of HSV; and the CHV inverted repeat regions (CIRs) are analogous to the HSV IR regions. CUS genes are CHV genes that are homologs of (i.e., genes that share some degree of similarity with) HSV genes located in the US region of the HSV genome. CUL genes are CHV genes that are homologs of HSV genes located in the UL region of the HSV genome. CIR genes are CHV genes that are homologs of HSV genes located in the IR regions of the HSV or EHV genome. It is also to be noted that although the UL, US, and IR designations refer to the respective genes' locations in the HSV genome, they do not necessarily refer to the respective genes' locations in the CHV genome. For example, while CUS2 is partially in the IR region of CHV, HSV US2 is entirely in the US region of HSV.

Another embodiment of the present invention is a recombinant CHV that is defective for reproduction in tissue culture. A reproduction defective CHV is a CHV that when inserted into an appropriate host cell is unable to form infectious virus. Such a defective CHV has at least one inactive gene that encodes a protein essential for reproduction, including, but not limited to proteins essential for viral entry, immediate early or early gene expression, DNA replication, capsid assembly, and viral egress. Suitable gene targets include any essential CHV gene, with preferred targets being genes encoding proteins involved in viral entry and/or egress. CHV defective in viral entry and/or egress are easy to complement and are advantageous over most other reproduction defective mutants in that such virus are able to undergo one round of viral replication. An essential CHV gene can be identified by altering a CHV gene within a CHV genome and demonstrating (a) that the altered genome is not capable of effecting self-reproduction in tissue culture under wild type conditions or, if a temperature sensitive mutant, at a non-permissive temperature; and (b) that the altered genome can reproduce in a complementing cell line that expresses an active protein corresponding to the essential gene defect on the CHV genome (assuming the defect can be complemented in trans), or at a permissive temperature. Preferred essential CHV genes to target include, but are not limited to, a CHV glycoprotein D (CgD) gene, a CHV glycoprotein B (CgB) gene, a CHV alpha trans-inducing factor UL48 (CUL48) gene, a CHV helicase/primase UL52 (CUL52) gene, a CHV glycoprotein L (CgL) gene and a CHV ICP4 (cICP4) gene. Particularly preferred essential genes to target include a CgD gene and a CgB gene.

The present invention also includes cell lines that complement replication defective CHVs and use of such cell lines to produce replication defective viruses. As such, the present invention includes canine cell lines that complement, or supplement, a CHV defect in a gene encoding CgD, CgB, CUL48, or CUL52, and/or CgL. Such cell lines can be produced by a variety of means known to those skilled in the art. For example, a cell capable of complementing a CgD negative, or CgD-, CHV (i.e., a virus with a CHV genome having an inactive CgD gene), can be produced by stable integration of an active CgD gene into the cellular genome or by co-transfection of the CgD-CHV with a nucleic acid molecule capable of complementing the defective CgD gene. Such a nucleic acid molecule can be a nucleic acid containing an active CgD gene operatively linked to regulatory sequences to enable expression of the CgD gene in the transfected cell. In another embodiment, such a nucleic acid molecule can be incorporated into a virus that is co-infected with the CgD-CHV. Such methods can also be used to produce cell lines complementing other replication defective CHVs of the present invention. Any canine cell line that CHV can infect and that expresses the complementary active protein can be used in the production of reproduction-defective CHV. Examples include, but are not limited to, the following cell lines available from American Type Culture Collection (ATCC), Rockville, Md.: ATCC CRL-1542 A-72 (Tumor, canine), ATCC CRL-1430 Cf2Th (*Thymus, canine, Canis familiaris*), ATCC CRL-10389 DH82 (Monocyte-macrophage, canine), ATCC CRL-8468 D17 (Osteogenic sarcoma, canine), ATCC CCL-183 D-17 (Primary osteogenic sarcoma, canine, *Canis familiaris*), ATCC CCL-34.1 DoCl1 (S+L-) (Kidney, canine, *Canis familiaris*), ATCC CCL-34 MDCK (NBL-2) (Kidney, canine, *Canis familiaris*), and ATCC CCL-34.2 MDCK/SF (Kidney, canine, *Canis familiaris*), such cell lines expressing, preferably in a stable manner, the desired essential gene(s) for complementation. Particularly preferred complementing cell lines include MDCK cells that stably express CgD, CgB, CUL48, CUL52 and/or CgL.

An additional preferred CHV open reading frame to inactivate, or disrupt, includes a CUS8.5 open reading frame.

While not being bound by theory, it is believed that a reproductive defective virus-based vaccine may be safer than a reproduction competent virus-based vaccine. On the other hand, a reproduction competent virus-based vaccine may be more efficacious than a reproduction defective virus-based vaccine. Since CHV, as disclosed above, exhibits low pathogenicity, a reproduction competent recombinant CHV is a preferred embodiment of the present invention.

As heretofore disclosed, one embodiment of the present invention is a recombinant CHV having one or more inactive genes. Preferred recombinant CHV of the present invention include genomes in which one or more of the following CHV genes have been inactivated, preferably using recombinant techniques: a CdUTPase gene, a CgC gene, a CgE gene, a CgG gene, a CgI gene, a CPK gene, a CTK gene, a CIR6 gene, a CUS2 gene, a CUS9 gene, a CUL49 gene, a CUL51 gene, a CUL45 gene, a CgD gene, a CgB gene, a CUL48 gene, and a CUL52 gene, a CgL gene, a CUL49.5 gene, a CICP0 gene, a CICP4 gene, and a CUS8.5 open reading frame. Other than the genes encoding CgD, CgB, CUL48, CUL52, CgL and CICP4, the preferred genes to inactivate are nonessential genes. Each of the preferred genes to inactivate is a preferred target for the insertion of heterologous nucleic acid molecules; such insertion is a preferred method to inactivate these genes. More preferred recombinant CHV include genomes in which one or more of the following CHV genes have been inactivated, preferably using recombinant techniques: a CdUTPase gene, a CgC gene, a CgE gene, a CgG gene, a CgI gene, a CUS2 gene, a CUS9 gene, a CgD gene, and/or a CgB gene being more preferred. Also preferred are the corresponding recombinant CHV genomes.

Particularly preferred recombinant CHV of this embodiment include a CdUTPase negative CHV, a CgC negative CHV, a CgE negative CHV, a CgG negative CHV, a CgI negative CHV, a CPK negative CHV, a CTK negative CHV, a CIR6 negative CHV, a CUS2 negative CHV, a CUS9 negative CHV, a CUL49 negative CHV, a CUL51 negative CHV, a CUL45 negative CHV, a CgD negative CHV, a CgB negative CHV, a CUL48 negative CHV, a CUL52 negative CHV, a CgL negative CHV, a CUL49.5 negative CHV, a CICP0 negative CHV, a CICP4 negative CHV, and a CUS8.5 negative CHV. Particularly preferred recombinant CHV include a CdUTPase negative CHV, a CgC negative CHV, a CgE negative CHV, a CgG negative CHV, a CgI negative CHV, a CUS2 negative CHV, a CUS9 negative CHV, a CgD negative CHV, and a CgB negative CHV. Also preferred are the corresponding recombinant CHV genomes, as well as recombinant CHV and CHV genomes having more than one of these preferred genes inactivated. Examples of such CHV include, but are not limited to: a CUS2 negative, CdUTPase negative CHV; a CUS2 negative, CdUTPase negative, CgG negative CHV; and a CUS2 negative, CdUTPase negative, CgG negative, CgC negative CHV, a CUL49.5, CdUTPase negative CHV.

One embodiment of the present invention includes a recombinant CHV comprising a recombinant CHV genome comprising a heterologous nucleic acid molecule; i.e., the recombinant CHV genome includes one or more heterologous nucleic acid molecule(s) located, or positioned, in the CHV genome. The present invention also includes a recombinant CHV genome having a heterologous nucleic acid molecule in the genome. Also included is the use of such a CHV and/or CHV genome as a therapeutic composition as well as in the production of a compound encoded by the heterologous nucleic acid molecule(s).

As used herein, a heterologous nucleic acid molecule is a nucleic acid molecule that is not derived from CHV; that is, a heterologous nucleic acid molecule is isolated from a source other than CHV. An isolated nucleic acid molecule of the present invention can be obtained from its natural source, can be produced using recombinant DNA technology (e.g., by amplification, such as by polymerase chain reaction (PCR) amplification and/or cloning) or can be produced by chemical synthesis.

In accordance with the present invention, a heterologous nucleic acid molecule can be inserted into a CHV genome simply to inactivate a CHV gene. A heterologous nucleic acid molecule can also be inserted into a CHV genome to serve as a target for the insertion of a second heterologous nucleic acid molecule, such as to introduce a restriction enzyme site or a recombination site otherwise not present in the CHV genome. For example, CHV strain D 004 (available from ATCC), which does not contain a Sse83871, I-Sce-I, or NotI restriction enzyme site, can be genetically engineered to include one or more sites by inserting into the genome a heterologous nucleic acid molecule containing a Sse83871, I-Sce-I, and/or NotI site(s). Such a heterologous nucleic acid molecule is a good target for the insertion of another heterologous nucleic acid molecule. Other restriction enzyme sites lacking in CHV can be identified using techniques known to those skilled in the art. Without being bound by theory, it is believed that CHV is more likely to lack GC-rich restriction enzyme sites than AT-rich sites, since the CHV genome is AT-rich, as disclosed above.

Another example of a heterologous nucleic acid molecule to insert into a CHV genome is a gene encoding a selectable marker, such as, but not limited to, an *E. coli* lacz gene, a green fluorescent protein gene, a chloramphenicol, transacetylase gene, a xanthine-guanine phosphoribosyl transferase gene, a β-glucuronidase gene, a neomycin resistance gene, an *E. coli* hygromycin resistance gene, and a heterologous thymidine kinase gene (e.g., HSV, FHV; assuming the CHV genome is a CTK negative genome). The presence of such a gene in a CHV genome allows for the selection of recombinant CHV having such a marker gene, and includes the ability to distinguish recombinant CHV from natural CHV isolates. In addition, a second heterologous nucleic acid molecule can be inserted into such a selectable marker gene, thereby inactivating the protein encoded by the marker gene, allowing for yet another method to select for CHV having a desirable heterologous nucleic acid molecule. Methods to select CHV having selectable marker genes, as well as for the inactivation of such markers, is known to those skilled in the art.

A preferred embodiment of the present invention is a recombinant CHV genome, and corresponding virus, in which the genome contains a heterologous nucleic acid molecule operatively linked to a transcription control sequence. As such, the heterologous nucleic acid molecule can be transcribed when transfected into a cell. A heterologous nucleic acid molecule can be joined to CHV transcription control sequences, can be joined to its own or other homologous transcription control sequences, and/or can be joined to transcription control sequences heterologous to both the heterologous nucleic acid molecule and CHV. The heterologous nucleic acid molecule can also be operatively linked to other regulatory sequences. Suitable regulatory sequences include any regulatory sequence that can function in the present invention. Preferred transcription control sequences include those sequences that can function in canine cells, including, but not limited to: mammalian, preferably canine; viral; or natural (i.e., endogenous to the heterologous nucleic acid molecule) transcription control sequences. Examples of transcription control sequences include antibiotic resistance gene, baculovirus, *Heliothis zea* insect virus, vaccinia virus, herpesvirus, poxvirus, adenovirus, simian virus 40, retrovirus, actin, Rous sarcoma virus, heat shock, and mammalian hormone transcription control sequences. Additional suitable transcription control sequences include tissue-specific promoters and enhancers as well as lymphokine-inducible promoters (e.g., promoters inducible by interferons or interleukins). In one embodiment, expression of a heterologous nucleic acid molecule inserted into a CHV genome is mediated, at least in part, by a human cytomegalovirus (CMV) immediate early promoter and a bovine growth hormone polyadenylation site.

A heterologous nucleic acid molecule of the present invention can be located in any region of the CHV genome (i.e., in the UL, US, and/or IR regions), including, but not limited to, in an essential gene, in a non-essential gene, or in an intergenic region. As such, a heterologous nucleic acid molecule can be located in a coding region, a regulatory region, an intron, an untranslated region, or a non-transcribed region of a gene. A heterologous nucleic acid molecule can also be located in a direct or inverted repeat, including direct and/or inverted repeats within the IR, US or UL regions of CHV. For example, a heterologous nucleic acid molecule can be located in one or more CHV origins of replication (Cori), such as in CoriS.

In one embodiment, a heterologous nucleic acid molecule is located in a CHV genome such that a gene is inactivated. Suitable and preferred gene targets are as disclosed above, with non-essential gene targets being preferred.

In another embodiment, a heterologous nucleic acid molecule is located in a region of the CHV genome spanning from about the 3' end of the coding region of the CUL41 gene through about the 3' end of the coding region of the CUL38 gene. CUL41 gene refers to the CHV homolog of the HSV virion host shutoff protein UL41 gene. CUL38 gene refers to the CHV homolog of the HSV capsid protein VP19C UL38 gene. In most herpesviruses analyzed by cloning and sequencing techniques to date, the region between UL41 and UL38 contains genes encoding the large and small subunits of ribonucleotide reductase. The inventors have found, however, that the ribonucleotide reductase genes appear to be at least partially deleted in CHV in such a manner that there is an intergenic target in that region for heterologous nucleic acid molecule insertion.

A preferred recombinant CHV genome of the present invention comprises a heterologous nucleic acid molecule located in a region of the genome such that the heterologous nucleic acid molecule-containing CHV genome can be easily distinguished from a CHV genome not containing the heterologous nucleic acid molecule; that is, the heterologous nucleic acid molecule is inserted into a selectable region of the genome. Suitable selectable regions include any region of the CHV genome that, upon introduction of a heterologous nucleic acid molecule, leads to a detectable (e.g., growth-related, biochemical, or molecular) change in the CHV genome or CHV containing the genome. Examples of such selectable regions include, but are not limited to, a CTK gene and a CdUTPase gene. CHV genomes in which a heterologous nucleic acid molecule is inserted into a CTK gene or a CdUTPase gene can be selected using methods known to those skilled in the art; see for example, Kit et al, 1983, *Virology* 130, 381–389; and Holliday et al, 1991, *Antiviral Research* 16, 197–203.

Additional examples of selectable regions include restriction endonuclease sites, such as the HindIII site or XbaI site in the CdUTPase gene and the AscI site in the CUS2 gene. The AscI site is particularly preferred as there are no other AscI sites in the CHV genome. As such, a particularly preferred CHV of the present invention is a recombinant CHV having a CHV genome including a heterologous nucleic acid molecule in an AscI site in the CHV genome. Even more preferred is recombinant CHV strain D 004 having a heterologous nucleic acid molecule in an AscI site in the CHV genome. Also preferred are the corresponding genomes. Examples of methods to insert a heterologous nucleic acid molecule into a genome, including into restriction endonuclease site(s) in the genome, are disclosed herein. Such methods are known to those skilled in the art.

One embodiment of the present invention is a recombinant CHV genome having a heterologous nucleic acid molecule in one of the following regions of the CHV genome: a region spanning the 9,300 nucleotide AscI restriction endonuclease fragment, denoted herein as nCAsc$_{9300}$ that apparently includes the entire US region; a region spanning the 10,000 nucleotide fragment from AscI to the end of the genome, denoted herein as nCAsc$_{10000}$, that apparently essentially comprises an IR region, including the CIR6 gene; a region spanning the 3,000 nucleotide HindIII fragment, denoted herein as nCHin$_{3000}$, that spans from a portion of CUL48 through a portion of the CdUTPase gene; a region spanning the 1,900 nucleotide HindIII fragment, denoted herein as nCHin$_{1900}$, that includes the remainder of the CdUTPase gene through a portion of CUL52; a region spanning the 5,500 nucleotide HindIII fragment, denoted herein as nCHin$_{5500}$, that includes at least a portion of CgL, CICP0, and CICP4; and/or a region spanning the 8,500 nucleotide HindIII fragment, denoted herein as nCHin$_{8500}$, that includes a portion of CUL48, CUL45 and CgC. Details regarding the production of these and certain other nucleic acid molecules of the present invention are provided in the Examples section.

Also included in the present invention is a recombinant CHV genome having a heterologous nucleic acid molecule in a region of the genome spanning at least one of the following: a CHV US region comprising nCUS$_{5495}$, a CHV UL region comprising nCgC/CUL45$_{21001}$ a CgE gene comprising nCgE$_{750}$, a CgI gene comprising nCgI$_{161}$, a CUS9 gene comprising nCUS9$_{579}$, a CHV UL region comprising nCdUTP/CUL51$_{743}$, a CTK gene comprising nCTK$_{280}$, a CUL48 gene comprising nCUL48$_{294}$, a CUL49 gene included in nCHin$_{3000}$, a CUL52 gene comprising nCUL52$_{146}$, a CHV UL region comprising nCUL$_{1823}$, a CHV UL region comprising nCUL49/CUL48$_{2044}$, a CHV IR region comprising nCICP4$_{626}$, a CHV UL region comprising nCgL$_{655}$, a CHV UL region comprising nCUL52$_{749}$, a CHV UL region comprising nCdUTP$_{3200}$, as well as allelic variants of such (i.e., said, any of these) regions. As such, the present invention also includes a recombinant CHV genome having a heterologous nucleic acid molecule in a region of the genome spanning at least one of the following: a CIR6 gene including nCIR6$_{552}$, a CUS2 gene including nCUS2$_{1176}$, a CPK gene including nCPK$_{1203}$, a CgG gene including nCgG$_{1248}$, a CgD gene including nCgD$_{357}$, a CdUTPase gene including nCdUTP$_{459}$, a CUL51 gene including nCUL51$_{261}$, a CgD gene including nCgD$_{1038}$, a CgI gene including nCgI$_{1095}$, a CgE gene including nCgE$_{1569}$, a CUS8.5 open reading frame including nCUS8.5$_{237}$, a CUS9 gene including nCUS9$_{360}$, a CUL49 gene including nCUL49$_{420}$, a CUL48 gene including nCUL48$_{1269}$, a CICP4 gene including nCICP4$_{626}$, a CgL gene including nCgL$_{655}$, a CdUTPase gene including nCdUTP$_{918}$, a CUL49 gene including nCUL49$_{255}$, a CUL49.5 gene including nCUL49.5$_{261}$, and a CUL52 gene including nCUL52$_{749}$, as well as allelic variants of such regions.

As used herein, an allelic variant of a nucleic acid molecule, or region, for which nucleic acid sequence is provided herein is a nucleic acid molecule, or region, that occurs at essentially the same locus in another CHV genome as the nucleic acid molecule in CHV strain D 004, and that, due to natural variation caused by, for example, mutation or recombination, has a similar but not identical nucleic acid sequence. A coding region allelic variant typically encodes a protein having similar activity to that of the protein encoded by the gene to which it is being compared. An allelic variant can also comprise an alteration in the 5' or 3' untranslated regions of the gene, such as in regulatory control regions. Allelic variants are well known to those skilled in the art and would be expected to be found among the family of canine herpesviruses.

The present invention also includes a recombinant CHV genome having a heterologous nucleic acid molecule in a region of the genome spanning at least one of the following nucleic acid molecules: $nCUS_{5495}$ (and, as such, $nCIR6_{552}$, $nCUS2_{1176}$, $nCPK_{1203}$, $nCgG_{1248}$, and/or $nCgD_{357}$), $nCgC/CUL45_{2100}$, $nCgE_{750}$, $nCgI_{161}$, $nCUS9_{579}$, $nCdUTP/CUL51_{743}$ (and, as such, $nCdUTP_{459}$ and $nCUL51_{261}$), $nCTK_{280}$, $nCUL48_{294}$, $nCUL52_{146}$, $nCUS_{10592}$, $nCgD_{1038}$, $nCgI_{1095}$, $nCgE_{1569}$, $nCUS8.5_{237}$, $nCUS9_{360}$, $nCUL49/CUL48_{2044}$, $nCUL49_{420}$, $nCUL48_{1269}$, $nCICP4_{626}$, $nCgL_{655}$, $nCUL_{1823}$, $nCdUTP_{918}$, $nCUL49.5_{261}$, $nCUL49_{255}$, $nCUL52_{749}$, and/or $nCdUTP_{3200}$, as well as allelic variants of such regions.

A particularly preferred CHV genome of the present invention includes a heterologous nucleic acid molecule located in a region of the CHV genome comprising (e.g., including, represented by, or identified by) at least one of the following nucleic acid sequences: SEQ ID NO:1, SEQ ID NO:2, SEQ ID NO:3, SEQ ID NO:5, SEQ ID NO:7, SEQ ID NO:9, SEQ ID NO:11, SEQ ID NO:13, SEQ ID NO:14, SEQ ID NO:15, SEQ ID NO:17, SEQ ID NO:19, SEQ ID NO:20, SEQ ID NO:21, SEQ ID NO:23, SEQ ID NO:24, SEQ ID NO:25, SEQ ID NO:27, SEQ ID NO:28, SEQ ID NO:29, SEQ ID NO:31, SEQ ID NO:32, SEQ ID NO:33, SEQ ID NO:35, SEQ ID NO:37, SEQ ID NO:38, SEQ ID NO:51, SEQ ID NO:52, SEQ ID NO:53, SEQ ID NO:55, SEQ ID NO:57, SEQ ID NO:59, SEQ ID NO:61, SEQ ID NO:63, SEQ ID NO:64, SEQ ID NO:65, SEQ ID NO:67, SEQ ID NO:69, SEQ ID NO:70, SEQ ID NO:71, SEQ ID NO:73, SEQ ID NO:74, SEQ ID NO:75, SEQ ID NO:77, SEQ ID NO:78, SEQ ID NO:79, SEQ ID NO:81, SEQ ID NO:83, SEQ ID NO:85, SEQ ID NO:86, and/or SEQ ID NO:87, as well as complements of such regions and allelic variants of such regions. The relationships between certain nucleic acid molecules and nucleic acid sequences of the present invention are detailed below. It should be noted that since nucleic acid sequencing technology is not entirely error-free, the sequences represented by the SEQ ID NOs in the present invention at best represent apparent nucleic acid or amino acid sequences of CHV nucleic acid molecules or proteins of the present invention. It is also to be noted that a double-stranded nucleic acid molecule of the present invention for which a nucleic acid sequence has been determined for one strand that is represented by a SEQ ID NO also comprises a complementary strand having a sequence that is a complement of that SEQ ID NO. As such, nucleic acid molecules of the present invention, which can be either double-stranded or single-stranded, include those nucleic acid molecules that form stable hybrids under stringent hybridization conditions with either a given SEQ ID NO denoted herein and/or with the complement of that SEQ ID NO, which may or may not be denoted herein. Methods to deduce a complementary sequence are known to those skilled in the art.

The present invention includes a recombinant CHV genome that includes a heterologous nucleic acid molecule that encodes a protective compound; the present invention also includes a recombinant CHV containing such a genome. As used herein, a protective compound is a compound that when administered to an animal protects that animal from a disease corresponding to that compound. For example, a compound derived from *Dirofilaria immitis* protects an animal from heartworm and other related infections, whereas a compound derived from a virus protects an animal from disease caused by that and related viruses. As used herein, the ability of a compound to protect an animal from a disease refers to the ability of that protective compound to treat, ameliorate and/or prevent the disease.

A protective compound of the present invention includes, but is not limited to, a protective protein and a protective RNA species. Essentially any heterologous nucleic acid molecule that encodes a protective protein or RNA can be used in the present invention. A protective protein of the present invention can be, for example, an immunogen that elicits an immune response which will protect an animal from the corresponding disease or some other compound (e.g., an immunomodulator, a toxin, an enzyme, an antibody, or other binding protein) that neutralizes and/or reduces the disease. A protective RNA of the present invention can be, for example, an RNA-based drug, a ribozyme, a molecule capable of triple helix formation, or an antisense RNA that effectively prevents the expression of a detrimental protein, thereby protecting an animal from disease.

It is within the scope of the present invention to produce therapeutic compositions against a variety of diseases, including infectious diseases, genetic diseases, and other metabolic diseases, including diseases that lead to abnormal cell growth, degenerative processes, and/or immunological defects. Therapeutic compositions of the present invention can protect animals from a variety of diseases including, but not limited to, allergies, autoimmune diseases, cancers, cardiovascular diseases, graft rejection, hematopoietic disorders, immunodeficiency diseases, immunoproliferative diseases, immunosuppressive disorders, infectious diseases, inflammatory diseases, jaundice, septic shock, other immunological defects, as well as other genetic or metabolic defects.

One preferred embodiment of the present invention is a recombinant CHV having a heterologous nucleic acid molecule within its genome that encodes a compound that protects a canid, or other animal susceptible to CHV infection, from infectious disease. Such disease can be caused by a variety of infectious agents, including, but not limited to, helminth parasites, protozoan parasites, ectoparasites, fungi (including yeast), bacteria and/or viruses. It should also be noted that although some infectious agents have not been definitively classified into one of these groups, such infectious agents are also included in the present invention. A preferred protective compound is derived from (e.g., obtained from natural source or produced using recombinant or synthetic chemistry techniques) an infectious agent.

Preferred helminth infectious agents to target include nematodes, cestodes and trematodes, with filariid, ascarid, capillarid, strongylid, strongyloides, trichostrongyle, and trichurid, parasitic helminths being more preferred, and filariid nematodes being even more preferred. More preferred parasitic helminths to target include the following: *Aelurostrongylus, Ancylostoma, Angiostrongylus, Ascaris, Brugia, Bunostomum, Capillaria, Chabertia, Cooperia, Crenosoma, Dictyocaulus, Dioctophyme, Dipetalonema, Diphyllobothrium, Diplydium, Dirofilaria* (e.g., *D. immitis*), *Dracunculus, Echinococcus, Enterobius, Filaroides, Haemonchus, Loa, Mansonella, Muellerius, Nanophyetus, Necator, Nematodirus, Oesophagostomum, Onchocerca, Opisthorchis, Ostertagia, Parafilaria, Paragonimus, Parascaris, Physaloptera, Protostrongylus, Setaria, Spirometra, Spirocera, Stephanofilaria, Strongyloides, Strongylus, Taenia, Thelazia, Toxascaris, Toxocara, Trichinella, Trichostrongylus, Trichuris. Uncinaria*, and *Wuchereria*. More preferred helminths to target, particularly with respect to being canine pathogens include *Ancylostoma, Angiostrongylus, Brugia, Capillaria, Crenosoma, Dioctophyme, Dipetalonema, Diphyllobothrium, Diplydium, Dirofilaria, Echinococcus, Filaroides, Nanophyetus, Opisthorchis, Paragonimus, Physaloptera, Spirometra, Spirocera, Strongyloides, Taenia, Toxascaris, Toxocara, Trichinella, Trichuris*, and *Uncinaria*.

Preferred protozoal infectious agents to target include *Acetospora, Apicoplexa, Ciliophora, Labyrinthomorphorpha, Microspora, Myxozoa and Sarcomastigophora, with Babesia, Balantidium, Besnoitia, Cryptosporidium, Eimeria, Encephalitozoon, Entamoeba, Giardia, Hammondia, Hepatozoon, Isospora, Leishmania, Microsporidia, Neospora, Nosema, Pentatrichomonas, Plasmodium, Pneumocystis, Sarcocystis, Schistosoma, Theileria, Toxoplasma*, and *Trypanosoma*, being more preferred. More preferred protozoans to target, particularly with respect to being canine pathogens, include *Babesia, Balantidium, Besnoitia, Cryptosporidium, Encephalitozoon, Entamoeba, Giardia, Hammondia, Hepatozoon, Isospora, Leishmania, Microsporidia, Neospora, Pentatrichomonas, Pneumocystis, Sarcocystis, Schistosoma, Toxoplasma*, and *Trypanosoma*.

Preferred ectoparasite infectious agents to target include fleas, flies, mosquitoes, ticks, mites, lice, spiders, ants and true bugs, with fleas being more preferred. More preferred are fleas of the genera *Ctenocephalides, Ctopsyllus, Diamanus, Echidnophaga Nosopsyllus, Pulex, Tunga*, and *Xenopsylla*, with *Ctenocephalides canis* and *Ctenocephalides felis* fleas being particularly preferred.

Preferred fungal agents include *Absidia, Acremonium, Alternaria, Aspergillus, Basidiobolus, Bipolaris, Blastomyces, Candida, Chlamydia, Coccidioides, Conidiobolus, Cryptococcus, Curvalaria, Epidermophyton, Exophiala, Geotrichum, Histoplasma, Madurella, Malassezia, Microsporum, Moniliella, Mortierella, Mucor, Paecilomyces, Penicillium, Phialemonium, Phialophora, Prototheca, Pseudallescheria, Pseudomicrodochium, Pythium, Rhinosporidium, Rhizopus, Scolecobasidium, Sporothrix, Stemphylium, Trichophyton, Trichosporon*, and *Xylohypha*.

Preferred bacterial infectious agents to target include *Actinomyces, Bacillus, Bacteroides, Bordetella, Bartonella* (e.g., *B. henselae*), Borrelia (e.g., *B. burgdorferi*), *Brucella, Campylobacter, Capnocytophaga, Clostridium, Corynebacterium, Coxiella, Dermatophilus, Enterococcus, Ehrlichia* (e.g., *E. canis*), *Escherichia, Francisella, Fusobacterium, Haemobartonella, Helicobacter, Klebsiella*, L-form bacteria, *Leptospira, Listeria, Mycobacteria, Mycoplasma, Neorickettsia, Nocardia, Pasteurella, Peptococcus, Peptostreptococcus, Proteus, Pseudomonas, Rickettsia, Rochalimaea, Salmonella, Shigella, Staphylococcus, Streptococcus*, and *Yersinia* (e.g., *Y. pestis*).

Preferred virus infectious agents to target include adenoviruses, caliciviruses, coronaviruses, distemper viruses, hepatitis viruses, herpesviruses, immunodeficiency viruses, infectious peritonitis viruses, leukemia viruses, oncogenic viruses, panleukopenia viruses, papilloma viruses, parainfluenza viruses, parvoviruses, rabies viruses, and reoviruses, as well as other cancer-causing or cancer-related viruses.

A preferred recombinant CHV of the present invention includes a recombinant CHV genome having a heterologous nucleic acid molecule encoding a protective compound that elicits an immune response. As used herein, a protective compound that elicits an immune response refers to a compound that when administered to an animal in an appropriate manner, known to those skilled in the art, leads to the production of an immune response in that animal against the protective compound. The immune response, which can include humoral and/or cell-mediated components, preferably protects the immunized animal against the disease(s) targeted by the protective compound. As such, preferred protective compounds include, but are not limited to, antigens associated with diseases, as disclosed herein. Particularly preferred protective compounds of the present invention include *Dirofilaria immitis* antigens, *Toxoplasma gondii* antigens, Sarcocystis antigens, *Bartonella henselae* antigens, *Yersinia pestis* antigens, flea antigens, flea allergens, viral antigens, and cancer antigens. Even more preferred protective compounds are those disclosed in the following patent applications and patent publications, which are incorporated by reference herein in their entireties: U.S. Pat. No. 5,356,622, issued Oct. 18, 1994; U.S. Pat. No. 5,399,485, issued Mar. 21, 1995; U.S. Pat. No. 5,418,137, issued May 23, 1995; PCT Publication No. WO 92/13560, published Aug. 20, 1992; PCT Publication No. WO 93/10225, published May 27, 1993; PCT Publication No. WO 93/23077, published Nov. 25, 1993; PCT Publication No. WO 94/15593, published Jul. 21, 1994; PCT Publication No. WO 94/17813, published Aug. 18, 1994; PCT Publication No. WO 94/17824, published Aug. 18, 1994; PCT Publication No. WO 95/24198, published Sep. 14, 1995; PCT Publication No. WO 95/32988, published Dec. 7, 1995; U.S. Ser. No. 08/401,509, filed Mar. 9, 1995; U.S. Ser. No. 08/415,365, filed Mar. 30, 1995; U.S. Ser. No. 08/450,944, filed May 23, 1995; U.S. Ser. No. 08/473,034, filed Jun. 6, 1995; U.S. Ser. No. 08/482,304, filed Jun. 7, 1995; U.S. Ser. No. 08/485,434, filed Jun. 7, 1995; U.S. Ser. No. 08/486,036, filed Jun. 7, 1995; U.S. Ser. No. 08/558,735 filed Nov. 16, 1995; PCT Serial No. PCT/US95/13200, filed Oct. 6, 1995; PCT Serial No. PCT/US95/14442, filed Oct. 18, 1995; U.S. Ser. No. 08/630,822, filed Apr. 10, 1996; U.S. Ser. No. 08/602,262, filed Feb. 15, 1996; PCT Serial No.: PCT/US96/03133, filed Mar. 8, 1996; U.S. Ser. No. 08/639,075, filed Apr. 24, 1996; PCT Serial No. PCT/US96/07709, filed May 23, 1996; and PCT Serial No. PCT/US96/09848, filed Jun. 7, 1996, and related filings.

Another preferred protective compound of the present invention is an immunomodulator. Suitable immunomodulators include compounds that enhance the immune response as well as compounds that suppress the immune response. Compounds that enhance the immune response include compounds that preferentially enhance humoral immunity as well as compounds that preferentially enhance cell-mediated immunity. Suitable compounds can be selected depending on the disease being targeted. Suitable immunomodulators include, but are not limited to, cytokines, chemokines, superantigens, and other immunomodulators as well as compounds that induce the production of cytokines, chemokines and other immunomodulators. Examples of such protective compounds include, but are not limited to, granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interferon gamma, interferon gamma inducing factor I (IGIF), transforming growth factor beta (TGF-$\beta$), RANTES (regulated upon activation, normal T-cell expressed and presumably secreted), macrophage inflammatory proteins (e.g., MIP-1 alpha and MIP-1 beta), and Leishmania elongation initiating factor (LEIF).

One preferred embodiment of the present invention is a recombinant CHV having more than one heterologous nucleic acid molecule included in the CHV genome. Such a CHV can include two or more heterologous nucleic acid molecules encoding two or more protective compounds to protect an animal from a given disease (e.g., two or more heartworm antigens), or can include two or more heterologous nucleic acid molecules encoding protective compounds each targeted against a different disease (e.g., a compound to protect an animal against heartworm and a compound to protect an animals against a viral infection). A preferred multivalent CHV can also include an heterologous nucleic acid molecule encoding a protective compound that elicits an immune response as well as an heterologous nucleic acid molecule encoding an immunomodulator to enhance the desired immune response. Also included in the present invention are protective compounds that are fusion, or multivalent, proteins comprising more than one functional domain.

The present invention also includes recombinant CHV genomes. As such, the invention includes any CHV genome disclosed herein, including those included in recombinant CHV of the present invention. Also included in the present invention are cells comprising recombinant CHV genomes of the present invention. As used herein, a cell comprising a recombinant CHV genome is a cell into which a recombinant CHV genome has been introduced. Such introduction can be accomplished by any method by which a nucleic acid molecule can be inserted into a cell. Such methods, known to those skilled in the art, include, but are not limited to, infection (i.e., with a virus comprising the genome), transfection, transformation, electroporation, microinjection, lipofection, adsorption, and protoplast fusion. A preferred cell comprises a recombinant CHV having a heterologous nucleic acid molecule, which preferably is operatively linked to a transcription control sequence. Cells containing CHV genomes are useful in the production of recombinant CHV. Methods to produce recombinant CHV are disclosed herein.

The present invention also includes isolated CHV nucleic acid molecules. As used herein, a CHV nucleic acid molecule is a nucleic acid molecule that is derived from CHV. As such, the nucleic acid molecule can be produced, for example, by recovery of such a nucleic acid molecule directly from a CHV genome, by recombinant DNA techniques, or by chemical synthesis. That the CHV nucleic acid molecule is isolated indicates that the molecule is removed from its natural milieu. An isolated CHV nucleic acid molecule can include DNA, RNA, or derivatives of either DNA or RNA.

A preferred CHV nucleic acid molecule of the present invention is a CHV nucleic acid molecule that hybridizes under stringent hybridization conditions with at least one of the following: with a CdUTPase gene, a CgC gene, a CgE gene, a CgG gene, a CgI gene, a CPK gene, a CTK gene, a CIR6 gene, a CUS2 gene, a CUS9 gene, a CUL49 gene, a CUL51 gene, a CUL45 gene, a CgD gene, a CUL48 gene, a CgL gene, a CUL49.5 gene, a CICP4 gene, a CUS8.5 open reading frame, and/or a CUL52 gene; with other regions of a CUS; and/or with a region of the CHV genome spanning from about the 3' end of the coding region of the CUL41 gene through about the 3' end of the coding region of the CUL38 gene. The identifying characteristics of such regions, including the CHV genes listed, are heretofore described.

As used herein, stringent hybridization conditions refer to standard hybridization conditions under which nucleic acid molecules, including oligonucleotides, are used to identify molecules having similar nucleic acid sequences. Stringent hybridization conditions typically permit isolation of nucleic acid molecules having at least about 70% nucleic acid sequence identity with the nucleic acid molecule being used as a probe in the hybridization reaction. Formulae to calculate the appropriate hybridization and wash conditions to achieve hybridization permitting 30% or less mis-match between two nucleic acid molecules are disclosed, for example, in Meinkoth et al, 1984, *Anal. Biochem* 138, 267–284; Meinkoth et al, ibid, is incorporated by reference herein in its entirety. An example of such conditions includes, but is not limited to, the following: Oligonucleotide probes of about 18–25 nucleotides in length with $T_m$'s ranging from about 50° C. to about 65° C., for example, can be hybridized to nucleic acid molecules typically immobilized on a filter (e.g., nitrocellulose filter) in a solution containing 2× SSPE, 1% Sarkosyl, 5× Denhardts and 0.1 mg/ml denatured salmon sperm DNA at a temperature as calculated using the formulae of Meinkoth et al., ibid. for about 2 to about 12 hours. The filters are then washed 3 times in a wash solution containing 2× SSPE, 1% Sarkosyl at about 55° C. for about 15 minutes each. The filters can be further washed in a wash solution containing 2× SSPE, 1% Sarkosyl at about 55° C. for about 15 minutes per wash.

A CHV nucleic acid molecule of the present invention can include an isolated natural CHV gene or a homolog thereof, the latter of which is described in more detail below. A CHV nucleic acid molecule of the present invention can include one or more regulatory regions, full-length or partial coding regions, or combinations thereof. The minimal size of a CHV nucleic acid molecule of the present invention is the minimal size that can form a stable hybrid with one of the aforementioned CHV genes and other regions under stringent hybridization conditions.

Isolated CHV nucleic acid molecules include natural nucleic acid molecules and homologs thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode a CHV protein of the present invention or to form stable hybrids under stringent conditions with natural gene iisolates.

A CHV nucleic acid molecule homolog can be produced using a number of methods known to those skilled in the art (see, for example, Sambrook et al., ibid.). CHV nucleic acid molecule homologs can be selected from a mixture of modified nucleic acids by screening for the function of the protein encoded by the nucleic acid molecule and/or by hybridization with a CHV region as defined above.

An isolated CHV nucleic acid molecule of the present invention can include a nucleic acid sequence that encodes at least one CHV protein of the present invention; such proteins are discussed in further detail below. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a CHV protein.

One embodiment of the present invention is a CHV nucleic acid molecule that, when administered to an animal, is capable of protecting that animal from CHV infection. Such a CHV nucleic acid molecule can be, or encode, an antisense RNA, a molecule capable of triple helix formation, a ribozyme, or other nucleic acid-based drug compound. In an additional embodiment, a CHV nucleic acid molecule of the present invention can encode a protective protein, the nucleic acid molecule being delivered to the animal by direct injection (i.e, as a naked nucleic acid) or in a vehicle such as a recombinant virus vaccine or a recombinant cell vaccine.

One embodiment of the present invention is a CHV nucleic acid molecule that hybridizes under stringent hybridization conditions with $nCUS_{5495}$, $nCgC/CUL45_{2100}$, $nCgE_{750}$, $nCgI_{161}$, $nCUS9_{579}$, $nCdUTP/CUL51_{743}$, $nCTK_{280}$, $nCUL48_{294}$, a nCUL49 included in $nCHin_{3000}$, $nCUL52_{146}$, $nCgI_{1095}$, $nCgE_{1569}$, $nCUS8.5_{237}$, $nCUS9_{360}$, $nCUL49/CUL48_{2044}$, $nCUL49_{420}$, $nCUL48_{1269}$, $nCICP4_{626}$, $nCgL_{655}$, $nCUL_{1823}$, $nCdUTP_{918}$, $nCUL49.5_{261}$, $nCUL49_{255}$, and/or $nCUL52_{749}$. Such a CHV nucleic acid molecule can also hybridize under stringent hybridization conditions with $nCAsc_{9300}$, $nCAsc_{10000}$, $nCHin_{3000}$, $nCHin_{1900}$, $nCHin_{5500}$, $nCHin_{8500}$, $nCIR6_{552}$, $nCUS2_{1176}$, $nCPK_{1203}$, $nCgG_{1248}$, $nCgD_{357}$, $nCdUTP_{459}$, $nCTK_{279}$, $nCUS9_{450}$, $nCUL48_{291}$, $nCUL51_{261}$, $nCUL52_{144}$, $nCgI_{159}$, $nCUS_{10592}$, $nCICP4_{624}$, $nCgL_{516}$, $nCUL52_{747}$, $nCdUTP_{858}$, and/or $nCdUTP_{3200}$. At least some of such CHV nucleic acid molecules can hybridize under stringent hybridization conditions with a nucleic acid molecule having nucleic acid sequence SEQ ID NO:1, SEQ ID NO:2, SEQ ID NO:13, SEQ ID NO:14, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:35, SEQ ID NO:37, SEQ ID NO:51, SEQ ID NO:52, SEQ ID NO:63, SEQ ID NO:64, SEQ ID NO:69, SEQ ID NO:70, SEQ ID NO:71, SEQ ID NO:73, SEQ ID NO:74, SEQ ID NO:77, SEQ ID NO:78, SEQ ID NO:85, SEQ ID NO:86, and/or SEQ ID NO:87, as well as complements of such sequences.

SEQ ID NO:1 and SEQ ID NO:2 represent the deduced nucleic acid sequences of the two complementary strands of $nCUS_{5495}$. Translation of SEQ ID NO:1 and SEQ ID NO:2 indicates that nucleic acid molecule $nCUS_{5495}$ encodes CIR6, CUS2, CPK and CgG proteins as well as a portion of a CgD protein. Specifically, SEQ ID NO:2 includes: a coding region for a CIR6 protein of about 183 amino acids, denoted herein as $nCIR6_{552}$ and represented by SEQ ID NO:3, assuming a start codon spanning about nucleotides 4566–4568 and a stop codon spanning about nucleotides 5115–5117 of SEQ ID NO:2; and a coding region for a CUS2 protein of about 391 amino acids, denoted herein as $nCUS2_{1176}$ and represented by SEQ ID NO:5, assuming a start codon spanning about nucleotides 3232–3234 and a stop codon spanning about nucleotides 4405–4407 of SEQ ID NO:2. The amino acid sequences of the respective encoded proteins $PCIR6_{183}$ and $PCUS2_{391}$ are represented by SEQ ID NO:4 and SEQ ID NO:6. SEQ ID NO:1 includes: a coding region for a CPK protein of about 400 amino acids, denoted herein as $nCPK_{1203}$ and represented by SEQ ID NO:7, assuming a start codon spanning about nucleotides 2384–2386 and a stop codon spanning about nucleotides 3584–3586 of SEQ ID NO:1; a coding region for a CgG protein of about 415 amino acids, denoted herein as $nCgG_{1248}$ and represented by SEQ ID NO:9, assuming a start codon spanning about nucleotides 3698–3700 and a stop codon spanning about nucleotides 4943–4945 of SEQ ID NO:1; and a partial coding region for a CgD protein of about 119 amino acids, denoted herein as $nCgD_{357}$ and represented by SEQ ID NO:11, assuming a start codon spanning about nucleotides 5137–5139. The amino acid sequences of the respective encoded proteins $PCPK_{400}$, $PCgG_{415}$, and $PCgD_{119}$ are represented by SEQ ID NO:8, SEQ ID NO:10 and SEQ ID NO:12.

SEQ ID NO:13 and SEQ ID NO:14 represent the deduced nucleic acid sequences of the two complementary strands of $nCdUTP/CUL51_{743}$. SEQ ID NO:13 includes a partial coding region for a CdUTPase protein of about 152 amino acids, denoted herein as $nCdUTP_{459}$ and represented by SEQ ID NO:15, assuming a first in-frame codon spanning about nucleotides 3–5, and a stop codon spanning about nucleotides 459–461 of SEQ ID NO:13. The amino acid sequence of the encoded protein $PCdUTP_{152}$ is represented by SEQ ID NO:16. SEQ ID NO:14 includes a partial coding region for a CUL51 protein of about 86 amino acids, denoted herein as $nCUL51_{261}$ and represented by SEQ ID NO:33, assuming a first in-frame codon spanning about nucleotides 1–3, and a stop codon spanning about nucleotides 259–261 of SEQ ID NO:14. The amino acid sequence of the encoded protein PCUL51$_{86}$ is represented by SEQ ID NO:34.

SEQ ID NO:17 and SEQ ID NO:19 represent the deduced nucleic acid sequences of the two complementary strands of nCUS9$_{579}$. SEQ ID NO:17 includes a coding region for a CUS9 protein of about 149 amino acids, denoted herein as nCUS9$_{450}$ and represented by SEQ ID NO:20, assuming a start codon spanning about nucleotides 54–56 and a stop codon spanning about nucleotides 501–503 of SEQ ID NO:17. The amino acid sequence of the encoded protein PCUS9$_{149}$ is represented by SEQ ID NO:18.

SEQ ID NO:21 and SEQ ID NO:23 represent the deduced nucleic acid sequences of the two complementary strands of nCUL48$_{294}$. SEQ ID NO:21 includes a partial coding region for a CUL48 protein of about 97 amino acids, denoted herein as nCUL48$_{29}$, and represented by SEQ ID NO:24, assuming a first in-frame codon spanning about nucleotides 3–5 of SEQ ID NO:21. The amino acid sequence of the encoded protein PCUL48$_{97}$ is represented by SEQ ID NO:22.

SEQ ID NO:25 and SEQ ID NO:27 represent the deduced nucleic acid sequences of the two complementary strands of nCUL52$_{146}$. SEQ ID NO:25 includes a partial coding region for a CUL52 protein of about 48 amino acids, denoted herein as nCUL52$_{144}$ and represented by SEQ ID NO:28, assuming a first in-frame codon spanning about nucleotides 1–3 of SEQ ID NO:25. The amino acid sequence of the encoded protein PCUL52$_{48}$ is represented by SEQ ID NO:26.

SEQ ID NO:29 and SEQ ID NO:31 represent the deduced nucleic acid sequences of the two complementary strands of nCgI$_{161}$. SEQ ID NO:29 includes a partial coding region for a CgI protein of about 53 amino acids, denoted herein as nCgI$_{159}$ and represented by SEQ ID NO:32, assuming a first in-frame codon spanning about nucleotides 3–5 of SEQ ID NO:29. The amino acid sequence of the encoded protein PCgI$_{53}$ is represented by SEQ ID NO:30.

SEQ ID NO:35 and SEQ ID NO:37 represent the deduced nucleic acid sequences of the two complementary strands of nCTK$_{280}$. SEQ ID NO:35 includes a partial coding region for a CTK protein of about 93 amino acids, denoted herein as nCTK$_{279}$ and represented by SEQ ID NO:38, assuming a first in-frame codon spanning about nucleotides 2–4 of SEQ ID NO:35. The amino acid sequence of the encoded protein PCTK$_{93}$ is represented by SEQ ID NO:36.

The identities of additional nucleic acid molecules, nucleic acid sequences, proteins, and amino acid sequences are presented in the Examples.

Comparison of the CHV nucleic acid sequences SEQ ID NO:1, SEQ ID NO:2, SEQ ID NO:3, SEQ ID NO:5, SEQ ID NO:7, SEQ ID NO:9, SEQ ID NO:13, SEQ ID NO:14, SEQ ID NO:15, SEQ ID NO:17, SEQ ID NO:19, SEQ ID NO:20, SEQ ID NO:21, SEQ ID NO:23, SEQ ID NO:24, SEQ ID NO:25, SEQ ID NO:27, SEQ ID NO:28,, SEQ ID NO:29, SEQ ID NO:31, SEQ ID NO:32, SEQ ID NO:33, SEQ ID NO:35, SEQ ID NO:37, SEQ ID NO:38, SEQ ID NO:51, SEQ ID NO:52, SEQ ID NO:55, SEQ ID NO:57, SEQ ID NO:59, SEQ ID NO:61, SEQ ID NO:63, SEQ ID NO:64, SEQ ID NO:65, SEQ ID NO:67, SEQ ID NO:69, SEQ ID NO:70, SEQ ID NO:71, SEQ ID NO:73, SEQ ID NO:74, SEQ ID NO:75, SEQ ID NO:77, SEQ ID NO:78, SEQ ID NO:79, SEQ ID NO:81, SEQ ID NO:83, SEQ ID NO:85, SEQ ID NO:86, and SEQ ID NO:87 with known sequences indicates that none of these CHV nucleic acid sequences share more than about 70% identity (many, if not all, sharing significantly less identity) with a known nucleic acid sequence. As such, a preferred CHV nucleic acid molecule has a nucleic acid sequence that is at least about 80%, preferably at least about 85%, more preferably at least about 90%, even more preferably at least about 95%, and even more preferably at least about 99% identical to nucleic acid sequence SEQ ID NO:1, SEQ ID NO:2, SEQ ID NO:3, SEQ ID NO:5, SEQ ID NO:7, SEQ ID NO:9, SEQ ID NO:13, SEQ ID NO:14, SEQ ID NO:15, SEQ ID NO:17, SEQ ID NO:19, SEQ ID NO:20, SEQ ID NO:21, SEQ ID NO:23, SEQ ID NO:24, SEQ ID NO:25, SEQ ID NO:27, SEQ ID NO:28, SEQ ID NO:29, SEQ ID NO:31, SEQ ID NO:32, SEQ ID NO:33, SEQ ID NO:35, SEQ ID NO:37, SEQ ID NO:38, SEQ ID NO:51, SEQ ID NO:52, SEQ ID NO:55, SEQ ID NO:57, SEQ ID NO:59, SEQ ID NO:61, SEQ ID NO:63, SEQ ID NO:64, SEQ ID NO:65, SEQ ID NO:67, SEQ ID NO:69, SEQ ID NO:70, SEQ ID NO:71, SEQ ID NO:73, SEQ ID NO:74, SEQ ID NO:75, SEQ ID NO:77, SEQ ID NO:78, SEQ ID NO:79, SEQ ID NO:81, SEQ ID NO:83, SEQ ID NO:85, SEQ ID NO:86, and/or SEQ ID NO:87, as well as complements of such sequences.

A more preferred CHV nucleic acid molecule of the present invention includes at least a portion of CHV nucleic acid molecule nCAsc$_{9300}$, nCAsc$_{10000}$, nCHin$_{3000}$, nCHin$_{1900}$, nCHin$_{5500}$, nCHin$_{8500}$, nCUS$_{5495}$, nCIR6$_{552}$, nCUS2$_{1176}$, nCPK$_{1203}$, nCgG$_{1248}$, nCdUTP/CUL51$_{743}$, nCdUTP$_{459}$, nCUS9$_{579}$, nCUS9$_{450}$, nCUL48$_{294}$, nCUL48$_{291}$, nCUL52$_{146}$, nCUL52$_{144}$, nCgI$_{161}$, nCgI$_{159}$, nCgE$_{750}$, nCTK$_{280}$, nCTK$_{279}$, nCUL51$_{261}$, nCUS$_{10592}$, nCgI$_{1095}$, nCgE$_{1569}$, nCUS8.5$_{237}$, nCUS9$_{360}$, nCUL49/CUL48$_{2044}$, nCUL49$_{420}$, nCUL48$_{1269}$, nCICP4$_{626}$, nCICP4$_{624}$, nCgL$_{655}$, nCgL$_{516}$, nCUL$_{1823}$, nCdUTP$_{918}$, nCUL49.5$_{261}$, nCUL49$_{255}$, nCUL52$_{749}$, nCUL52$_{747}$, nCdUTP$_{858}$, and/or nCdUTP$_{3200}$, as well as allelic variants of those CHV nucleic acid molecules. Such CHV nucleic acid molecules can include nucleotides in addition to those included in the defined fragments; examples of such CHV nucleic acid molecules include full-length genes, full-length coding regions, or nucleic acid molecules encoding multivalent proteins. Particularly preferred CHV nucleic acid molecules are nCAsc$_{9300}$, nCAsc$_{10000}$, nCHin$_{3000}$, nCHin$_{1900}$, nCHin$_{5500}$, nCHin$_{8500}$, nCUS$_{5495}$, nCIR6$_{552}$, nCUS2$_{1176}$, nCPK$_{1203}$, nCgG$_{1248}$, nCdUTP/CUL51$_{743}$, nCdUTP$_{459}$, nCUS9$_{579}$, nCUS9$_{450}$, nCUL48$_{294}$, nCUL48$_{291}$, nCUL52$_{146}$, nCUL52$_{144}$, nCgI$_{161}$, nCgI$_{159}$, nCgE$_{750}$, nCTK$_{280}$, nCTK$_{279}$, nCUL51$_{261}$, nCUS$_{10592}$, nCgI$_{1095}$, nCgE$_{1569}$, nCUS8.5$_{237}$, nCUS9$_{360}$, nCUL49/CUL48$_{2044}$, nCUL49$_{420}$, nCUL48$_{1269}$, nCICP4$_{626}$, nCICP4$_{624}$, nCgL$_{655}$, nCgL$_{516}$, nCUL$_{1823}$, nCdUTP$_{918}$, nCUL49.5$_{261}$, nCUL49$_{255}$, nCUL52$_{749}$, nCUL52$_{747}$, nCdUTP$_{858}$, and/or nCdUTP$_{3200}$.

Similarly, a preferred CHV nucleic acid molecule of the present invention includes at least a portion of nucleic acid sequence SEQ ID NO:1, SEQ ID NO:2, SEQ ID NO:3, SEQ ID NO:5, SEQ ID NO:7, SEQ ID NO:9, SEQ ID NO:13, SEQ ID NO:14, SEQ ID NO:15, SEQ ID NO:17, SEQ ID NO:19, SEQ ID NO:20, SEQ ID NO:21, SEQ ID NO:23, SEQ ID NO:24, SEQ ID NO:25, SEQ ID NO:27, SEQ ID NO:28, SEQ ID NO:29, SEQ ID NO:31, SEQ ID NO:32, SEQ ID NO:33, SEQ ID NO:35, SEQ ID NO:37, SEQ ID NO:38, SEQ ID NO:51, SEQ ID NO:52, SEQ ID NO:55, SEQ ID NO:57, SEQ ID NO:59, SEQ ID NO:61, SEQ ID NO:63, SEQ ID NO:64, SEQ ID NO:65, SEQ ID NO:67, SEQ ID NO:69, SEQ ID NO:70, SEQ ID NO:71, SEQ ID NO:73, SEQ ID NO:74, SEQ ID NO:75, SEQ ID NO:77, SEQ ID NO:78, SEQ ID NO:79, SEQ ID NO:81, SEQ ID NO:83, SEQ ID NO:85, SEQ ID NO:86, and/or SEQ ID NO:87; or a complement of SEQ ID NO:3, SEQ ID NO:5, SEQ ID NO:7, SEQ ID NO:9, SEQ ID NO:15, SEQ ID NO:20, SEQ ID NO:24, SEQ ID NO:28, SEQ ID NO:32, SEQ ID NO:33, SEQ ID NO:38, SEQ ID NO:55, SEQ ID NO:57, SEQ ID NO:59, SEQ ID NO:61, SEQ ID NO:65, SEQ ID NO:67, SEQ ID NO:71, SEQ ID NO:75, SEQ ID NO:79, SEQ ID NO:81, SEQ ID NO:83, and/or SEQ ID NO:87; as well as allelic variants of such nucleic acid molecules. More preferred is a nucleic acid molecule that includes at least one of the following nucleic acid sequences: SEQ ID NO:1, SEQ ID NO:2, SEQ ID NO:3, SEQ ID NO:5, SEQ ID NO:7, SEQ ID NO:9, SEQ ID NO:13, SEQ ID NO:14, SEQ ID NO:15, SEQ ID NO:17, SEQ ID NO:19, SEQ ID NO:20, SEQ ID NO:21, SEQ ID NO:23, SEQ ID NO:24, SEQ ID NO:25, SEQ ID NO:27, SEQ ID NO:28, SEQ ID NO:29, SEQ ID NO:31, SEQ ID NO:32, SEQ ID NO:33, SEQ ID NO:35, SEQ ID NO:37, SEQ ID NO:38, SEQ ID NO:51, SEQ ID NO:52, SEQ ID NO:55, SEQ ID NO:57, SEQ ID NO:59, SEQ ID NO:61, SEQ ID NO:63, SEQ ID NO:64, SEQ ID NO:65, SEQ ID NO:67, SEQ ID NO:69, SEQ ID NO:70, SEQ ID NO:71, SEQ ID NO:73, SEQ ID NO:74, SEQ ID NO:75, SEQ ID NO:77, SEQ ID NO:78, SEQ ID NO:79, SEQ ID NO:81, SEQ ID NO:83, SEQ ID NO:85, SEQ ID NO:86, and/or SEQ ID NO:87; or a complement of SEQ ID NO:3, SEQ ID NO:5, SEQ ID NO:7, SEQ ID NO:9, SEQ ID NO:15, SEQ ID NO:20,, SEQ ID NO:24, SEQ ID NO:28, SEQ ID NO:32, SEQ ID NO:33, SEQ ID NO:38, SEQ ID NO:55, SEQ ID NO:57, SEQ ID NO:59, SEQ ID NO:61, SEQ ID NO:65, SEQ ID NO:67, SEQ ID NO:71, SEQ ID NO:75, SEQ ID NO:79, SEQ ID NO:81, SEQ ID NO:83, and/or SEQ ID NO:87; also included are nucleic acid molecules that are allelic variants of nucleic acid molecules having those nucleic acid sequences. Such nucleic acid molecules can include nucleotides in addition to those included in the SEQ ID NOs.

The present invention also includes CHV nucleic acid molecules encoding a protein, including nucleic acid molecules that have been modified to accommodate codon usage properties of the cells in which such nucleic acid molecules are to be expressed. CHV proteins of the present invention are described in more detail below. Particularly preferred nucleic acid molecules are those that encode a protein having at least one of the following amino acid sequences: SEQ ID NO:4, SEQ ID NO:6, SEQ ID NO:8, SEQ ID NO:10, SEQ ID NO:16, SEQ ID NO:18, SEQ ID NO:22, SEQ ID NO:26, SEQ ID NO:30, SEQ ID NO:34, SEQ ID NO:36, SEQ ID NO:56, SEQ ID NO:58, SEQ ID NO:60, SEQ ID NO:62, SEQ ID NO:66, SEQ ID NO:68, SEQ ID NO:72, SEQ ID NO:76, SEQ ID NO:80, SEQ ID NO:82, SEQ ID NO:84, and/or SEQ ID NO:88.

The present invention also includes CHV nucleic acid molecules that are oligonucleotides capable of hybridizing, under stringent hybridization conditions, with complementary regions of other, preferably longer, CHV nucleic acid molecules of the present invention. Oligonucleotides of the present invention can be RNA, DNA, or derivatives of either. The minimal size of such oligonucleotides is the size required to form a stable hybrid between a given oligonucleotide and the complementary sequence on another nucleic acid molecule of the present invention. Minimal size characteristics are disclosed herein. The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to inhibit CHV infection as disclosed herein.

The present invention also includes an isolated CHV protein encoded by a CHV nucleic acid molecule of the present invention. As such, the present invention includes a CHV protein encoded by a CHV nucleic acid molecule that hybridizes under stringent hybridization conditions with at least one of the following: a CdUTPase gene, a CgC gene, a CgE gene, a CgG gene, a CgI gene, a CPK gene, a CTK gene, a CIR6 gene, a CUS2 gene, a CUS9 gene, a CUL49 gene, a CUL51 gene, a CUL45 gene, a CgD gene, a CUL48 gene, and/or a CUL52 gene; and/or with other portions of a CUS region; and/or with a CgL gene, a CUL49.5 gene, a CICP4 gene, and/or a CUS8.5 open reading frame.

According to the present invention, an isolated, or biologically pure, protein, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology or can be produced by chemical synthesis. As used herein, a CHV protein can be a full-length protein or any homolog of such a protein. Examples of CHV homologs include CHV proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homolog retains a desired activity of the natural protein, such as, but not limited to, enzymatic activity, activity important for viral growth, and/or ability to elicit an immune response. These activities can be measured using techniques known to those skilled in the art.

CHV protein homologs can be the result of natural allelic variation or natural mutation. CHV protein homologs of the present invention can also be produced using techniques known in the art including, but not limited to, direct modifications to the protein or modifications to the gene encoding the protein using, for example, classic or recombinant DNA techniques to effect random or targeted mutagenesis.

The minimal size of a CHV protein homolog of the present invention is a size sufficient to be encoded by a nucleic acid molecule capable of forming a stable hybrid (i.e., hybridize under stringent hybridization conditions) with the complementary sequence of a nucleic acid molecule encoding the corresponding natural protein. As such, the size of the nucleic acid molecule encoding such a protein homolog is dependent on nucleic acid composition and percent homology between the nucleic acid molecule and complementary sequence. It should also be noted that the extent of homology required to form a stable hybrid can vary depending on whether the homologous sequences are interspersed throughout the nucleic acid molecules or are clustered (i.e., localized) in distinct regions on the nucleic acid molecules. The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode a CHV protein homolog of the present invention is from about 12 to about 18 nucleotides in length. There is no limit, other than a practical limit, on the maximal size of such a nucleic acid molecule in that the nucleic acid molecule can include a portion of a gene, an entire gene, or multiple genes, or portions thereof. Similarly, the minimal size of a CHV protein homolog of the present invention is from about 4 to about 6 amino acids in length, with preferred sizes depending on whether full-length, fusion, or other functional portions of such proteins are desired.

One embodiment of the present invention is a CHV protein that can protect an animal from disease, preferably by eliciting an immune response against CHV, and/or can detect CHV infection in an animal. The minimum size of such a protein is a minimum size sufficient to form an epitope, a size that typically is at least from about 5 to about 9 amino acids. As is appreciated by those skilled in the art, an epitope can include amino acids that naturally are contiguous to each other as well as amino acids that, due to the tertiary structure of the natural protein, are in sufficiently close proximity to form an epitope.

The present invention also includes mimetopes of CHV proteins that can be used in accordance with methods as disclosed for CHV proteins of the present invention. As used herein, a mimetope of a CHV protein of the present invention refers to any compound that is able to mimic the activity of such a CHV protein, often because the mimetope has a structure that mimics the CHV protein. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

One embodiment of the present invention is a fusion, or multivalent, protein that includes a CHV protein-containing domain attached to another functional domain. Such a domain can be an entire protein, or function portion thereof. Examples of such domains include not only protective compounds as disclosed above, but also domains that enhance a protein's stability (e.g., during production, storage and/or use) or that aid in protein purification.

A preferred isolated protein of the present invention is a protein encoded by a nucleic acid molecule that hybridizes under stringent hybridization conditions with $nCIR6_{552}$, $nCUS2_{1176}$, $nCPK_{1203}$, $nCgG_{1248}$, $nCgD_{357}$, $nCgC/CUL45_{2100}$, $nCdUTP_{459}$, $nCUS9_{450}$, $nCUL48_{291}$, $nCUL52_{144}$, $nCgI_{159}$, $nCgE_{750}$, $nCTK_{279}$, $nCUL51_{261}$, $nCgI_{1095}$, $nCgE_{1569}$, $nCUS8.5_{237}$, $nCUS9_{360}$, $nCUL49/CUL48_{2044}$, $nCUL49_{420}$, $nCUL48_{1269}$, $nCICP4_{626}$, $nCgL_{655}$, $nCUL_{1823}$, $nCdUTP_{918}$, $nCUL49.5_{261}$, $nCUL49_{255}$, and/or $nCUL52_{749}$. Also included is a protein that hybridizes under stringent hybridization conditions with $nCAsc_{9300}$, $nCAsc_{10000}$, $nCHin_{3000}$, $nCHin_{1900}$, $nCHin_{5500}$ and/or $nCHin_{8500}$. A further preferred isolated protein is encoded by a nucleic acid molecule that hybridizes under stringent hybridization conditions with a nucleic acid molecule having the complement of nucleic acid sequence SEQ ID NO:3, SEQ ID NO:5, SEQ ID NO:7, SEQ ID NO:9, SEQ ID NO:11, SEQ ID NO:15, SEQ ID NO:20, SEQ ID NO:24, SEQ ID NO:28, SEQ ID NO:32, SEQ ID NO:33, SEQ ID NO:38, SEQ ID NO:55, SEQ ID NO:57, SEQ ID NO:59, SEQ ID NO:61, SEQ ID NO:65, SEQ ID NO:67, SEQ ID NO:71, SEQ ID NO:75, SEQ ID NO:79, SEQ ID NO:81, SEQ ID NO:83, and/or SEQ ID NO:87, or by an allelic variant of any of such nucleic acid molecules. Proteins encoded by nucleic acid sequences SEQ ID NO:3, SEQ ID NO:5, SEQ ID NO:7, SEQ ID NO:9, SEQ ID NO:11, SEQ ID NO:15, SEQ ID NO:20, SEQ ID NO:24, SEQ ID NO:28, SEQ ID NO:32, SEQ ID NO:33, SEQ ID NO:38, SEQ ID NO:55, SEQ ID NO:57, SEQ ID NO:59, SEQ ID NO:61, SEQ ID NO:65, SEQ ID NO:67, SEQ ID NO:71, SEQ ID NO:75, SEQ ID NO:79, SEQ ID NO:81, SEQ ID NO:83, and SEQ ID NO:87 have amino acid sequences SEQ ID NO:4, SEQ ID NO:6, SEQ ID NO:8, SEQ ID NO:10, SEQ ID NO:12, SEQ ID NO:16, SEQ ID NO:18, SEQ ID NO:22, SEQ ID NO:26, SEQ ID NO:30, SEQ ID NO:34, SEQ ID NO:36, SEQ ID NO:26, SEQ ID NO:58, SEQ ID NO:60, SEQ ID NO:62, SEQ ID NO:66, SEQ ID NO:68, SEQ ID NO:72, SEQ ID NO:76, SEQ ID NO:80, SEQ ID NO:82, SEQ ID NO:84, and SEQ ID NO:88, respectively.

Comparison of the CHV amino acid sequences SEQ ID NO:4, SEQ ID NO:6, SEQ ID NO:8, SEQ ID NO:10, SEQ ID NO:16, SEQ ID NO:18, SEQ ID NO:22, SEQ ID NO:26, SEQ ID NO:30, SEQ ID NO:34, SEQ ID NO:36, SEQ ID NO:56, SEQ ID NO:58, SEQ ID NO:60, SEQ ID NO:62, SEQ ID NO:66, SEQ ID NO:68, SEQ ID NO:72, SEQ ID NO:76, SEQ ID NO:80, SEQ ID NO:82, SEQ ID NO:84, and SEQ ID NO:88 with known sequences indicates that none of these CHV amino acid sequences share more than about 75% identity (many, if not all, sharing significantly less identity) with a known amino acid sequence.

A preferred CHV protein has an amino acid sequence that is at least about 80%, preferably at least about 85%, more preferably at least about 90%, even more preferably at least about 95%, and even more preferably at least about 99% identical to amino acid sequence SEQ ID NO:4, SEQ ID NO:6, SEQ ID NO:8, SEQ ID NO:10, SEQ ID NO:16, SEQ ID NO:18, SEQ ID NO:22, SEQ ID NO:26, SEQ ID NO:30, SEQ ID NO:34, SEQ ID NO:36, SEQ ID NO:56, SEQ ID NO:58, SEQ ID NO:60, SEQ ID NO:62, SEQ ID NO:66, SEQ ID NO:68, SEQ ID NO:72, SEQ ID NO:76, SEQ ID NO:80, SEQ ID NO:82, SEQ ID NO:84, and/or SEQ ID NO:88.

A more preferred CHV protein includes at least a portion of $PCIR6_{183}$, $PCUS2_{391}$, $PCPK_{400}$, $PCgG_{415}$, $PCdUTP_{152}$, $PCUS9_{149}$, $PCUL48_{97}$, $PCUL52_{48}$, $PCUL51_{86}$, $PCgI_{53}$, $PCTK_{93}$, $PCgI_{364}$, $PCgE_{522}$, $PCUS8.5_{78}$, $PCUS9_{119}$, $PCUL49_{139}$, $PCUL48_{422}$, $PCICP4_{208}$, $PCgL_{171}$, $PCdUTP_{305}$, $PCUL49.5_{86}$, $PCUL49_{85}$, and/or $PCUL52_{249}$, as well as proteins encoded by allelic variants of the nucleic acid molecules encoding such proteins. Also preferred are proteins including at least a portion of CgE and/or CUL49 proteins. A particularly preferred CHV protein includes $PCIR6_{183}$, $PCUS2_{391}$, $PCPK_{400}$, $PCgG_{415}$, $PCdUTP_{152}$, $PCUS9_{149}$, $PCUL48_{97}$, $PCUL52_{48}$, $PCUL51_{86}$, $PCgI_{53}$, $PCTK_{93}$, $PCgI_{364}$, $PCgE_{522}$, $PCUS8.5_{78}$, $PCUS9_{119}$, $PCUL49_{139}$, $PCUL48_{422}$, $PCICP4_{208}$, $PCgL_{171}$, $PCdUTP_{305}$, $PCUL49.5_{86}$, $PCUL49_{85}$, and/or $PCUL52_{249}$ (including, but not limited to the encoded proteins, full-length proteins, processed proteins, multivalent proteins).

Similarly, a preferred CHV protein of the present invention includes at least a portion of SEQ ID NO:4, SEQ ID NO:6, SEQ ID NO:8, SEQ ID NO:10, SEQ ID NO:16, SEQ ID NO:18, SEQ ID NO:22, SEQ ID NO:26, SEQ ID NO:30, SEQ ID NO:34, SEQ ID NO:36, SEQ ID NO:56, SEQ ID NO:58, SEQ ID NO:60, SEQ ID NO:62, SEQ ID NO:66, SEQ ID NO:68, SEQ ID NO:72, SEQ ID NO:76, SEQ ID NO:80, SEQ ID NO:82, SEQ ID NO:84, and/or SEQ ID NO:88. A particularly preferred CHV protein includes SEQ ID NO:4, SEQ ID NO:6, SEQ ID NO:8, SEQ ID NO:10, SEQ ID NO:16, SEQ ID NO:18, SEQ ID NO:22, SEQ ID NO:26, SEQ ID NO:30, SEQ ID NO:34, SEQ ID NO:36, SEQ ID NO:56, SEQ ID NO:58, SEQ ID NO:60, SEQ ID NO:62, SEQ ID NO:66, SEQ ID NO:68, SEQ ID NO:72, SEQ ID NO:76, SEQ ID NO:80, SEQ ID NO:82, SEQ ID NO:84, and/or SEQ ID NO:88. Also included are proteins encoded by allelic variants of the nucleic acid molecules encoding such proteins.

The present invention also includes a recombinant vector, which includes at least one isolated CHV nucleic acid molecule inserted into any vector capable of delivering the CHV nucleic acid molecule into a host cell. The vector can be either RNA or DNA, either prokaryotic or eukaryotic, and typically is a virus or a plasmid. Recombinant vectors can be used in the cloning, sequencing, and/or otherwise manipulating of CHV nucleic acid molecules of the present invention. Suitable and preferred CHV nucleic acid molecules to include in a recombinant vector are disclosed herein.

One embodiment of the present invention is a recombinant vector comprising an inactive CHV gene. Such a recombinant vector, also referred to as a transfer vector, can be used to produce a CHV comprising a CHV genome having an inactive gene by, for example, co-transfecting such a transfer vector with a CHV genome into a host cell and selecting for a CHV comprising a recombinant CHV genome having an inactive gene. Such a recombinant CHV genome is produced in the host cell by homologous recombination between the inactive gene on the transfer vector and the corresponding active gene on the transfected CHV genome. Transfection, culturing and purification methods to obtain recombinant CHV and CHV genomes are known to the art; see, for example, Graham et al., 1973, *Virology* 52:456–467; Graham et al, ibid. is incorporated by reference herein in its entirety.

Another embodiment of the present invention is a recombinant vector comprising a CHV nucleic acid molecule that includes a heterologous nucleic acid molecule (i.e., a heterologous nucleic acid molecule is located within a CHV nucleic acid molecule). Suitable and preferred heterologous nucleic acid molecules are disclosed herein. Such a heterologous nucleic acid molecule can be operatively linked to a transcription control sequence, as disclosed above. A recombinant vector comprising a CHV nucleic acid molecule into which a heterologous nucleic acid molecule is inserted is also a transfer vector. Such a transfer vector can be co-transfected with a CHV genome into a host cell to produce a recombinant CHV having a CHV genome including a heterologous nucleic acid molecule, using methods as described above. Recombinant CHV can be selected by identifying those CHV that have the heterologous nucleic acid molecule. If the recombinant vector comprises a selectable marker into which the heterologous nucleic acid molecule is inserted, selection methods as disclosed herein can also be used to identify recombinant CHV. A preferred embodiment is a recombinant vector comprising a CHV nucleic acid molecule having a heterologous nucleic acid molecule in which a majority of the CHV nucleic acid molecule is deleted; a sufficient size of the CHV nucleic acid molecule is retained to allow homologous recombination to occur with the corresponding target gene on the CHV genome. Examples of insertion of a heterologous nucleic acid molecule into a CHV genomic restriction site and into a CHV gene, as well as use of a selectable marker are provided in the Examples section.

Transfer vectors of the present invention are preferably able to replicate in bacterial, and particularly *E. coli*, hosts, thereby enabling easy manipulation of the CHV nucleic acid molecules, and, if included, heterologous nucleic acid molecules, prior to insertion of such CHV nucleic acid molecules into a CHV genome. Such manipulations, including culturing of *E. coli* comprising such vectors, is described, for example, in Sambrook et al, ibid.

In one embodiment, recombinant CHV are produced by co-transfection of a set of overlapping cosmid clones comprising the entire viral CHV genome, at least one of the cosmid clones having been genetically engineered to, for example, contain an inactive CHV gene and/or a heterologous nucleic acid molecule. Details of such a method are presented in the Examples.

Any canid host cell is suitable for recombinant CHV production. Examples of suitable and preferred host cells are provided herein. After transfection, transfected cells are cultured in an effective medium, using techniques such as those described in Graham et al, ibid. As used herein, an effective medium refers to any medium in which the transfected cells can produce recombinant CHV. An effective medium is typically an aqueous medium comprising assimilable carbohydrate, nitrogen and phosphate sources, as well as appropriate salts, minerals, metals and other nutrients, such as vitamins, growth factors and hormones. Culturing is carried out at a temperature, pH and oxygen content appropriate for the transfected cell. Such culturing conditions are well within the expertise of one of ordinary skill in the art.

Recombinant CHV can be recovered from the cultured transfected cells using a combination of standard techniques such as, but not limited to, freeze/thaw cycles, sonication, sucrose gradient centrifugation, and/or high speed centrifugation. Recombinant CHV genomes can be recovered from the cultured transfected cells using a combination of standard techniques such as, but not limited to, those described by Walboomers et al, 1976, *Virology* 74, 256–258.

Preferably, a recombinant CHV or recombinant CHV genome of the present invention is recovered in "substantially pure" form. As used herein, "substantially pure" refers to a purity that allows for the effective use of the recombinant CHV or CHV genome as a vaccine without substantial negative side effects.

The present invention also includes a method to increase recombinant CHV plaque forming efficiency, thereby facilitating the production of recombinant CHV and CHV genomes. The phrase to increase recombinant CHV plaque forming efficiency refers to the ability to increase, or enhance, the production of CHV above the frequency of plaque forming units produced when a CHV genome is transfected into a cell in the absence of additional factors. The method includes the step of expressing the CHV alpha transinducing factor gene (i.e., CUL48 gene, also called the CHV alpha-tif gene) when a CHV genome is introduced into a canine cell.

Herpesviruses studied to date carry into infected cells a transcriptional activator called alpha transinducing factor (also called VP16 or Vmw65); see, for example, Batterson et al., 1983, *J. Virol.*, 46:371–377. This transactivator protein interacts, along with cellular proteins, with a cis-acting sequence element present in the upstream regulatory regions of herpesvirus immediate early genes. Since purified herpesvirus DNA is infectious in the absence of alpha-tif, it is not absolutely required for expression of immediate early genes, but its presence in stably transfected cell lines has been shown to enhance infectivity of herpes simplex virus type-1 viral DNA; see, for example, Werstuck et al., 1990, *J. Virol.*, 64:984–991.

Expression of the CHV alpha-tif gene can be accomplished in a variety of ways, including, but not limited to, the following. In one embodiment, a recombinant CHV genome is introduced into a canine cell expressing CHV alpha transinducing factor and the cells are cultured to produce recombinant CHV. A canine cell expressing CHV alpha-tif is a canine cell that has been genetically engineered to produce CHV alpha-tif in either a stable or transient manner. Such a canine cell can be produced by introducing a CUL48 nucleic acid molecule of the present invention into a canine cell line in such a manner that the CUL48 nucleic acid molecule can direct the expression of active alpha-tif. An example of a useful CUL48 nucleic acid molecule is such nCUL48$_{1269}$. Details regarding the production of an alpha-tif-expressing canine cell and the use such a cell in the production of recombinant CHV and CHV genomes is present in the Examples.

In another embodiment, recombinant CHV plaque forming efficiency is increased by co-introducing a recombinant CHV genome and a CHV alpha transinducing factor gene into a canine cell and culturing the cell to produce recombinant CHV. The CHV alpha transinducing factor gene can be introduced as part of a recombinant molecule of the present invention. Details regarding this method are also presented in the Examples.

The present invention all includes canine cell lines that include a CHV alpha-tif gene; such cell lines are able to express alpha-tif, thereby facilitating CHV production. One example of such a cell line is a canine cell line transfected with CHV nucleic acid molecule $nCUL48_{1269}$.

One embodiment of the present invention is a recombinant molecule that includes a CHV nucleic acid molecule operatively linked to a transcription control sequence. Such a recombinant molecule, when introduced into a host cell, can direct the expression of the CHV nucleic acid molecule(s), thereby leading to the production of one or more CHV protein of the present invention. Such a recombinant molecule preferably is replication competent. Suitable and preferred CHV nucleic acid molecules to include in such a recombinant molecule are as disclosed herein for suitable and preferred CHV nucleic acid molecules per se.

Isolated CHV proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell that is capable of expressing one or more CHV proteins, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Suitable and preferred CHV nucleic acid molecules with which to transform a cell are as disclosed herein for suitable and preferred CHV nucleic acid molecules per se.

Suitable host cells to transform include any cell that can be transformed with a CHV nucleic acid molecule of the present invention. Host cells can be either untransformed cells or cells that are already transformed with at least one nucleic acid molecule. Host cells of the present invention either can be endogenously (i.e., naturally) capable of producing CHV proteins of the present invention or can be capable of producing such proteins after being transformed with at least one CHV nucleic acid molecule of the present invention. Host cells of the present invention can be any cell capable of producing at least one protein of the present invention, and include bacterial, fungal (including yeast), parasite (including helminth, protozoa and ectoparasite), insect, other animal and plant cells. Preferred host cells include bacterial, yeast, insect and mammalian cells. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, insect and mammalian cells, such as, but not limited to, tac, lac, trp, trc, oxy-pro, omp/lpp, rrnB, bacteriophage lambda (such as lambda $p_L$and lambda $p_R$ and fusions that include such promoters), bacteriophage T7, T7lac, bacteriophage T3, bacteriophage SP6, bacteriophage SP01, metallothionein, alpha-mating factor, Pichia alcohol oxidase, alphavirus, phosphate-regulated and nitrate-regulated transcription control sequences as well as other sequences capable of controlling gene expression in prokaryotic or eukaryotic cells, including those disclosed herein for expression of heterologous nucleic acid molecules, including endogenous CHV transcription control regions.

Recombinant cells of the present invention can be used to produce one or more proteins by culturing such cells under conditions effective to produce such a protein, and recovering the protein. Effective conditions to produce a protein include, but are not limited to, appropriate media, bioreactor, temperature, pH and oxygen conditions that permit protein production. Such culturing conditions are well within the expertise of one of ordinary skill in the art.

Depending on the vector and host system used for production, resultant CHV proteins may either remain within the recombinant cell; be secreted into the fermentation medium; be secreted into a space between two cellular membranes, such as the periplasmic space in *E. coli;* or be retained on the outer surface of a cell or viral membrane.

The phrase "recovering the protein" refers simply to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and should be capable of stimulating the production of antibodies in a treated animal.

The present invention also includes isolated antibodies capable of selectively binding to a CHV protein of the present invention or to a mimetope thereof. Such antibodies are also referred to herein as anti-CHV antibodies. Isolated antibodies are antibodies that have been removed from their natural milieu. The term "isolated" does not refer to the state of purity of such antibodies. As such, isolated antibodies can include anti-sera containing such antibodies, or antibodies that have been purified to varying degrees.

As used herein, the term "selectively binds to" refers to the ability of antibodies of the present invention to preferentially bind to specified proteins and mimetopes thereof of the present invention. Binding can be measured using a variety of methods known to those skilled in the art.

Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein or mimetope used to obtain the antibodies. Antibodies of the present invention also include chimeric antibodies that can bind to more than one epitope. Preferred antibodies are raised in response to proteins, or mimetopes thereof, that are encoded, at least in part, by a nucleic acid molecule of the present invention.

A preferred method to produce antibodies of the present invention includes (a) administering to an animal an effective amount of a protein or mimetope thereof of the present invention to produce the antibodies and (b) recovering the antibodies. In another method, antibodies of the present invention are produced recombinantly using techniques as heretofore disclosed to produce CHV proteins of the present invention. Antibodies raised against defined proteins or mimetopes can be advantageous because such antibodies are not substantially contaminated with antibodies against other substances that might otherwise cause interference in a diagnostic assay or an assay to monitor recombinant CHV administration, or side effects if used in a therapeutic composition.

Antibodies of the present invention have a variety of potential uses that are within the scope of the present invention. For example, such antibodies can be used (a) as compounds to monitor recombinant CHV or recombinant CHV genome administration, (b) as therapeutic compounds to passively immunize an animal in order to protect the animal from CHV infection, and/or (c) as reagents in assays to detect CHV infection.

One embodiment of the present invention is a therapeutic composition that includes a recombinant CHV, a recombinant CHV genome, or a mixture (i.e., combination) of one or more recombinant CHVs and/or recombinant CHV genomes. As used herein, a therapeutic composition, or vaccine, is a formulation that, when administered to an animal in an effective manner, is capable of protecting that animal from a disease against which the therapeutic composition is targeted. Some therapeutic compositions of the present invention can modulate (i.e., either elicit or suppress) an immune response to protect an animal from disease, whereas other therapeutic compositions can protect an animal in other ways, as disclosed herein. A therapeutic composition of the present invention can be used to prevent and/or treat a disease depending on whether the composition is administered as a prophylactic or after the animal has the disease.

A therapeutic composition of the present invention, when administered to an animal in an effective manner, can infect the cells of the animal (in a manner essentially harmless to the animal) and direct the production of a protective compound able to protect the animal from a disease targeted by the therapeutic composition. If a recombinant CHV includes a protective compound in its envelope and/or capsid, the CHV can function as an immunogen per se.

As disclosed herein, therapeutic compositions can be designed to target a variety of diseases, depending on the nature of the heterologous nucleic acid molecule(s) included in such recombinant CHV and recombinant CHV genomes. Examples of such diseases, and the nature of the corresponding heterologous nucleic acid molecules, are disclosed herein. Furthermore, therapeutic compositions of the present invention can comprise multivalent vaccines. For example, a CHV genome can encode a variety of protective compounds, and/or more than one recombinant CHV genome and/or recombinant CHV can be administered. The present invention also includes the use of a recombinant CHV or recombinant CHV genome to protect an animal against CHV infection. Such a therapeutic composition can, but need not, include a heterologous nucleic acid molecule.

A therapeutic composition of the present invention is preferably administered to a canid, due to the host range specificity of CHV. Suitable canids include dogs (including domesticated and wild dogs), foxes, wolves, jackals, coyotes, and other members of the family Canidae. Particularly preferred canids to treat include domesticated dogs.

It is, however, also within the scope of the present invention to administer therapeutic compositions to other animals. Recombinant CHV can be administered to any animal susceptible to such therapy. Without being bound by theory, it is believed that sufficiently high doses of a recombinant CHV composition of the present invention may be infectious in other animals, particularly other mammals. Mink and other mink-like mammals (e.g., those of the family Mustelidae, such as ermines, ferrets, fishers, martens, otters, and weasels), in particular, may be susceptible to CHV infection, as suggested by the ability of CHV to infect mink lung cells. The host range of recombinant CHV of the present invention can also be altered, as disclosed herein, to infect other animal cells. It is also to be noted that CHV genomes of the present invention can be administered as naked DNA vaccines or in association with other carriers (e.g., liposomes). In accordance with these embodiments, any animal, including, but not limited to, mammals, birds, amphibians, and arthropods (including arachnids and insects) can be administered a therapeutic composition of the present invention. Preferred animals to treat include dogs, cats, humans, ferrets, prairie dogs, other rodents, horses, cattle, sheep, pigs, and poultry, as well as other pets, work animals, economic food animals and zoo animals.

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, the vaccine can also include an adjuvant and/or a carrier. One advantage of live virus-based vaccines, such as the recombinant CHVs of the present invention, is that adjuvants and carriers are not required to produce an efficacious vaccine, and in some cases, the advantages of recombinant CHV vaccines of the present invention would be precluded by the use of some adjuvants. However, it should be noted that use of adjuvants or carriers is not precluded by the present invention. Adjuvants are typically substances that generally enhance the immune response of an animal to a specific antigen. Suitable adjuvants include, but are not limited to, other bacterial cell wall components; aluminum-based salts; calcium-based salts; silica; polynucleotides; toxoids; serum proteins; other viral coat proteins; other bacterial-derived preparations; block copolymer adjuvants, such as Hunter's Titermax™ adjuvant (Vaxcel™, Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark). Carriers are typically compounds that increase the half-life of a therapeutic composition in the treated animal. Suitable carriers include, but are not limited to, polymeric controlled release formulations, biodegradable implants, liposomes, bacteria, viruses, oils, esters, and glycols.

In one embodiment, a therapeutic composition of the present invention is administered to an animal in an effective manner to enable the animal to produce sufficient protective compound(s) and/or to directly mount a sufficient immune response to protect the animal from disease. Acceptable protocols to administer therapeutic compositions in an effective manner include enumeration of individual dose size, number of doses, frequency of dose administration, and mode of administration. Determination of such protocols can be accomplished by those skilled in the art. A suitable single dose is a dose that is capable of protecting an animal from disease when administered one or more times over a suitable time period.

A preferred single dose of a recombinant CHV of the present invention is from about $1 \times 10^4$ to about $1 \times 10^7$ virus plaque forming units (pfu) per kilogram body weight of the animal. Booster vaccinations can be administered from about 2 weeks to several years after the original vaccination. Booster vaccinations preferably are administered when the immune response of the animal becomes insufficient to protect the animal from disease. A preferred administration schedule is one in which from about $1 \times 10^4$ to about $1 \times 10^7$ virus plaque forming units per kilogram (kg) body weight of the animal are administered from about 1 to about 2 times over a time period of from about 12 to about 18 months. Modes of administration can include, but are not limited to, subcutaneous, intradermal, intravenous, intranasal, oral, transdermal and intramuscular routes.

A recombinant CHV genome can be administered in a variety of ways, with intramuscular, subcutaneous, intradermal, transdermal, intranasal and oral routes of administration being preferred. A preferred single dose of a recombinant CHV genome ranges from about 1 nanogram (ng) to about 100 micrograms (µg), depending on the route of administration and/or method of delivery, as can be determined by those skilled in the art; see, for example, Wolff et al., 1990, *Science* 247, 1465–1468. Suitable delivery methods include, for example, injection, as drops, aerosolized and/or topical administration. Suitable excipients include, for example, physiologically acceptable aqueous solutions (e.g., phosphate buffered saline as well as others disclosed above), liposomes (including neutral or cationic liposomes), and other lipid membrane-based vehicles (e.g., micelles or cellular membranes).

In one embodiment, a therapeutic composition of the present invention is administered to a dam to protect her offspring from disease. In this method, the dam is administered the therapeutic composition at such a time as to be able to develop an immune response such that she can passively transfer antibodies produced against a protective compound of the present invention to her offspring. Such a method can also be used to protect offspring from CHV infection and is particularly useful since neonates are most affected by CHV infection.

The efficacy of a therapeutic composition of the present invention to protect an animal from disease can be tested in a variety of ways including, but not limited to, detection of protective protein or RNA within the treated animal, detection of protective antibodies within the treated animal, detection of cellular immunity within the treated animal, or challenge of the treated animal with an appropriate infectious agent, or other disease component, to determine whether the animal is now protected from the disease caused by such an agent or other component. Such techniques are known to those skilled in the art. In one embodiment, anti-CHV antibodies of the present invention are used to monitor recombinant CHV infection and can be used to distinguish wild type infections from infections using recombinant CHV of the present invention (i.e., by using antibodies that specifically recognize either recombinant CHV of the present invention or wild type virus).

In one embodiment, the efficacy of a therapeutic composition of the present invention may be improved by co-administering (a) a recombinant CHV or recombinant CHV genome and (b) a protective compound (e.g., subunit vaccine) encoded by a CHV nucleic acid molecule or heterologous nucleic acid molecule present in the CHV genome. While not being bound by theory, it is believed that administration of a protective compound in conjunction with the recombinant CHV or CHV genome can boost the immune response, particularly the antibody titer. The protective compound can be administered prior to, concomitant with, and/or following administration of the recombinant CHV or CHV genome. The protective compound can be either produced naturally, recombinantly, or synthetically. The protective compound should be sufficiently pure to allow for effective use of the compound as a vaccine; i.e., it should not cause substantial side effects. The protective compound can be joined (i.e., conjugated) to a carrier or other material that enhances the immunogenicity of the compound.

The present invention also includes the use of CHV nucleic acid molecules, CHV proteins, and anti-CHV antibodies as therapeutic compositions to protect animals from CHV infection. Methods to administer such compositions to canids are known to those skilled in the art. For example, a preferred single dose of a protein, mimetope or antibody therapeutic composition is from about 1 microgram (µg) to about 10 milligrams (mg) of the therapeutic composition per kilogram body weight of the animal. Booster vaccinations can be administered from about 2 weeks to several years after the original administration. Booster vaccinations preferably are administered when the immune response of the animal becomes insufficient to protect the animal from disease. A preferred administration schedule is one in which from about 10 µg to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, oral, transdermal and intramuscular routes. A CHV nucleic acid molecule, including recombinant molecules, can be administered as described herein for administration of CHV genomes or CHV of the present invention. Recombinant molecules including heterologous nucleic acid molecules can also be used as therapeutic compositions to protect an animal from disease, using methods as disclosed herein.

It is also within the scope of the present invention to use isolated CHV proteins, mimetopes, CHV nucleic acid molecules and anti-CHV antibodies of the present invention as diagnostic reagents to detect CHV infection. Methods to use such diagnostic reagents to diagnose infection are well known to those skilled in the art.

The following examples are provided for the purposes of illustration and are not intended to limit the scope of the present invention.

EXAMPLES

It is to be noted that the Examples include a number of molecular biology, virology, microbiology, immunology and biochemistry techniques considered to be known to those skilled in the art. Disclosure of such techniques can be found, for example, in Sambrook et al., ibid.; Ausubel et al, 1993, *Current Protocols in Molecular Biology*, Greene/Wiley Interscience, New York, N.Y.; Graham et al, ibid.; and related references. Ausubel et al, ibid. is incorporated by reference herein in its entirety. Nucleic acid and amino acid sequences of the present invention were compared to known sequences using BLAST (NCBI) and DNAsis (Hitachi Software, San Bruno, Calif.).

Example 1

This Example demonstrates the isolation of certain CHV nucleic acid molecules of the present invention.

The disclosed CHV nucleic acid molecules were amplified from a CHV genome by PCR amplification using a variety of primers designed in view of published herpesvirus sequences. The following PCR conditions were used: 0.2 millimolar (mM) dNTPs, 1 µM of each primer, 1× PCR buffer (available from Perkin Elmer Cetus, Emeryville, Calif.), 50 ng of CHV DNA (isolated from CHV strain D 004 as described in Example 2) and 0.5 µl of a thermostable DNA polymerase, all in an about 100 μl total volume. The PCR reactions included an initial denaturation for 3 minutes at 95° C., five cycles of 1 minute each at 95° C., 35° C. for 1 minute, 72° C. for 1 minute, 35 cycles of 1 minute each at 95° C., 37° C. for 1 minute, 72° C. for 1 minute, and finally 10 minutes at 72° C. The resultant PCR products were directly cloned into the pCRII TA cloning vector (available from Invitrogen Corp., San Diego, Calif.) according to the manufacturer's specifications. Primers which were successful in amplifying fragments from a CHV genome, which was determined to be very AT-rich compared to other herpesvirus genomes, are described below.

A. Isolation of a Nucleic Acid Molecule Including a Partial CHV dUTPase Gene and a Partial CHV UL51 Gene The following primers were designed using dUTPase protein sequence derived from HSV-1 (McGeoch et al, 1988, *J. Gen. Virol.* 69, 1531–1574), EHV-4 (Riggio et al, 1993, *Arch. Virol.* 133, 171–178), BHV-1 (Liang et al, 1993, *Virology* 195, 42–50), and EBV (Lees et al, 1993, *Virology* 195, 578–586: Primer 212S (dUTPase forward) having nucleic acid sequence 5' GG CGA ATT CCI AAR MGI GAI GAR GAY G 3', denoted herein as SEQ ID NO:39; and Primer 365A (dUTPase reverse) having nucleic acid sequence 5' C GCG GATi CCI GTI SWI CCY AAI CC 3', denoted herein as SEQ ID NO:40. These primers led to the amplification of an about 743 nucleotide fragment, which was significantly larger than expected. Nucleic acid sequence analysis, described in Example 3,indicated that the 743 nucleotide fragment contained part of the CUL51 gene as well as part of the CdUTPase gene; as such, the fragment was denoted $nCdUTP/CUL51_{743}$. Nucleic acid sequence analysis also indicated that the dUTPase reverse primer actually hybridized to a region of the CHV DNA genome within the CUL51 gene rather than within the CdUTPase gene. It is believed that the mispriming was due to nucleotide position 19 of SEQ ID NO:40 being a Y instead of an R; the latter sequence would have matched more closely to the targeted priming region, about 290 nucleotides upstream from the 3' end of nucleic acid molecule $nCdUTP/CUL51_{743}$. This result demonstrates the sensitivity of PCR amplification to primer design.

B. Isolation of a CHV gE Nucleic Acid Molecule

The following primers were designed using gE protein sequence derived from FHV-1 (Spatz et al, 1994, *J Gen. Virol.* 75, 1235–1244), EHV-1 (Elton et al, 1991, *Gene* 101, 203–208), and BHV-1 (Leung-Tack et al, 1994, *Virology* 199, 409–421): Primer 197S (gE forward) having nucleic acid sequence 5' GGC GAA TTC TAY CAY WSI CAY GTI TA 3', denoted herein as SEQ ID NO:41; and Primer 441A (gE reverse) having nucleic acid sequence 5' CGC GGA TCC RTC RTT ISW IGG DAI ISW IGT 3', denoted herein as SEQ ID NO:42. These primers led to the amplification of an about 750 nucleotide fragment, referred to herein as $nCgE_{750}$.

C. Isolation of a CHV TK Nucleic Acid Molecule

The following primers were designed using TK protein sequence derived from HSV-1 (McGeoch et al., 1988, ibid.), HSV-2 (Kit et al, 1987, *Antimicrob. Agents Chemother.* 31, 1483–1490, BHV-1 (Kit et al, U.S. Pat. No. 4,703,011, issued Oct. 27, 1987), FHV-1 (Nunberg et al, 1989, *J. Virol.* 63, 3240–3249), EHV-1 (Robertson et al, 1988, *Nuc. Acids Res.* 16, 11303–11317), and PRV (Prieto et al, 1991, *J. Gen. Virol.* 72, 1435–1439): Primer EJH 002 (TK forward) having nucleic acid sequence 5' GGC GAA TTC GGI AAR WSI ACI RC 3', denoted herein as SEQ ID NO:43; and Primer EJH004 (TK reverse) having nucleic acid sequence 5' GGC GGA TCC GGT TGI CKR TC 3', denoted herein as SEQ ID NO:44. These primers led to the amplification of an about 280 nucleotide fragment, referred to herein as $nCTK_{280}$.

D. Isolation of a Nucleic Acid Molecule Including CHV gC and CHV UL45 genes

The following primers were designed using gC and UL45 sequences derived from Limbach et al., ibid.: Primer gC sense, having nucleic acid sequence 5' CGCGGATCCAAGGTAATAAGTCAAAATGAG 3', denoted herein as SEQ ID NO:45; and Primer gC ant, having nucleic acid sequence 5' CGCGGATCCGACAAAAACAAAAAGTAATG 3', denoted herein as SEQ ID NO:46. These primers led to the amplification of an about 2100 nucleotide fragment, referred to herein as $nCgC/CUL45_{2100}$.

E. Attempt to Isolate a CHV Ribonucleotide Reductase Gene

The following primers were designed using ribonucleotide subunit small subunit protein sequence derived from HSV-1 (McGeoch et al, 1988, ibid.), PRV (Dewind et al, 1993, *J. Gen. Virol.* 74, 351–359), EHV-1 (Telford et al, 1992, *Virology* 189, 04–316) and BHV-1 (Simard et al, 1992, *Virology* 190, 689–701): Primer EJH 021 (RR forward) having nucleic acid sequence 5' CCG AAT TCY TIA TGA THY TIA THG ARG G 3', denoted herein as SEQ ID NO:47; and Primer EJH022 (RR reverse) having nucleic acid sequence 5' CCG GAT CCY TCR AAR AAR TTI GTR TGY TT 3', denoted herein as SEQ ID NO:48. These primers did not lead to the amplification of a fragment under a variety of magnesium and amplification conditions, suggesting the lack of a coding region for a ribonucleotide reductase small subunit in CHV. As a control, these primers were shown to be able to easily amplify a ribonucleotide reductase small subunit fragment from an FHV genome.

Example 2

This Example describes the production of CHV genomic libraries.

Canine herpesvirus strain D 004 (Binn, et al., 1967, *Proc. Soc. Exp. Biol. Med.* 126, 140) was obtained from ATCC. Virus were propagated on Madin-Darby Canine Kidney (MDCK) cells according to standard virological procedures. Viral DNA was prepare from CHV-infected MDCK cells by previously described methods; see, for example, Walboomers et al, ibid. The viral DNA was digested with restriction endonucleases HindIII, PstI, EcoRI or XbaI, and the resultant digests were cloned into either vector pSP72 (available from Promega Corp., Madison, Wis.), or pLitmus 28 or 38 (available from New England Biolabs, Beverly, Mass.). DNA was prepared from the resultant recombinant plasmids and the inserts were sorted according to size.

Example 3

This Example describes the isolation of genomic HindIII restriction fragment nucleic acid molecules containing CdUTPase nucleic acid sequences and the nucleic acid sequencing of at least regions of these nucleic acid molecules.

Nucleic acid molecule nCdUTP/CUL$51_{743}$, produced as described in Example 1, was labelled with either $^{32}P$ or digoxigenin (available from Boehringer Mannheim Biochemicals (BMB), Indianapolis, Ind.) and used to screen the CHV HindIII fragment-containing library, either by colony hybridization or Southern blotting. Two clones hybridized with nCdUTP/CUL$51_{743}$, one containing a HindIII fragment of about 3000 nucleotides, referred to herein as $nCHin_{3000}$, and another containing a HindIII fragment of about 1,900 nucleotides, referred to herein as $nCHin_{1900}$. The HindIII fragments were further characterized by restriction mapping, as shown in FIG. 1. Also shown is the relative location of nCdUTP/CUL$51_{743}$ (referred to therein as $nCdUTP_{743}$) with respect to the HindIII fragments.

Nucleic acid molecules nCdUTP/CUL$51_{743}$, $nCHin_{3000}$, and $nCHin_{1900}$ were submitted to DNA sequence analysis, using a sequencing strategy as depicted in FIG. 1. Among sequences obtained were SEQ ID NO:13 and SEQ ID NO:14, which include SEQ ID NO:15 and SEQ ID NO:33, as well as SEQ ID NO:21, SEQ ID NO:23, SEQ ID NO:25 and SEQ ID NO:27. The relative locations of genes included in these sequences (i.e., the CUL52, CUL51, CdUTPase and CUL48 genes) are shown in FIG. 1. Also shown is the apparent location of the CUL49 gene.

SEQ ID NO:13 and SEQ ID NO:14 represent the deduced nucleic acid sequences of the two complementary strands of nCdUTP/CUL$51_{743}$. SEQ ID NO:13 includes a partial coding region for a CdUTPase protein of about 152 amino acids, denoted herein as $nCdUTP_{459}$ and represented by SEQ ID NO:15, assuming a first in-frame codon spanning about nucleotides 3–5, and a stop codon spanning about nucleotides 459–461 of SEQ ID NO:13. The amino acid sequence of the encoded protein $PCdUTP_{152}$ is represented by SEQ ID NO:16. SEQ ID NO:14 includes a partial coding region for a CUL51 protein of about 86 amino acids, denoted herein as $nCUL51_{261}$ and represented by SEQ ID NO:33, assuming a first in-frame codon spanning about nucleotides 1–3, and a stop codon spanning about nucleotides 259–261 of SEQ ID NO:14. The amino acid sequence of the encoded protein $PCUL51_{86}$ is represented by SEQ ID NO:34.

SEQ ID NO:21 and SEQ ID NO:23 represent the deduced nucleic acid sequences of the two complementary strands of $nCUL48_{294}$. SEQ ID NO:21 includes a partial coding region for a CUL48 protein of about 97 amino acids, denoted herein as $nCUL48_{291}$, and represented by SEQ ID NO:24, assuming a first in-frame codon spanning about nucleotides 3–5 of SEQ ID NO:21. The amino acid sequence of the encoded protein $PCUL48_{97}$ is represented by SEQ ID NO:22.

SEQ ID NO:25 and SEQ ID NO:27 represent the deduced nucleic acid sequences of the two complementary strands of $nCUL52_{146}$. SEQ ID NO:25 includes a partial coding region for a CUL52 protein of about 48 amino acids, denoted herein as $nCUL52_{144}$ and represented by SEQ ID NO:28, assuming a first in-frame codon spanning about nucleotides 1–3 of SEQ ID NO:25. The amino acid sequence of the encoded protein $PCUL52_{48}$ is represented by SEQ ID NO:26.

Example 4

This Example describes a method to identify restriction enzymes that effect limited cleavage of the CHV genome. Also described is the isolation and sequencing of an AscI fragment containing the entire US region of CHV.

CHV DNA was evaluated for recognition sites for several restriction enzymes with 8-base, or larger, recognition sites. No sites were found for enzymes Sse8387I, I-Sce-I, or NotI. Two AscI sites were found, which were mapped to sites within the inverted repeats surrounding the US region, specifically within CHV gene US2 (see FIG. 2). The AscI fragments, of 9.3, 10.0 and approximately 100–120 kilobases (kb), were cloned into pLitmus 38 and submitted to restriction enzyme mapping analysis. The restriction map of the 9.3-kb AscI fragment, denoted herein as nCAsc9300 is shown in FIG. 2; this fragment apparently contains the entire CUS region, as well as small portions of the internal and terminal IR regions. The 10.0-kb AscI-blunt fragment, denoted herein as nCAsc10000, contains most of the terminal IR region and is shown in FIG. 3. The about 100–120-kb AscI-blunt fragment contains the remainder of the CHV genome. Both AscI sites are located just 5' of the diploid copies of the CHV homolog of the EHV-1 IR6 gene (Breeden et al, 1992, *Virology* 191, 649–660), and the orf1 of BHV-1 (Leung-Tack et al, ibid.). The AscI sites appear to be located within an open reading frame that is the homolog of the EHV US1 gene (Breeden et al ibid.) and the HSV-1 US2 gene (McGeoch et al, 1985, *J. Mol. Biol* 181, 1–13), although the size is somewhat different from these other genes. No function has been ascribed to the HSV-1 US2 gene product, but it has been shown to be dispensable for growth in tissue culture and to attenuate the virus (Meignier et al, 1988, *Virology* 162, 251–254).

Nucleic acid molecules $nCAsc_{9300}$ and $nCAsc_{10000}$ were submitted to DNA sequence analysis using a strategy as depicted in FIG. 2 and FIG. 3. Among sequences obtained were SEQ ID NO:1, SEQ ID NO:2, SEQ ID NO:17, SEQ ID NO:19, SEQ ID NO:29, and SEQ ID NO:31 The relative locations of genes included in these sequences (i.e., the CUS9, CgI, CgD, CgG, CPK, CUS2, and C!R6 genes) are shown in FIG. 2 and FIG. 3. Also shown is the putative location of the CgE gene.

SEQ ID NO:1 and SEQ ID NO:2 represent the deduced nucleic acid sequences of the two complementary strands of $nCUS_{5495}$. Translation of SEQ ID NO:1 and SEQ ID NO:2 indicates that nucleic acid molecule $nCUS_{5495}$ encodes CIR6, CUS2, CPK and CgG proteins as well as a portion of a CgD protein. Specifically, SEQ ID NO:2 includes: a coding region for a CIR6 protein of about 183 amino acids, denoted herein as $nCIR6_{552}$ and represented by SEQ ID NO:3, assuming a start codon spanning about nucleotides 4566–4568 and a stop codon spanning about nucleotides 5115–5117 of SEQ ID NO:2; and a coding region for a CUS2 protein of about 391 amino acids, denoted herein as $nCUS2_{1176}$ and represented by SEQ ID NO:5, assuming a start codon spanning about nucleotides 3232–3234 and a stop codon spanning about nucleotides 4405–4407 of SEQ ID NO:2. The amino acid sequences of the respective encoded proteins $PCIR6_{183}$ and $PCUS2_{391}$ are represented by SEQ ID NO:4 and SEQ ID NO:6. SEQ ID NO:1 includes: a coding region for a CPK protein of about 400 amino acids, denoted herein as $nCPK_{1203}$ and represented by SEQ ID NO:7, assuming a start codon spanning about nucleotides 2384–2386 and a stop codon spanning about nucleotides 3584–3586 of SEQ ID NO:1; a coding region for a CgG protein of about 415 amino acids, denoted herein as $nCgG_{1248}$ and represented by SEQ ID NO:9, assuming a start codon spanning about nucleotides 3698–3700 and a stop codon spanning about nucleotides 4943–4945 of SEQ ID NO:1; and a partial coding region for a CgD protein of about 119 amino acids, denoted herein as $nCgD_{357}$ and represented by SEQ ID NO:11, assuming a start codon spanning about nucleotides 5137–5139. The amino acid sequences of the respective encoded proteins $PCPK_{400}$, $PCgG_{415}$, and $PCgD_{119}$ are represented by SEQ ID NO:8, SEQ ID NO:10 and SEQ ID NO:12.

SEQ ID NO:17 and SEQ ID NO:19 represent the deduced nucleic acid sequences of the two complementary strands of $nCUS9_{579}$. SEQ ID NO:17 includes a coding region for a CUS9 protein of about 149 amino acids, denoted herein as $nCUS9_{450}$ and represented by SEQ ID NO:20, assuming a start codon spanning about nucleotides 54–56 and a stop codon spanning about nucleotides 501–503 of SEQ ID NO:17. The amino acid sequence of the encoded protein $PCUS9_{149}$ is represented by SEQ ID NO:18.

SEQ ID NO:29 and SEQ ID NO:31 represent the deduced nucleic acid sequences of the two complementary strands of $nCgI_{161}$. SEQ. ID NO:29 includes a partial coding region for a CgI protein of about 53 amino acids, denoted herein as $nCgI_{159}$ and represented by SEQ ID NO:32, assuming a first in-frame codon spanning about nucleotides 3–5 of SEQ ID NO:29. The amino acid sequence of the encoded protein $PCgI_{53}$ is represented by SEQ ID NO:30.

Example 5

This Example describes the nucleic acid sequencing of additional nucleic acid molecules of the present invention.

Nucleic acid molecule $nCTK_{280}$, produced as described in Example 1, was submitted to DNA sequence analysis to obtain the following sequences. SEQ ID NO:35 and SEQ ID NO:37 represent the deduced nucleic acid sequences of the two complementary strands of $nCTK_{280}$. SEQ ID NO:35 includes a partial coding region for a CTK protein of about 93 amino acids, denoted herein as $nCTK_{279}$ and represented by SEQ ID NO:38, assuming a first in-frame codon spanning about nucleotides 2–4 of SEQ ID NO:35. The amino acid sequence of the encoded protein $PCTK_{93}$ is represented by SEQ ID NO:36.

Example 6

This Example discloses the production of a recombinant CHV genome and recombinant CHV of the present invention.

A cassette including the human CMV immediate early promoter and the poly-adenylation signal from bovine growth hormone separated by a polylinker was PCR amplified from plasmid pcDNA3 (available from Invitrogen) using forward primer EJH058 having nucleic acid sequence 5' TCCCCCGGGGGCGCGCCTTGACATTGAT-TATTGAC 3', denoted SEQ ID NO:49, and reverse primer EJH059 having nucleic acid sequence 5' GCCCT-TAAGGGGCGCGCCAATGCGATGCAATTTCC 3', denoted SEQ ID NO:50. EJH058 has SmaI and AscI sites attached to the 5' end of pcDNA3 homologous sequences, and EJH059 has AflII and AscI sites attached to the 5' end of pcDNA3 homologous sequences. The resultant PCR amplified fragment of about 930 nucleotides was digested with SmaI and AflII and ligated into the SnaBI and AflII sites of plasmid pLitmus 38. This cloning procedure eliminated the entire polylinker region of pLitmus38. The resulting recombinant plasmid, denoted herein as pAscCMV/BGH, contains the CMV promoter—BGH polyadenylation signal cassette, with its original polylinker, in a plasmid such that the entire cassette can be excised with enzyme AscI. This cassette plasmid can also be prepared with other rare-cutting enzyme sites flanking the cassette.

Plasmid pAscCMV/BGH allows for the insertion of heterologous nucleic acid molecules between the CMV promoter and the BGH polyadenylation signal. The resulting heterologous nucleic acid molecule-containing cassette was excised from the plasmid for insertion into a CHV genome. For example, a heterologous nucleic acid molecule containing a lacZ gene was inserted into the polylinker region of pAscCMV/BGH such that the lacZ gene is expressed by the CMV promoter in a eukaryotic system. The cassette containing the lacZ gene, referred to herein as AscCMV/lacZ/BGH is then excised from the plasmid by AscI digestion and gel purified by standard methods.

About 5–10 µg of CHV DNA is digested with AscI, resulting in three fragments as disclosed herein. The DNA fragments are dephosphorylated with calf intestine alkaline phosphatase (available from BMB) for 10 minutes at 37° C.; the enzyme is then inactivated for by incubation for 10 minutes at 65° C. The phosphatase-treated digested CHV DNA is then subjected to extraction with phenol and phenol/chloroform and precipitated with ethanol.

The phosphatase-treated digested CHV genomic DNA is mixed with the gel-purified AscCMV/lacZ/BGH cassette at a molar ratio of approximately 1:2 under standard ligation conditions. Since the viral DNA is dephosphorylated, it should not be able to self ligate; thus all resultant ligated viral molecules should contain two copies of the inserted cassette. The ligated DNA is then subjected to phenol extraction and ethanol precipitated.

The precipitated ligated DNA is resuspended in hepes-buffered saline and submitted to standard viral transfection conditions, such as that described by Graham et al., ibid., along with appropriate controls (e.g., undigested viral DNA, digested and dephosphorylated viral DNA that was self-ligated, and no DNA). Resultant viral plaques are screened under an X-gal overlay for expression of β-galactosidase.

Example 7

This Example discloses the production of another recombinant CHV genome and recombinant CHV of the present invention.

A recombinant, or transfer, vector to be used in the production of a recombinant CHV having a heterologous nucleic acid molecule in a TK gene of the CHV genome is constructed as follows. A CHV TK nucleic acid molecule of the present invention (e.g., $nCTK_{280}$) is ligated into a pLitmus plasmid to produce a pCTK-Litmus plasmid. An expression cassette including a heterologous nucleic acid molecule (e.g., a lacZ gene or a nucleic acid molecule encoding an antigen isolated from a pathogenic organism) ligated to a CMV immediate early promoter and a BHV polyadenylation site in such a manner that the heterologous nucleic acid molecule is expressed in a eukaryotic cell is inserted into the CTK nucleic acid molecule within pCTK-Litmus such that there are CTK flanking sequences on either side of the expression cassette (e.g., into a restriction site internal to $nCTK_{280}$).

A recombinant CHV is produced by co-transfecting the recombinant vector and CHV DNA into canine MDCK cells using previously described methods; see, for example, Graham et al, ibid. Recombinant TK negative CHV are selected for by passage in bromodeoxyuridine; see, for example, Kit et al., 1983, *Virology* 130, 381–389. If the heterologous nucleic acid molecule is the lacZ gene, such recombinant CHV can also be selected as described in Example 6.

Example 8

This Example discloses the production of another recombinant CHV genome and recombinant CHV of the present invention.

A recombinant, or transfer, vector to be used in the production of a recombinant CHV having a heterologous nucleic acid molecule in a dUTPase gene of the CHV genome is constructed as follows. A CHV dUTPase nucleic acid molecule of the present invention (e.g., $nCdUTP_{459}$) is ligated into a pLitmus plasmid to produce a pCdUTP-Litmus plasmid. An expression cassette including a heterologous nucleic acid molecule (e.g., a lacZ gene or a nucleic acid molecule encoding an antigen isolated from a pathogenic organism) ligated to a CMV immediate early promoter and a BHV polyadenylation site in such a manner that the heterologous nucleic acid molecule is expressed in a eukaryotic cell is inserted into the CdUTP nucleic acid molecule within pCdUTP-Litmus such that there are CdUTPase flanking sequences on either side of the expression cassette (e.g., into a restriction site internal to $nCdUTP_{459}$).

A recombinant CHV is produced by co-transfecting the recombinant vector and CHV DNA into canine MDCK cells as described in Example 7. Recombinant dUTPase negative CHV are selected for by passage in mercurithio analogs of deoxyuridine; see, for example, Holliday et al, 1991, *Antiviral Research* 16, 197–203. If the heterologous nucleic acid molecule is the lacZ gene, such recombinant CHV can also be selected as described in Example 6. Recombinant virus carrying the foreign DNA of interest can also be selected by either by plaque hybridizations, or by dot-blot hybridizations of infected cell cultures. Verification of the proper insert within the CHV genome is conducted by Southern hybridization analysis.

Example 9

This Example discloses the production of a recombinant CHV by co-transfection of a set of overlapping cosmid clones comprising the entire viral CHV genome.

A library of CHV cosmid clones is created in the cosmid vector SuperCos (available from Stratagene Cloning Systems, La Jolla, Calif.) according to manufacturer's specifications, except that the vector is modified to contain one for more restriction sites not present in CHV genomic DNA (e.g., Sse83871, I-Sce-I, or NotI) so that the cosmid inserts can be excised prior to cotransfection. A heterologous nucleic acid molecule in an expression cassette, such as one of those described in Examples 6–8, is inserted into a cosmid clone using standard procedures. A recombinant CHV is produced by co-transfection of a set of overlapping cosmid clones comprising the entire viral CHV genome, including the cosmid comprising a heterologous nucleic acid molecule, using techniques as described in van Zihl et al., 1988, *J. Virol.* 62, 2191–2195.

Example 10

This Example describes the nucleic acid sequencing of additional nucleic acid molecules of the present invention.

Nucleic acid molecules $nCAsc_{9300}$ and $nCAsc_{10000}$, produced as described in Example 4, were submitted to additional DNA sequence analysis. The resultant nucleic acid sequences were compiled to produce SEQ ID NO:51 and SEQ ID NO:52. SEQ ID NO:51 and SEQ ID NO:52 represent the deduced nucleic acid sequences of the two complementary strands of a nucleic acid molecule referred to herein as $nCUS_{10592}$. Nucleic acid molecule $nCUS_{10592}$ includes the entire US region of CHV plus terminal repeat and internal repeat sequences. Analysis of SEQ ID NO:51 indicates that the US region spans from nucleotides about 2047 through about 9724 of SEQ ID NO:51, whereas the terminal repeat sequences and inverted repeat sequences span from nucleotides about 1 through about 2046 and from nucleotides about 9725 through about 10592, respectively, of SEQ ID NO:51.

Translation of SEQ ID NO:51 and SEQ ID NO:52 indicates that nucleic acid molecule $nCUS_{10592}$ contains at least the following open reading frames: CIR6, CUS2, CPK, CgG, CgD, CgI, CgE, CUS8.5 and CUS9. The relative locations of these open reading frames is shown in FIG. 4.

Specifically, SEQ ID NO:52 includes: the coding strand of $nCIR6_{552}$ (having SEQ ID NO:3) which encodes a CIR6 protein of about 183 amino acids, assuming a start codon spanning about nucleotides 9672–9674 and a stop codon spanning about nucleotides 10221–10223 of SEQ ID NO:52; and the coding strand of $nCUS2_{1176}$ (having SEQ ID NO:5) which encodes a CUS2 protein of about 391 amino acids, assuming a start codon spanning about nucleotides 8338–8340 and a stop codon spanning about nucleotides 9511–9513 of SEQ ID NO:52. Nucleic acid molecules $nCIR6_{552}$ and $nCUS2_{1176}$ are also described in Example 4 in relation to $nCUS_{5495}$, as are the corresponding nucleic acid sequences and amino acid sequences they encode.

SEQ ID NO:51 includes: the coding strand of $nCPK_{1203}$ (having SEQ ID NO:7) which encodes a CPK protein of about 400 amino acids, assuming a start codon spanning about nucleotides 2375–2377 and a stop codon spanning about nucleotides 3575–3577 of SEQ ID NO:51; the coding strand of $nCgG_{1248}$ (having SEQ ID NO:9) which encodes a CgG protein of about 415 amino acids, assuming a start codon spanning about nucleotides 3689–3691 and a stop codon spanning about nucleotides 4934–4936 of SEQ ID NO:51; the coding strand of nCgD$_{1038}$ (having SEQ ID NO:53, and including SEQ ID NO:11) which encodes a CgD protein of about 345 amino acids, assuming a start codon spanning about nucleotides 5128–5130 and a stop codon spanning about nucleotides 6163–6165 of SEQ ID NO:51; the coding strand of nCgI$_{1095}$ (having SEQ ID NO:55, and including SEQ ID NO:29) which encodes a CgI protein of about 364 amino acids, assuming a start codon spanning about nucleotides 6225–6227 and a stop codon spanning about nucleotides 7317–7319 of SEQ ID NO:51; the coding strand of nCgE$_{1569}$ (having SEQ ID NO:57) which encodes a CgE protein of about 522 amino acids, assuming a start codon spanning about nucleotides 7467–7469 and a stop codon spanning about nucleotides 9033–9035 of SEQ ID NO:51; the coding strand of nCUS8.5$_{237}$ (having SEQ ID NO:59) which encodes a CUS8.5 protein of about 78 amino acids, assuming a start codon spanning about nucleotides 9028–9030 and a stop codon spanning about nucleotides 9262–9264 of SEQ ID NO:51; and the coding strand of nCUS9$_{360}$ (having SEQ ID NO:61) which encodes a CUS9 protein of about 119 amino acids, assuming a start codon spanning about nucleotides 9376–9378 and a stop codon spanning about nucleotides 9733–9735 of SEQ ID NO:51. SEQ ID NO:61 differs from the coding region reported for CUS9 in Example 4 (e.g., SEQ ID NO:20), in that additional sequence analysis indicated that SEQ ID NO:17 included a sequencing error resulting in a frameshift, leading to a longer deduced open reading frame. Nucleic acid molecules nCPK$_{1203}$ and nCgG$_{1248}$ are also described in Example 4 in relation to nCUS$_{5495}$, as are the corresponding nucleic acid sequences and amino acid sequences they encode. The amino acid sequences of the respective encoded proteins PCgD$_{345}$, PCgI$_{364}$, PCgE$_{522}$, PCUS8.5$_{78}$, and PCUS9$_{119}$ are represented by SEQ ID NO:54, SEQ ID NO:56, SEQ ID NO:58, SEQ ID NO:60 and SEQ ID NO:62, respectively.

Example 11

This Example describes the nucleic acid sequencing of additional nucleic acid molecules of the present invention.

Figure 5:
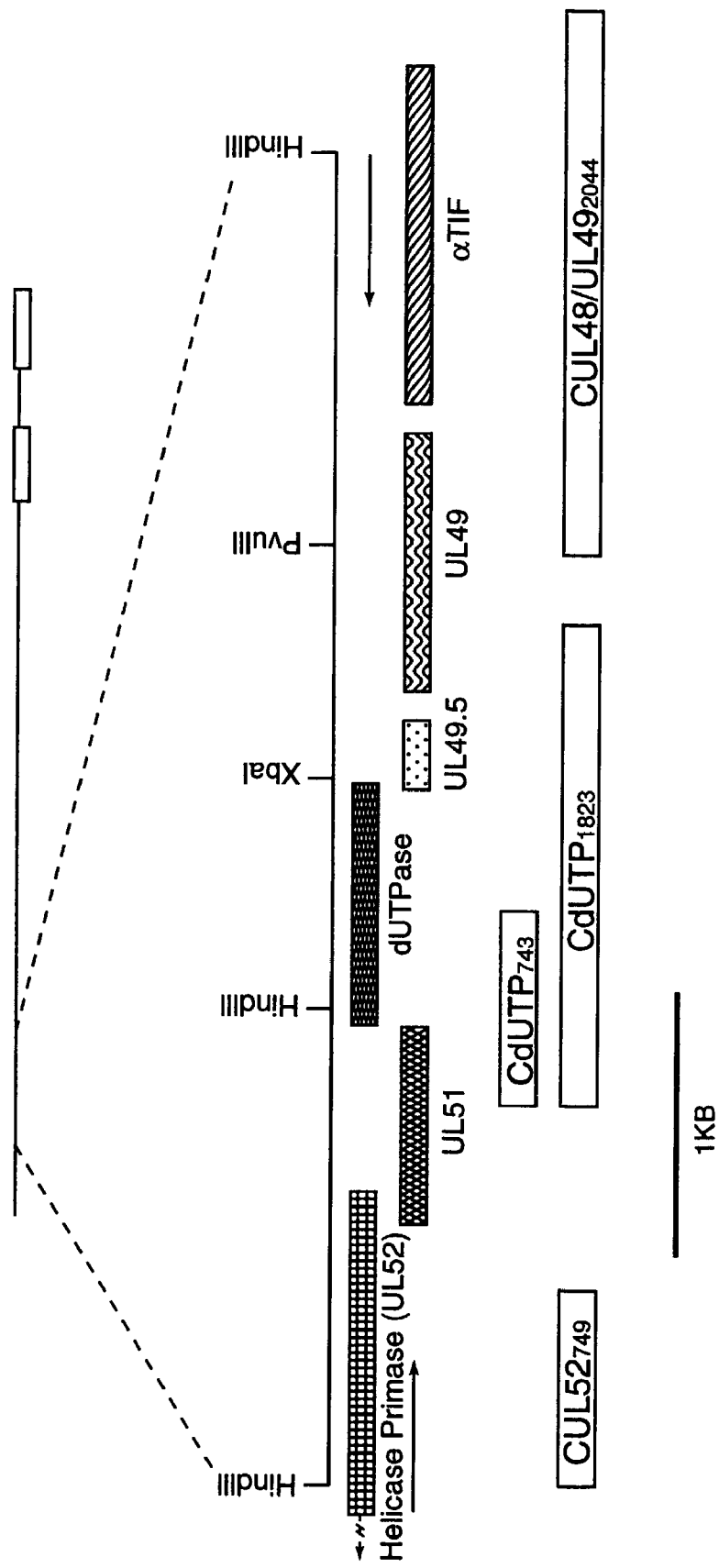
FIG. 5 depicts a schematic map of a region of the CHV genome spanning at least from a portion of the CUL52 gene through at least a portion of the CUL48 gene.

Nucleic acid molecules nCHin$_{3000}$, and nCHin$_{1900}$, produced as described in Example 3, were submitted to additional DNA sequence analysis. Also submitted to additional nucleic acid sequence analysis was nucleic acid molecule nCHin$_{8500}$, a HindIII fragment shown to include the 3' end of CUL48 as well as CgC and CUL45. The resultant nucleic acid sequences were compiled to produce SEQ ID NO:63, SEQ ID NO:64, SEQ ID NO:77, SEQ ID NO:78, SEQ ID NO:85, and SEQ ID NO:86. SEQ ID NO:63 and SEQ ID NO:63 represent the deduced nucleic acid sequences of the two complementary strands of a nucleic acid molecule referred to herein as nCUL49/CUL48$_{2044}$. Translation of SEQ ID NO:63 and SEQ ID NO:64 indicates that nucleic acid molecule nCUL49/CUL48$_{2044}$ contains at least the following open reading frames: CUL48 and the 3' end of CUL49. SEQ ID NO:77 and SEQ ID NO:78 represent the deduced nucleic acid sequences of the two complementary strands of a nucleic acid molecule referred to herein as nCUL$_{1823}$. Translation of SEQ ID NO:77 and SEQ ID NO:78 indicates that nucleic acid molecule nCUL$_{1823}$ contains at least the following open reading frames: CUL51, CdUTPase, CUL49.5, and the 5' end of CUL49. SEQ ID NO:85 and SEQ ID NO:86 represent the deduced nucleic acid sequences of the two complementary strands of a nucleic acid molecule referred to herein as nCUL52$_{749}$. Translation of SEQ ID NO:85 and SEQ ID NO:86 indicates that nucleic acid molecule nCUL52$_{749}$ contains a partial open reading frame for CUL52, the 3' end of which is included in SEQ ID NO:28. The relative location of each of these open reading frames is shown in FIG. 5.

Specifically, SEQ ID NO:63 includes: the coding strand of nCUL49$_{420}$ (having SEQ ID NO:65) which encodes a non-full length CUL49 protein of about 139 amino acids, assuming a stop codon spanning about nucleotides 419–421 of SEQ ID NO:63; and the coding strand of nCUL48$_{1269}$ (having SEQ ID NO:67, and including SEQ ID NO:24) which encodes a CUL48 protein of about 422 amino acids, assuming a start codon spanning about nucleotides 541–543 and a stop codon spanning about nucleotides 1807–1809 of SEQ ID NO:63. The amino acid sequences of the respective encoded proteins PCUL49$_{139}$ and PCUL48$_{422}$ are represented by SEQ ID NO:66 and SEQ ID NO:68, respectively.

SEQ ID NO:77 includes the coding strand of nCdUTP$_{918}$ (having SEQ ID NO:79 and including SEQ ID NO:15) which encodes a CdUTPase protein of about 305 amino acids, assuming a start codon spanning about nucleotides 624–626 and a stop codon spanning about nucleotides 1539–1541 of SEQ ID NO:77. The amino acid sequence of the respective encoded protein PCdUTP$_{305}$ is represented by SEQ ID NO: 80.

SEQ ID NO:78 includes: the coding strand of nCUL51$_{261}$ (having SEQ ID NO:33) which encodes a non-full length CUL51 protein of about 86 amino acids, assuming translation begins at about nucleotide 1 and a stop codon spanning about nucleotides 259–261 of SEQ ID NO:78; the coding strand of nCUL49.5$_{261}$ (having SEQ ID NO:81) which encodes a CUL49.5 protein of about 86 amino acids, assuming a start codon spanning about nucleotides 1175–1177 and a stop codon spanning about nucleotides 1433–1435 of SEQ ID NO:78; and the coding strand of nCUL49$_{255}$ (having SEQ ID NO:83) which encodes a non-full length CUL49 protein of about 85 amino acids, assuming a start codon spanning about nucleotides 1586–1588 of SEQ ID NO:78. The amino acid sequence of the respective encoded proteins PCUL51$_{86}$, PCUL49.5$_{86}$, and PCUL49$_{85}$ are represented by SEQ ID NO:34, SEQ ID NO:82 and SEQ ID NO:84, respectively.

SEQ ID NO:85 includes the coding strand of nCUL52$_{747}$ (having SEQ ID NO:87) which encodes a non-full length CUL52 protein of about 249 amino acids, assuming translation begins at about nucleotide 1 of SEQ ID NO:85. The amino acid sequence of the respective encoded protein PCUL52$_{249}$ is represented by SEQ ID NO:88.

Example 12

This Example discloses the production of another recombinant CHV genome and recombinant CHV of the present invention.

A 3.2 kb fragment containing the entire CdUTPase sequence was amplified from CHV genomic DNA using forward primer RSF009 having nucleic acid sequence 5' GCCGGTACCAGGCTTTGGACGAGATTTAGG 3', denoted SEQ ID NO:89, and reverse primer RSF008 having nucleic acid sequence 5' GCCGAATTCAATATAAT-TAATAAACTCTC3', denoted SEQ ID NO:90. RSF009 has an Asp718 site attached to the 5' end of CHV homologous sequences, and RSF008 has an EcoRI site attached to the 5' end of CHV homologous sequences. The resultant PCR-amplified fragment of about 3.2 kb, referred to herein as $nCdUTP_{3200}$, was digested with Asp718 and EcoRI and ligated into plitmus28 (available from New England Biolabs). The resultant recombinant plasmid, denoted herein as p28CdUTP$_{3200}$, was verified by end-sequencing and restriction mapping. Plasmid p28CdUTP$_{3200}$ was then digested with HindIII and XbaI, releasing an 858 base-pair fragment, referred to herein as nCdUTP$_{858}$, containing all of the dUTPase open reading frame except 108 bp at the 3' end. The XbaI site was found to be 49 nucleotides upstream of the start codon of the dUTPase ORF (open reading frame), and is also 70 nucleotides into the UL49.5 ORF on the opposite strand, which overlaps the dUTPase ORF. Previous studies have shown that the UL49.5 ORF in other herpesviruses encodes a membrane protein, and is nonessential for growth in tissue culture (e.g., Liang et al, ibid.).

The cohesive ends on the remaining 2.3 kb fragment of p28CdUTP$_{3200}$, minus the 858 bp HindIII/XbaI fragment, were filled in using Klenow fragment and dNTPs according to standard methods. The resulting blunt-ended fragment was gel purified by standard methods. A heterologous nucleic acid sequence operatively linked to transcription control regions, in this case an AscCMV/lacZ/BGH cassette described in Example 6, was isolated from its plasmid by digestion with AscI, and the cohesive ends were filled in by Klenow fragment and dNTPs. This cassette was ligated to the HindIII and XbaI-digested p28CdUTP$_{3200}$ fragment described above by standard methods resulting in a plasmid containing flanking regions to the CHV dUTPase gene and with the lacZ gene, operatively linked to transcription control regions, inserted into a deletion of the dUTPase gene, herein denoted as pdUTP/lacZ.

A recombinant CHV is produced by co-transfecting the plasmid with the deleted dUTPase gene and the inserted heterologous nucleic acid molecule, in this case pdUTP/lacZ, and CHV DNA into canine cells using previously described methods; see, for example, Graham et al, ibid.). Alternatively, a recombinant CHV is produced by transfecting canine cells with the aforementioned plasmid as described, and then infecting the cells with CHV. Recombinant dUTPase-negative CHV are selected for by passage in mercurithio analogs of deoxyuridine as described in Example 8. If the heterologous nucleic acid molecule is the lacZ gene, such a recombinant CHV can be selected as described in Example 6.

Example 13

This example discloses a method for obtaining higher plaque forming efficiencies to facilitate the production of recombinant CHV genomes and recombinant CHV of the present invention. The method involves the expression of the CHV alpha-tif gene in the presence of CHV genomes introduced into canine cells during CHV production.

The alpha-tif gene of CHV (denoted herein as $nCUL48_{1269}$) was identified to lie on two CHV clones described herein: namely, $nCHin_{3000}$ and $nCHin_{8500}$. Nucleotide sequencing from the ends of these two fragments using universal primers and internal primers designed based on previous sequences was used to determine the entire sequence. A single fragment including the complete alpha-tif gene was PCR amplified from CHV viral DNA using forward primer RSF014 having nucleic acid sequence 5' CCGGAATTCGCTTAGTGAGAGTATAAAC 3', denoted SEQ ID NO 91, and reverse primer RSF016 having nucleic acid sequence 5' CCGGAATTCCCTCATATTATATAC-TAAC 3', denoted SEQ ID NO:92. Both primers have EcoRI sites attached to the 5' end of the CHV homologous sequences. The resultant PCR amplified fragment of about 1351 base pairs was digested with EcoRI and ligated into EcoRI-digested pCDNA3 (available from Invitrogen, described in Example 6). This plasmid contains a neomycin-resistance gene for selection of stably transformed cell lines by techniques well known to those skilled in the art. Resulting plasmids were checked for the proper orientation by digestion with HindIII. A plasmid consisting of pcDNA3 with the alpha-tif gene inserted in the proper orientation for expression was found, and is designated herein as $pATIF_{1351}$. Expression of CHV alpha-tif from $pATIF_{1351}$ was verified by cell-free transcription/translation using T7 RNA polymerase and a rabbit reticulocyte lysate system. These techniques are readily apparent to those skilled in the art, and are available in kit form, for example, from Amersham. Improved CHV DNA infectivity is then achieved by cotransfection of $pATIF_{1351}$ with from about 1 to about 5 μg of CHV DNA by methods such as described in Examples 6–9 and Example 12.

Alternatively, cell lines that stably express CHV alpha-tif are derived. Three canine cell lines, A72, D17 and CF2Th (all available from ATCC) were transfected with $pATIF_{1351}$ by standard methods, see, for example, Graham et al, ibid. The cells are then subjected to selection using varying amounts of the antibiotic G418 (available from BMB), determined empirically for each cell line. Cloned G418-resistant cell lines are then derived by standard dilution methods. Cell lines stably expressing CHV alpha-tif are then used for standard CHV DNA transfections or co-transfections such as those described in Examples 6–9 and Example 12.

Example 14

This Example describes the identification and sequencing of additional CHV nucleic acid molecules of the present invention.

CHV nucleic acid molecule $nCHin_{5500}$, a CHV HindIII fragment derived as described in Example 2, was submitted to nucleic acid sequence analysis. Sequences derived from the sequence analysis include SEQ ID NO:69, SEQ ID NO:70, SEQ ID NO:73 and SEQ ID NO:74. Translation of these sequences indicated that $nCHin_{5500}$ includes at least a portion of the CgL and CICP4 coding regions. The nucleic acid molecule also apparently contains the CICP0 coding region.

SEQ ID NO:69 and SEQ ID NO:70 represent the deduced nucleic acid sequences of the two complementary strands of a CHV ICP4 nucleic acid molecule referred to herein as $nCICP4_{626}$. Translation of SEQ ID NO:69 indicates that $nCICP4_{626}$ encodes a non-full length CICP4 protein of about 208 amino acids, denoted herein as $PCICP4_{208}$, having an amino acid sequence represented by SEQ ID NO:72. The coding region for $PCICP4_{208}$ is denoted herein as $nCICP4_{624}$, having nucleic acid sequence SEQ D NO:71.

SEQ ID NO:73 and SEQ ID NO:74 represent the deduced nucleic acid sequences of the two complementary strands of a CHV gL nucleic acid molecule referred to herein as $nCgL_{655}$. Translation of SEQ ID NO:74 indicates that $nCgL_{655}$ encodes a non-full length CgL protein of about 171 amino acids, denoted herein as $PCgL_{171}$, having an amino acid sequence represented by SEQ ID NO:76. The coding region for $PCgL_{171}$ is denoted herein as $nCgL_{516}$, having nucleic acid sequence SEQ D NO:75, assuming that the open reading frame spans about nucleotides 1 through 516 of SEQ ID NO:74, with a stop codon spanning about nucleotides 514–516.

Example 15

This example describes the mapping of messenger RNA molecules transcribed from nucleic acid molecules of the present invention. These transcripts are useful for verifying expression (or lack of expression) of various genes.

Figure 4:
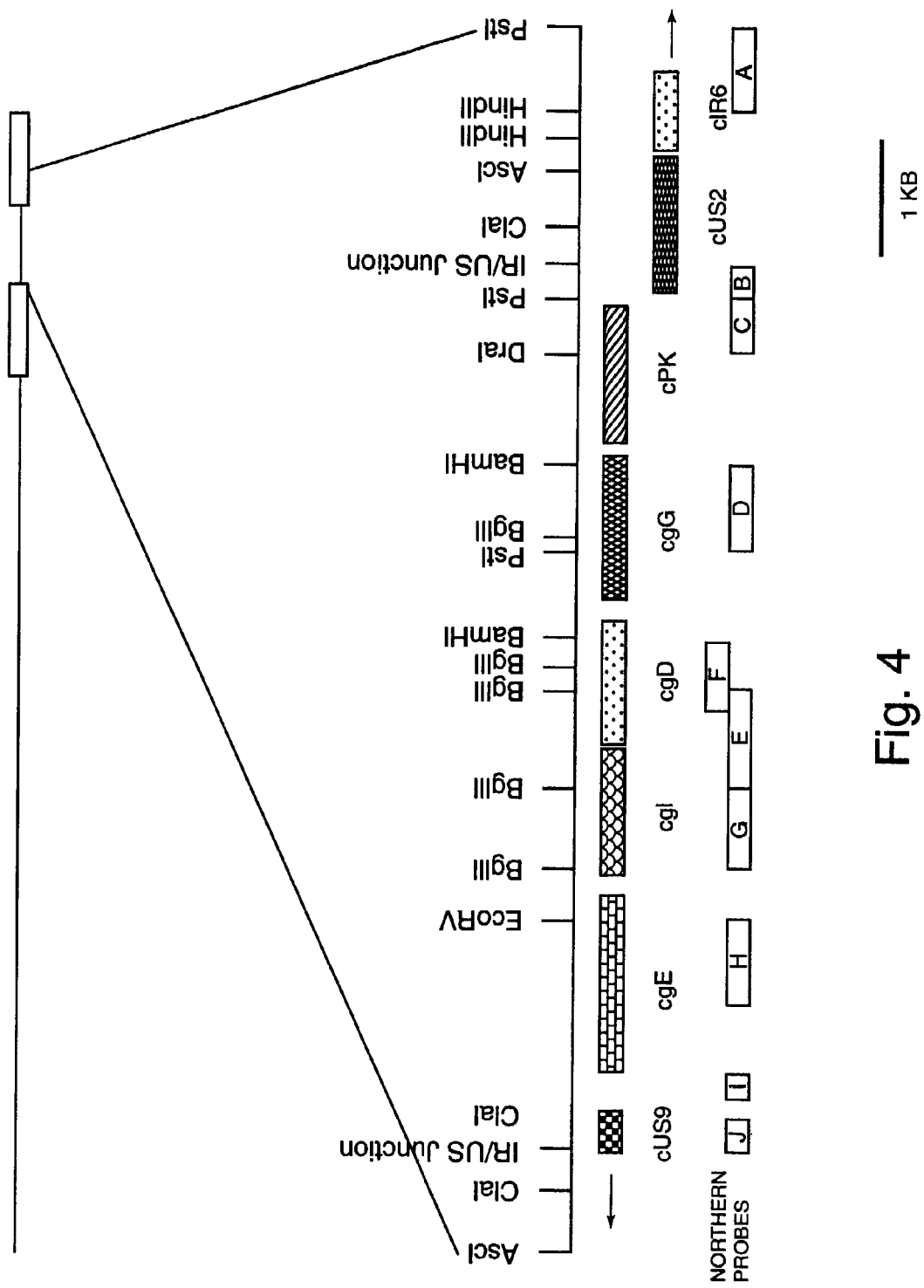
FIG. 4 depicts a schematic map of a region of the CHV genome spanning at least from the CUS9 gene through the CIR6 gene.

Total RNA was prepared from CHV-infected cells using a phenol/guanidine extraction method familiar to those skilled in the art. See, for example, Chomczynski et al, 1987, *Anal. Biochem.* 162, 156–159. Multiple samples of RNA were separated on formaldehyde/agarose gels and transferred to nitrocellulose by standard methods. Based on the sequences of $nCUS_{10592}$, designated SEQ ID NO:51 and SEQ ID NO:52, nucleic acid fragments were isolated for use as probes, such that they would hybridize to sequences homologous to the open reading frames $nCPK_{1203}$ (SEQ ID NO:7), $nCgG_{1248}$ (SEQ ID NO:9), $nCgD_{1038}$ (SEQ ID NO:53), $nCgG_{1095}$ (SEQ ID NO:55), $nCgE_{1569}$ (SEQ ID NO:57), nCUS8.5237 (SEQ ID NO:59), $nCUS9_{360}$ (SEQ ID NO:61), $nCIR6_{552}$ (SEQ ID NO:3), and $nCUS2_{1176}$ (SEQ ID NO:5). The probes were as follows: to hybridize with an $nCIR6_{552}$ (SEQ ID NO:3) transcript, a PstI-HindIII restriction fragment extending from about nucleotide 1 to about nucleotide 685 in $nCUS_{10592}$ herein denoted as probe A; to hybridize with an $nCUS2_{1176}$ (SEQ ID NO:5) transcript, a PCR-amplified fragment extending from about nucleotide 2056 to about nucleotide 2273 in $nCUS_{10592}$ herein denoted as probe B; to hybridize with an $nCPK_{1203}$ (SEQ ID NO:7) transcript, a PstI-DraI restriction fragment extending from about nucleotide 2326 to about nucleotide 2788 in $nCUS_{10592}$ herein denoted as probe C; to hybridize with an $nCgG_{1248}$ (SEQ ID NO:9) transcript, a BamHI-PstI restriction fragment extending from about nucleotide 3766 to about nucleotide 4494 in $nCUS_{10592}$ herein denoted as probe D; to hybridize with an $nCgD_{1038}$ (SEQ ID NO:53) transcript, either a BglII-BglII restriction fragment extending from about nucleotide 5728 to about nucleotide 6561 in $nCUS_{10592}$ (this piece slightly overlaps $nCgI_{1095}$) herein denoted as probe E, or a PCR-amplified fragment that will extend from about nucleotide 5295 to about nucleotide 5885 in $nCUS_{10592}$ herein denoted as probe F; to hybridize with an $nCgI_{1095}$ (SEQ ID NO:55) transcript, a BglII-BglII restriction fragment extending from about nucleotide 6561 to about nucleotide 7263 in $nCUS_{10592}$ herein denoted as probe G; to hybridize with an $nCgE_{1569}$ (SEQ ID NO:57) transcript, a deletion subclone extending from about nucleotide 7667 to about nucleotide 8425 in $nCUS_{10592}$ herein denoted as probe H; to hybridize with a putative ncus85237 (SEQ ID NO:59) transcript, a PCR-amplified fragment extending from about nucleotide 9023 to about nucleotide 9242 in $nCUS_{10592}$ herein denoted as probe I; to hybridize to an $nCUS9_{360}$ (SEQ ID NO:61) transcript, a PCR-amplified fragment extending from about nucleotide 9447 to about nucleotide 9715 in $nCUS_{10592}$ herein denoted as probe J. These probes are shown graphically in FIG. 4. The probes were labelled with $^{32}P$ DATP using random priming, a technique well known to those skilled in the art. Hybridization of the probes to the RNA samples on nitrocellulose and washing at stringent temperatures were done according to well known methods.

The main transcript sizes that hybridized to the various probes were as follows: probe A hybridized strongly to a transcript of about 0.7 kb, but also hybridized weakly to transcripts of about 1.7, 2.2 and 2.6 kb; probe B hybridized with a transcript of about 2.2 kb; probe C hybridized to a transcript of about 2.6 kb; probe D hybridized to two transcripts of about 1.9 kb and 2.6 kb; probe E hybridized to two transcripts of about 4.2 kb and 3.2 kb; probe G hybridized to two transcripts of about 4.2 kb and 3.2 kb; probe H hybridized to three transcripts of about 1.9 kb, 3.2 kb, and 4.2 kb; probe I hybridized to the same three transcripts as probe H; probe J hybridized to a transcript of about 2.1 kb. These data suggest that the transcripts of US2, US9, and IR6, although starting at different points, terminated in a common general area in the inverted repeats, since probe A hybridized to transcripts that were generally the same size as the US2 and US9 transcripts. Furthermore, these data suggest that the PK and gG transcripts overlapped, probably terminating at a common 3' terminus, since probe C hybridized to only a 2.6 kb transcript but probe D hybridized with both the 2.6 kb transcript and the 1.4 kb transcript. This result was even more likely because only one polyadenylation consensus sequence (AATAAA) was found downstream of the gG ORF, but before the gD ORF. This polyadenylation signal was found from nucleotide 4935–4940 of $nCUS_{10592}$. Similarly, these data indicate the gI and gE transcripts overlapped, probably terminating at a common 3' terminus since probe G hybridized to a transcript of 2.6 kb, while probe H hybridized both to the 2.6 kb transcript and the 1.9 kb transcript. Probes E, G, and H also all hybridized to a 4.2 kb transcript, suggesting that the gD transcript also overlapped the gI and gE transcripts, probably terminating at a common 3' terminus. Verification of this result is if probe F hybridizes only to the 4.2 kb transcript. Probe I hybridized to only the 4.2, 2.6 and 2.9 kb transcripts suggesting two things; first, that these three transcripts probably terminated at polyadenylation signals at about 9186–9181, 9256–9261 or 9260–9265 of $nCUS_{10592}$, also that the putative US8.5 open reading frame is not transcribed to levels detectable by Northern analysis.

What is claimed is:

1. An isolated nucleic acid molecule comprising a nucleic acid sequence that is at least about 90% identical to SEQ ID NO:21, SEQ ID NO:24 or SEQ ID NO:67, wherein said nucleic acid molecule encodes a herpesvirus (CHV) alpha transducing factor capable of increasing CHV plaque forming efficiency.

2. The nucleic acid molecule of claim 1, comprises $nCUL48_{1269}$.

3. The isolated nucleic acid molecule of claim 1, wherein said nucleic acid molecule comprises a nucleic acid sequence at least about 90% identical to SEQ ID NO:67.

4. An isolated nucleic acid molecule comprising the nucleotide sequence of SEQ ID NO:21, SEQ ID NO:24 or SEQ ID NO:67, wherein said nucleic acid molecule encodes a CHV alpha transducing factor capable of increasing CHV plaque forming efficiency.

5. The isolated nucleic acid molecule of claim 1, wherein said nucleic acid molecule comprises the nucleotide sequence of SEQ ID NO:24.

6. The isolated nucleic acid molecule of claim 1, wherein said nucleic acid molecule comprises the nucleotide sequence of SEQ ID NO:67.

7. The isolated molecule of claim 1, wherein said nucleic acid molecule comprises the nucleotide sequence of SEQ ID NO:21.

8. An canine cell line comprising the nucleic acid molecule of claim 1.

9. The cell line of claim 8, wherein said nucleic acid molecule is operatively linked to a transcription control region.

10. The cell line of claim 8, wherein said cell line is selected from the group consisting of MDCK cells, A72 cells, D17 cells, and CF2Th cells.

11. The cell line of claim 8, wherein said cell line is resistant to antibiotic G418.

12. A method to produce the canine cell line of claim 8, said method comprising the steps of:

(a) obtaining a recombinant plasmid, said plasmid comprising a the isolated nucleic acid molecule of claim 1 molecule operatively linked to a eukaryotic transcription control region, said plasmid further comprising an antibiotic resistance gene operatively linked to a eukaryotic transcription control region;
(b) transfecting a canine cell line with said recombinant plasmid;
(c) culturing the transfected cells in a culture medium comprising an antibiotic corresponding to the resistance gene carried by said recombinant plasmid; and
(d) selecting cloned antibiotic-resistant cell lines.

13. The method of claim 12 wherein said canine cell line is selected from the group consisting of MDCK cells, A72 cells, D17 cells, and CF2Th cells.

14. A recombinant plasmid comprising the nucleic acid molecule of claim 1 operatively linked to a transcription control region.

15. The method of claim 12, wherein said antibiotic is G418.

16. The method of claim 12, wherein said nucleic acid molecule comprises $nCUL48_{1269}$.

17. The method of claim 12, wherein said nucleic acid molecule is $nCUL48_{1269}$.

* * * * *